United States Patent
Liu et al.

(10) Patent No.: US 10,988,487 B2
(45) Date of Patent: Apr. 27, 2021

(54) SUBSTITUTED N'-HYDROXYCARBAMIMIDOYL-1,2,5-OXADIAZOLE COMPOUNDS AS INDOLEAMINE 2,3-DIOXYGENASE (IDO) INHIBITORS

(71) Applicant: Merck Sharp & Dohme Corp., Rahway, NJ (US)

(72) Inventors: Kun Liu, Needham, MA (US); Abdelghani Achab, Melrose, MA (US); Purakkattle Biju, Westwood, MA (US); Timothy A. Cernak, Boston, MA (US); Yongqi Deng, Newton, MA (US); Xavier Fradera, Needham, MA (US); Liangqin Guo, Monroe, NJ (US); Yongxin Han, Needham, MA (US); Shuwen He, Fanwood, NJ (US); Joseph Kozlowski, Princeton, NJ (US); Derun Li, West Roxbury, MA (US); Guoqing Li, Belle Mead, NJ (US); Qinglin Pu, Needham, MA (US); Zhi-Cai Shi, Monmouth Junction, NJ (US); Wensheng Yu, Edison, NJ (US); Hongjun Zhang, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 111 days.

(21) Appl. No.: 16/326,408

(22) PCT Filed: Aug. 24, 2017

(86) PCT No.: PCT/US2017/048314
§ 371 (c)(1),
(2) Date: Feb. 19, 2019

(87) PCT Pub. No.: WO2018/044663
PCT Pub. Date: Mar. 8, 2018

(65) Prior Publication Data
US 2020/0231606 A1    Jul. 23, 2020

Related U.S. Application Data

(60) Provisional application No. 62/481,321, filed on Apr. 4, 2017, provisional application No. 62/380,626, filed on Aug. 29, 2016.

(51) Int. Cl.
C07F 5/02 (2006.01)
C07D 271/08 (2006.01)
C07D 413/12 (2006.01)

(52) U.S. Cl.
CPC ............ *C07F 5/025* (2013.01); *C07D 271/08* (2013.01); *C07D 413/12* (2013.01)

(58) Field of Classification Search
None
See application file for complete search history.

(56) References Cited

U.S. PATENT DOCUMENTS

2014/0377292 A1  12/2014 Combs et al.

FOREIGN PATENT DOCUMENTS

WO    WO2004094409 A1    11/2004

OTHER PUBLICATIONS

Khalilullah, H., 1,3,4-Oxadiazole: A Biologically Active Scaffold, Mini-Revie in Medicinal Chemistry, 2012, pp. 789-801, 12.

Primary Examiner — Kamal A Saeed
(74) Attorney, Agent, or Firm — Yong Zhao; Anna L. Cocuzzo

(57) ABSTRACT

Disclosed herein is a compound of formula (I), or a pharmaceutically acceptable salt thereof: Formula (I). Also disclosed herein are uses of the compounds disclosed herein in the potential treatment or prevention of an IDO-associated disease or disorder. Also disclosed herein are compositions comprising a compound disclosed herein. Further disclosed herein are uses of the compositions in the potential treatment or prevention of an IDO-associated disease or disorder.

20 Claims, No Drawings

SUBSTITUTED N'-HYDROXYCARBAMIMIDOYL-1,2,5-OXADIAZOLE COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2017/048314, filed Aug. 24, 2017, which claims the benefit of U.S. Provisional Application No. 62/380,626, filed Aug. 29, 2016, and U.S. Provisional Application No. 62/481,321, filed Apr. 4, 2017, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517~24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppresses T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV.

Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salts thereof:

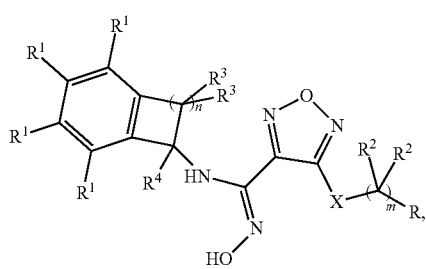

(I)

wherein:
m is 0, 1, 2, or 3; n is 1, 2, or 3,
X is —S— or —NH—;
R is selected from the group consisting of:
(a) hydrogen,
(b) $C_{1-6}$alkyl, optionally substituted with one to three substituents independently selected from the group consisting of (i) —OH, (ii) halogen, and (iii) —NH₂,
(c) $C_{3-6}$cycloalkyl, optionally substituted with one to three substituents independently selected from the group consisting of (i) NH₂, (ii) —NH—S(O)₂—NH₂ and (iii) —NH—C(O)—$C_{1-6}$alkyl, optionally substituted with —OH,
(d) $C_{4-6}$cycloalkenyl, optionally substituted with an oxo,
(e) —(C=O)—NH—$R^a$, wherein $R^a$ is selected from the group consisting of:
  (i) hydrogen,
  (ii) —$C_{1-6}$alkyl, optionally substituted with one to three substituents independently selected from the group consisting of (1) halogen, (2) —OH and (3) —S(O)₂—$C_{1-6}$alkyl,
  (iii) —$C_{1-6}$alkoxy, and
  (iv) —$C_{3-6}$cycloalkyl,
(f) —$NR^xR^y$, wherein each of $R^x$ and $R^y$ is independently selected from the group consisting of:
  (i) hydrogen,
  (ii) —(C=O)—$R^a$, wherein $R^a$ is selected from the group consisting of (1) hydrogen, and (2) —$C_{1-6}$alkyl, optionally substituted with one to three substituents independently selected from halogen and —CN, (3) —NH₂, (4) —NH—$C_{1-6}$alkyl, optionally substituted with —OH, —O-methyl, or —CN, (5) —NH—$C_{3-6}$cycloalkyl, and (6) heterocyclyl, optionally substituted with —OH,
  (iii) —S(O)₂—NH₂,
  (iv) —S(O)₂—CH₃, and
  (v) $C_{4-5}$cycloalkenyl, optionally substituted with one to four substituents independently selected from the group consisting of (1) oxo, (2) —$C_{1-6}$alkyl, and (3) —NH—$C_{1-6}$alkyl, and
(g) a 4-, 5- or 6-membered heterocyclyl, optionally substituted with one to four substituents independently selected from the group consisting of (i) halogen, (ii) $C_{1-6}$alkyl, (iii) oxo, (iv) —C(O)—$C_{1-6}$alkyl, optionally substituted with one to three groups independently selected from —OH and —O—$C_{1-6}$alkyl, (v) —S(O)₂—NH₂ and (vi) —S(O)₂—NH—$C_{1-6}$alkyl, optionally substituted with —OH,
(h) —S(O)₂—$C_{1-6}$alkyl, optionally substituted with one to three —OH groups,
(i) —O—S(O)₂—NH₂;
(j)

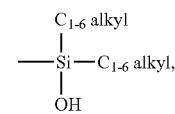

(k) a 7-, 8-, 9- or 10-membered bi-cyclic heterocyclyl, optionally substituted with one to three substituents independently selected from the group consisting of (i) halogen, (ii) $C_{1-6}$alkyl and (iii) oxo,
(l) aryl, optionally substituted with one to three substituents independently selected from the group consisting of (i) halogen and (ii) —B(OH)₂;

each occurrence of $R^1$ is independently selected from the group consisting of (a) hydrogen, (b) halogen, (c) —CN, and (d) $C_{1-6}$ alkyl, optionally substituted with 1 to 3 halogens;

each occurrence of $R^2$ is independently selected from the group consisting of (a) hydrogen, (b) halogen, (c) —OH, (d) —NH$_2$ and (e) $C_{1-6}$ alkyl, optionally substituted with —OH;

each occurrence of $R^3$ is independently selected from the group consisting of (a) hydrogen, (b) halogen, (c) $C_{1-6}$ alkyl, and (d) —O—$C_{1-6}$ alkyl; and $R^4$ is selected from the group consisting of (a) hydrogen and (b) $C_{1-4}$ alkyl.

In one embodiment of formula (I), m is 0, 1, 2, or 3; n is 1, 2, or 3;

X is —S— or —NH—;

R is selected from the group consisting of:
(a) hydrogen,
(b) $C_{1-6}$alkyl, optionally substituted with one to three substituents independently selected from the group consisting of (i) —OH, (ii) halogen, and (iii) —NH$_2$,
(c) $C_{3-6}$cycloalkyl, optionally substituted with one to three substituents independently selected from the group consisting of (i) NH$_2$, (ii) —NH—S(O)$_2$—NH$_2$ and (iii) —NH—C(O)—$C_{1-6}$alkyl, optionally substituted with —OH,
(d) $C_{4-6}$cycloalkenyl, optionally substituted with an oxo,
(e) —(C=O)—NH—$R^a$, wherein $R^a$ is selected from the group consisting of:
 (i) hydrogen,
 (ii) —$C_{1-6}$alkyl, optionally substituted with one to three substituents independently selected from the group consisting of (1) halogen, (2) —OH and (3) —S(O)$_2$—$C_{1-6}$alkyl,
 (iii) —$C_{1-6}$alkoxy, and
 (iv) —$C_{3-6}$cycloalkyl,
(f) —NR$^x$R$^y$, wherein each of R$^x$ and R$^y$ is independently selected from the group consisting of:
 (i) hydrogen,
 (ii) —(C=O)—$R^a$, wherein $R^a$ is selected from the group consisting of (1) hydrogen, and (2) —$C_{1-6}$alkyl, optionally substituted with one to three substituents independently selected from halogen and —CN, (3) —NH$_2$, (4) —NH—$C_{1-6}$alkyl, optionally substituted with —OH, —O-methyl, or —CN, and (5) —NH—$C_{3-6}$cycloalkyl,
 (iii) —S(O)$_2$—NH$_2$,
 (iv) —S(O)$_2$—CH$_3$, and
 (v) $C_{4-5}$cycloalkenyl, optionally substituted with one to four substituents independently selected from the group consisting of (1) oxo, (2) —$C_{1-6}$alkyl, and (3) —NH—$C_{1-6}$alkyl, and
(g) a 4-, 5- or 6-membered heterocyclyl, optionally substituted with one to four substituents independently selected from the group consisting of (i) halogen, (ii) $C_{1-6}$alkyl, (iii) oxo and (iv) —C(O)—$C_{1-6}$alkyl, optionally substituted with optionally substituted with one to three —OH groups;

each occurrence of $R^1$ is independently selected from the group consisting of (a) hydrogen, (b) halogen, (c) —CN, and (d) $C_{1-6}$ alkyl, optionally substituted with 1 to 3 halogens;

each occurrence of $R^2$ is independently selected from the group consisting of (a) hydrogen, (b) halogen, and (c) —OH;

each occurrence of $R^3$ is independently selected from the group consisting of (a) hydrogen, (b) halogen, (c) $C_{1-6}$ alkyl, and (d) —O—$C_{1-6}$ alkyl; and $R^4$ is selected from the group consisting of (a) hydrogen and (b) $C_{1-4}$ alkyl.

In one embodiment of formula (I), m is 1 or 2; and n is 1 or 2.

In one embodiment of formula (I), R is selected from the group consisting of:
(a) $C_{1-4}$alkyl, optionally substituted with one to two —OH groups,
(b) $C_{3-4}$cycloalkyl,
(c) —(C=O)—NH—$R^a$, wherein $R^a$ is selected from the group consisting of:
 (i) hydrogen,
 (ii) —$C_{1-6}$alkyl,
 (iii) —$C_{1-6}$alkoxy, and
 (iv) —$C_{3-6}$cycloalkyl,
(d) —NR$^x$R$^y$, wherein each of R$^x$ and R$^y$ is independently selected from the group consisting of:
 (i) hydrogen,
 (ii) —(C=O)—$C_{1-6}$alkyl,
 (iii) —S(O)$_2$—NH$_2$, and
 (iv) cyclobutenyl, optionally substituted with one to three substituents independently selected from the group consisting of (1) oxo, (2) —$C_{1-4}$alkyl, and (3) —NH—$C_{1-4}$alkyl, and
(e) a 5- or 6-membered heterocyclyl, optionally substituted with one to four substituents independently selected from the group consisting of (i) $C_{1-6}$alkyl, and (ii) oxo.

In one embodiment of formula (I), R is selected from the group consisting of:
(a) methyl, ethyl or propyl, each of which is optionally substituted with one to two —OH groups,
(b) cyclopropyl,
(c) —(C=O)—NH—$R^a$, wherein $R^a$ is selected from the group consisting of (i) hydrogen, (ii) methyl, (iii) ethyl, (iv) methoxy and (v) ethoxy,
(d) —NR$^x$R$^y$, wherein each of R$^x$ and R$^y$ is independently selected from the group consisting of (i) hydrogen, (ii) —(C=O)-methyl, (iii) —(C=O)-ethyl, (iv) —(C=O)-propyl, (v) —S(O)$_2$—NH$_2$, and (vi) cyclobutenyl, optionally substituted with one to three substituents independently selected from the group consisting of (i) oxo, (ii) methyl, (iii) ethyl, (ii) —NH-methyl, and (iii) —NH-ethyl, and
(e) a 5- or 6-membered heterocyclyl selected from pyridinyl, pyrimidinyl, piperidinyl, triazolyl, and thiazolyl, each of which is optionally substituted with one to four substituents independently selected from the group consisting of (i) $C_{1-6}$alkyl, and (ii) oxo.

In one embodiment of formula (I), R is a 5- or 6-membered heterocyclyl selected from the group consisting of pyridinyl, pyrimidinyl, piperidinyl, triazolyl and thiazolyl; wherein the 5- or 6-membered heterocyclyl is optionally substituted with one to four substituents independently selected from the group consisting of (i) $C_{1-6}$alkyl, and (ii) oxo.

In one embodiment of formula (I), each occurrence of $R^1$ is independently selected from the group consisting of (a) hydrogen, (b) halogen, (c) —CN, and (d) $C_{1-4}$ alkyl, optionally substituted with 1 to 3 halogens.

In one embodiment of formula (I), each occurrence of $R^2$ is independently selected from the group consisting of (a) hydrogen, and (b) —OH.

In one embodiment of formula (I), each occurrence of $R^3$ is independently selected from the group consisting of (a) hydrogen, (b) $C_{1-4}$ alkyl, and (c) —O—$C_{1-4}$ alkyl.

In one embodiment of formula (I):

R is selected from the group consisting of:
(a) $C_{1-4}$alkyl, optionally substituted with one to two —OH groups,
(b) $C_{3-4}$cycloalkyl,
(c) —(C=O)—NH—$R^a$, wherein $R^a$ is selected from the group consisting of (i) hydrogen, and (ii) —$C_{1-6}$alkyl,
(d) —$NR^xR^y$, wherein each of $R^x$ and $R^y$ is independently selected from the group consisting of (i) hydrogen, (ii) —(C=O)—$C_{1-6}$alkyl, and (iii) —$S(O)_2$—$NH_2$, and
(e) 5- or 6-membered heterocyclyl, optionally substituted with one to four substituents independently selected from the group consisting of (i) $C_{1-6}$alkyl and (ii) oxo each occurrence of $R^1$ is independently selected from the group consisting of (a) hydrogen, (b) halogen, (c) —CN, and (d) $C_{1-4}$ alkyl, optionally substituted with 1 to 3 halogens;

each occurrence of $R^2$ is independently selected from the group consisting of (a) hydrogen, and (b) —OH;

each occurrence of $R^3$ is independently selected from the group consisting of (a) hydrogen, (b) $C_{1-4}$ alkyl, and (c) —O—$C_{1-4}$ alkyl; and $R^4$ is selected from the group consisting of (a) hydrogen, and (b) $C_{1-6}$ alkyl.

In one embodiment of formula (I):
m is 0, 1, 2, or 3; n is 1, 2, or 3,
X is —S— or —NH—;
R is selected from the group consisting of:
(a) hydrogen,
(b) $C_{1-6}$alkyl, optionally substituted with one to three substituents independently selected from the group consisting of (i) hydroxy, (ii) halogen, and (iii) —$NH_2$,
(c) $C_{3-6}$cycloalkyl,
(d) —(C=O)—NH—$R^a$, wherein $R^a$ is selected from the group consisting of:
 (i) hydrogen,
 (ii) —$C_{1-6}$alkyl, optionally substituted with one to three halogens,
 (iii) —$C_{1-6}$alkoxy, and
 (iv) —$C_{3-6}$cycloalkyl,
(e) —$NR^xR^y$, wherein each of $R^x$ and $R^y$ is independently selected from the group consisting of:
 (i) hydrogen,
 (ii) —(C=O)—$R^a$, wherein $R^a$ is selected from the group consisting of (1) hydrogen, and (2) —$C_{1-6}$alkyl, optionally substituted with one to three halogens, (3) —NH—$C_{1-6}$alkyl, optionally substituted with —OH or —O-methyl, and (4) —NH—$C_{3-6}$cycloalkyl,
 (iii) —$S(O)_2$—$NH_2$,
 (iv) —$S(O)_2$—$CH_3$, and
 (v) $C_{4-5}$cycloalkenyl, optionally substituted with one to four substituents independently selected from the group consisting of (1) oxo, (2) —$C_{1-6}$alkyl, and (3) —NH—$C_{1-6}$alkyl, and
(f) a 5- or 6-membered heterocyclyl, optionally substituted with one to four substituents independently selected from the group consisting of (i) halogen, (ii) $C_{1-6}$alkyl, and (iii) oxo;

each occurrence of $R^1$ is independently selected from the group consisting of (a) hydrogen, (b) halogen, (c) —CN, and (d) $C_{1-6}$ alkyl, optionally substituted with 1 to 3 halogens;

each occurrence of $R^2$ is independently selected from the group consisting of (a) hydrogen, (b) halogen, and (c) hydroxy;

each occurrence of $R^3$ is independently selected from the group consisting of (a) hydrogen, (b) halogen, (c) $C_{1-6}$ alkyl, and (d) —O—$C_{1-6}$ alkyl; and $R^4$ is selected from the group consisting of (a) hydrogen and (b) $C_{1-4}$ alkyl.

In one embodiment, a compound disclosed herein is of formula (Ia):

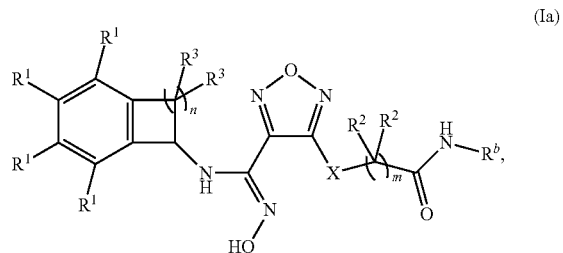

(Ia)

wherein:
m is 1, 2, or 3; n is 1 or 2;
X is —S— or —NH—;
$R^b$ is selected from the group consisting of:
(a) $C_{1-6}$alkyl, optionally substituted with one to two —OH groups,
(b) $C_{3-6}$cycloalkyl,
(c) $C_{1-6}$alkoxy, and
(d) —$NR^xR^y$, wherein each of $R^x$ and $R^y$ is independently selected from the group consisting of (i) hydrogen, (ii) —$C_{1-6}$alkyl, (iii) —$C_{3-6}$cycloalkyl and (iv) —(C=O)—$C_{1-6}$alkyl;

each occurrence of $R^1$ is independently selected from the group consisting of (a) hydrogen, (b) halogen, (c) —CN, and (d) $C_{1-4}$ alkyl, optionally substituted with 1 to 3 halogens;

each occurrence of $R^2$ is independently selected from the group consisting of (a) hydrogen, and (b) —OH; and each occurrence of $R^3$ is independently selected from the group consisting of (a) hydrogen, (b) $C_{1-6}$alkyl, and (c) —O—$C_{1-6}$alkyl.

In one embodiment of formula (Ia):
$R^b$ is selected from the group consisting of:
(a) $C_{1-4}$alkyl, optionally substituted with one to two —OH groups,
(b) $C_{3-4}$cycloalkyl,
(c) $C_{1-4}$alkoxy, and
(d) —NH—$R^a$, wherein $R^a$ is selected from the group consisting of (i) hydrogen, and (ii) —$C_{1-6}$alkyl.

In one embodiment of formula (Ia), $R^b$ is selected from the group consisting of methyl, ethyl, propyl, iso-propyl, methoxy, ethoxy, propoxy and cyclopropyl.

In one embodiment of formula (Ia):
each occurrence of $R^1$ is independently selected from the group consisting of (a) hydrogen, (b) halogen, (c) —CN, and (d) —$CF_3$.

In one embodiment of formula (Ia):
each occurrence of $R^2$ is hydrogen.

In one embodiment of formula (Ia):
each occurrence of $R^3$ is independently selected from the group consisting of (a) hydrogen, (b) methyl, (c) ethyl, (d) —O-methyl, and (e) —O-ethyl.

In one embodiment, a compound disclosed herein is of formula (Ib):

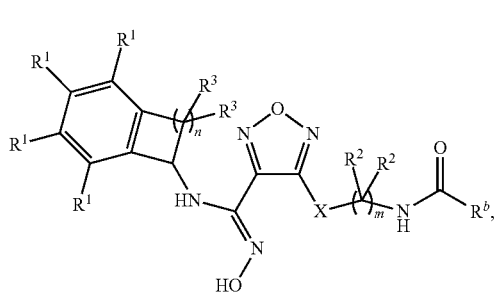

(Ib)

wherein
m is 1, 2, or 3; n is 1 or 2;
X is —S— or —NH—,
$R^b$ is selected from the group consisting of:
  (a) $C_{1-6}$alkyl, optionally substituted with one to two —OH groups, and
  (b) $C_{3-6}$cycloalkyl;
each occurrence of $R^1$ is independently selected from the group consisting of (a) hydrogen, (b) halogen, and (c) —CN;
each occurrence of $R^2$ is independently selected from the group consisting of (a) hydrogen, and (b) —OH; and
each occurrence of $R^3$ is independently selected from the group consisting of (a) hydrogen, (b) $C_{1-6}$alkyl, and (c) —O—$C_{1-6}$alkyl.

In one embodiment of formula (Ib):
each occurrence of $R^1$ is independently selected from the group consisting of (a) hydrogen, (b) halogen, and (c) —CN.

In one embodiment of formula (Ib):
each occurrence of $R^2$ is hydrogen and each occurrence of $R^3$ is independently selected from the group consisting of (a) hydrogen, (b) methyl, and (c) ethyl.

In one embodiment, a compound disclosed herein is selected from the group consisting of the compounds exemplified in Examples 1 to 242; or a pharmaceutically acceptable salt thereof.

Also disclosed herein is a pharmaceutical composition comprising a compound of formula I, (Ia), or (Ib) and at least one pharmaceutically acceptable carrier.

Also disclosed herein is a method of inhibiting activity of indoleamine 2,3-dioxygenase (IDO) comprising contacting IDO with a compound of formula I, (Ia), or (Ib), or a pharmaceutically acceptable salt thereof.

Also disclosed herein is a method of inhibiting immunosuppression in a patient comprising administering to said patient an effective amount of a compound of formula I, (Ia), or (Ib), or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound of formula I, (Ia), or (Ib), or a pharmaceutically acceptable salt thereof.

Also disclosed herein is a method of treating melanoma in a patient comprising administering to said patient an effective amount of a compound of Formula I, or a pharmaceutically acceptable salt thereof.

Further disclosed herein is a compound of formula I, (Ia), or (Ib), or a pharmaceutically acceptable salt thereof, for use in therapy. In one embodiment, disclosed herein is the use of a compound of formula I, (Ia), or (Ib), or a pharmaceutically acceptable salt thereof, for the preparation of a medicament for use in therapy.

As used herein, "alkenyl" refers to both branched- and straight-chain unsaturated aliphatic hydrocarbon groups of 2 to 12 carbon atoms and having at least one carbon-carbon double bond. Alkenyl groups may be optionally substituted with one or more substituents as defined herein. Examples of such groups include, but are not limited to, ethenyl, propenyl, n-butenyl, 3-methylbut-2-enyl, n-pentenyl, octenyl and decenyl. "$C_{2-6}$alkenyl" refers to an alkenyl group as defined herein having 2 to 6 carbon atoms.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is boron, oxygen, sulfur, or nitrogen. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4- oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

Optical Isomers—Diastereomers—Geometric Isomers—Tautomers

Included herein are various isomers of the compounds of formula (I). The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound of formula (I) may have one or more asymmetric carbon atom and may occur as mixtures (such as a racemic mixture) or as individual enantiomers or diastereomers. All such isomeric forms are included herein, including mixtures thereof. If a compound of formula (I) contains a double bond, the substituent may be in the E or Z configuration. If a compound of formula (I) or (Ia) contains a disubstituted cycloalkyl, the cycloalkyl substituent may have a cis- or trans-configuration. All tautomeric forms are also intended to be included.

Any asymmetric atom (e.g., carbon) of a compound of formula (I), can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis—(Z)— or trans—(E)—form.

A compound of formula (I), can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds of formula I, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds of formula (I), can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I), is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds of the invention can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I).

One embodiment of the present invention provides for a method of treating a disease or disorder associated with IDO enzyme activity comprising administration of an effective amount of a compound of formula (I) to a subject in need of treatment thereof. In one embodiment, the disease or disorder associated with an IDO enzyme is a cell proliferation disorder.

In one embodiment, disclosed herein is the use of a compound of formula (I) in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound of formula (I), or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, poly epsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I) and one or more other active agent(s) together in the same pharmaceutical composition, or a compound of formula (I), and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I), and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I), for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound of formula (I).

The invention also provides the use of a compound of formula (I) for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound of formula (I). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—(R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyridinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

Experimental

The following examples are intended to be illustrative only and not limiting in any way. Abbreviations used are those conventional in the art or the following.

| ACN | acetonitrile |
|---|---|
| ° C. | degree Celsius |
| DCM | dichloromethane |
| DMA | dimethylamine |
| DMF | N,N-dimethylformamide |
| DMSO | dimethylsulfoxide |
| EtOAc | ethyl acetate |
| EtOH | ethanol |
| g | gram |
| h | hour(s) |
| HPLC | high pressure liquid chromatography |
| kg | kilogram |
| L | liter |
| LC | liquid chromatography |
| LCMS | liquid chromatography and mass spectrometry |
| MeOH | methanol |
| MS | mass spectrometry |
| MTBE | methyl tert-butyl ether |
| min | minutes |
| mL | milliliter(s) |
| m/z | mass to charge ratio |
| nm | nanometer |
| nM | nanomolar |
| N | normal |
| MR | nuclear magnetic resonance |
| RT or rt | room temperature |
| sat. | saturated |
| TEA | triethyl amine |
| FA | trifluoroacetic acid |
| THF | tetrahydrofuran |

Intermediates

Intermediate A: 4-Amino-N'-hydroxy-1,2,5-oxadiazole-3-carboximidamide

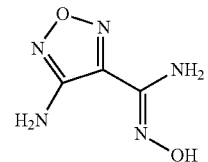

Malononitrile (15 g, 227 mmol) in 2N HCl (200 ml) was stirred till dissolved. With the reaction temperature kept between 15° C.-20° C., a solution of sodium nitrite (31.3 g, 454 mmol) in 45 ml of water was added dropwise and stirred at ambient for a further 16 h. An aqueous solution of hydroxylamine hydrochloride (35.0 g, 504 mmol) in 25 ml of water was added and the pH of the solution was brought to about 10 by addition of 10 N NaOH while maintaining the temperature below 20° C. The temperature of the reaction was brought to 30° C. for 1 h then refluxed for 3 h. Heating was discontinued and the reaction gradually warmed to RT overnight. The reaction was cooled in an ice bath, pH adjusted to 8 with 6N HCl and stirred for 30 min. The solids were filtered and washed with cold water to afford the title compound. MS: 144 (M+1). $^{13}$C NMR (500 MHz, CD3OD): δ 154.5, 144.3, 139.8.

Intermediate B:
4-Amino-N-hydroxy-1,2,5-oxadiazole-3-carbimidoyl chloride

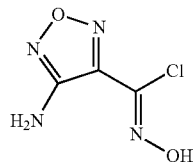

To a solution of (Z)-4-amino-N'-hydroxy-1,2,5-oxadiazole-3-carboximidamide (5.09 g, 35.6 mmol) in 70 ml of water was added AcOH (35 ml) and 6N hydrogen chloride (17.78 ml, 107 mmol). The reaction mixture was warmed to 40° C. till all solids were dissolved. The reaction was cooled to ambient and solid sodium chloride (6.24 g, 107 mmol) was added, stirred, then the reaction mixture was cooled to 0° C. A solution of sodium nitrite (2.5 g, 35.6 mmol) in 8.4 ml of water was added dropwise over 3 h and the reaction was stirred at 0° C. for a further 1.5 h, then warmed to 15° C. for 15 min. The solid precipitates were filtered and washed with cold water to afford the title product. MS: 163 (M+1). $^{13}$C NMR (500 MHz, DMSO-$d_6$): δ 154.4, 142.3, 126.8. $^1$HNMR (500 MHz, DMSO-$d_6$): δ 13.41 (s, 1H), 6.29 (s, 2H).

Intermediate C:
4-Amino-1,2,5-oxadiazole-3-carbonitrile

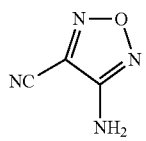

To a solution of (Z)-4-amino-N'-hydroxy-1,2,5-oxadiazole-3-carboximidamide (5.0 g, 34.9 mmol) in acetic acid (30 mL), CH3CN (3 mL) and water (3 mL) was added manganese(IV) oxide (3.04 g, 34.9 mmol). The mixture was stirred at 35° C. for 5 min, then stirred at 55° C. for 20 min. The mixture was concentrated under reduced pressure, partitioned between water (30 mL) and EtOAc (50 mL×2). The combined organic layers were washed with brine (20 mL), dried over Na$_2$SO4, filtered and concentrated under reduced pressure. The crude product was purified by column chromatography (SiO$_2$, petroleum ether/ethyl acetate 10:1-5:1 as eluent) to give the title compound as white solid. $^1$H NMR (400 MHz, CDCl3) δ 4.66 (broad s, 2H)

Intermediate D:
4-Nitro-1,2,5-oxadiazole-3-carbonitrile

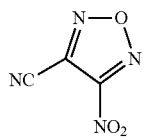

To a solution of 4-amino-1,2,5-oxadiazole-3-carbonitrile (500 mg, 4.54 mmol) in 0.8 mL of conc. H$_2$SO$_4$ at 0° C. was added dropwise a mixture of 30% H$_2$O$_2$ (0.25 mL, 4.54 mmol) in 0.2 mL of conc. H$_2$SO$_4$ (98%). The reaction was stirred for 15 min at 0° C., warmed to RT, and stirred for 16 h, poured over ice, diluted with ice cold water, extracted with CH$_2$Cl$_2$ (30 mL×2). The combined CH$_2$Cl$_2$ layers were washed with water (20 mL×2), sat. aqueous NaHCO$_3$, dried, and concentrated in vacuo. The residue was purified by column chromatography (SiO$_2$, petroleum ether/ethyl acetate 20:1 to 10:1 as eluent) to give the title compound as an oil. $^{13}$C NMR (101 MHz, CDCl$_3$) δ159.09-159.89 (m, 1C) 128.55 (s, 1C) 103.77 (s, 1C).

Intermediate E: 4-Fluorobicyclo[4.2.0]octa-1(6),2,4-trien-7-amine hydrochloride

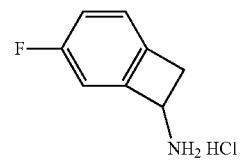

Step 1: 3-(2-bromo-4-fluorophenyl)acrylonitrile

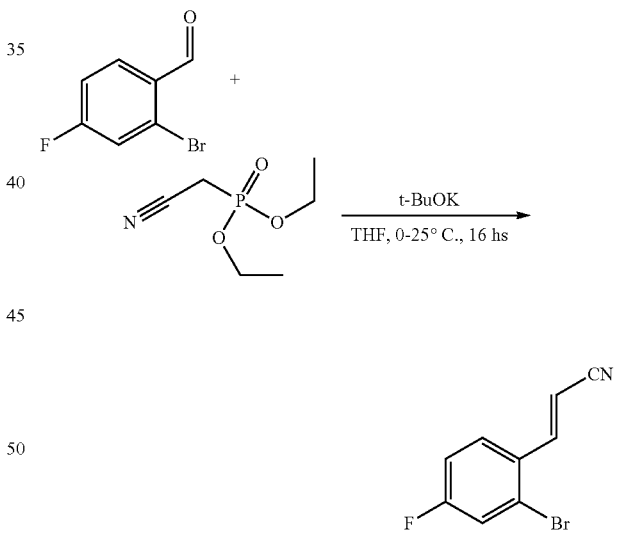

To a solution of 2-bromo-4-fluorobenzaldehyde (400.0 g, 1.97 mol) and diethyl (cyanomethyl)phosphonate (401.0 g, 2.266 mol) in THF (7 L) was added potassium 2-methylpropan-2-olate (254 g, 2.266 mol) portion-wise at 0° C. After 16 h at 25° C., water (2.5 L) was added and the mixture was stirred for another 10 min. Layers were separated. The aqueous layer was extracted with ethyl acetate (1.5 L×3). The combined organic layers were washed with brine (2.0 L), dried over anhydrous Na$_2$SO$_4$, filtered, and concentrated in vacuo. The residue was purified by column chromatography on silica gel (SiO$_2$, eluting with petroleum) to give the title compound.

Step 2: 3-(2-bromo-4-fluorophenyl)propanenitrile

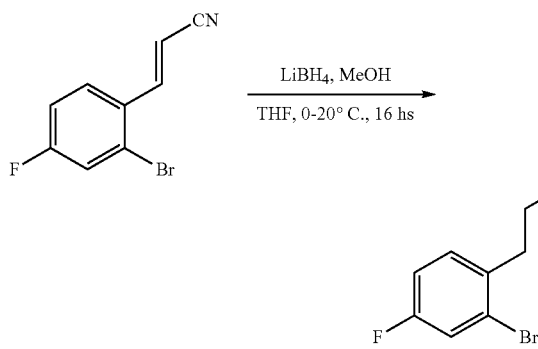

To a solution of 3-(2-bromo-4-fluorophenyl)acrylonitrile (160.0 g, 708 mmol) in THF (1.5 L) was added LiBH$_4$ (30.0 g, 1377 mmol) at 0° C. in portions over 5 min. The mixture was stirred at the 0° C. for 30 min, followed by the addition of methanol (20 mL) dropwise, warmed to 20° C., and stirred for 16 h. The mixture was quenched by adding 2.0 M KH$_2$PO$_4$ aqueous solution until pH-7, extracted with ethyl acetate (500 mL×2). The organic layers were washed with brine (sat. 100 mL), dried over anhydrous sodium sulfate, filtered, and concentrated under reduce pressure. The residue was purified by column chromatography on silica gel (SiO$_2$, eluting with petroleum ether/ethyl acetate=50:1 to 30:1) to give the title compound as an oil. $^1$H NMR (400 MHz, CDCl$_3$) δ 7.28-7.40 (m, 2H), 7.04 (td, J=8.0, 2.8 Hz, 1H), 3.07 (t, J=7.2 Hz, 2H), 2.67 (t, J=7.2 Hz, 2H).

Step 3: 4-fluorobicyclo[4.2.0]octa-1,3,5-triene-7-carbonitrile

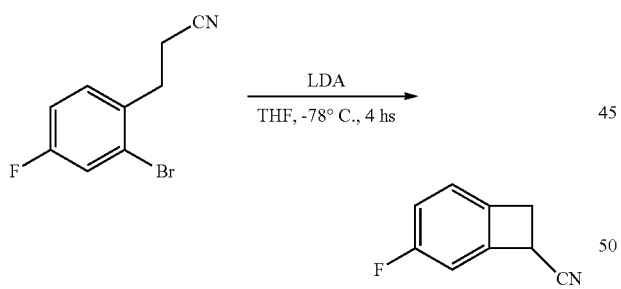

To a stirred solution of diisopropylamine (0.222 L, 1579 mmol) in THF (1.5 L) was added n-BuLi (0.631 L, 1579 mmol) (2.5 M, in hexane) dropwise at −78° C. under N$_2$ atmosphere. After the addition was finished, the reaction was stirred at −78° C. for 30 min before 3-(2-bromo-4-fluorophenyl)propanenitrile (90.0 g, 395 mmol) in THF (500 mL) was added dropwise under N$_2$ atmosphere. The mixture was stirred at −78° C. for 3 h, warmed to RT, quenched with aq. HCl (1.7 L, 1 M) to pH-8, extracted by ethyl acetate (500 mL×2). The organic layers were washed with brine (200 mL), dried over Na$_2$SO$_4$, filtered, and concentrated under reduce pressure. The residue was purified by column chromatography on silica gel (SiO$_2$, eluting with petroleum ether/ethyl acetate=50:1 to 30:1) to give title compound as an oil. $^1$H NMR (400 MHz, CDCl$_3$) δ 7.04-7.16 (m, 2H), 6.92-7.00 (m, 1H), 4.21-4.25 (m, 1H), 3.62-3.68 (m, 1H), 3.45-3.53 (m, 1H)

Step 4: 4-Fluorobicyclo[4.2.0]octa-1,3,5-triene-7-carboxylic acid

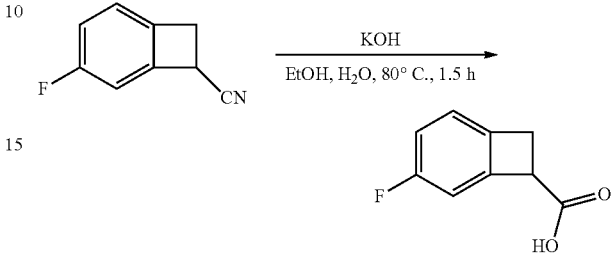

To a stirred solution of 4-fluorobicyclo[4.2.0]octa-1,3,5-triene-7-carbonitrile (73.0 g, 496 mmol) in EtOH (700 mL) and water (140 mL) was added potassium hydroxide (97.0 g, 1736 mmol) at 25° C. After the addition was finished, the reaction mixture was stirred at 80° C. for 1.5 h, cooled to RT, and concentrated under reduced pressure. The residue was dissolved in water (500 mL) and extracted by DCM (300 mL). The aqueous phase was acidified by adding aqueous HCl (6M) to a pH value of ~3, then extracted by ethyl acetate (800 mL×2). The organic layers were washed with brine (400 mL), dried over Na$_2$SO$_4$, filtered, and concentrated in vacuo to give the title compound as a solid. $^1$H NMR (400 MHz, CDCl$_3$) δ 7.04-7.07 (m, 1H), 6.92-6.97 (m, 2H), 4.30 (t, J=4.0 Hz, 1H), 3.43-3.45 (m, 2H).

Step 5: tert-Butyl (4-fluorobicyclo[4.2.0]octa-1(6),2,4-trien-7-yl)carbamate

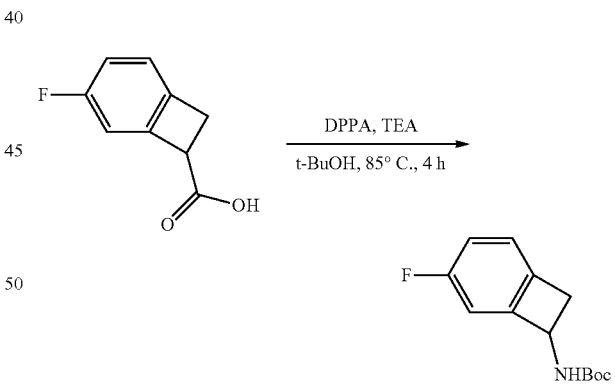

To a stirred solution of 4-fluorobicyclo[4.2.0]octa-1,3,5-triene-7-carboxylic acid (26.0 g, 156 mmol) in t-BuOH (100 mL) were added triethylamine (32.7 mL, 235 mmol) and diphenyl phosphorazidate (51.7 g, 188 mmol). The mixture was stirred at 85° C. for 4 h under N$_2$ atmosphere, cooled to RT, and concentrated under reduced pressure. The residue was purified by silica chromatography (petroleum ether/ethyl acetate=50:1~30:1) to afford the title compound. $^1$H NMR (400 MHz, CD$_3$OD) δ 7.07-7.14 (m, 1H), 6.96-7.03 (m, 1H), 6.94 (dd, J=7.9, 2.2 Hz, 1H), 5.07 (br s, 1H), 3.54 (br dd, J=14.1, 4.4 Hz, 1H), 2.97 (br d, J=14.1 Hz, 1H), 1.49 (s, 9H).

Step 6: 4-Fluorobicyclo[4.2.0]octa-1(6),2,4-trien-7-amine hydrochloride

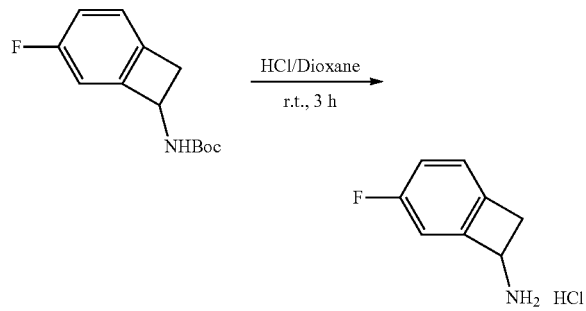

To a solution of tert-butyl (4-fluorobicyclo[4.2.0]octa-1,3,5-trien-7-yl)carbamate (25 g, 105 mmol) in EtOAc (200 mL) was added HCl (100 mL, 400 mmol) (4 M in dioxane) at RT. The mixture was stirred for 2 h at RT (~26° C.). LCMS and TLC (petroleum ether:ethyl acetate=5:1) showed no starting material. The precipitate was collected by filtration to give 4-fluorobicyclo [4.2.0]octa-1,3,5-trien-7-amine hydrochloride (16.0 g, 92 mmol) as a solid. ESI MS m/z 138.1 [M+H$^+$]. $^1$H NMR (400 MHz, CD$_3$OD) δ 7.24-7.30 (m, 1H), 7.15-7.22 (m, 1H), 7.12 (dd, J=7.5, 2.2 Hz, 1H), 4.79-4.84 (m, 1H), 3.63-3.71 (m, 1H), 3.24 (br d, J=14.5 Hz, 1H).

Intermediates F and G: (S)- and (R)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one

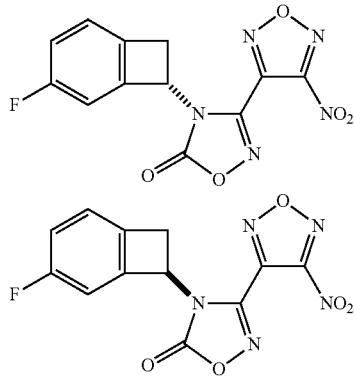

Step 1: 4-amino-N-(4-fluorobicyclo[4.2.0]octa-1(6),2,4-trien-7-yl)-N'-hydroxy-1,2,5-oxadiazole-3-carboximidamide

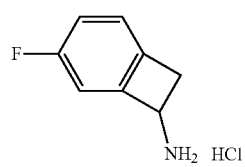

+

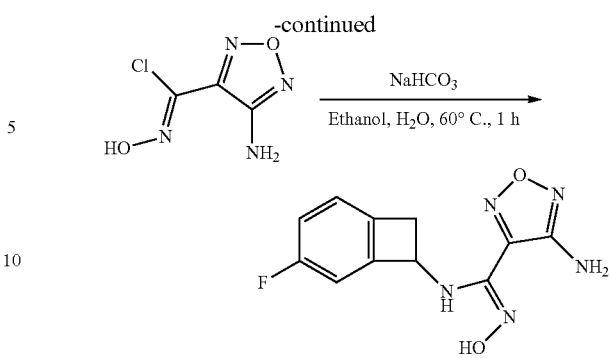

To a solution of 4-fluorobicyclo[4.2.0]octa-1,3,5-trien-7-amine hydrochloride (15 g, 86 mmol) in EtOH (150 mL) were added 4-amino-N-hydroxy-1,2,5-oxadiazole-3-carbimidoyl chloride (16.85 g, 104 mmol) and sodium hydrogencarbonate (18.15 g, 216 mmol). The mixture was stirred at 60° C. for 1 h, cooled to RT, and concentrated in vacuo. The residue was purified by silica chromatography (SiO$_2$, petroleum ether/AcOEt: 10:1 to 4:1) to afford the title compound (18.0 g, 68.4 mmol) as a solid. LC/MS: MS (ESI) m/z: 264.1 [M+H$^+$].

Step 2: 3-(4-amino-1,2,5-oxadiazol-3-yl)-4-(4-fluorobicyclo[4.2.0]octa-1(6),2,4-trien-7-yl)-1,2,4-oxadiazol-5(4H)-one

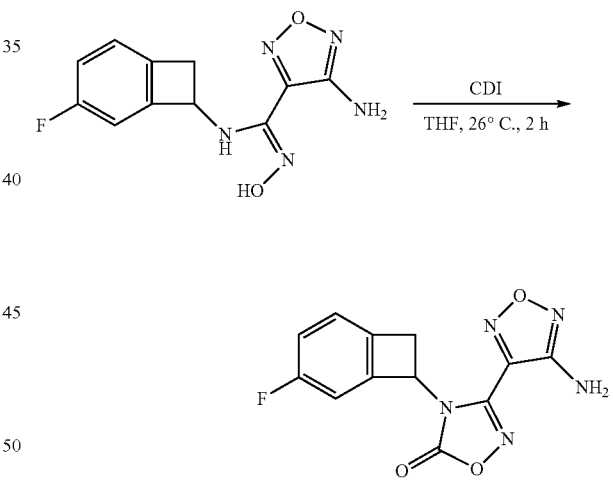

To a solution of 4-amino-N-(4-fluorobicyclo[4.2.0]octa-1(6),2,4-trien-7-yl)-N'-hydroxy-1,2,5-oxadiazole-3-carboximidamide (18.0 g, 68.4 mmol) and CDI (11.09 g, 68.4 mmol) in THF (180 ml) was added Et$_3$N (19.06 ml, 137 mmol). The reaction mixture was stirred at 26° C. for 2 h under N$_2$ atmosphere (balloon), then concentrated under reduced pressure. The residue was partitioned between water (300 mL) and DCM (300 mL). The aqueous layer was extracted with DCM (300 mL*2). The combined organic layers were washed with brine (300 mL), dried over Na$_2$SO$_4$, filtered, and concentrated under reduced pressure. The residue was purified by column chromatography (SiO$_2$, Pet.ether/ethyl acetate 10:1-3:1 as eluent) to give the title compound (16.5 g, 57.0 mmol) as a solid.

Step 3: 4-(4-fluorobicyclo[4.2.0]octa-1(6),2,4-trien-7-yl)-3-(4-nitro-1,2,5-oxadiazol-3-yl)-1,2,4-oxadiazol-5(4H)-one

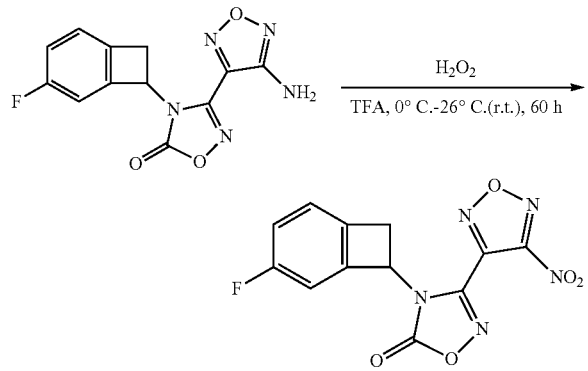

To a stirred solution of 3-(4-amino-1,2,5-oxadiazol-3-yl)-4-(4-fluorobicyclo[4.2.0]octa-1,3,5-trien-7-yl)-1,2,4-oxadiazol-5(4H)-one (15 g, 51.9 mmol) in TFA (1000 mL) was added hydrogen peroxide (174 mL, 51.9 mmol, 30%) at 0° C. The reaction was stirred at 15° C. for 15 h, extracted with DCM (1500 mL*8). The organic layers were washed with brine (200 ml*3), dried over $Na_2SO_4$, filtered, and concentrated in vacuo to give the title compound (70.2% yield) as a solid. $^1$H NMR (400 MHz, $CD_3Cl$) δ 7.05 (br d, J=6.6 Hz, 2H), 6.73 (br d, J=6.8 Hz, 1H), 5.65 (br d, J=3.1 Hz, 1H), 3.79 (ddd, J=1.5, 5.0, 14.7 Hz, 1H), 3.41 (br d, J=14.8 Hz, 1H)

Step 4: (S)- and (R)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one

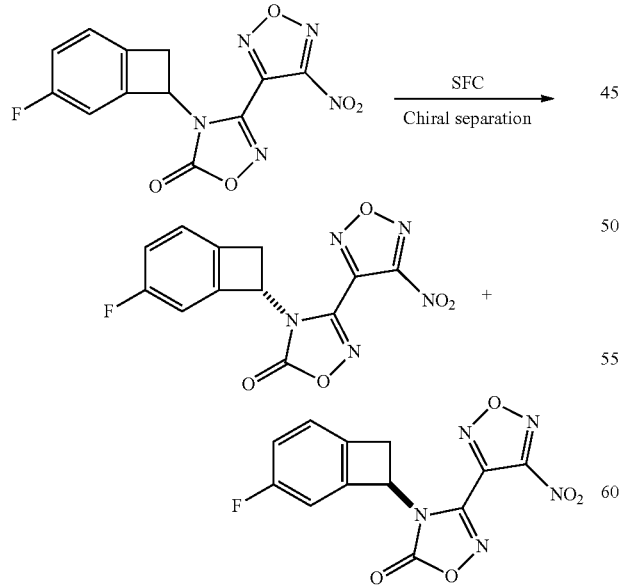

The above racemic compound was submitted to SFC chiral separation (Column OD 250 mm*50 mm, 10 um;

Mobile phase: A: $CO_2$ B: ethanol; Gradient: 15% B; Flow rate: 180 ml/min). The two chiral intermediates F and G were obtained as solids:

Intermediate F (peak 1): $^1$H NMR (400 MHz, $CD_3Cl$) δ 7.05 (br d, J=6.6 Hz, 2H), 6.73 (br d, J=6.8 Hz, 1H), 5.65 (br d, J=3.1 Hz, 1H), 3.79 (ddd, J=1.5, 5.0, 14.7 Hz, 1H), 3.41 (br d, J=14.8 Hz, 1H)

Intermediate G (peak 2): $^1$H NMR (400 MHz, $CD_3Cl$) δ 7.05 (br d, J=6.6 Hz, 2H), 6.73 (br d, J=6.8 Hz, 1H), 5.65 (br d, J=3.1 Hz, 1H), 3.79 (ddd, J=1.5, 5.0, 14.7 Hz, 1H), 3.41 (br d, J=14.8 Hz, 1H)

General Synthetic Schemes

The compounds of formula I, (Ia), or (Ib) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes. Exemplary synthetic schemes are described below.

Scheme 1.

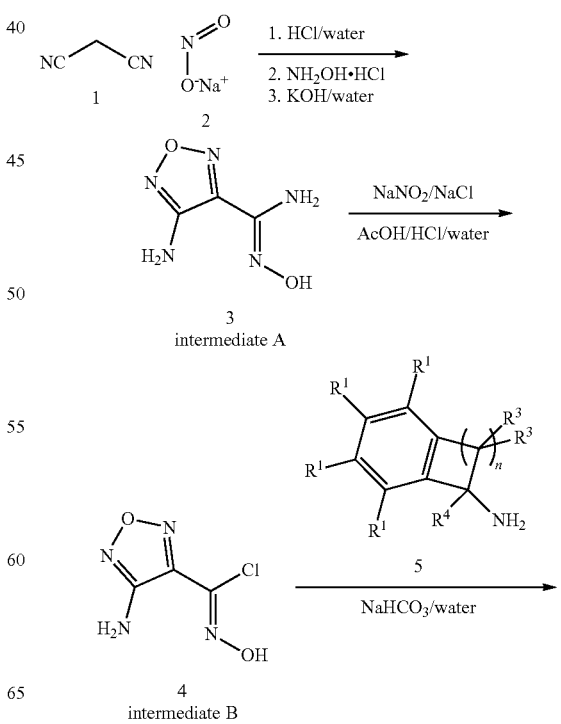

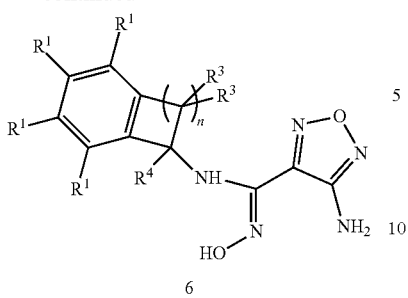

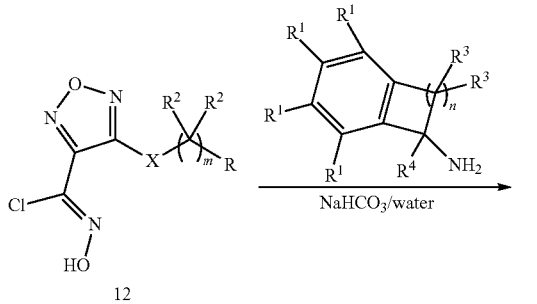

Intermediate A is prepared according to Scheme 1 via nitrosation of malononitrile in aqueous acid followed by the addition of hydroxylamine hydrochloride and subsequent pH adjustment to 9-11. Treatment of intermediate A with $NaNO_2$ and NaCl generates intermediate B, which can react with bicyclic amines 5 to give product 6.

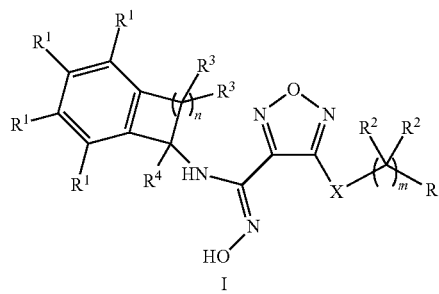

In Scheme 2, processes for preparing compounds, for example those in Examples 1-9 and 29-54, are described in more detail below in the Examples section.

Scheme 3.

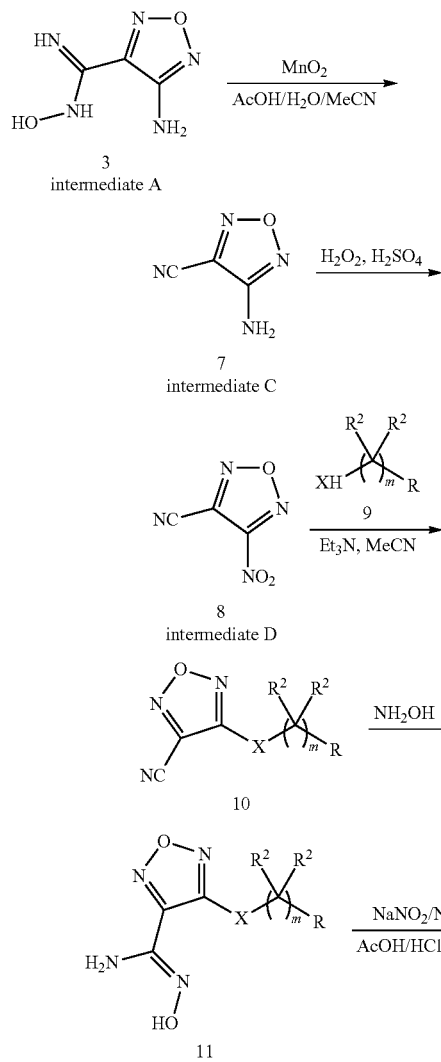

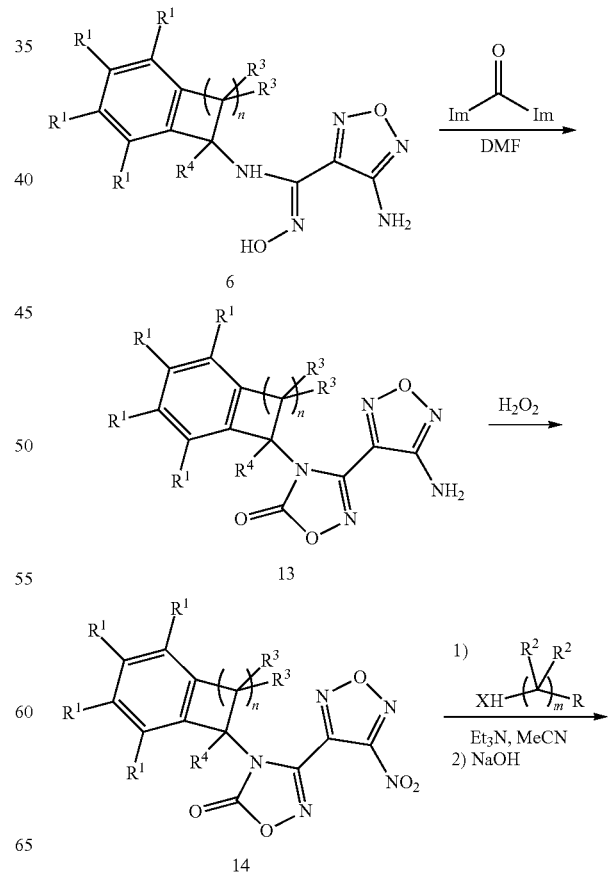

-continued

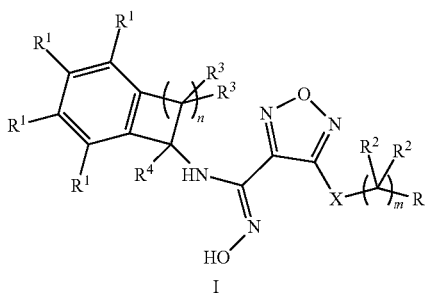

In Scheme 3, processes for preparing compounds, for example those in Examples 1-9 and 29-54, are described in more detail below in the Examples section.

Scheme 4.

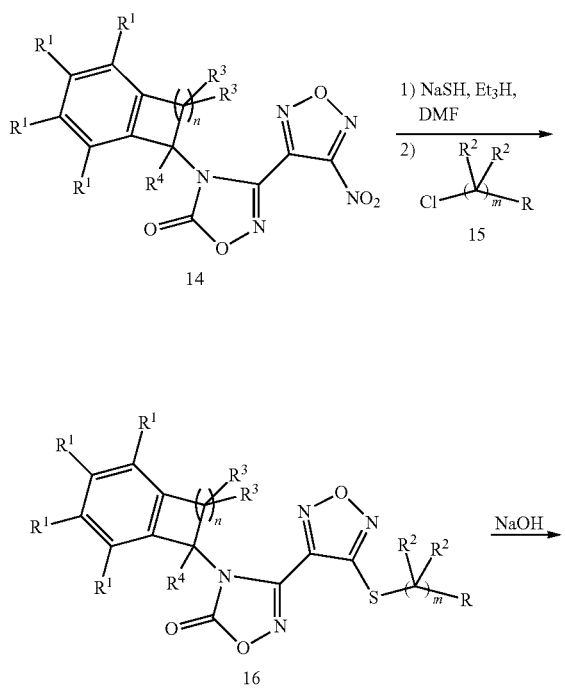

In Scheme 4, processes for preparing compounds, for example those in Examples 1-9 and 29-54, are described in more detail below in the Examples section.

EXAMPLES

Example 1. 4-Amino-N-(4-fluorobicyclo[4.2.0]octa-1,3,5-trien-7-yl)-N'-hydroxy-1,2,5-oxadiazole-3-carboximidamide

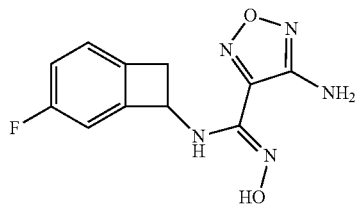 [SMILES: Nc1nonc1/C(=N/O)NC1Cc2ccc(F)cc21]

Step 1. Tert-butyl (4-fluorobicyclo[4.2.0]octa-1,3,5-trien-7-yl)-carbamate

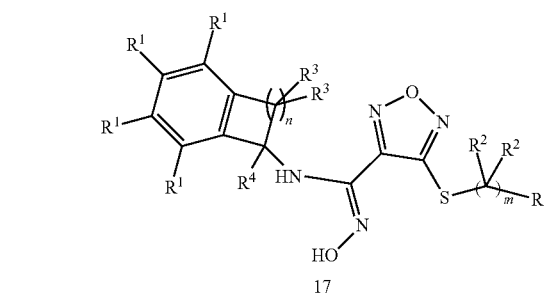

A mixture of 4-fluorobicyclo[4.2.0]octa-1,3,5-triene-7-carboxylic acid (300 mg, 1.806 mmol), diphenylphosphoryl azide (427 μL, 1.986 mmol), Et$_3$N (302 μL, 2.167 mmol) in t-BuOH (3.5 mL) was refluxed at 85° C. for 3 h. The mixture was cooled down, quenched with sat. NaHCO$_3$, and extracted with ether. The organic layer was separated, washed with brine, dried over MgSO$_4$, and concentrated. The residue was then purified by silica gel chromatography (RediSepRf 40 g column, 0-50% ethyl acetate in hexanes) to give tert-butyl (4-fluorobicyclo[4.2.0]octa-1,3,5-trien-7-yl) carbamate (188 mg, 0.792 mmol) as an oil.

Step 2. 4-Fluorobicyclo[4.2.0]octa-1,3,5-trien-7-amine hydrochloride

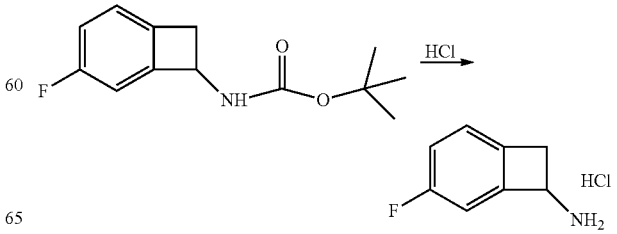

To a solution of tert-butyl (4-fluorobicyclo[4.2.0]octa-1,3,5-trien-7-yl)carbamate (188 mg, 0.792 mmol) in dioxane (2641 µl) was added HCl (4M in dioxane) (990 µl, 3.96 mmol) at ambient temperature for 1 h. The reaction mixture was stirred at ambient temperature overnight and concentrated to afford 4-fluorobicyclo[4.2.0]octa-1,3,5-trien-7-amine hydrochloride (138 mg, 0.792 mmol) as a powder.

Step 3. 4-Amino-N-(4-fluorobicyclo[4.2.0]octa-1,3,5-trien-7-yl)-N'-hydroxy-1,2,5-oxadiazole-3-carboximidamide

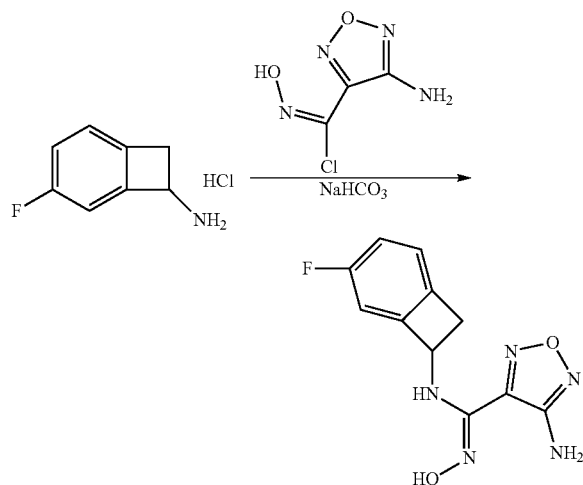

To the solution of 4-fluorobicyclo[4.2.0]octa-1,3,5-trien-7-amine hydrochloride (133 mg, 0.766 mmol) in ethanol (3830 µL) was added 4-amino-N-hydroxy-1,2,5-oxadiazole-3-carbimidoyl chloride (249 mg, 1.532 mmol). The reaction was stirred at 66° C. overnight. The resulting mixture was then purified by reverse phase HPLC (H$_2$O/CH$_3$CN containing 0.1% TFA) to afford racemic 4-amino-N-(4-fluorobicyclo[4.2.0]octa-1,3,5-trien-7-yl)-N'-hydroxy-1,2,5-oxadiazole-3-carboximidamide 2,2,2-trifluoroacetate (53 mg, 0.140 mmol) as a solid. MS: 264.1 (M+1). $^1$HNMR (600 MHz, DMSO-d$_6$): δ 10.84 (s, 1H), 7.22 (m, 1H), 7.12 (t, J=9 Hz, 1H), 6.96 (d, J=6 Hz, 1H), 6.81 (d, J=6 Hz, 1H), 6.39 (s, 2H), 5.46 (s, 1H), 3.52 (dd, J=6.12 Hz, 1H), 3.24 (d, J=18 Hz, 1H).

Examples 2 and 3. (R)-4-Amino-N-(4-fluorobicyclo[4.2.0]octa-1,3,5-trien-7-yl)-N'-hydroxy-1,2,5-oxadiazole-3-carboximidamide and (S)-4-Amino-N-(4-fluorobicyclo[4.2.0]octa-1,3,5-trien-7-yl)-N'-hydroxy-1,2,5-oxadiazole-3-carboximidamide

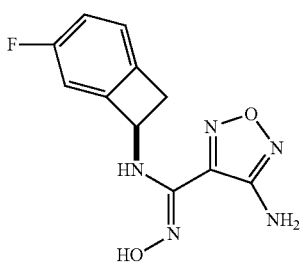

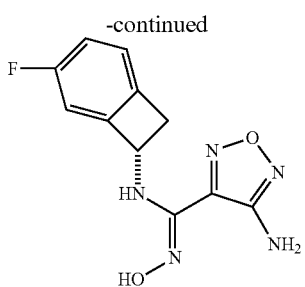

The above racemic Example 1 was submitted for chiral separation (Chiralcel OJ-H, 21×250 (mm) as column, methanol+0.25% dimethyl ethyl amine as modifier, 20% modifier in CO$_2$) to afford Example 2 (peak 1) (18.5 mg, 0.070 mmol) and Example 3 (peak 2).

Example 2: MS: 264.1 (M+1). $^1$HNMR (600 MHz, DMSO-d$_6$): δ 10.84 (s, 1H), 7.22 (m, 1H), 7.12 (t, J=9 Hz, 1H), 6.96 (d, J=6 Hz, 1H), 6.81 (d, J=6 Hz, 1H), 6.39 (s, 2H), 5.46 (s, 1H), 3.52 (dd, J=6.12 Hz, 1H), 3.24 (d, J=18 Hz, 1H).

Example 3: MS: 264.1 (M+1). $^1$HNMR (600 MHz, DMSO-d$_6$): δ 10.84 (s, 1H), 7.22 (m, 1H), 7.12 (t, J=9 Hz, 1H), 6.96 (d, J=6 Hz, 1H), 6.81 (d, J=6 Hz, 1H), 6.39 (s, 2H), 5.46 (s, 1H), 3.52 (dd, J=6.12 Hz, 1H), 3.24 (d, J=18 Hz, 1H).

Examples 4 and 5: (S)-4-amino-N-(bicyclo[4.2.0]octa-1,3,5-trien-7-yl)-N'-hydroxy-1,2,5-oxadiazole-3-carboximidamide and (R)-4-amino-N-(bicyclo[4.2.0]octa-1,3,5-trien-7-yl)-N'-hydroxy-1,2,5-oxadiazole-3-carboximidamide

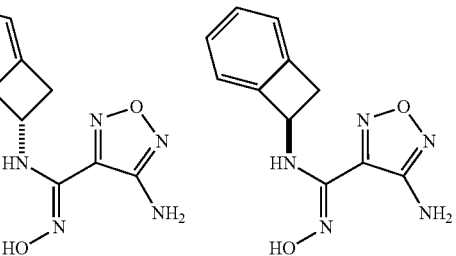

To the solution of bicyclo[4.2.0]octa-1,3,5-trien-7-amine hydrochloride (450 mg, 2.89 mmol) in ethanol (15 mL) was added 4-amino-N-hydroxy-1,2,5-oxadiazole-3-carbimidoyl chloride (940 mg, 5.78 mmol) and sodium bicarbonate (486 mg, 5.78 mmol) at ambient temperature. The reaction mixture was heated up to 66° C. and stirred for 1 h. After the reaction completed, the reaction mixture was concentrated and diluted with sat. NaHCO$_3$ solution and extracted with ethyl acetate twice. The combined organic layers were washed with brine, dried over MgSO$_4$ and concentrated. The material was then purified by silica gel chromatography (RediSepRf 40 g column, 0-100% ethyl acetate in hexanes) to afford racemic 4-amino-N-(bicyclo[4.2.0]octa-1,3,5-trien-7-yl)-N'-hydroxy-1,2,5-oxadiazole-3-carboximidamide (525 mg, 2.141 mmol) as a solid.

The above compound was submitted for chiral separation (LUX-4 as column, MeOH+0.25% DMEA as modifier) to afford Example 4 (peak 1) (9.4 mg, 0.038 mmol) as a solid and Example 5 (peak 2) (14.2 mg, 0.058 mmol) as a solid.

Example 4: MS: 246.1 (M+1). ¹HNMR (600 MHz, DMSO-d₆): δ 10.84 (s, 1H), 7.30 (t, J=6 Hz, 1H), 7.23 (t, J=6 Hz, 1H), 7.20 (d, J=6 Hz, 1H), 7.08 (d, J=6 Hz, 1H), 6.67 (d, J=6 Hz, 1H), 6.39 (s, 2H), 5.50 (s, 1H), 3.58 (dd, J=6.12 Hz, 1H), 3.29 (d, J=18 Hz, 1H).

Example 5: MS: 246.1 (M+1). ¹HNMR (600 MHz, DMSO-d₆): δ 10.84 (s, 1H), 7.30 (t, J=6 Hz, 1H), 7.23 (t, J=6 Hz, 1H), 7.20 (d, J=6 Hz, 1H), 7.08 (d, J=6 Hz, 1H), 6.67 (d, J=6 Hz, 1H), 6.39 (s, 2H), 5.50 (s, 1H), 3.58 (dd, J=6.12 Hz, 1H), 3.29 (d, J=18 Hz, 1H).

Example 6: 4-Amino-N'-hydroxy-N-(7-methylbicyclo[4.2.0]octa-1,3,5-trien-7-yl)-1,2,5-oxadiazole-3-carboximidamide

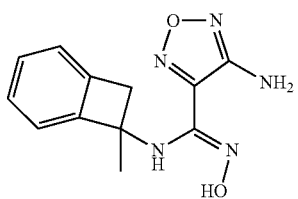 [SMILES: CC1(N/C(=N\O)c2nonc2N)Cc2ccccc21]

To the solution of 7-methylbicyclo[4.2.0]octa-1,3,5-trien-7-amine hydrochloride (50 mg, 0.295 mmol) in ethanol (1474 μl) was added 4-amino-N-hydroxy-1,2,5-oxadiazole-3-carbimidoyl chloride (96 mg, 0.589 mmol) and sodium bicarbonate (99 mg, 1.179 mmol) at ambient temperature. The resulting mixture was heated up to 66° C. for 2 h. After the reaction completed, the reaction mixture was concentrated and diluted with NaHCO₃ sat. solution and extracted with ethyl acetate twice. The combined organic layers were washed with brine, dried over MgSO₄ and concentrated. The material was then purified by silica gel chromatography (RediSepRf 12 g gold column, 0-100% 3:1 ethyl acetate:ethanol in hexanes) to afford racemic 4-amino-N'-hydroxy-N-(7-methylbicyclo[4.2.0]octa-1,3,5-trien-7-yl)-1,2,5-oxadiazole-3-carboximidamide (56 mg, 0.205 mmol) as a solid. MS: 260.1 (M+1). ¹HNMR (600 MHz, DMSO-d₆): δ 10.89 (s, 1H), 7.27 (t, J=6 Hz, 1H), 7.21 (t, J=6 Hz, 1H), 7.17 (m, 2H), 6.48 (s, 1H), 6.27 (s, 2H), 3.35 (d, J=12 Hz, 1H), 3.24 (d, J=12 Hz, 1H), 1.73 (s, 3H).

Examples 7 and 8: (S)-4-amino-N'-hydroxy-N-(7-methylbicyclo[4.2.0]octa-1,3,5-trien-7-yl)-1,2,5-oxadiazole-3-carboximidamide and (R)-4-amino-N'-hydroxy-N-(7-methylbicyclo[4.2.0]octa-1,3,5-trien-7-yl)-1,2,5-oxadiazole-3-carboximidamide

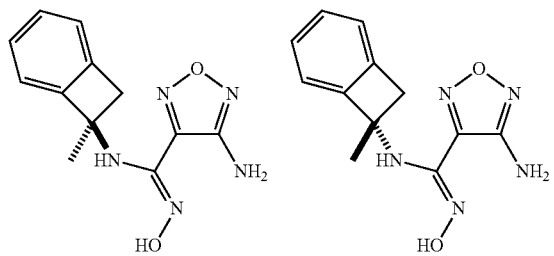 [SMILES: C[C@@]1(N/C(=N\O)c2nonc2N)Cc2ccccc21 ; C[C@]1(N/C(=N\O)c2nonc2N)Cc2ccccc21]

The racemic Example 6 was submitted for SFC chiral separation (Chiralpak IF, 21×250 (mm) as column, methanol+0.25% dimethyl ethyl Amine as modifier, 15% modifier in CO₂) to afford Example 7 (peak 1) (17.6 mg, 0.068 mmol) as a solid and Example 8 (peak 2) (19.9 mg, 0.077 mmol) as a solid.

Example 7: MS: 260.1 (M+1). ¹HNMR (600 MHz, DMSO-d₆): δ 10.89 (s, 1H), 7.27 (t, J=6 Hz, 1H), 7.21 (t, J=6 Hz, 1H), 7.17 (m, 2H), 6.48 (s, 1H), 6.27 (s, 2H), 3.35 (d, J=12 Hz, 1H), 3.24 (d, J=12 Hz, 1H), 1.73 (s, 3H).

Example 8: MS: 260.1 (M+1). ¹HNMR (600 MHz, DMSO-d₆): δ 10.89 (s, 1H), 7.27 (t, J=6 Hz, 1H), 7.21 (t, J=6 Hz, 1H), 7.17 (m, 2H), 6.48 (s, 1H), 6.27 (s, 2H), 3.35 (d, J=12 Hz, 1H), 3.24 (d, J=12 Hz, 1H), 1.73 (s, 3H).

Example 9: (S)-4-Amino-N-(2,3-dihydro-1H-inden-1-yl)-N'-hydroxy-1,2,5-oxadiazole-3-carboximidamide

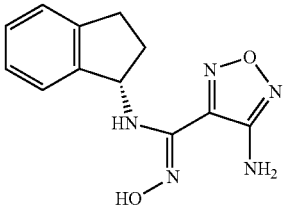 [SMILES: Nc1nonc1/C(=N/O)N[C@H]1CCc2ccccc21]

To a microwave reaction vial was added 4-amino-N-hydroxy-1,2,5-oxadiazole-3-carbimidoyl chloride (439 mg, 2.70 mmol), (S)-2,3-dihydro-1H-inden-1-amine (300 mg, 2.25 mmol), EtOH (4.5 mL), and Et₃N (942 μl, 6.76 mmol). The vial was sealed and the reaction mixture was heated at 80° C. for 1 h. The mixture was cooled down, diluted with sat. NaHCO₃, and extracted with EtOAc. The organic layer was separated, washed with brine, dried over MgSO₄, and concentrated. The residue was purified by flash chromatography (0-80% EtOAc/hexanes) to give (S)-4-amino-N-(2,3-dihydro-1H-inden-1-yl)-N'-hydroxy-1,2,5-oxadiazole-3-carboximidamide (243 mg). MS: 259 (M+1)

Example 10: (R)-4-Amino-N-(2,3-dihydro-1H-inden-1-yl)-N'-hydroxy-1,2,5-oxadiazole-3-carboximidamide

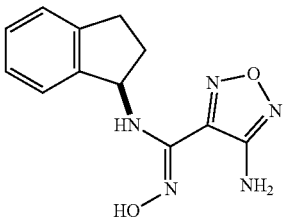 [SMILES: Nc1nonc1/C(=N/O)N[C@@H]1CCc2ccccc21]

This compound was prepared following the procedure for Example 9, using (R)-2,3-dihydro-1H-inden-1-amine as the starting material. MS: 259 (M+1)

Example 11: 4-Amino-N-(8-fluorobicyclo[4.2.0]
octa-1(6),2,4-trien-7-yl)-N'-hydroxy-1,2,5-oxadiazole-3-carboximidamide

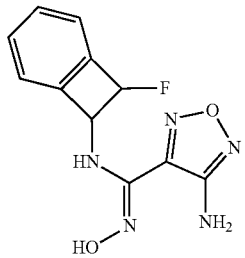 [SMILES: Nc1nonc1/C(=N/O)NC1c2ccccc2C1F]

Step 1: 5-(2-Bromobenzylidene)-2,2,3,3,7,7,8,8-octamethyl-4,6-dioxa-3,7-disilanonane

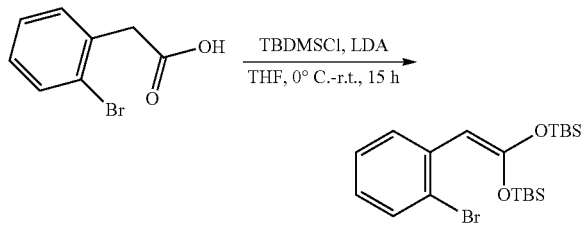

A solution of 2-(2-bromophenyl)acetic acid (4.80 g, 22.32 mmol) and tert-butylchlorodimethylsilane (7.68 g, 51.0 mmol) in THF (75 ml) was stirred at 0° C. under N$_2$. LDA (24 ml, 48.0 mmol) (2 M in heptane) was added to the mixture dropwise. The reaction was stirred at 0° C. for 30 min, warmed to RT and stirred for another 15 h. The solvent was removed in vacuo and the residue was used directly in the next step without further purification.

Step 2: 2-(2-Bromophenyl)-2-fluoroacetic acid

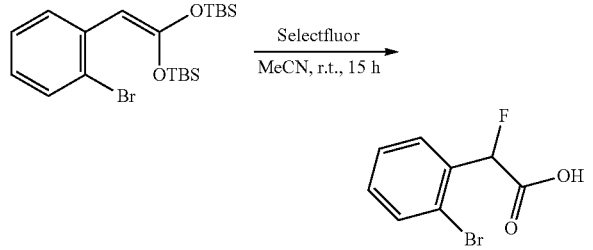

To a solution of 5-(2-bromobenzylidene)-2,2,3,3,7,7,8,8-octamethyl-4,6-dioxa-3,7-disilanonane (9.90 g) in acetonitrile (100 mL) was added selectfluor (10.08 g, 28.5 mmol) in acetonitrile (200 mL) dropwise at RT. The mixture was stirred for 15 h. The solvent was removed in vacuo. The residue was diluted with EtOAc (200 mL), washed with 1N HCl (100 mL). The organic layer was dried over Na$_2$SO$_4$, filtered and concentrated. The residue was purified by reverse phase HPLC on a GILSON 281 instrument fitted with a Phenomenex Synergi C18 (250×21.2 mm×4 μm) using water (0.1% TFA) and acetonitrile as eluents (Mobile phase A water (0.1% TFA), Mobile phase B acetonitrile, Detective wavelength: 220 nm) to afford 2-(2-bromophenyl)-2-fluoroacetic acid (3.60 g, 10.35 mmol) as a solid.

Step 3: 2-(2-Bromophenyl)-2-fluoro-N-methoxy-N-methylacetamide

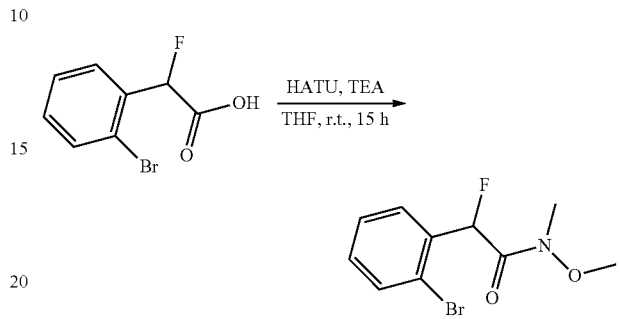

To a solution of 2-(2-bromophenyl)-2-fluoroacetic acid (1.80 g, 7.72 mmol) in THF (10 mL) were added HATU (3.23 g, 8.50 mmol), N,O-dimethylhydroxylamine hydrochloride (0.904 g, 9.27 mmol) and TEA (4.31 mL, 30.9 mmol). The mixture was stirred at 25° C. for 16 h. The solvent was removed in vacuo. The residue was partitioned between ethyl acetate (50 mL) and water (50 mL). The organic layer was washed with brine (20 mL), concentrated in vacuo to give a residue which was purified by column chromatography (SiO$_2$, Petroleum ether:ethyl acetate=10:1 to 5:1) to give the crude product, then re-purified by reverse phase HPLC on a GILSON 281 instrument fitted with a Phenomenex Synergi C18 (250×21.2 mm×4 m) using water (0.1% TFA) and acetonitrile as eluents (Mobile phase A water (0.1% TFA), Mobile phase B acetonitrile, Detective wavelength: 220 nm) followed by lyophilization to afford 2-(2-bromophenyl)-2-fluoro-N-methoxy-N-methylacetamide (900 mg, 3.10 mmol) as an oil.

Step 4: 8-Fluorobicyclo[4.2.0]octa-1,3,5-trien-7-one

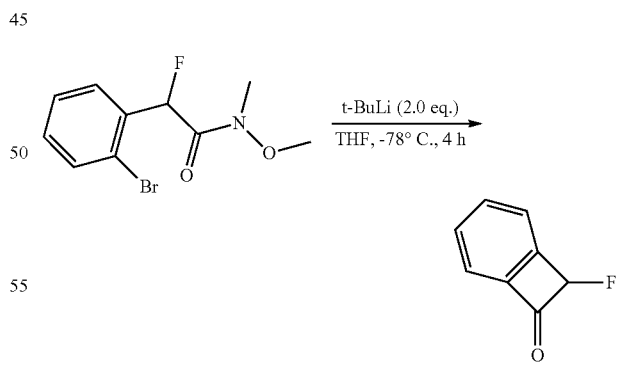

To a stirred solution of 2-(2-bromophenyl)-2-fluoro-N-methoxy-N-methylacetamide (624 mg, 2.260 mmol) in THF (7 mL) was added tert-butyllithium (3.48 mL, 4.52 mmol) (1.3 M in pentane) dropwise at −78° C. under nitrogen. Stirring was continued at −78° C. for 4 h. The reaction was quenched at −10° C. with saturated ammonium chloride (2 mL), concentrated in vacuum. The residue was diluted with EtOAc (20 mL), washed with brine (10 mL), concentrated in vacuo. The residue was purified by column chromatography (SiO₂, Pet.ether/EtOAc=20:1 as eluent) to afford 8-fluorobicyclo[4.2.0]octa-1,3,5-trien-7-one (160 mg, 0.999 mmol) as an oil.

Step 5: 8-Fluorobicyclo[4.2.0]octa-1,3,5-trien-7-amine

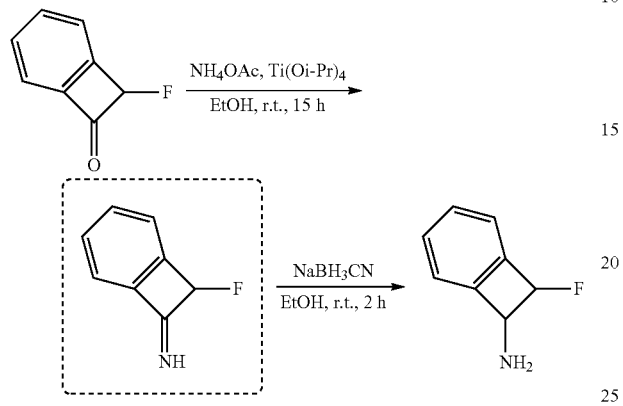

To a solution of 8-fluorobicyclo[4.2.0]octa-1,3,5-trien-7-one (46 mg, 0.338 mmol) in ethanol (2 ml) were added NH₄OAc (260 mg, 3.38 mmol) and tetraisopropoxytitanium (115 mg, 0.406 mmol). The reaction mixture was stirred at 15° C. for 15 h before NaBH₃CN (20 mg, 0.318 mmol) was added. The reaction was stirred at 15° C. for 3 h. The solvent was removed in vacuo to give the crude 8-fluorobicyclo[4.2.0]octa-1,3,5-trien-7-amine (40 mg, 0.292 mmol) as a solid, which was used in the next step without further purification.

Step 6: (Z)-4-Amino-N-(8-fluorobicyclo[4.2.0]octa-1(6),2,4-trien-7-yl)-N'-hydroxy-1,2,5-oxadiazole-3-carboximidamide

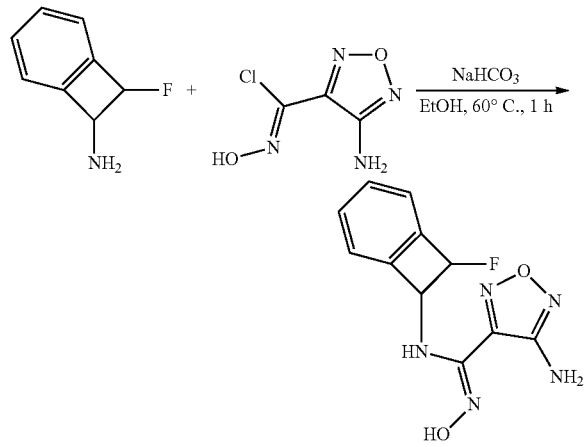

To a solution of 8-fluorobicyclo[4.2.0]octa-1,3,5-trien-7-amine (20 mg, 0.146 mmol) in EtOH (2 ml) were added 4-amino-N-hydroxy-1,2,5-oxadiazole-3-carbimidoyl chloride (50 mg, 0.308 mmol) and NaHCO₃ (50 mg, 0.595 mmol) then the mixture was stirred at 60° C. for 1 h. After removing the solvent, the residue was purified by reverse phase HPLC on a GILSON 281 instrument fitted with a Phenomenex Synergi C18 (250×21.2 mm×4 μm) using water (0.1% TFA) and acetonitrile as eluents (Mobile phase A water (0.1% TFA), Mobile phase B acetonitrile) to afford 4-amino-N-(8-fluorobicyclo[4.2.0]octa-1(6),2,4-trien-7-yl)-N'-hydroxy-1,2,5-oxadiazole-3-carboximidamide (3 mg, 10.02 μmol) as a solid. m/z: 264.1 [M+H]⁺; ¹H NMR (400 MHz, CD₃OD) δ 7.35-7.50 (m, 3H), 7.31 (br d, J=6.8 Hz, 1H), 5.98-6.17 (m, 1H), 5.95 (br s, 1H).

Example 12: 4-Amino-N-(8,8-difluorobicyclo[4.2.0]octa-1(6),2,4-trien-7-yl)-N'-hydroxy-1,2,5-oxadiazole-3-carboximidamide

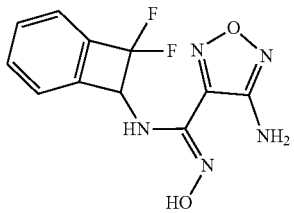 [SMILES: Nc1nonc1/C(=N/O)NC1c2ccccc2C1(F)F]

Step 1: Ethyl 2-(2-bromophenyl)-2,2-difluoroacetate

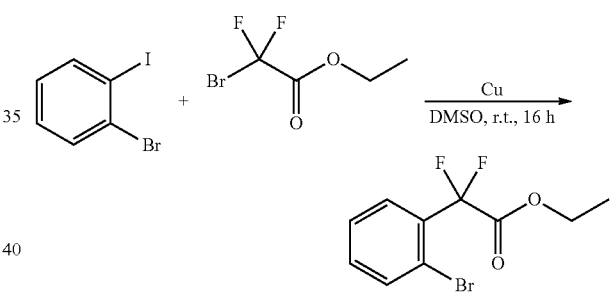

To a suspension of copper (0.898 g, 14.14 mmol) in DMSO (10 mL) was added ethyl 2-bromo-2,2-difluoroacetate (1.435 g, 7.07 mmol) at RT. The mixture was stirred for 1 h at RT under N₂ before 1-bromo-2-iodobenzene (1.0 g, 3.53 mmol) was added. The reaction was stirred for another 16 h at RT, quenched with sat. NH₄Cl solution (50 mL), and extracted with CH₂Cl₂ (50 mL×3). The combined organic extracts were washed with H₂O (30 mL) and brine (30 mL), dried over anhydrous Na₂SO₄ and concentrated under reduced pressure to obtain the crude product. Purification by silica gel column chromatography (eluting with 2.5 percent EtOAc/petroleum ether) afforded the ethyl 2-(2-bromophenyl)-2,2-difluoroacetate (510 mg, 1.827 mmol) as an oil.

Step 2: 2-(2-Bromophenyl)-2,2-difluoroacetic acid

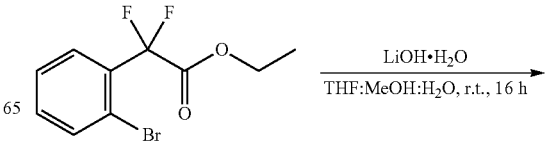

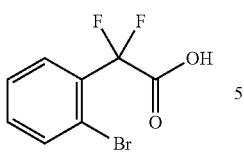

To a solution of ethyl 2-(2-bromophenyl)-2,2-difluoroacetate (510 mg, 1.827 mmol) in THF (10 mL), MeOH (10 mL) and water (5 mL) was added lithium hydroxide hydrate (153 mg, 3.65 mmol). The mixture was stirred at 20° C. for 1 h. The mixture was acidified to a pH value of 2, extracted with ethyl acetate (30 ml×3). The combined organic layers were washed with brine (20 mL), and then dried over Na$_2$SO$_4$, filtered and concentrated under reduced pressure to give 2-(2-bromophenyl)-2,2-difluoroacetic acid (430 mg, 1.542 mmol) as an oil. The crude was used in the next step without further purification.

Step 3. 2-(2-Bromophenyl)-2,2-difluoro-N-methoxy-N-methylacetamide

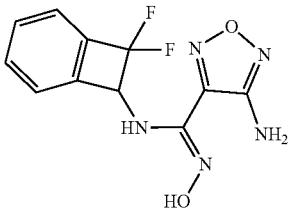 [SMILES: Nc1nonc1/C(=N/O)NC1c2ccccc2C1(F)F]

To a solution of 2-(2-bromophenyl)-2,2-difluoroacetic acid (450 mg, 1.793 mmol) in DCM (20 mL) were added oxalyl chloride (0.3 mL, 3.43 mmol) and a catalytic amount of DMF at 20° C. After stirring for 3 h, the solvent was removed under reduced pressure to afford 2-(2-bromophenyl)-2,2-difluoroacetyl chloride (450 mg, 1.670 mmol) as an oil, which was used in the next step without further purification.

To a solution of N,O-dimethylhydroxylamine hydrochloride (179 mg, 1.837 mmol) in DCM (10 mL) was added Et$_3$N (0.698 ml, 5.01 mmol) at 0° C. After stirring for 5 min, a solution of 2-(2-bromophenyl)-2,2-difluoroacetyl chloride (450 mg, 1.670 mmol) in DCM (5 mL) was added slowly. The mixture was stirred for 16 h at RT and concentrated in vacuo. The residue was purified by silica gel column chromatography using (petroleum ether/ethyl acetate 10:1~3:1 to give 2-(2-bromophenyl)-2,2-difluoro-N-methoxy-N-methylacetamide (360 mg, 1.224 mmol) as a solid.

Steps 4-6: 4-Amino-N-(8,8-difluorobicyclo[4.2.0]octa-1(6),2,4-trien-7-yl)-N'-hydroxy-1,2,5-oxadiazole-3-carboximidamide This compound was prepared following the procedures of steps 4-6 for Example 11, using 2-(2-bromophenyl)-2,2-difluoro-N-methoxy-N-methylacetamide as the starting material. LCMS: 282.1 [M+H]$^+$; $^1$H NMR (400 MHz, CD$_3$OD) δ 7.57-7.64 (m, 1H), 7.48-7.55 (m, 2H), 7.41-7.47 (m, 1H), 6.17 (d, J=1.8 Hz, 1H).

Example 13: 4-Amino-N-(6-fluoro-2,3-dihydro-1H-inden-1-yl)-N'-hydroxy-1,2,5-oxadiazole-3-carboximidamide

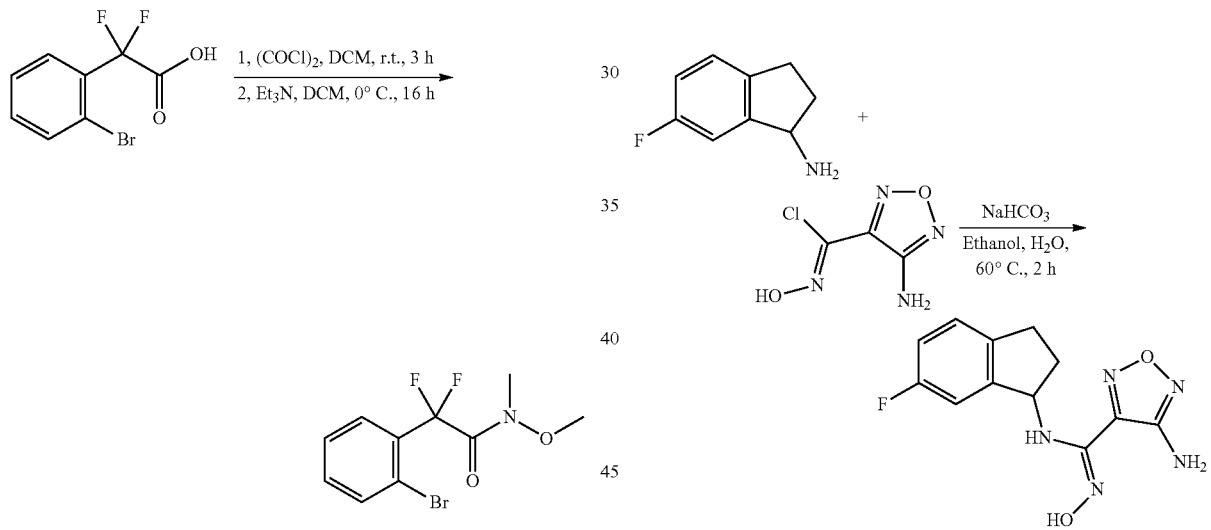

To a solution of 6-fluoro-2,3-dihydro-1H-inden-1-amine (1.00 g, 6.61 mmol) and 4-amino-N-hydroxy-1,2,5-oxadiazole-3-carbimidoyl chloride (1.075 g, 6.61 mmol) in EtOH (20 mL) was added sodium bicarbonate (0.834 g, 9.92 mmol). The reaction mixture was stirred at 60° C. for 1 h. Detected by LCMS, the starting material was consumed. The mixture was concentrated, diluted with water (50 mL), extracted with EtOAc (50 mL×3). The combined organic layers were dried over MgSO$_4$, filtered, and concentrated in vacuo. The residue was purified by column chromatography (Pet. ether:EtOAc=5:1 as eluent) to give 4-amino-N-(6-fluoro-2,3-dihydro-1H-inden-1-yl)-N'-hydroxy-1,2,5-oxadiazole-3-carboximidamide (550 mg, 1.587 mmol) as an oil. m/z=: 278.1 [M+H]$^+$; $^1$H NMR (400 MHz, CDCl3) δ 7.13 (t, J=5.2 Hz, 1H), 6.97 (dd, J=2.0 Hz, 8.8 Hz, 1H), 6.88 (t, J=5.2 Hz, 1H), 5.72 (t, J=8.0 Hz, 1H), 3.33 (s, 1H), 2.85-2.89 (m, 1H), 2.70-2.83 (m, 1H), 2.57-2.65 (m, 1H), 1.82-1.91 (m, 1H).

Using the general methodology disclosed in the schemes, Examples 1-13, and general knowledge in organic synthesis, compounds in Table 1 were prepared.

TABLE 1

Examples 14-28

| Ex. # | Structure | Chemical Name | Mass [M + H]+ |
|---|---|---|---|
| 14 | 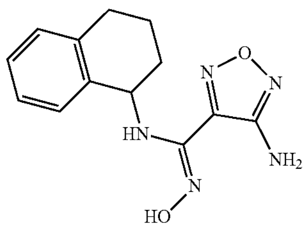 [SMILES: Nc1nonc1/C(=N/O)NC1CCCc2ccccc21] | 4-amino-N'-hydroxy-N-(1,2,3,4-tetrahydronaphthalen-1-yl)-1,2,5-oxadiazole-3-carboximidamide | 274.1 |
| 15 | 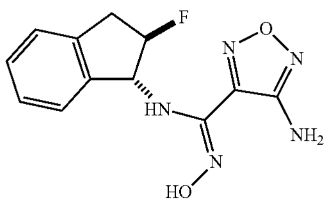 [SMILES: Nc1nonc1/C(=N/O)N[C@@H]1c2ccccc2C[C@H]1F] | trans-4-amino-N-((1R,2R)-2-fluoro-2,3-dihydro-1H-inden-1-yl)-N'-hydroxy-1,2,5-oxadiazole-3-carboximidamide | 278.1 |
| 16 | 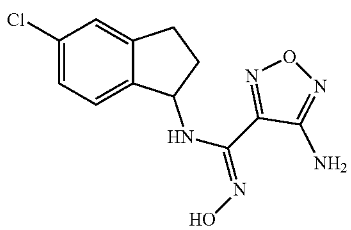 [SMILES: Nc1nonc1/C(=N/O)NC1CCc2cc(Cl)ccc21] | 4-amino-N-(5-chloro-2,3-dihydro-1H-inden-1-yl)-N'-hydroxy-1,2,5-oxadiazole-3-carboximidamide | 294.1 |
| 17 | 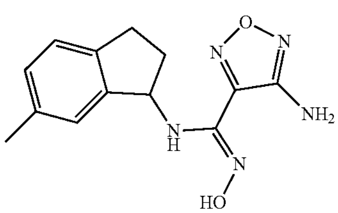 [SMILES: Cc1ccc2c(c1)C(N/C(=N\O)c1nonc1N)CC2] | 4-amino-N'-hydroxy-N-(6-methyl-2,3-dihydro-1H-inden-1-yl)-1,2,5-oxadiazole-3-carboximidamide | 274.1 |
| 18 | 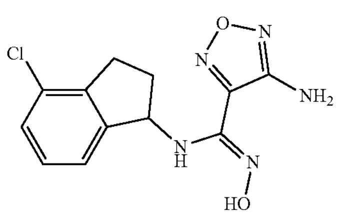 [SMILES: Nc1nonc1/C(=N/O)NC1CCc2c(Cl)cccc21] | 4-amino-N-(4-chloro-2,3-dihydro-1H-inden-1-yl)-N'-hydroxy-1,2,5-oxadiazole-3-carboximidamide | 294.1 |
| 19 | 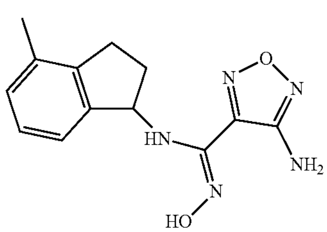 [SMILES: Cc1cccc2c1CCC2N/C(=N\O)c1nonc1N] | 4-amino-N'-hydroxy-N-(4-methyl-2,3-dihydro-1H-inden-1-yl)-1,2,5-oxadiazole-3-carboximidamideidamide | 274.1 |

TABLE 1-continued

Examples 14-28

| Ex. # | Structure | Chemical Name | Mass [M + H]+ |
|---|---|---|---|
| 20 | 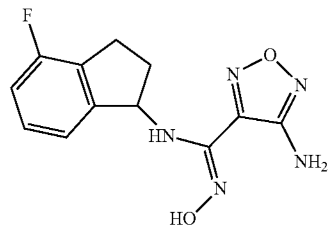 [SMILES: Nc1nonc1/C(=N/O)NC1CCc2c(F)cccc21] | 4-amino-N-(4-fluoro-2,3-dihydro-1H-inden-1-yl)-N'-hydroxy-1,2,5-oxadiazole-3-carboximidamide | 278.1 |
| 21 | 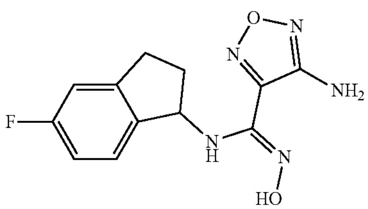 [SMILES: Nc1nonc1/C(=N/O)NC1CCc2cc(F)ccc21] | 4-amino-N-(5-fluoro-2,3-dihydro-1H-inden-1-yl)-N'-hydroxy-1,2,5-oxadiazole-3-carboximidamide | 278.1 |
| 22 | 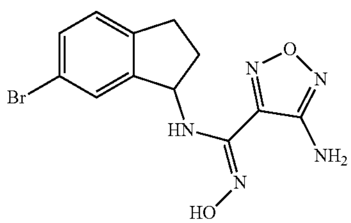 [SMILES: Nc1nonc1/C(=N/O)NC1CCc2ccc(Br)cc21] | 4-amino-N-(6-bromo-2,3-dihydro-1H-inden-1-yl)-N'-hydroxy-1,2,5-oxadiazole-3-carboximidamide | 338.1 |
| 23 | 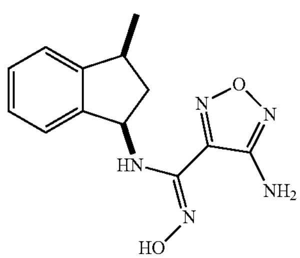 [SMILES: C[C@H]1C[C@@H](N/C(=N\O)c2nonc2N)c2ccccc21] | cis-4-amino-N'-hydroxy-N-(3-methyl-2,3-dihydro-1H-inden-1-yl)-1,2,5-oxadiazole-3-carboximidamide | 274.1 |
| 24 | 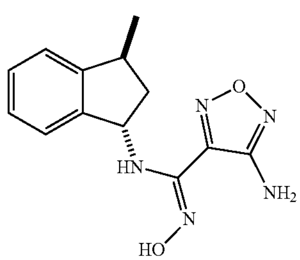 [SMILES: C[C@H]1C[C@H](N/C(=N\O)c2nonc2N)c2ccccc21] | trans-4-amino-N'-hydroxy-N-(3-methyl-2,3-dihydro-1H-inden-1-yl)-1,2,5-oxadiazole-3-carboximidamide | 274.1 |
| 25 | 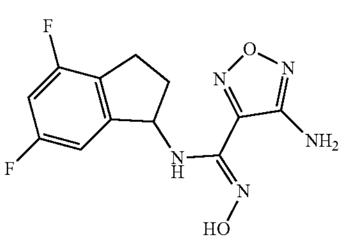 [SMILES: Nc1nonc1/C(=N/O)NC1CCc2c(F)cc(F)cc21] | 4-amino-N-(4,6-difluoro-2,3-dihydro-1H-inden-1-yl)-N'-hydroxy-1,2,5-oxadiazole-3-carboximidamide | 296.1 |

TABLE 1-continued

Examples 14-28

| Ex. # | Structure | Chemical Name | Mass [M + H]+ |
|---|---|---|---|
| 26 | 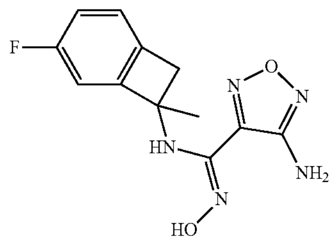 [SMILES: CC1(N/C(=N\O)c2nonc2N)Cc2ccc(F)cc21] | 4-amino-N-(4-fluoro-7-methylbicyclo[4.2.0]octa-1(6),2,4-trien-7-yl)-N'-hydroxy-1,2,5-oxadiazole-3-carboximidamide | 278.1 |
| 27 | 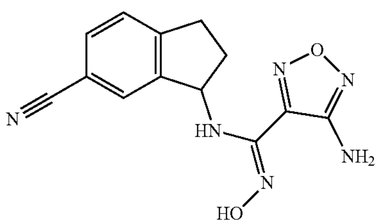 [SMILES: N#Cc1ccc2c(c1)C(N/C(=N\O)c1nonc1N)CC2] | 4-amino-N-(6-cyano-2,3-dihydro-1H-inden-1-yl)-N'-hydroxy-1,2,5-oxadiazole-3-carboximidamide | 285.1 |
| 28 | 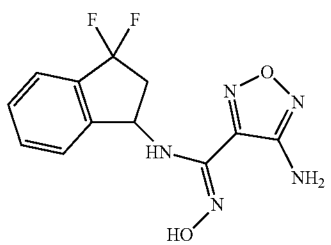 [SMILES: Nc1nonc1/C(=N/O)NC1CC(F)(F)c2ccccc21] | (4-amino-N-(3,3-difluoro-2,3-dihydro-1H-inden-1-yl)-N'-hydroxy-1,2,5-oxadiazole-3-carboximidamide | 296.1 |

Example 29. N-(6-fluoro-2,3-dihydro-1H-inden-1-yl)-N'-hydroxy-4-((2-(sulfamoylamino)ethyl)thio)-1,2,5-oxadiazole-3-carboximidamide

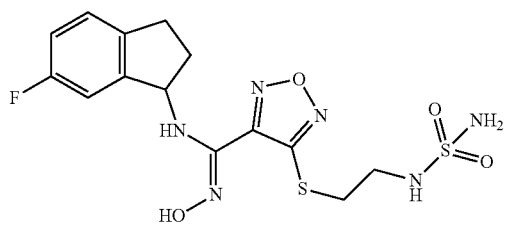 [SMILES: NS(=O)(=O)NCCSc1nonc1/C(=N/O)NC1CCc2ccc(F)cc21]

Step 1. 3-(4-Amino-1,2,5-oxadiazol-3-yl)-4-(6-fluoro-2,3-dihydro-1H-inden-1-yl)-1,2,4-oxadiazol-5(4H)-one

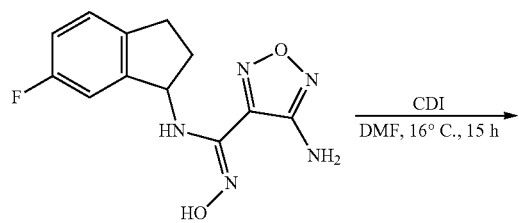

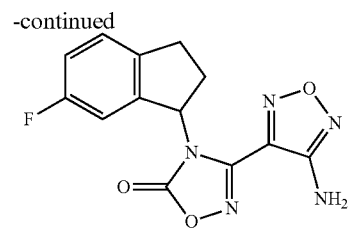

To a solution of 4-amino-N-(6-fluoro-2,3-dihydro-1H-inden-1-yl)-N'-hydroxy-1,2,5-oxadiazole-3-carboximidamide (Example 13, 550 mg, 1.587 mmol) and CDI (283 mg, 1.746 mmol) in DMF (15 mL) was added Et₃N (0.442 mL, 3.17 mmol). The reaction mixture was stirred at RT for 15 h under N₂ atmosphere. The mixture was concentrated in vacuo, diluted with EtOAc (100 mL), and washed with water (50 mL×3). The combined organic layers were concentrated in vacuo. The residue was purified by column chromatography (Pet. ether:EtOAc=5:1 as eluent) to give 3-(4-amino-1,2,5-oxadiazol-3-yl)-4-(6-fluoro-2,3-dihydro-1H-inden-1-yl)-1,2,4-oxadiazol-5(4H)-one (220 mg, 0.653 mmol) as a solid.

An alternative procedure for the synthesis of the title compound is described below:

To a solution of 4-amino-N-(6-fluoro-2,3-dihydro-1H-inden-1-yl)-N'-hydroxy-1,2,5-oxadiazole-3-carboximidamide (75.5 g) and CDI (44.2 g) in THF (150 mL) was added Et₃N (76 mL). The reaction mixture was stirred at 20° C. for 2 h under N₂ atmosphere (balloon), then concentrated under reduced pressure. The residue was partitioned between water (300 mL) and CH$_2$Cl$_2$ (500 mL). The aqueous layer was extracted with CH$_2$Cl$_2$ (500 mL). The combined organic layers were washed with brine (200 mL), dried over Na$_2$SO$_4$, filtered, and concentrated under reduced pressure. The residue was recrystallized to give the title compound (73.5 g) as a solid. $^1$H NMR (400 MHz, CDCl$_3$) δ 7.2-7.3 (m, 1H), 7.2-7.3 (m, 1H), 7.2-7.3 (m, 1H), 7.0 (td, J=8.7, 2.4 Hz, 1H), 6.8 (dd, J=8.3, 2.2 Hz, 1H), 6.4 (t, J=7.8 Hz, 1H), 5.2 (br s, 2H), 3.2-3.4 (m, 1H), 3.0 (dt, J=15.8, 7.80 Hz, 1H), 2.5-2.8 (m, 2H).

Step 2. 4-(6-Fluoro-2,3-dihydro-1H-inden-1-yl)-3-(4-nitro-1,2,5-oxadiazol-3-yl)-1,2,4-oxadiazol-5(4H)-one

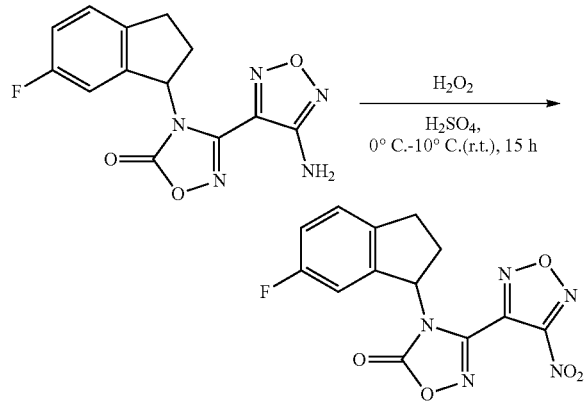

To a solution of 3-(4-amino-1,2,5-oxadiazol-3-yl)-4-(6-fluoro-2,3-dihydro-1H-inden-1-yl)-1,2,4-oxadiazol-5(4H)-one (110 mg, 0.363 mmol) in 30% hydrogen peroxide (1.0 mL) was added sulfuric acid (1.2 mL) at 0° C. The reaction mixture was warmed to RT and stirred for 15 h, poured to ice slowly, diluted with ice cold water (30 mL), extracted with EtOAc (30 mL×3). The combined organic layers were concentrated under reduced pressure. The residue was purified by column chromatography (SiO$_2$, Pet. ether: EtOAc=5:1 as eluent) to give 4-(6-fluoro-2,3-dihydro-1H-inden-1-yl)-3-(4-nitro-1,2,5-oxadiazol-3-yl)-1,2,4-oxadiazol-5(4H)-one (30 mg, 0.077 mmol) as a solid.

An alternative procedure for the synthesis of the title compound is described below:

To a solution of 3-(4-amino-1,2,5-oxadiazol-3-yl)-4-(6-fluoro-2,3-dihydro-1H-inden-1-yl)-1,2,4-oxadiazol-5(4H)-one (50.0 g, 165 mmol) in TFA (450 mL) was added hydrogen peroxide (166 mL, 165 mmol, 30% aqueous solution) slowly at 0° C. The reaction mixture was warmed to RT and stirred for 16 h, then diluted by water (300 mL0 at 0° C., extracted with CH$_2$Cl$_2$ (300 mL) twice. The combined organic layers were washed with brine (200 mL), dried over Na$_2$SO$_4$, filtered, and concentrated under reduced pressure. The residue was purified by column chromatography (SiO$_2$, petroleum ether/ethyl acetate 20:1 to 15:1 as eluent) to give the title compound (21.5 g) as a solid. $^1$H NMR (400 MHz, CDCl$_3$) δ 7.1 (dd, J=8.2, 5.1 Hz, 1H), 7.0 (td, J=8.6, 2.4 Hz, 1H), 6.8 (dd, J=7.8, 2.0 Hz, 1H), 5.7 (dd, J=9.0, 5.1 Hz, 1H), 2.9-3.1 (m, 2H), 2.8 (dtd, J=14.3, 8.9, 8.9, 5.9 Hz, 1H), 2.4 (ddt, J=14.3, 9.1, 5.5, 5.5 Hz, 1H).

Step 3. Tert-butyl (2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)carbamate

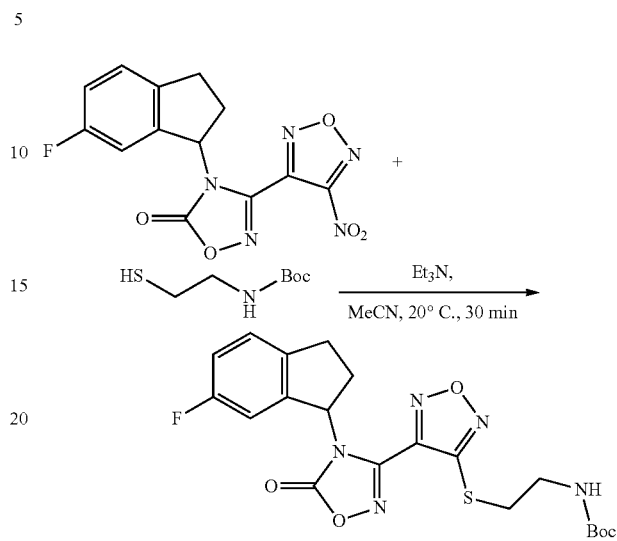

To a solution of 4-(6-fluoro-2,3-dihydro-1H-inden-1-yl)-3-(4-nitro-1,2,5-oxadiazol-3-yl)-1,2,4-oxadiazol-5(4H)-one (30 mg, 0.090 mmol) in MeCN (2 mL) were added triethylamine (9.11 mg, 0.090 mmol) and tert-butyl (2-mercaptoethyl)carbamate (15.96 mg, 0.090 mmol) and the mixture was stirred at 20° C. for 30 min. The solvent was removed in vacuo. The residue was purified by prep-TLC (Pet.ether/ethyl acetate=3:1) to give tert-butyl (2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)carbamate (22 mg, 0.047 mmol) as an oil.

Step 4. 3-(4-((2-Aminoethyl)thio)-1,2,5-oxadiazol-3-yl)-4-(6-fluoro-2,3-dihydro-1H-inden-1-yl)-1,2,4-oxadiazol-5(4H)-one hydrochloride

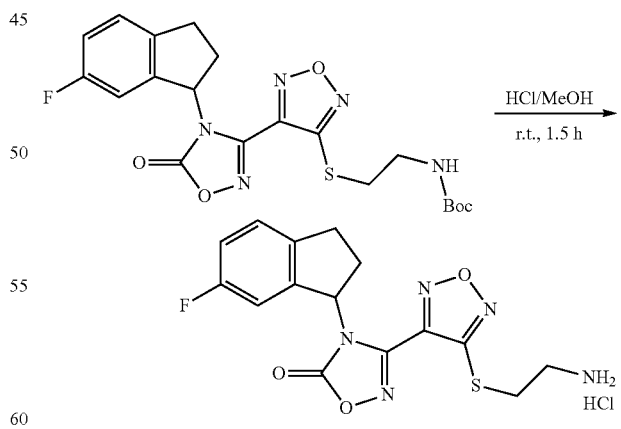

A solution of tert-butyl (2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)carbamate (22 mg, 0.047 mmol) in 4 M HCl—CH$_3$OH (2.0 mL) was stirred at 20° C. for 1.5 h. The mixture was concentrated under reduced pressure to give 3-(4-((2-aminoethyl)thio)-1,2,5-oxadiazol- 3-yl)-4-(6-fluoro-2,3-dihydro-1H-inden-1-yl)-1,2,4-oxadi-azol-5(4H)-one hydrochloride (19 mg, 0.047 mmol) as a solid which was used in the next step directly without further purification.

Step 5. N-(6-fluoro-2,3-dihydro-1H-inden-1-yl)-N'-hydroxy-4-((2-(sulfamoylamino)ethyl)thio)-1,2,5-oxadiazole-3-carboximidamide

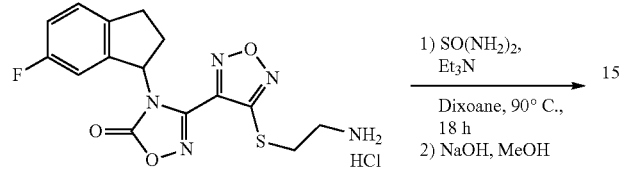

1) SO(NH$_2$)$_2$, Et$_3$N

Dixoane, 90° C., 18 h
2) NaOH, MeOH

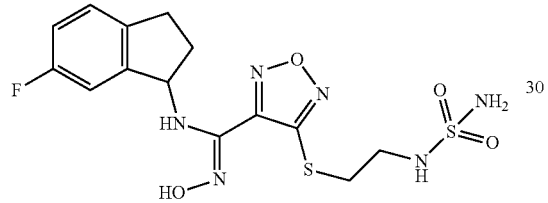

To a solution of 3-(4-((2-aminoethyl)thio)-1,2,5-oxadi-azol-3-yl)-4-(6-fluoro-2,3-dihydro-1H-inden-1-yl)-1,2,4-oxadiazol-5(4H)-one hydrochloride (19 mg, 0.047 mmol) in 1,4-dioxane (3.0 mL) were added Et$_3$N (0.017 mL, 0.125 mmol). After stirring at 20° C. for 30 min, sulfuric diamide (12.02 mg, 0.125 mmol) was added. The reaction mixture was stirred at 90° C. for 18 h under N$_2$ atmosphere, cooled to RT, concentrated under reduced pressure. The residue (21 mg) was dissolved in MeOH (3.0 mL). To the resultant solution was added aq. NaOH (2.0 M, 1.0 mL, 2.0 mmol). The reaction mixture was stirred at 20° C. for 6 h, concentrated under reduced pressure. The residue was purified by prep-HPLC (Column Agela ASB 150×25 mm×5 um, Condition water (0.225% FA)-ACN Begin B 32, End B 62 Gradient Time (min) 10, 100% B Hold Time (min) 2, Flow Rate (mL/min) 25, Injections 3) and acetonitrile as eluents (Mobile phase A water (0.2% Formic acid), Mobile phase B acetonitrile, Detective wavelength: 220 nm.) followed by lyophilization to give N-(6-fluoro-2,3-dihydro-1H-inden-1-yl)-N'-hydroxy-4-((2-(sulfamoylamino)ethyl)thio)-1,2,5-oxadiazole-3-carboximidamide (7 mg, 0.016 mmol) as a solid. m/z=: 417.0 [M+H]$^+$ $^1$H NMR (400 MHz, METHANOL-d4) δ 7.13-7.25 (m, 1H), 6.85-7.03 (m, 2H), 5.34 (t, J=8.0 Hz, 1H), 3.44 (br d, J=6.4 Hz, 2H), 3.38 (br d, J=6.4 Hz, 2H), 2.87-2.99 (m, 1H), 2.70-2.82 (m, 1H), 2.50-2.61 (m, 1H), 1.87-2.00 (m, 1H).

Examples 30 and 31. (S)—N-(2-((4-(N-(2,3-di-hydro-1H-inden-1-yl)-N'-hydroxycarbamimidoyl)-1,2,5-oxadiazol-3-yl)thio)ethyl)acetamide and (R)—N-(2-((4-(N-(2,3-dihydro-1H-inden-1-yl)-N'-hydroxycarbamimidoyl)-1,2,5-oxadiazol-3-yl)thio)ethyl)acetamide

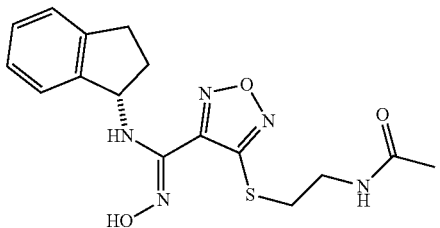

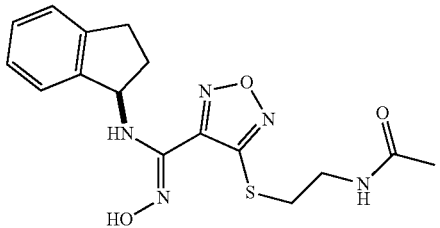

Step 1. N-(2-((4-Cyano-1,2,5-oxadiazol-3-yl)thio)ethyl)acetamide

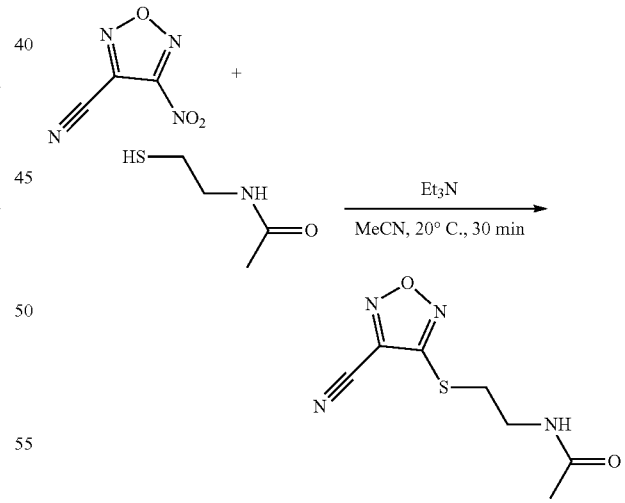

To a solution of 4-nitro-1,2,5-oxadiazole-3-carbonitrile (200 mg, 1.428 mmol) in CH$_3$CN (5 mL) were added Et$_3$N (289 mg, 2.86 mmol) and N-(2-mercaptoethyl)acetamide (170 mg, 1.428 mmol). The mixture was stirred at 20° C. for 30 min, concentrated under reduced pressure. The residue was purified by column chromatography (CH$_3$OH/CH$_2$Cl$_2$ 1:30-1:20 as eluent) to give the title compound (112 mg, 0.475 mmol) as a solid.

Step 2. N-(2-((4-(N-Hydroxycarbamimidoyl)-1,2,5-oxadiazol-3-yl)thio)ethyl)acetamide

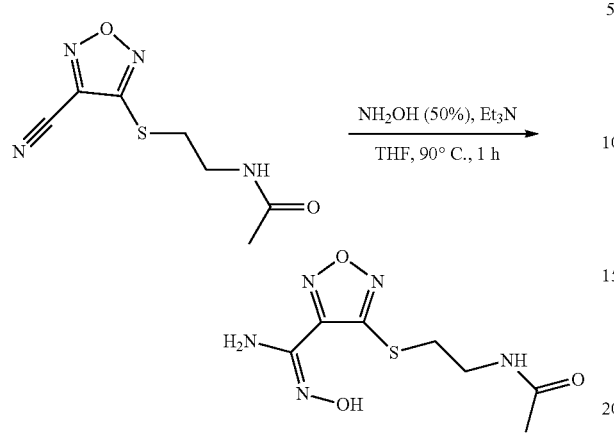

To a solution of N-(2-((4-cyano-1,2,5-oxadiazol-3-yl)thio)ethyl)acetamide (112 mg, 0.528 mmol) in THF (10 mL) were added Et$_3$N (0.79 mL, 5.68 mmol) and 50% aqueous NH$_2$OH (0.14 mL, 2.285 mmol). The mixture was stirred at 90° C. for 1 h, cooled to RT, concentrated under reduced pressure. The residue was purified by column chromatography (CH$_3$OH/CH$_2$Cl$_2$ 1:10 as eluent) to give the title compound (117 mg, 0.429 mmol) as a solid.

Step 3. 4-((2-Acetamidoethyl)thio)-N-hydroxy-1,2,5-oxadiazole-3-carbimidoyl chloride

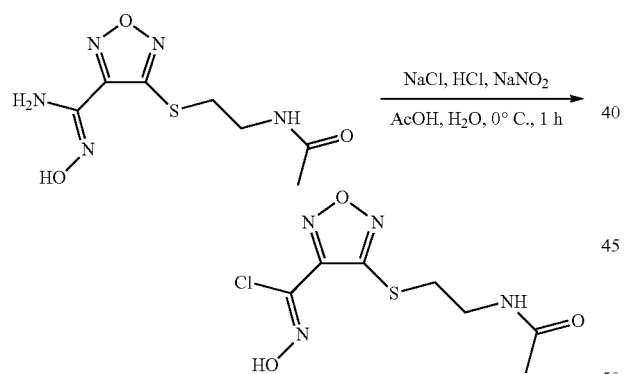

N-(2-((4-(N-hydroxycarbamimidoyl)-1,2,5-oxadiazol-3-yl)thio)ethyl)acetamide (117 mg, 0.477 mmol) was added to a mixture of water (2.0 mL), AcOH (1.0 mL) and 6 M HCl (0.24 mL, 1.440 mmol). The suspension was stirred at 45° C. until a clear solution was achieved. NaCl (84 mg, 1.431 mmol) was then added. The reaction was cooled using an ice/water/methanol bath before a solution of sodium nitrite (33 mg, 0.478 mmol) in water (10 mL) was added over 10 min while maintaining the temperature below 0° C. After stirring for another 1.5 h, the reaction mixture was allowed to warm to RT. The precipitate was collected by filtration, washed well with water (10 mL), taken in ethyl acetate (30 mL×2), treated with anhydrous sodium sulfate. This suspension was filtered through sodium sulfate and the filtrate was concentrated to give the title compound (100 mg, 0.340 mmol) as a solid.

Step 4. N-(2-((4-(N-(2,3-Dihydro-1H-inden-1-yl)-N'-hydroxycarbamimidoyl)-1,2,5-oxadiazol-3-yl)thio)ethyl)acetamide

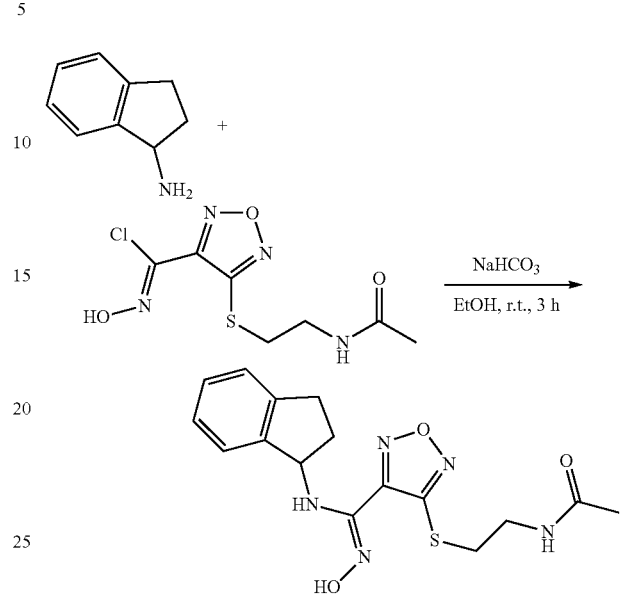

To a solution of 4-((2-acetamidoethyl)thio)-N-hydroxy-1,2,5-oxadiazole-3-carbimidoyl chloride (100 mg, 0.378 mmol) in ethanol (5 mL) were added 2,3-dihydro-1H-inden-1-amine (51 mg, 0.383 mmol) and NaHCO$_3$ (79 mg, 0.945 mmol). The mixture was stirred at 20° C. for 1 h. The mixture was concentrated under reduced pressure. The residue was purified by HPLC on a GILSON 281 instrument fitted with a Phenomenex Synergi C18 (250×21.2 mm×4 m) using water (0.225% FA)-CH$_3$CN, Mobile phase B acetonitrile, Detective wavelength: 220 nm) to give the title compound (80 mg, 0.216 mmol) as a solid.

Step 5. (S)—N-(2-((4-(N-(2,3-dihydro-1H-inden-1-yl)-N'-hydroxycarbamimidoyl)-1,2,5-oxadiazol-3-yl)thio)ethyl)acetamide and (R)—N-(2-((4-(N-(2,3-dihydro-1H-inden-1-yl)-N'-hydroxycarbamimidoyl)-1,2,5-oxadiazol-3-yl)thio)ethyl)acetamide

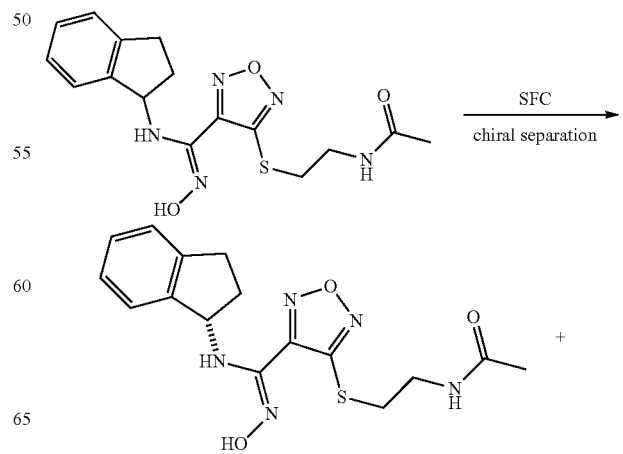

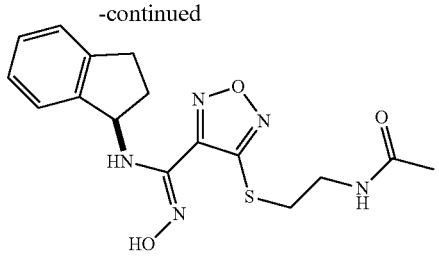

Two chiral isomers were obtained after SFC separation of 120 mg racemate compound above. The absolute stereochemistry was not determined.

SFC method: Chiralpak AD-3 100×4.6 mm I.D., 3 um; Mobile phase: A: CO2 B: ethanol (0.05% DEA) Gradient: from 5% to 40% of B in 4.5 min and hold 40% for 2.5 min, then 5% of B for 1 min Flow rate: 2.8 mL/min; Column temperature: 40° C.

Example 30 (Peak 1): $^1$H NMR (400 MHz, CD$_3$OD) δ 7.23-7.30 (m, 1H), 7.14-7.23 (m, 1H), 5.32 (t, J=7.4 Hz, 1H), 3.52-3.61 (m, 2H), 3.27-3.30 (m, 2H), 2.96 (ddd, J=15.8, 8.9, 2.7 Hz, 1H), 2.79 (dt, J=15.9, 8.3 Hz, 1H), 2.45-2.55 (m, 1H), 1.91 (s, 3H), 1.81-1.90 (m, 1H). ESI MS m/z: 383.9 [M+Na]$^+$.

Example 31 (Peak 2): $^1$H NMR (400 MHz, CD$_3$OD) δ 7.24-7.30 (m, 1H), 7.15-7.23 (m, 3H), 5.32 (t, J=7.4 Hz, 1H), 3.57 (t, J=6.3 Hz, 2H), 3.28-3.30 (m, 2H), 2.96 (ddd, J=15.6, 8.6, 2.7 Hz, 1H), 2.79 (dt, J=16.0, 8.4 Hz, 1H), 2.45-2.55 (m, 1H), 1.91 (s, 3H), 1.81-1.89 (m, 1H). ESI MS m/z: 383.9 [M+Na]$^+$. HPLC purity: 95.5%.

Examples 32 and 33. (S)—N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide and (R)—N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide

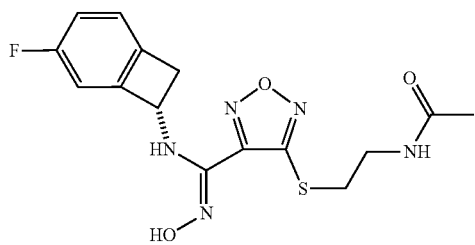

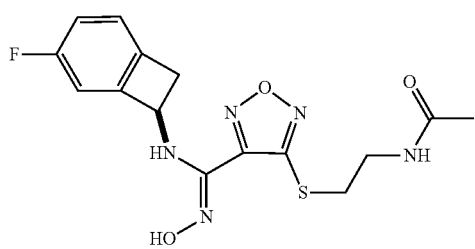

Step 1. Methyl 2-(2-bromo-5-fluorophenyl)acetate

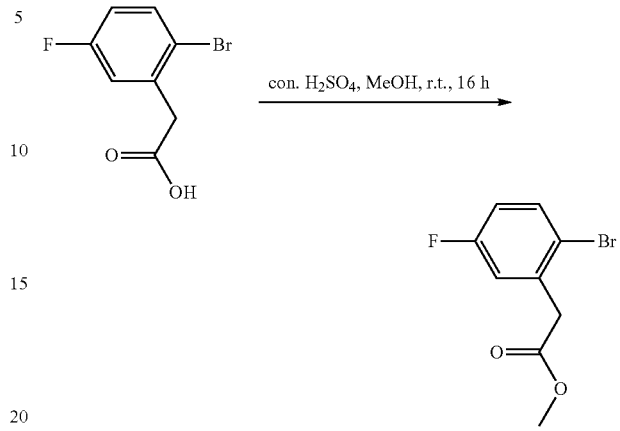

H$_2$SO$_4$ (5 mL, 94 mmol) was added cautiously to a solution of 2-(2-bromo-5-fluorophenyl) acetic acid (20.0 g, 86 mmol) in MeOH (100 mL) and the resulting mixture was stirred overnight at RT. Saturated aqueous Na$_2$CO$_3$ solution was added slowly to adjust the pH of the mixture to ~14. After extraction with DCM (200 mL×2). The combined organic layers were dried over anhydrous Na$_2$SO$_4$. The mixture was filtered and concentrated under reduced pressure to give methyl 2-(2-bromo-5-fluorophenyl) acetate (19.0 g, 77 mmol) as a solid, which was used in the next step without further purification.

Step 2. Dimethyl 2-(2-bromo-5-fluorophenyl)malonate

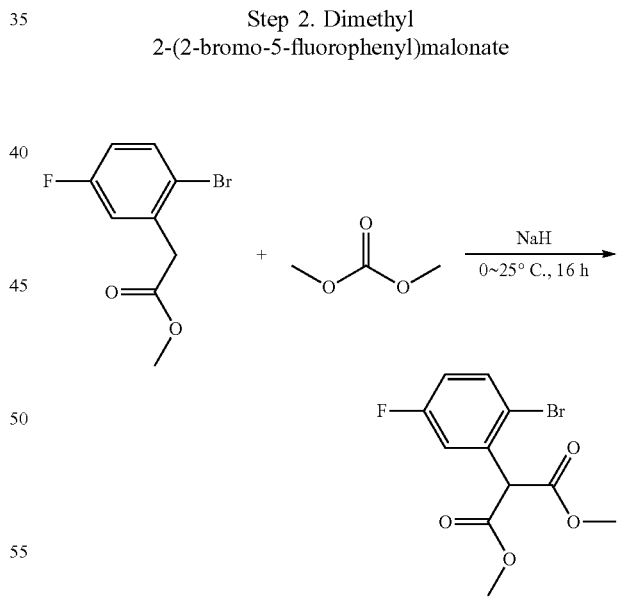

To a stirred solution of methyl 2-(2-bromo-5-fluorophenyl)acetate (19.0 g, 77 mmol) in dimethyl carbonate (DMC) (100 mL) under N$_2$ was added NaH (6.15 g, 154 mmol) (60% in oil) in three portions at 0° C. Then the reaction mixture was warmed up to 20° C. and stirred for 16 h. The reaction mixture was quenched by the addition of H$_2$O (~50 mL) slowly at 0° C. After extraction with ethyl acetate (100 mL×2), the combined organic phase was dried over Na$_2$SO$_4$ and concentrated under reduced pressure. The residue was purified by flash chromatography (ethyl acetate/petroleum ether=1/30 to 1/10) to afford dimethyl 2-(2-bromo-5-fluorophenyl)malonate (21.0 g, 68.8 mmol) as a solid.

Step 3. Dimethyl 2-(2-bromo-5-fluorophenyl)-2-methylmalonate

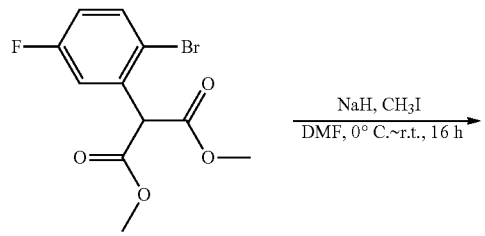

A solution of the dimethyl 2-(2-bromo-5-fluorophenyl)malonate (10.0 g, 32.8 mmol) in freshly distilled DMF (10 mL) was added dropwise at 0° C. to a mixture of sodium hydride (1.966 g, 49.2 mmol) (60% in oil) in freshly distilled DMF (40 mL). The mixture was stirred for 30 min and iodomethane (13.96 g, 98 mmol) was added dropwise. After stirring at 20° C. for 16 h, the reaction mixture was quenched with a saturated aq. solution of NH4Cl (500 mL) and the aqueous layer was extracted with Petroleum ether (300 mL×3). The combined organic layers were washed with brine (100 mL), dried over Na2SO4 and concentrated in vacuo. The residue was purified by silica chromatography (SiO2, Petroleum ether/AcOEt: 10/1 to 4:1) to afford dimethyl 2-(2-bromo-5-fluorophenyl)-2-methylmalonate (9.2 g, 28.8 mmol) as a solid.

Step 4. Dimethyl 4-fluorobicyclo[4.2.0]octa-1(6),2,4-triene-7,7-dicarboxylate

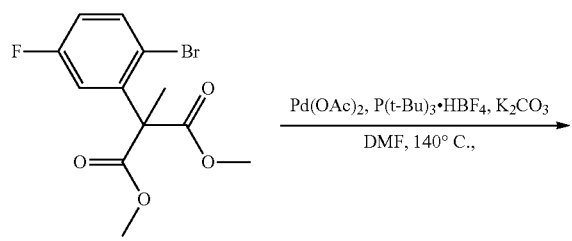

To a solution of dimethyl 2-(2-bromo-5-fluorophenyl)-2-methylmalonate (6.0 g, 18.80 mmol) in DMF (30 mL) were added potassium carbonate (3.38 g, 24.44 mmol), tri-tert-butylphosphonium tetrafluoroborate (1.091 g, 3.76 mmol) and diacetoxypalladium (0.422 g, 1.880 mmol). The mixture was degassed with argon twice, then the mixture was stirred at 140° C. (preheated oil bath) for 1.5 h. The mixture was diluted with EtOAc (~40 mL) and filtered through Celite. The organic solution was washed with brine (300 mL), dried over MgSO4, and concentrated in vacuo. The residue was purified by silica chromatography (petroleum ether/ethyl acetate=50:1) to afford the mixture of dimethyl 2-fluorobicyclo[4.2.0]octa-1(6),2,4-triene-7,7-dicarboxylate and dimethyl 4-fluorobicyclo[4.2.0]octa-1(6),2,4-triene-7,7-dicarboxylate (1.8 g, 6.80 mmol) as an oil (~1:3 ratio).

Step 5. 4-Fluorobicyclo[4.2.0]octa-1(6),2,4-triene-7-carboxylic acid

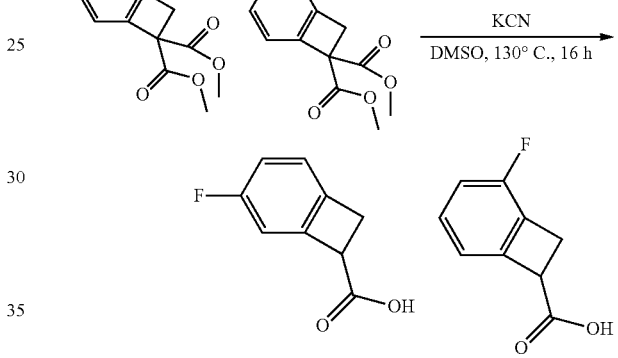

To a solution of dimethyl 4/2-fluorobicyclo[4.2.0]octa-1(6),2,4-triene-7,7-dicarboxylate (1.8 g, 7.56 mmol, as a mixture) in DMSO (36 mL) was added KCN (1.476 g, 22.67 mmol). The resulting mixture was heated to 130° C. and stirred for 12 h under Ar atmosphere. The reaction mixture was cooled to RT. 1 N aq. solution of HCl (~60 mL) and 2-methoxy-2-methylpropane (80 mL) was then cautiously added to the reaction mixture and the mixture was stirred for 1 h. The organic phase was then washed with 1N aq. solution of NaOH (80 mL×3). The combined aqueous were acidified to pH=2 with aq. solution of HCl at 20° C. and extracted with tert-butyl methyl ether (300 mL×3). The extracts were then dried over Na2SO4 and evaporated under reduced pressure. The residue was used in the next step without further purification.

Step 6. Tert-Butyl (4/2-fluorobicyclo[4.2.0]octa-1(6),2,4-trien-7-yl)carbamate

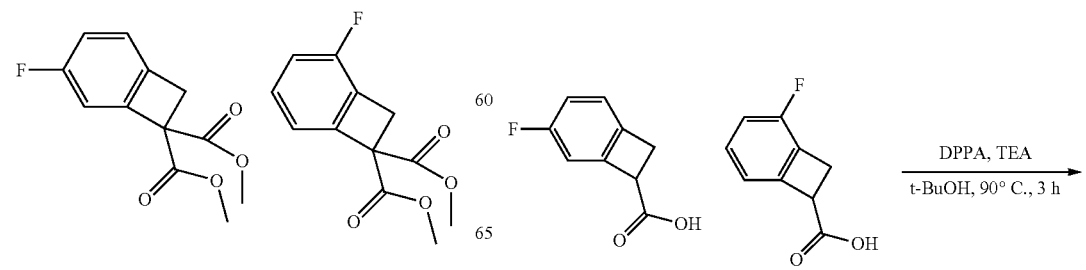

-continued

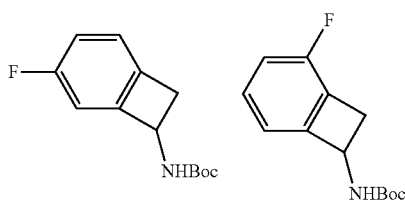

To a stirred solution of 4/2-fluorobicyclo[4.2.0]octa-1,3,5-triene-7-carboxylic acid (800 mg, 4.81 mmol) in t-BuOH (5 mL) were added TEA (0.805 mL, 5.78 mmol) and DPPA (1.0 mL, 4.81 mmol) and the mixture was stirred at 85° C. for 6 h under $N_2$ atmosphere. The mixture was evaporated under reduced pressure. The residue was purified by silica chromatography (petroleum ether/ethyl acetate=50: 1-30:1) to afford tert-butyl (4/2-fluorobicyclo[4.2.0]octa-1,3,5-trien-7-yl) carbamate (500 mg, 1.686 mmol) as a solid.

Step 7. 4/2-Fluorobicyclo[4.2.0]octa-1(6),2,4-trien-7-amine hydrochloride

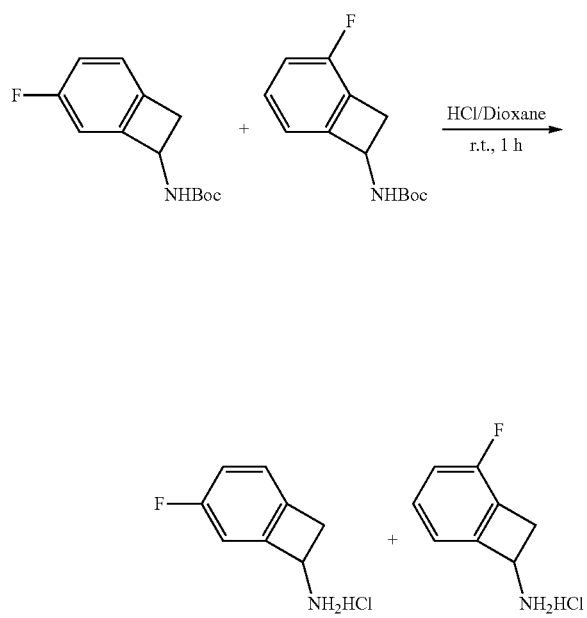

A mixture of tert-butyl (4/2-fluorobicyclo[4.2.0]octa-1,3,5-trien-7-yl)carbamate (200 mg, 0.843 mmol, 3:1 mixture) and HCl (5 ml, 20.00 mmol) (4 M in dioxane) was stirred at 20° C. for 1 h. The mixture was concentrated to afford 4/2-fluorobicyclo[4.2.0]octa-1,3,5-trien-7-amine hydrochloride (140 mg, 0.806 mmol, 3:1 mixture) as a solid which was used without further purification.

Step 8. N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide and N-(2-((4-(N-(2-fluorobicyclo[4.2.0]octa-1(6),2,4-trien-7-yl)-N'-hydroxycarbamimidoyl)-1,2,5-oxadiazol-3-yl)thio)ethyl)acetamide

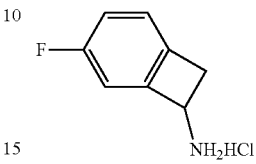

or

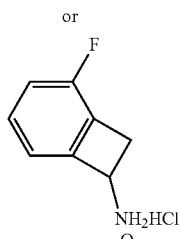

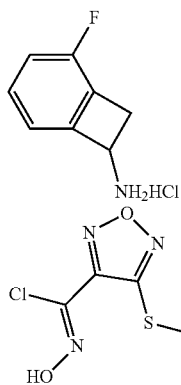

or

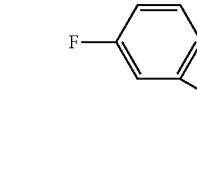

To a solution of 4/2-fluorobicyclo[4.2.0]octa-1,3,5-trien-7-amine hydrochloride (150 mg, 0.864 mmol) in EtOH (5 ml) were added 4-((2-acetamidoethyl)thio)-N-hydroxy-1,2,5-oxadiazole-3-carbimidoyl chloride (229 mg, 0.864 mmol) (Step 3, Example 30) and sodium bicarbonate (218 mg, 2.59 mmol). The mixture was stirred at 20° C. for 16 h. After the solvent was removed in vacuo, the residue was purified by reverse phase HPLC on a GILSON 281 instrument fitted with a Phenomenex Synergi C18 (250×21.2 mm×4 m) using water (0.1% FA) and acetonitrile as eluents (Mobile phase A water (0.1% FA), Mobile phase B acetonitrile, Detective wavelength: 220 nm) followed by lyophilization to afford N-(2-((4-(N-(4/2-fluorobicyclo[4.2.0]octa-1(6),2,4-trien-7-yl)-N'-hydroxycarbamimidoyl)-1,2,5-oxadiazol-3-yl)thio)

ethyl)acetamide (120 mg, 0.328 mmol) as a solid. ¹H NMR (400 MHz, MeOD) δ 7.06-7.15 (m, 1H), 6.93-7.02 (m, 2H), 5.36 (br s, 1H), 3.51-3.60 (m, 4H), 3.01 (br d, J=13.69 Hz, 1H), 1.91 (s, 3H). MS (ESI m/z) 366.1 [M+H]⁺

Step 9. (S)—N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide and (R)—N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide

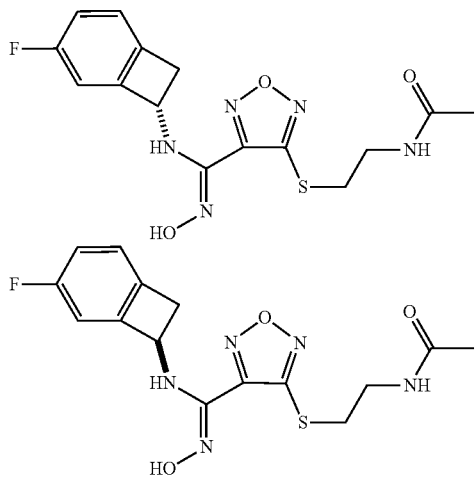

The above racemic mixture was submitted for chiral SFC separation (Column AD (250 mm×30 mm, 5 um), methanol+0.1% NH3H2O as modifier) to afford Example 32 (peak 1) (30 mg) and Example 33 (peak 2) (30 mg).

Example 32 (peak 1): MS (ESI m/z) 366.1 [M+H]⁺; ¹H NMR (400 MHz, MeOD) δ 7.11 (dd, J=7.9, 4.6 Hz, 1H), 6.96-7.03 (m, 1H), 6.92 (br d, J=7.7 Hz, 1H), 5.38 (br d, J=2.7 Hz, 1H), 3.53-3.60 (m, 3H), 3.26-3.30 (m, 2H), 3.03 (br d, J=14.1 Hz, 1H), 1.93 (s, 3H).

Example 33 (peak 2): MS (ESI m/z) 366.1 [M+H]⁺; ¹H NMR (400 MHz, MeOD) δ 7.11 (dd, J=7.9, 4.6 Hz, 1H), 6.96-7.03 (m, 1H), 6.92 (br d, J=7.7 Hz, 1H), 5.38 (br d, J=2.7 Hz, 1H), 3.53-3.60 (m, 3H), 3.26-3.30 (m, 2H), 3.03 (br d, J=14.1 Hz, 1H), 1.93 (s, 3H).

Example 34. (S)— or (R)—N-(2-((4-(N-(2-fluorobicyclo[4.2.0]octa-1(6),2,4-trien-7-yl)-N'-hydroxycarbamimidoyl)-1,2,5-oxadiazol-3-yl)thio)ethyl)acetamide

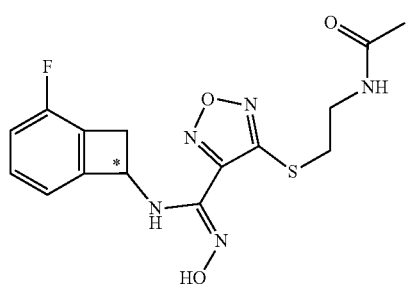 [SMILES: CC(=O)NCCSc1nonc1/C(=N/O)NC1Cc2c(F)cccc21]

Example 34 (peak 3, 10 mg) was isolated from the above SFC separation. The absolute stereochemistry was not determined. MS (ESI m/z) 366.1 [M+H]⁺;

¹H NMR (400 MHz, MeOD) δ 7.25 (br d, J=4.5 Hz, 1H), 6.90-7.01 (m, 2H), 5.44 (br s, 1H), 3.64 (br dd, J=13.7, 4.50 Hz, 1H), 3.56 (br d, J=6.3 Hz, 2H), 3.24-3.27 (m, 2H), 3.11 (br d, J=13.5 Hz, 1H), 1.91 (s, 3H).

Examples 35 and 36. (S)- and (R)—N-(4-fluorobicyclo[4.2.0]octa-1,3,5-trien-7-yl)-N'-hydroxy-4-(((6-oxo-1,6-dihydropyridin-2-yl)methyl)thio)-1,2,5-oxadiazole-3-carboximidamide

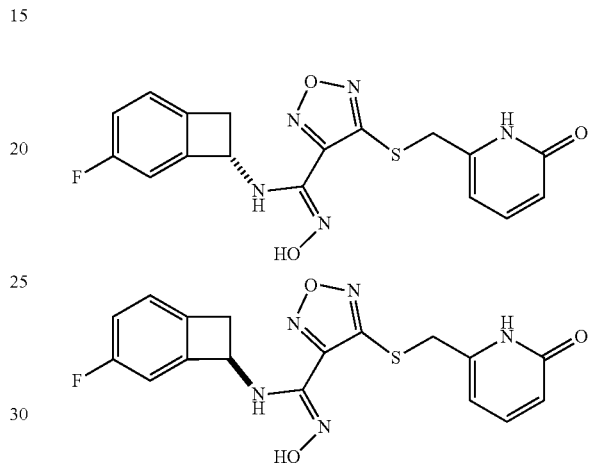

Step 1: 4-(((6-oxo-1,6-dihydropyridin-2-yl)methyl)thio)-1,2,5-oxadiazole-3-carbonitrile

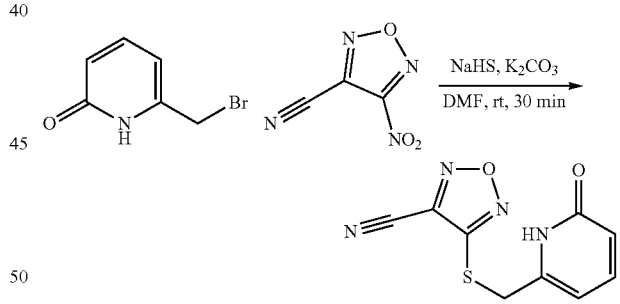

To a solution of 4-nitro-1,2,5-oxadiazole-3-carbonitrile (298 mg, 2.127 mmol) in DMF (15 ml) at 20° C. was added sodium hydrogensulfide (179 mg, 3.19 mmol). The mixture was stirred at 20° C. for 30 min before potassium carbonate (294 mg, 2.127 mmol) and 6-(bromomethyl)pyridin-2(1H)-one (400 mg, 2.127 mmol) were added. The mixture was stirred at 20° C. for 30 min, diluted with water (150 ml), extracted with EtOAc (3×60 ml). The combined organic layers were washed with brine (2×50 ml), dried over Na₂SO₄, filtered and concentrated. The residue was purified by column chromatography (MeOH in DCM: 0 to 10%) to afford 4-(((6-oxo-1,6-dihydropyridin-2-yl)methyl)thio)-1,2,5-oxadiazole-3-carbonitrile (200 mg, 0.854 mmol) as a solid.

Step 2: N-hydroxy-4-(((6-oxo-1,6-dihydropyridin-2-yl)methyl)thio)-1,2,5-oxadiazole-3-carboximidamide

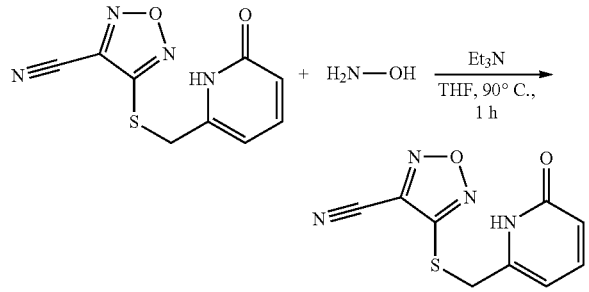

To a solution of 4-(((6-oxo-1,6-dihydropyridin-2-yl)methyl)thio)-1,2,5-oxadiazole-3-carbonitrile (200 mg, 0.854 mmol) in THF (15 ml) were added triethylamine (1.188 ml, 8.54 mmol) and hydroxylamine (50% aqueous, 0.262 ml, 4.27 mmol). The mixture was stirred at 90° C. for 1 h, cooled to RT, concentrated under reduced pressure. The residue was purified by column chromatography (SiO$_2$, MeOH/CH$_2$Cl$_2$=1:10 as eluent) to give N-hydroxy-4-(((6-oxo-1,6-dihydropyridin-2-yl)methyl)thio)-1,2,5-oxadiazole-3-carboximidamide (144 mg, 0.485 mmol) as a solid.

Step 3: N-hydroxy-4-(((6-oxo-1,6-dihydropyridin-2-yl)methyl)thio)-1,2,5-oxadiazole-3-carbimidoyl chloride

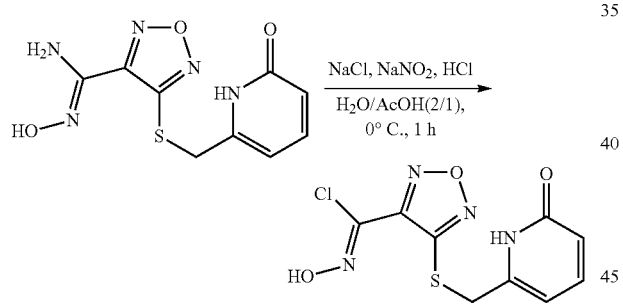

N-hydroxy-4-(((6-oxo-1,6-dihydropyridin-2-yl)methyl)thio)-1,2,5-oxadiazole-3-carboximidamide (144 mg, 0.485 mmol) was added to a mixture of water (2.0 ml) and 6 M hydrogen chloride (0.25 ml, 1.500 mmol), and this suspension was stirred at 45° C. until a clear solution was formed. Sodium chloride (85 mg, 1.455 mmol) was added and the reaction was cooled in an ice/water/methanol bath. A solution of sodium nitrite (33.5 mg, 0.485 mmol) in water (0.3 mL) was added over 10 min while maintaining the temperature below 0° C. After complete addition stirring was continued in the ice bath for 1 h and then the reaction mixture was allowed to warm to RT. The precipitate was collected by filtration, washed well with water (10 mL), taken in ethyl acetate (30 mL×2), treated with anhydrous sodium sulfate. This suspension was filtered through sodium sulfate and the filtrate was concentrated to give N-hydroxy-4-(((6-oxo-1,6-dihydropyridin-2-yl)methyl)thio)-1,2,5-oxadiazole-3-carbimidoyl chloride (133 mg, 0.441 mmol) as a solid.

Step 4. N-(4-Fluorobicyclo[4.2.0]octa-1,3,5-trien-7-yl)-N'-hydroxy-4-(((6-oxo-1,6-dihydropyridin-2-yl)methyl)thio)-1,2,5-oxadiazole-3-carboximidamide

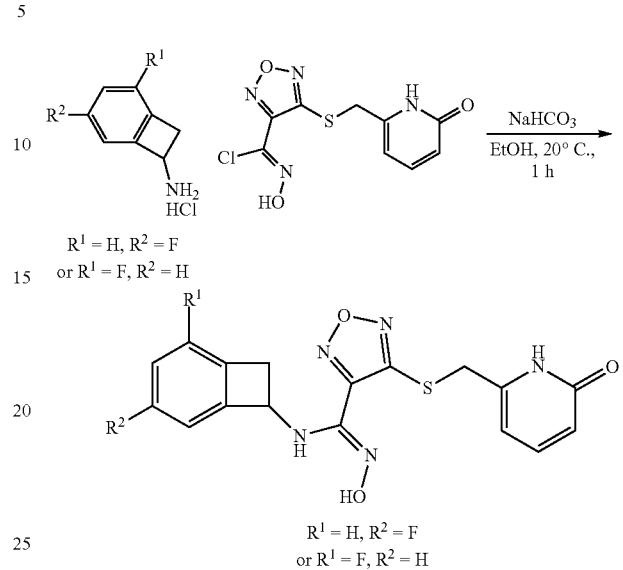

To a solution of N-hydroxy-4-(((6-oxo-1,6-dihydropyridin-2-yl)methyl)thio)-1,2,5-oxadiazole-3-carbimidoyl chloride (184 mg, 0.610 mmol) in ethanol (10 ml) was added 4-fluorobicyclo[4.2.0]octa-1,3,5-trien-7-amine hydrochloride (98 mg, 0.564 mmol) (Step 7, Example 32) and NaHCO$_3$ (145 mg, 1.727 mmol). The mixture was stirred at 20° C. for 1 h, concentrated under reduced pressure. The residue was purified by HPLC (Column: Phenomenex Synergi C18 150×30 mm×4 um; Condition: water (0.225% FA)-ACN; Gradient Time (min): 11; 100% B Hold Time (min): 2; Flow Rate (ml/min): 25) to provide N-(4-fluorobicyclo[4.2.0]octa-1,3,5-trien-7-yl)-N'-hydroxy-4-(((6-oxo-1,6-dihydropyridin-2-yl)methyl)thio)-1,2,5-oxadiazole-3-carboximidamide (75 mg, 0.192 mmol) as a solid.

Step 5: (S)- and (R)—N-(4-fluorobicyclo[4.2.0]octa-1,3,5-trien-7-yl)-N'-hydroxy-4-(((6-oxo-1,6-dihydropyridin-2-yl)methyl)thio)-1,2,5-oxadiazole-3-carboximidamide

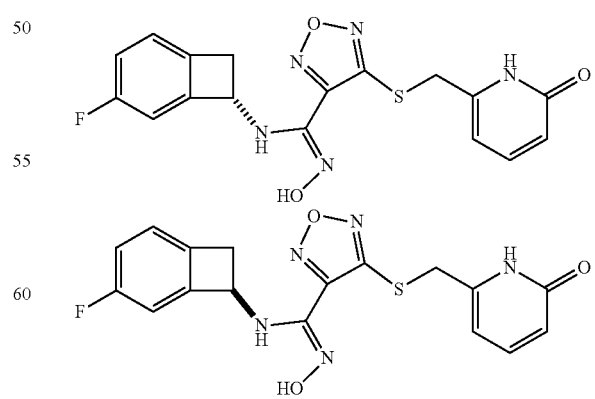

The above racemic mixture was submitted to SFC chiral separation (SFC12(Column: OJ (250 mm×30 mm, 5 um);

Condition: 0.1% NH₃H₂O MEOH; B: 40%; Flow Rate (ml/min): 60) to afford Examples 35 and 36 (7 mg each) as a solid.

Example 35 (peak 1): ¹H NMR (400 MHz, CD₃OD) δ 7.52 (dd, J=7.0, 9.2 Hz, 1H), 7.11 (dd, J=4.4, 7.7 Hz, 1H), 6.95-7.03 (m, 1H), 6.88 (br d, J=7.7 Hz, 1H), 6.54 (d, J=7.2 Hz, 1H), 6.44 (d, J=9.0 Hz, 1H), 5.47 (br s, 1H), 4.30 (s, 2H), 3.55 (dd, J=3.4, 13.6 Hz, 1H), 3.02 (br d, J=14.3 Hz, 1H). m/z: 388.2 [M+H]⁺.

Example 36 (peak 2): ¹H NMR (400 MHz, CD₃OD) δ 7.52 (dd, J=7.0, 9.2 Hz, 1H), 7.11 (dd, J=4.4, 7.7 Hz, 1H), 6.95-7.03 (m, 1H), 6.88 (br d, J=7.7 Hz, 1H), 6.54 (d, J=7.2 Hz, 1H), 6.44 (d, J=9.0 Hz, 1H), 5.47 (br s, 1H), 4.30 (s, 2H), 3.55 (dd, J=3.4, 13.6 Hz, 1H), 3.02 (br d, J=14.3 Hz, 1H). m/z: 388.2 [M+H]⁺.

Examples 37 and 38. (S)- and (R)—N-(2-((4-(N-(2-Chlorobicyclo[4.2.0]octa-1(6),2,4-trien-7-yl)-N'-hydroxycarbamimidoyl)-1,2,5-oxadiazol-3-yl)thio)ethyl)acetamide

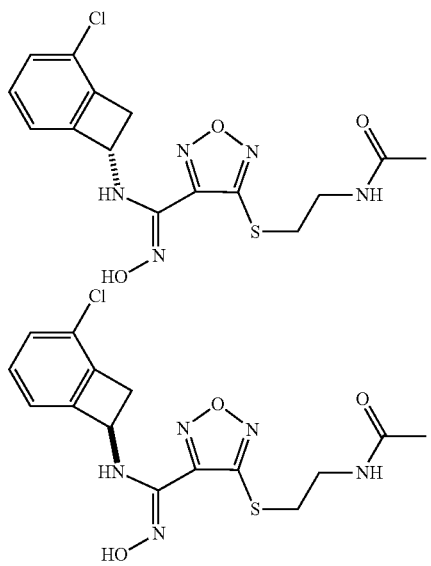

Step 1: Tert-butyl (2-chlorobicyclo[4.2.0]octa-1(6),2,4-trien-7-yl)carbamate

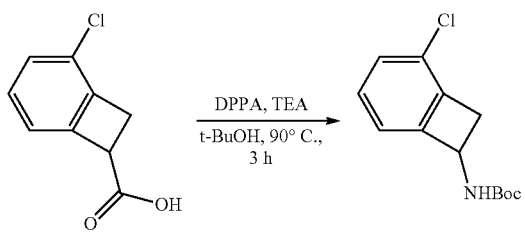 [SMILES: O=C(O)C1Cc2c(Cl)cccc21 ; CC(C)(C)OC(=O)NC1Cc2c(Cl)cccc21]

To a stirred solution of 2-chlorobicyclo[4.2.0]octa-1,3,5-triene-7-carboxylic acid (500 mg, 2.74 mmol) in t-BuOH (5 mL) were added TEA (0.46 mL, 3.29 mmol) and DPPA (0.62 mL, 2.88 mmol). The mixture was stirred under reflux (~90° C.) for 6 h under N₂ atmosphere, cooled, and concentrated in vacuo. The resultant residue was purified by reverse phase HPLC on a GILSON 281 instrument fitted with a Phenomenex Synergi C18 (250×21.2 mm×4 m) using water (0.1% TFA) and acetonitrile as eluents (Mobile phase A water (0.1% TFA), Mobile phase B acetonitrile, Detective wavelength: 220 nm) followed by lyophilization to give tert-butyl (2-chlorobicyclo[4.2.0]octa-1,3,5-trien-7-yl)carbamate (180 mg, 0.638 mmol) as a solid.

Step 2: 2-Chlorobicyclo[4.2.0]octa-1(6),2,4-trien-7-amine hydrochloride

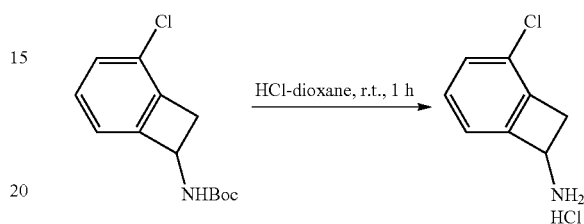

A mixture of tert-butyl (2-chlorobicyclo[4.2.0]octa-1,3,5-trien-7-yl)carbamate (60 mg, 0.236 mmol) and HCl (3 mL, 12.00 mmol) (4 M in dioxane) was stirred at ~15° C. for 1 h. The mixture was concentrated to afford 2-chlorobicyclo[4.2.0]octa-1,3,5-trien-7-amine hydrochloride (45 mg, 0.237 mmol) as a solid which was used without further purification.

Step 3: N-(2-((4-(N-(2-Chlorobicyclo[4.2.0]octa-1(6),2,4-trien-7-yl)-N'-hydroxycarbamimidoyl)-1,2,5-oxadiazol-3-yl)thio)ethyl)acetamide

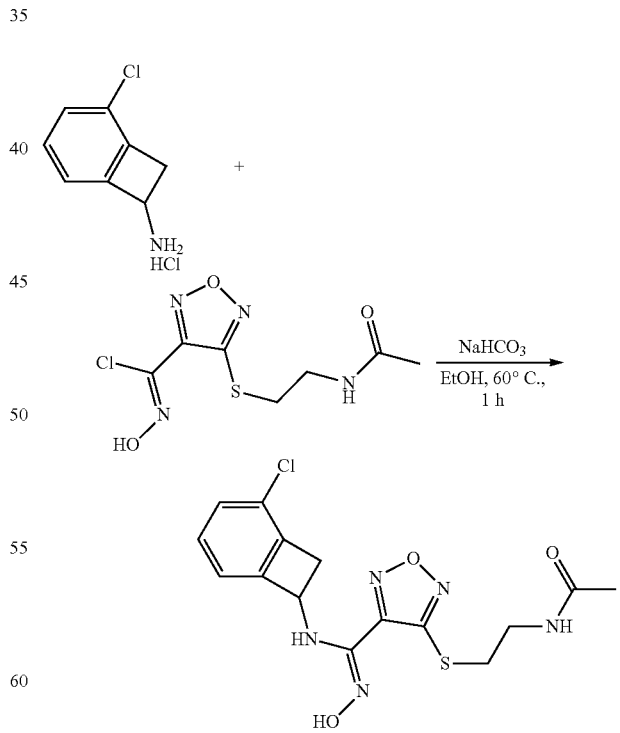

To a solution of 2-chlorobicyclo[4.2.0]octa-1,3,5-trien-7-amine hydrochloride (45 mg, 0.237 mmol) in EtOH (5 mL) were added 4-((2-acetamidoethyl)thio)-N-hydroxy-1,2,5-oxadiazole-3-carbimidoyl chloride (63 mg, 0.238 mmol)

and NaHCO₃ (50 mg, 0.595 mmol). The mixture was stirred at 60° C. for 1 h. After the solvent was removed in vacuo, the residue was purified by reverse phase HPLC on a GILSON 281 instrument fitted with a Phenomenex Synergi C18 (250×21.2 mm×4 μm) using water (0.1% TFA) and acetonitrile as eluents (Mobile phase A water (0.1% TFA), Mobile phase B acetonitrile, Detective wavelength: 220 nm) followed by lyophilization to give N-(2-((4-(N-(2-chlorobicyclo[4.2.0]octa-1(6),2,4-trien-7-yl)-N'-hydroxycarbamimidoyl)-1,2,5-oxadiazol-3-yl)thio)ethyl)acetamide (30 mg, 0.076 mmol) as a solid.

Step 4: (S)- and (R)—N-(2-((4-(N-(2-Chlorobicyclo[4.2.0]octa-1(6),2,4-trien-7-yl)-N'-hydroxycarbamimidoyl)-1,2,5-oxadiazol-3-yl)thio)ethyl)acetamide

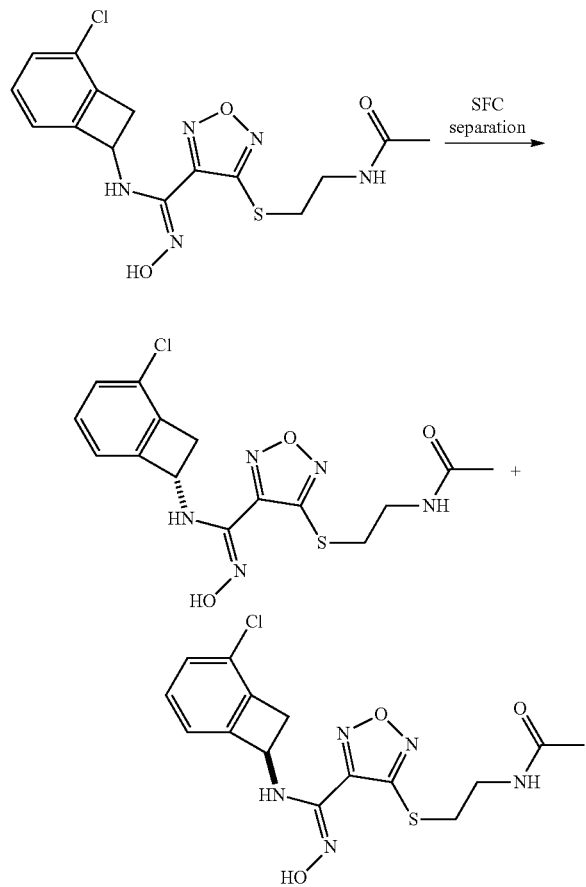

The above racemic mixture was submitted to SFC chiral separation (Column: AD (250 mm×30 mm, 5 um) Conditions: Neu-ETOH) to afford Examples 37 and 38 (10 mg each).

Example 37 (Peak 1): ¹H NMR (400 MHz, CD₃OD) δ 7.16-7.27 (m, 2H), 7.04-7.12 (m, 1H), 5.41 (d, J=2.4 Hz, 1H), 3.51-3.65 (m, 3H), 3.26 (brs., 2H), 3.09 (dd, J=14.5, 2.0 Hz, 1H), 1.91 (s, 3H).

Example 38 (Peak 2): ¹H NMR (400 MHz, CD₃OD) δ 7.18-7.29 (m, 2H), 7.05-7.14 (m, 1H), 5.42 (d, J=2.65 Hz, 1H), 3.55-3.64 (m, 3H), 3.28 (brs., 2H), 3.10 (dd, J=14.3, 2.0 Hz, 1H), 1.93 (s, 3H).

Example 39. (R)— or (S)—N-Ethyl-2-((4-(N-(6-fluoro-2,3-dihydro-1H-inden-1-yl)-N'-hydroxycarbamimidoyl)-1,2,5-oxadiazol-3-yl)thio)acetamide

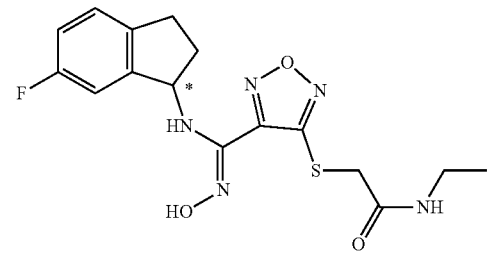 [SMILES: CCNC(=O)CSc1nonc1/C(=N/O)NC1CCc2ccc(F)cc21]

Step 1: (S)- and (R)-4-(6-Fluoro-2,3-dihydro-1H-inden-1-yl)-3-(4-nitro-1,2,5-oxadiazol-3-yl)-1,2,4-oxadiazol-5(4H)-one

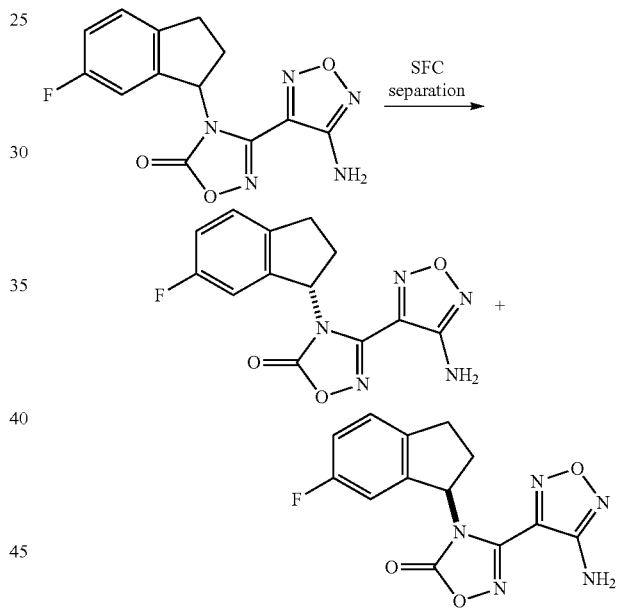

The racemic 4-(6-fluoro-2,3-dihydro-1H-inden-1-yl)-3-(4-nitro-1,2,5-oxadiazol-3-yl)-1,2,4-oxadiazol-5(4H)-one (1.0 g, 3.00 mmol, prepared according to step 2, Example 29) was submitted to chiral SFC separation (Column OD (250 mm×30 mm×5 um); Condition 0.1% NH3H2O ETOH Begin B 15%) to afford two chiral isomers (470 mg each) as an oil.

Isomer 1 (peak 1): ¹H NMR (400 MHz, CHLOROFORM-d) δ ppm 7.1 (dd, J=8.31, 4.99 Hz, 1H) 7.0 (td, J=8.56, 2.05 Hz, 1H) 6.8 (dd, J=8.12, 2.05 Hz, 1H) 5.8 (dd, J=8.51, 5.18 Hz, 1H) 2.9-3.1 (m, 2H) 2.8 (dtd, J=14.35, 8.82, 8.82, 5.58 Hz, 1H) 2.4 (ddt, J=14.21, 8.88, 5.48, 5.48 Hz, 1H).

Isomer 2 (peak 2): ¹H NMR (400 MHz, CHLOROFORM-d) δ ppm 7.1 (dd, J=8.31, 4.99 Hz, 1H) 7.0 (td, J=8.56, 2.05 Hz, 1H) 6.8 (dd, J=8.02, 1.96 Hz, 1H) 5.7 (dd, J=8.61, 5.09 Hz, 1H) 2.9-3.0 (m, 2H) 2.7-2.8 (m, 1H) 2.4 (ddt, J=14.21, 8.88, 5.48, 5.48 Hz, 1H).

Step 2. N-Ethyl-2-mercaptoacetamide

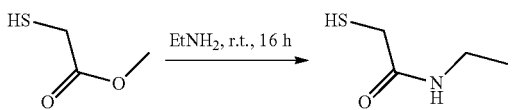

A mixture of methyl 2-mercaptoacetate (16.85 ml, 188 mmol) and ethanamine (27.7 g, 399 mmol) (25%, in water) was stirred at 18° C. for 16 h, extracted with $CH_2Cl_2$ (100 mL×3). The combined organic layers were dried over $Na_2SO_4$, filtered, and concentrated under reduced pressure to give crude N-ethyl-2-mercaptoacetamide (12 g, 101 mmol) as a solid.

Step 3. 2-((4-Cyano-1,2,5-oxadiazol-3-yl)thio)-N-ethylacetamide

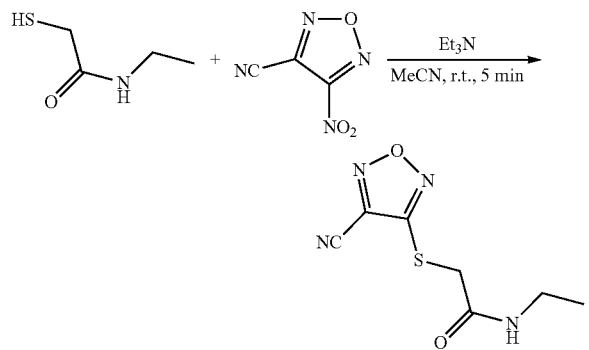

To a solution of 4-nitro-1,2,5-oxadiazole-3-carbonitrile (200 mg, 1.43 mmol) in MeCN (15 mL) were added triethylamine (0.40 ml, 2.86 mmol) and N-ethyl-2-mercaptoacetamide (153 mg, 1.29 mmol) in MeCN (5 mL) at 18° C. The mixture was stirred at 18° C. for 10 min, then concentrated under reduced pressure. The residue was purified by Pre-TLC (MeOH/CH2Cl2 1:20 as eluent) to give 2-((4-cyano-1,2,5-oxadiazol-3-yl)thio)-N-ethylacetamide (120 mg, 0.565 mmol) as a solid. LCMS: 213.0 [M+H]$^+$

Step 4. (Z)—N-Ethyl-2-((4-(N'-hydroxycarbamimidoyl)-1,2,5-oxadiazol-3-yl)thio)acetamide

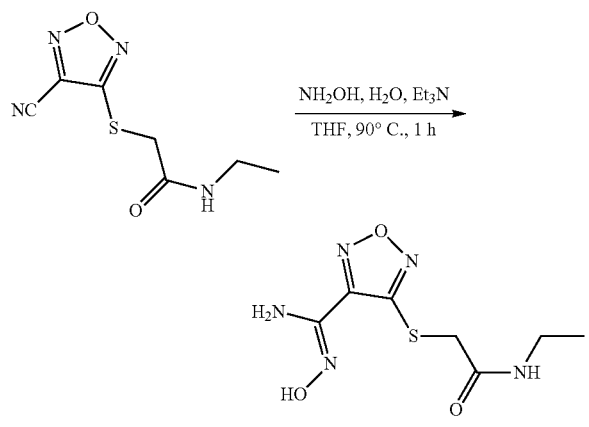

To a solution of 2-((4-cyano-1,2,5-oxadiazol-3-yl)thio)-N-ethylacetamide (200 mg, 0.94 mmol) in THF (15 ml) were added triethylamine (1313 µL, 9.42 mmol) and hydroxylamine (311 mg, 4.71 mmol). The mixture was stirred at 90° C. for 2 h, cooled to RT, and concentrated under reduced pressure. The residue was purified by column chromatography (SiO2, MeOH/CH2Cl2 1:20 as eluent) to give N-ethyl-2-((4-(N'-hydroxycarbamimidoyl)-1,2,5-oxadiazol-3-yl)thio)acetamide (200 mg, 0.815 mmol) as a solid.

Step 5: 4-((2-(Ethylamino)-2-oxoethyl)thio)-N-hydroxy-1,2,5-oxadiazole-3-carbimidoyl chloride

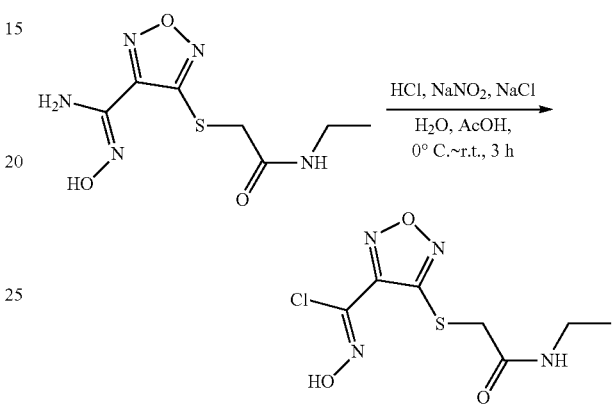

N-ethyl-2-((4-(N'-hydroxycarbamimidoyl)-1,2,5-oxadiazol-3-yl)thio)acetamide (200 mg, 0.82 mmol) was added to a mixture of water (4 mL), AcOH (2 mL) and 6 M HCl (0.4 mL, 2.45 mmol). The suspension was stirred at 45° C. until a clear solution was formed. Sodium chloride (143 mg, 2.45 mmol) was added and the reaction was cooled in an ice/water/methanol bath. A solution of sodium nitrite (56 mg, 0.82 mmol) in water (0.3 mL) was added over 10 min while maintaining the temperature below 0° C. After complete addition stirring was continued for 1 h. The reaction mixture was allowed to warm to ~20° C. The precipitate was collected by filtration, washed with water (10 mL), taken in ethyl acetate (30 mL×2), treated with anhydrous sodium sulfate. This suspension was filtered through sodium sulfate and the filtrate was concentrated to give 4-((2-(ethylamino)-2-oxoethyl)thio)-N-hydroxy-1,2,5-oxadiazole-3-carbimidoyl chloride (200 mg, 0.756 mmol) as a solid.

Step 6. (S)— or (R)—N-ethyl-2-((4-(N-(6-fluoro-2,3-dihydro-1H-inden-1-yl)-N'-hydroxycarbamimidoyl)-1,2,5-oxadiazol-3-yl)thio)acetamide

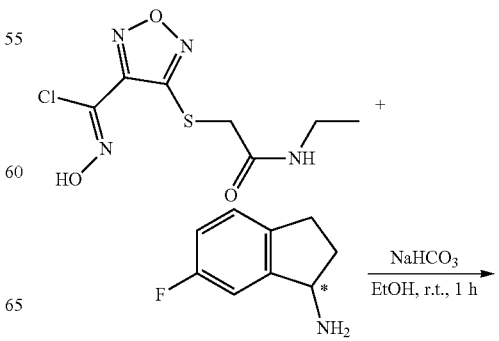

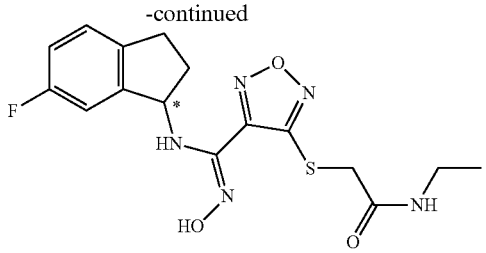

NaHCO₃ (69.5 mg, 0.827 mmol) was added to a mixture of 4-((2-(ethylamino)-2-oxoethyl)thio)-N-hydroxy-1,2,5-oxadiazole-3-carbimidoyl chloride (88 mg, 0.33 mmol) and 6-fluoro-2,3-dihydro-1H-inden-1-amine (50 mg, 0.33 mmol) (Isomer 1, Step 1) in EtOH (10 ml). The resulting mixture was stirred at 18° C. for 1 h, then concentrated under reduced pressure. The residue was purified by HPLC (on a GILSON 281 instrument fitted with a Waters XSELECT C18 (150×30 mm×5 m) using water (0.1% TFA)-MeCN, Mobile phase B acetonitrile, Detective wavelength: 220 nm)) to give (S)— or (R)—N-ethyl-2-((4-(N-(6-fluoro-2,3-dihydro-1H-inden-1-yl)-N'-hydroxycarbamimidoyl)-1,2,5-oxadiazol-3-yl)thio)acetamide (25 mg, 0.07 mmol) as a solid.

LCMS: 380.1 [M+H]⁺; ¹H NMR (400 MHz, CD₃OD) δ ppm 7.21 (dd, J=8.3, 5.0 Hz, 1H), 6.87-7.01 (m, 2H) 5.48 (t, J=7.8 Hz, 1H), 3.90 (s, 2H), 3.18-3.29 (m, 2H), 2.95 (br dd, J=13.1, 8.6 Hz, 1H), 2.72-2.83 (m, 1H), 2.52-2.63 (m, 1H), 1.95 (dq, J=12.7, 8.7 Hz, 1H), 1.12 (t, J=7.24 Hz, 3H)

Examples 40 and 41. (S)- and (R)—N-(4-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide

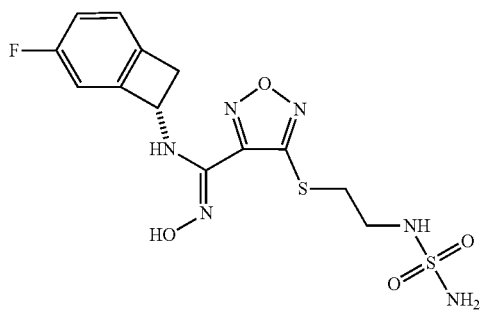

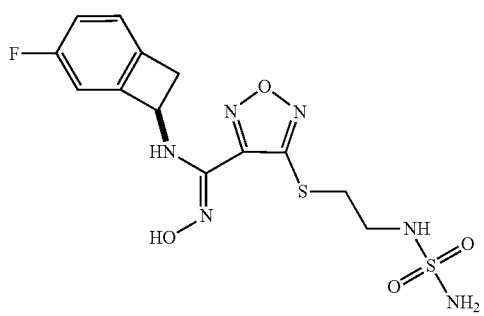

Step 1. 4-Amino-N-(4/2-fluorobicyclo[4.2.0]octa-1(6),2,4-trien-7-yl)-N'-hydroxy-1,2,5-oxadiazole-3-carboximidamide

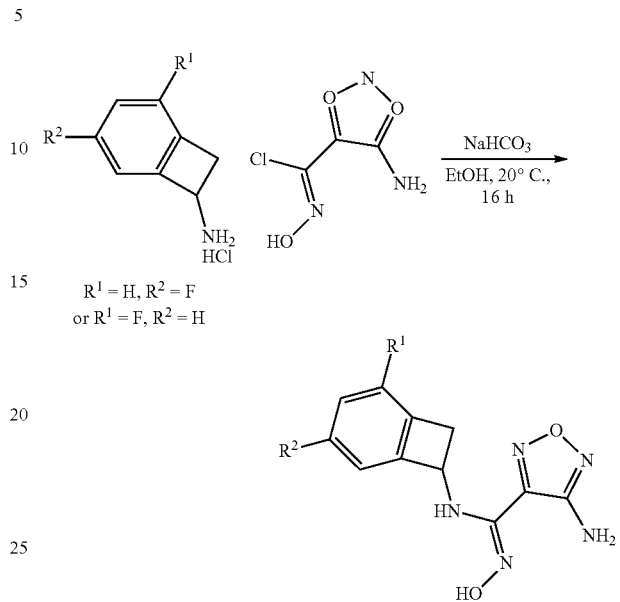

To a solution of 4/2-fluorobicyclo[4.2.0]octa-1,3,5-trien-7-amine hydrochloride (900 mg, 5.18 mmol, ~3:1 mixture) (Step 7, Example 32) in EtOH (20 ml) were added 4-amino-N-hydroxy-1,2,5-oxadiazole-3-carbimidoyl chloride (843 mg, 5.18 mmol) and NaHCO₃ (1306 mg, 15.55 mmol). The mixture was stirred at 20° C. for 16 h, and concentrated in vacuo. The residue was purified by silica chromatography (Petroleum ether/AcOEt: 10/1 to 4:1) to afford 4-amino-N-(4/2-fluorobicyclo[4.2.0]octa-1(6),2,4-trien-7-yl)-N'-hydroxy-1,2,5-oxadiazole-3-carboximidamide (1.1 g, 4.18 mmol, 3:1 mixture) as a solid.

Step 2. 3-(4-Amino-1,2,5-oxadiazol-3-yl)-4-(4/2-fluorobicyclo[4.2.0]octa-1(6),2,4-trien-7-yl)-1,2,4-oxadiazol-5(4H)-one

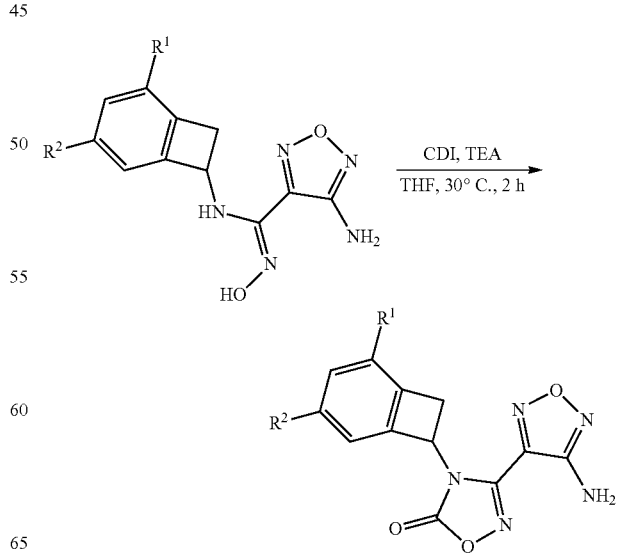

To a solution of 4-amino-N-(4/2-fluorobicyclo[4.2.0]octa-1(6),2,4-trien-7-yl)-N'-hydroxy-1,2,5-oxadiazole-3-carboximidamide (1.1 g, 4.18 mmol) and CDI (0.678 g, 4.18 mmol) in THF (30 ml) was added TEA (1.165 ml, 8.36 mmol). The reaction mixture was stirred at 30° C. for 2 h under N₂ atmosphere, concentrated under reduced pressure, diluted with water (100 mL), extracted with DCM (150 mL×2). The combined organic layers were washed with brine (100 mL) and dried over Na₂SO₄, filtered, and concentrated under reduced pressure. The residue was purified by column chromatography (Pet.ether/ethyl acetate 10:1-5:1 as eluent) to give 3-(4-amino-1,2,5-oxadiazol-3-yl)-4-(4/2-fluorobicyclo[4.2.0]octa-1(6),2,4-trien-7-yl)-1,2,4-oxadiazol-5(4H)-one (1.1 g, 3.80 mmol) as a solid.

Step 3. 4-(4/2-Fluorobicyclo[4.2.0]octa-1,3,5-trien-7-yl)-3-(4-nitro-1,2,5-oxadiazol-3-yl)-1,2,4-oxadiazol-5(4H)-one

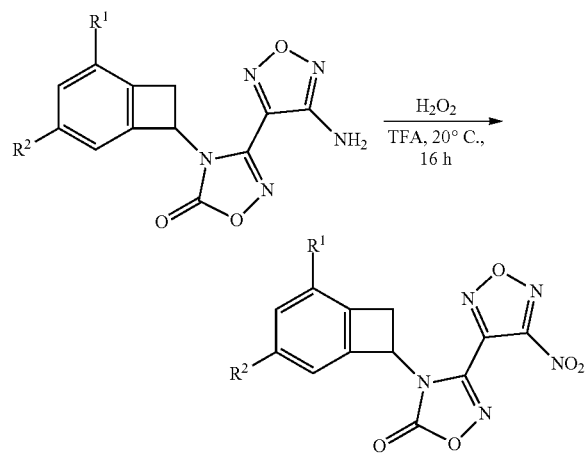

To a solution of 3-(4-amino-1,2,5-oxadiazol-3-yl)-4-(4/2-fluorobicyclo[4.2.0]octa-1,3,5-trien-7-yl)-1,2,4-oxadiazol-5(4H)-one (1.1 g, 3.80 mmol)) in TFA (20 ml) was added hydrogen peroxide (10 ml, 30%) at 0° C. The reaction mixture was stirred at 20° C. for 16 h, extracted with DCM (100 mL×3). The organic layer was concentrated under the reduced pressure. The residue was purified by column chromatography (Pet. ether:EtOAc, from pure Pet. ether to 5:1 as eluent) to give 4-(4/2-fluorobicyclo[4.2.0]octa-1,3,5-trien-7-yl)-3-(4-nitro-1,2,5-oxadiazol-3-yl)-1,2,4-oxadiazol-5(4H)-one (500 mg, 1.566 mmol) as a solid.

Step 4. Tert-Butyl (2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)carbamate

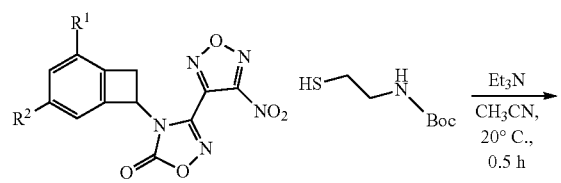

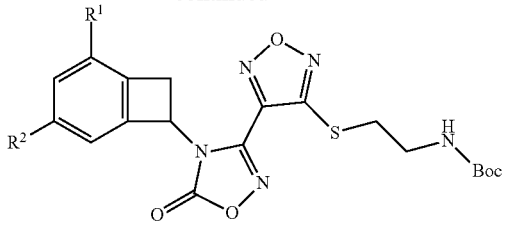

To a solution of 4-(4/2-fluorobicyclo[4.2.0]octa-1(6),2,4-trien-7-yl)-3-(4-nitro-1,2,5-oxadiazol-3-yl)-1,2,4-oxadiazol-5(4H)-one (400 mg, 1.253 mmol) in MeCN (10 ml) were added TEA (0.524 ml, 3.76 mmol) and tert-butyl (2-mercaptoethyl)carbamate (444 mg, 2.506 mmol). The mixture was stirred at 20° C. for 30 min, concentrated under reduced pressure. The residue was purified by column chromatography (Pet. ether/EtOAc 5:1 to 4:1 as eluent) to give tert-butyl (2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)carbamate (500 mg, 1.112 mmol) as a solid.

Step 5. Tert-butyl N-(2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate

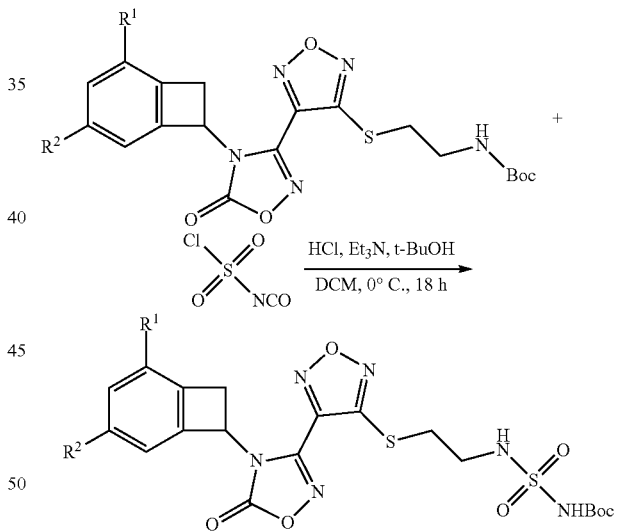

To a solution of tert-butyl (2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)carbamate (300 mg, 0.67 mmol) in dioxane (3 ml) was added hydrogen chloride (1.7 ml, 6.67 mmol, 4 M in dioxane). The reaction mixture was stirred for 30 min, and concentrated in vacuo. The residue was dissolved in DCM (10 mL). TEA (0.3 ml, 2.20 mmol) was added at 0° C., and the solution was stirred at 0° C. for 10 min.

To a mixture of t-BuOH (59.4 mg, 0.801 mmol) and CH₂Cl₂ (10 mL) was added sulfurisocyanatidic chloride (109 mg, 0.768 mmol) slowly at 0° C. After stirred at 0° C. for 1 h, this solution was added to the above solution slowly at 0° C. The reaction mixture was allowed to warm to RT and stirred for 16 h, quenched by the addition of water, and extracted with EtOAc (30 mL×3). The combined organic layers were washed with brine (100 mL) and dried over Na$_2$SO$_4$, filtered, and concentrated under reduced pressure. The residue was purified by column chromatography (pet. ether/EtOAc=10:1 to 3:1) to give tert-butyl N-(2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate (200 mg, 0.38 mmol) as a solid.

Step 6. Tert-butyl N-(2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate

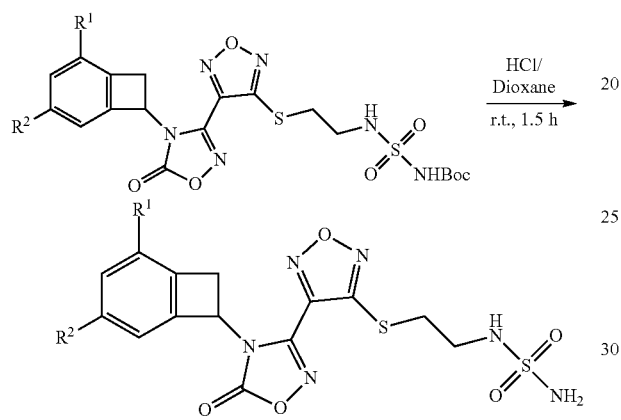

A solution of tert-butyl N-(2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate (290 mg, 0.55 mmol) in HCl-Dioxane (4M, 2 ml) was stirred at RT for 2 h, then concentrated under reduced pressure. The residue was used directly in the next step without further purification.

Step 7. N-(4/2-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide

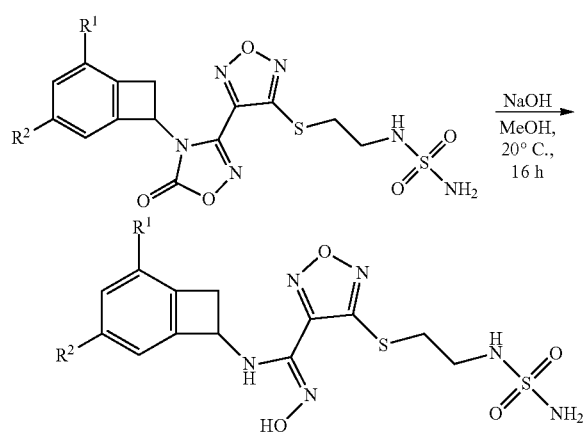

To a solution of tert-butyl N-(2-((4-(4-(4/2-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate (300 mg, 0.70 mmol) in MeOH (10 ml) was added sodium hydroxide (2.0 M aq. Solution, 3.15 ml, 6.30 mmol). The mixture was stirred at RT for 16 h. The pH value was adjusted to 7 using 1 M HCl. The solvent was removed in vacuo. The residue was purified by reverse phase HPLC on a GILSON 281 instrument fitted with a Phenomenex Synergi C18 (150×30 mm×5 m) using water (0.1% TFA)-ACN (Mobile phase A water (0.1% TFA), Mobile phase B acetonitrile, Detective wavelength: 220 nm) to give N-(4/2-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide (85 mg, 0.211 mmol) as an oil.

Step 8. (S)- and (R)—N-(4-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide

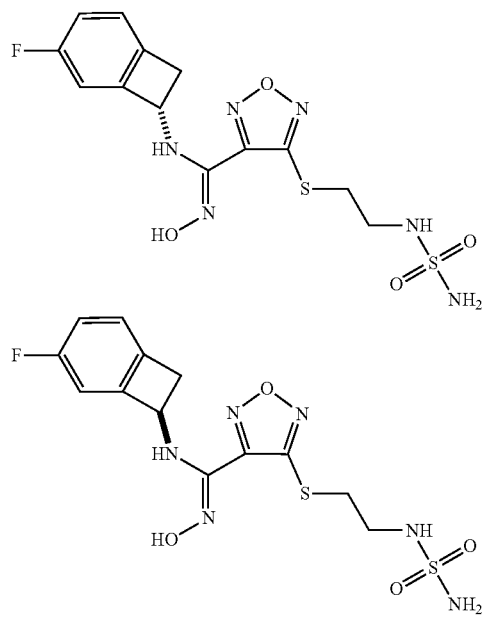

The above racemic mixture was submitted to SFC chiral separation. (Chiralpak AD-3 100×4.6 mm I.D., 3 um; Mobile phase: A: CO$_2$ B: ethanol (0.05% DEA); Gradient: from 5% to 40% of B in 4.5 min and hold 40% for 2.5 min, then 5% of B for 1 min; Flow rate: 2.8 mL/min; Column temperature: 40° C.). The two chiral isomers of Examples 40 and 41 were obtained (~20 mg each, 0.082 mmol) as a solid.

Example 40 (peak 1): $^1$H NMR (400 MHz, CD$_3$OD) δ 7.11 (dd, J=8.0, 4.7 Hz, 1H), 6.96-7.03 (m, 1H), 6.92 (br d, J=7.6 Hz, 1H), 5.38 (br d, J=2.5 Hz, 1H), 3.56 (dd, J=14.2, 4.8 Hz, 1H), 3.41-3.47 (m, 2H), 3.34-3.39 (m, 1H), 3.34-3.39 (m, 1H), 3.04 (br d, J=13.7 Hz, 1H) ESI MS: 403.0 [M+H]$^+$ Example 41 (peak 2): $^1$H NMR (400 MHz, CD$_3$OD) δ 7.11 (dd, J=8.0, 4.7 Hz, 1H), 6.96-7.03 (m, 1H), 6.92 (br d, J=7.6 Hz, 1H), 5.38 (br d, J=2.5 Hz, 1H), 3.56 (dd, J=14.2, 4.8 Hz, 1H), 3.41-3.47 (m, 2H), 3.34-3.39 (m, 1H), 3.34-3.39 (m, 1H), 3.04 (br d, J=13.7 Hz, 1H) ESI MS: 403.0 [M+H]$^+$ An alternative route for the synthesis of Example 40 is depicted below:

Step 1: (S)-tert-butyl N-(2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate

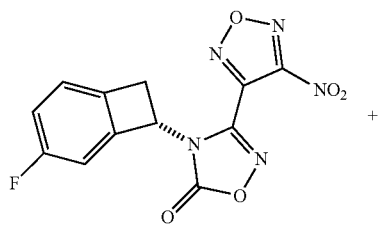

To a stirred solution of (S)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one (5.5 g, 17.23 mmol) in CH₃CN (100 mL) were added TEA (7.20 mL, 51.7 mmol) and tert-butyl N-(2-mercaptoethyl)sulfamoylcarbamate (5.3 g, 20.68 mmol) at 15° C. The reaction mixture was stirred at 15° C. for 30 min, then concentrated under reduced pressure. The residue was purified by column chromatography on silica gel (SiO₂, eluting with petroleum ether/ethyl acetate 10:1-5:1-1:1) to give the title compound as a solid. ¹H NMR (400 MHz, CDCl₃) δ 7.1-7.2 (m, 1H), 7.0-7.1 (m, 1H), 6.9 (br d, J=6.58 Hz, 1H), 6.1 (br s, 1H), 3.7-3.8 (m, 2H), 3.5-3.6 (m, 2H), 3.5-3.5 (m, 2H), 1.5 (s, 9H). ESI MS m/z: 551.0 [M+Na⁺].

Step 2: (S)—N-(2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylamine

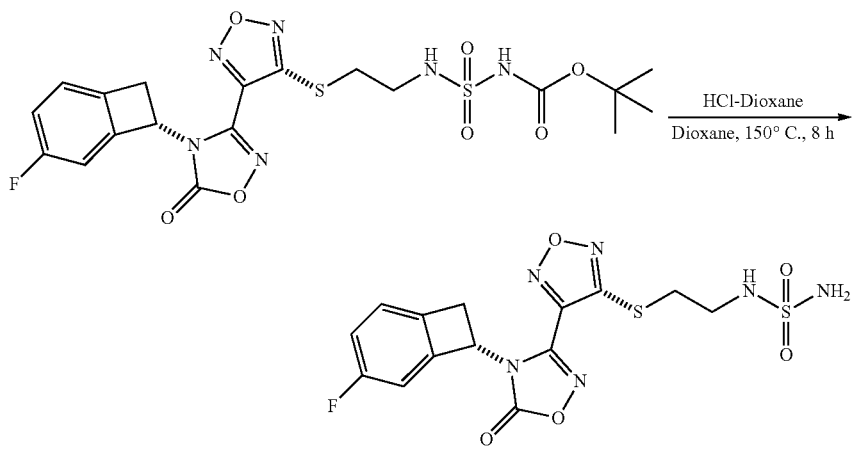

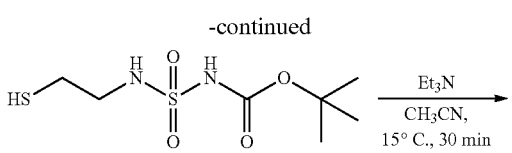

To a stirred solution of (S)-tert-butyl N-(2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylcarbamate (12.5 g, 23.65 mmol) in 1,4-dioxane (150 mL) was added hydrogen chloride (150 mL, 600 mmol, 4.0 M in dioxane) at 0° C. The reaction mixture was stirred at 15° C. for 8 h, then concentrated in vacuo to give the crude title compound (10.99 g, 23.65 mmol) as a solid.

Step 3: (S)—N-(4-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide

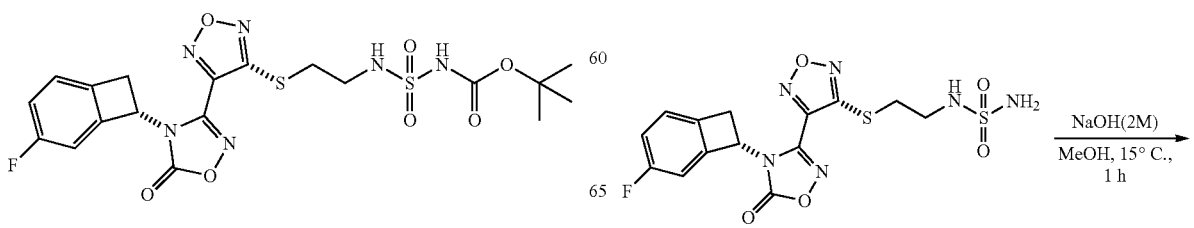

81

-continued

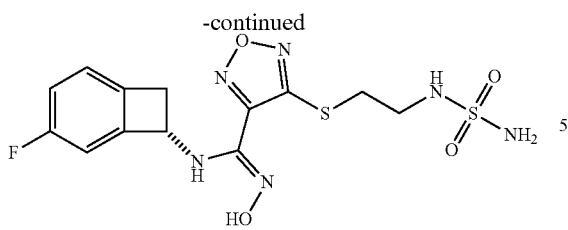

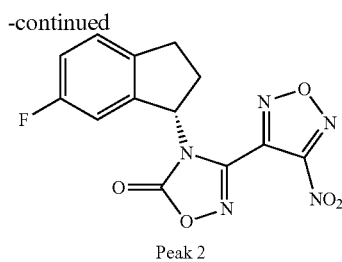

Peak 2

To a stirred solution of (S)—N-(2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)ethyl)sulfamoylamine (8.99 g, 19.34 mmol) in CH$_3$OH (300 mL) was added sodium hydroxide (116 mL, 232 mmol, 2.0 M aqueous solution) at 15° C. The reaction mixture was stirred at 15° C. for 1 h, quenched with 2.0 M HCl aqueous solution until pH~6, partially concentrated in vacuo, then extracted by EtOAc (100 mL*2). The organic layers were washed with brine (50 mL), dried over Na$_2$SO$_4$, filtered, and concentrated in vacuo. The residue was purified by HPLC on a GILSON 281 instrument fitted with a Phenomenex Synergi Max-RP 150*50 mm*10 um using water (0.1% TFA)-CH$_3$CN to give the title compound as a solid. $^1$H NMR (400 MHz, CD$_3$OD) δ 7.11 (dd, J=7.9, 4.6 Hz, 1H), 6.99-7.02 (m, 1H), 6.91-6.93 (m, 1H), 5.39-5.40 (m, 1H), 3.6 (br dd, J=14.1, 3.5 Hz, 1H) 3.4-3.5 (m, 2H), 3.4 (m, 2H), 3.0 (br d, J=14.1 Hz, 1H). ESI MS m/z: 402.9 [M+H$^+$]

Example 42. (S)—N-(6-fluoro-2,3-dihydro-1H-inden-1-yl)-N'-hydroxy-4-((2-ureidoethyl)thio)-1,2,5-oxadiazole-3-carboximidamide

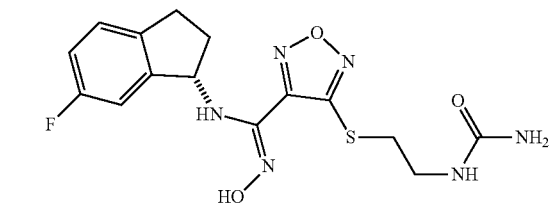 [SMILES: NC(=O)NCCSc1nonc1/C(=N/O)N[C@H]1CCc2ccc(F)cc21]

Step 1: (R)- and (S)-4-(6-fluoro-2,3-dihydro-1H-inden-1-yl)-3-(4-nitro-1,2,5-oxadiazol-3-yl)-1,2,4-oxadiazol-5(4H)-one

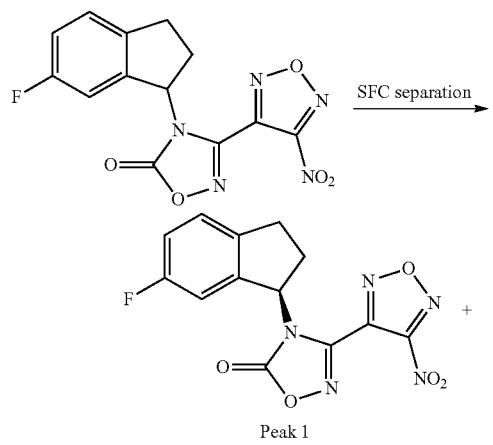

Racemic 4-(6-fluoro-2,3-dihydro-1H-inden-1-yl)-3-(4-nitro-1,2,5-oxadiazol-3-yl)-1,2,4-oxadiazol-5(4H)-one (110.0 g) was resolved by SFC separation to give (R)-4-(6-fluoro-2,3-dihydro-1H-inden-1-yl)-3-(4-nitro-1,2,5-oxadiazol-3-yl)-1,2,4-oxadiazol-5(4H)-one (48.4 g) (Peak 1) as a solid and (S)-4-(6-fluoro-2,3-dihydro-1H-inden-1-yl)-3-(4-nitro-1,2,5-oxadiazol-3-yl)-1,2,4-oxadiazol-5(4H)-one (50.7 g) (Peak 2) as a solid.

The SFC conditions: Column OJ (250 mm*50 mm, 10 um); Mobile phase: A: CO$_2$ B: ethanol; Gradient: 15% B; Flow rate: 200 ml/min.

Peak 1: $^1$H NMR (400 MHz, CDCl$_3$) δ 7.1 (dd, J=8.4, 5.0 Hz, 1H), 7.0 (td, J=8.6, 2.4 Hz, 1H), 6.8-6.9 (m, 1H), 5.7 (dd, J=8.9, 5.2 Hz, 1H), 2.9-3.1 (m, 2H), 2.7-2.8 (m, 1H), 2.4 (ddt, J=14.3, 8.9, 5.4, 5.4 Hz, 1H).

Peak 2: $^1$H NMR (400 MHz, CDCl$_3$) δ 7.1 (dd, J=8.4, 5.0 Hz, 1H), 7.0 (td, J=8.5, 2.3 Hz, 1H), 6.8 (dd, J=8.0, 2.2 Hz, 1H), 5.7 (dd, J=8.9, 5.2 Hz, 1H), 2.9-3.0 (m, 2H), 2.7-2.9 (m, 1H), 2.4 (ddt, J=14.3, 8.9, 5.5, 5.5 Hz, 1H).

Step 2: (S)-tert-Butyl (2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)carbamate

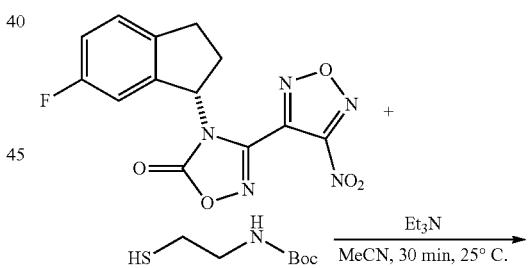

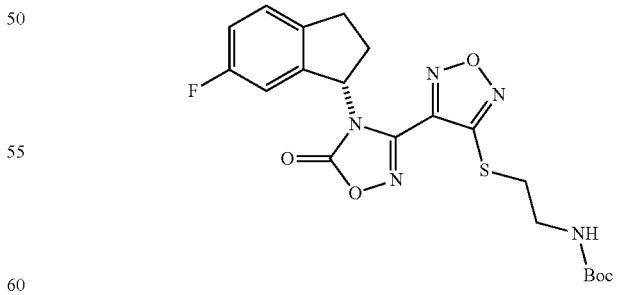

To a solution of chirally (S)-4-(6-fluoro-2,3-dihydro-1H-inden-1-yl)-3-(4-nitro-1,2,5-oxadiazol-3-yl)-1,2,4-oxadiazol-5(4H)-one (Peak 2, Step 1) (160 mg, 480.5 umol) in MeCN (10 mL) were added tert-butyl (2-mercaptoethyl)carbamate (94 mg, 528.16 umol) and Et$_3$N (0.2 mL, 1.437 mol). The mixture was stirred at 25° C. for 30 minutes, concentrated under reduced pressure. The residue was purified by column chromatography (Petroleum ether:ethyl acetate=5:1-3:1 as eluent) to give the title compound (210 mg) as a solid.

Step 3. (S)-3-(4-((2-aminoethyl)thio)-1,2,5-oxadiazol-3-yl)-4-(6-fluoro-2,3-dihydro-1H-inden-1-yl)-1,2,4-oxadiazol-5(4H)-one

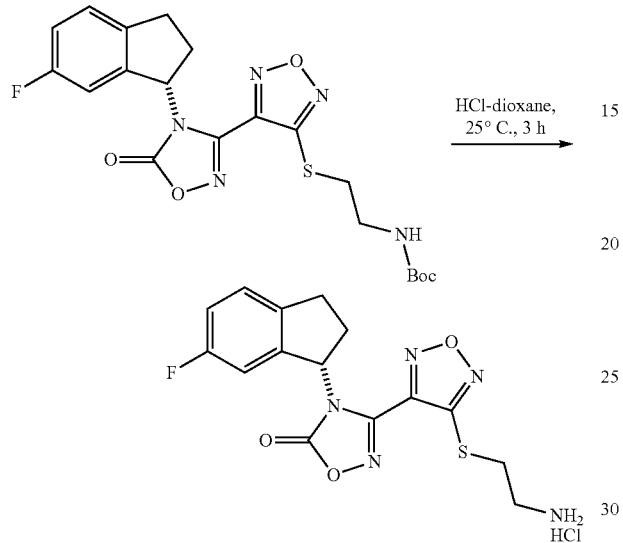

A mixture of (S)-tert-butyl (2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)carbamate (200 mg) in 4M HCl-dioxane (5 mL) was stirred at 25° C. for 3 h. The solvent was removed under reduced pressure to give the title compound (172 mg) as an oil, which was used in the next step without further purification.

Step 4. (S)-1-(2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)urea

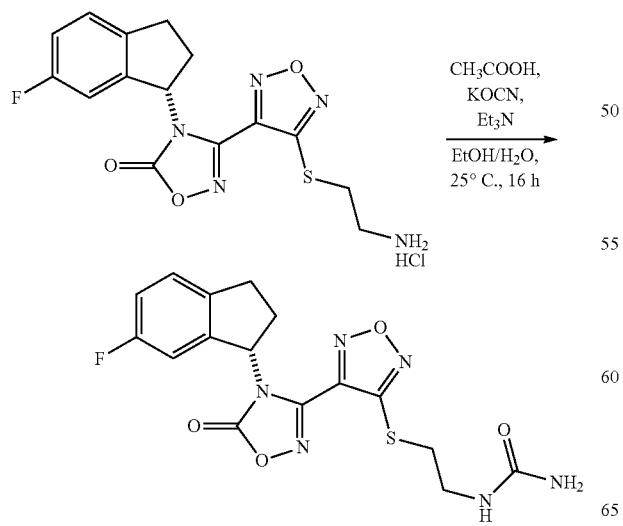

To a solution of (S)-3-(4-((2-aminoethyl)thio)-1,2,5-oxadiazol-3-yl)-4-(6-fluoro-2,3-dihydro-1H-inden-1-yl)-1,2,4-oxadiazol-5(4H)-one hydrochloride (172 mg, 430.19 umol) in EtOH (1.2 mL) and water (1.2 mL) were added Et3N (44 mg, 430.19 umol), potassium cyanate (47 mg, 580.75 umol), and CH3COOH (33 mg, 550.64 umol). The reaction mixture was stirred at 25° C. for 16 h, concentrated under reduced pressure. The residue was purified by column chromatography (MeOH:DCM=1:20~1:10 as eluent) to give the title compound (165 mg, 406.3 umol) as an oil.

Step 5. (S)—N-(6-fluoro-2,3-dihydro-1H-inden-1-yl)-N'-hydroxy-4-((2-ureidoethyl)thio)-1,2,5-oxadiazole-3-carboximidamide

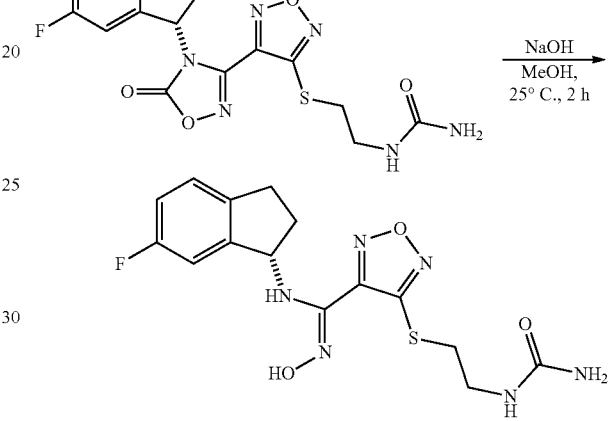

To a solution of (S)-1-(2-((4-(4-(6-fluoro-2,3-dihydro-1H-inden-1-yl)-5-oxo-4,5-dihydro-1,2,4-oxadiazol-3-yl)-1,2,5-oxadiazol-3-yl)thio)ethyl)urea (165 mg) in MeOH (4 mL) was added 2M NaOH aqueous solution (1.02 mL). The mixture was stirred at 25° C. for 2 h. The pH value was adjusted to ~7 by adding 3 N HCl aqueous solution. The solvent was removed under reduced pressure. The residue was purified by reserved HPLC on a GILSON 281 instrument fitted with a phenomenex Synergi C18 (250×21.2 mm×4 um) using water (0.2% formic acid) and acetonitrile as eluents to afford the title compound (87 mg) as a solid.

1H NMR (400 MHz, CD$_3$OD) δ 7.20 (dd, J=8.1, 5.0 Hz, 1H), 6.90-7.00 (m, 2H), 5.33 (t, J=7.7 Hz, 1H), 3.51 (t, J=6.6 Hz, 2H), 3.26-3.30 (m, 2H), 2.94 (br dd, J=15.2, 6.4 Hz, 1H), 2.77 (dt, J=16.0, 8.2 Hz, 1H), 2.51-2.60 (m, 1H), 1.94 (dq, J=12.6, 8.7 Hz, 1H) MS (ESI) m/z: 380.1 [M+H]$^+$

Example 43. 2-((4-(N-(6-fluoro-2,3-dihydro-1H-inden-1-yl)-N'-hydroxycarbamimidoyl)-1,2,5-oxadiazol-3-yl)thio)-N-(2-hydroxyethyl)acetamide

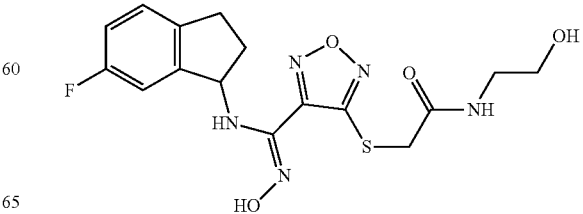

85

Step 1. N-(2-hydroxyethyl)-2-mercaptoacetamide

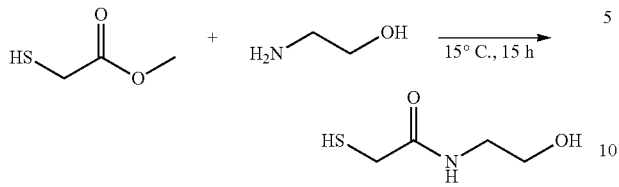

A mixture of methyl 2-mercaptoacetate (13.3 mL, 149 mmol) and 2-aminoethanol (19.99 g, 327 mmol) was stirred at 15° C. for 15 h. The mixture was washed with $CCl_4$ (100 mL). The organic layer was concentrated under reduced pressure to give crude N-(2-hydroxyethyl)-2-mercaptoacetamide (28 g, 62.1 mmol) as an oil.

Step 2. 2-((4-Cyano-1,2,5-oxadiazol-3-yl)thio)-N-(2-hydroxyethyl)acetamide

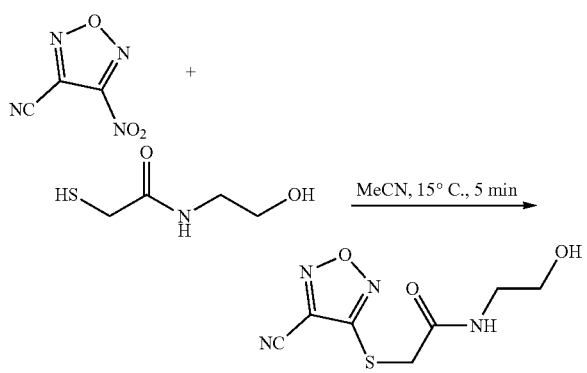

A mixture of 4-nitro-1,2,5-oxadiazole-3-carbonitrile (100 mg, 0.714 mmol) and N-(2-hydroxyethyl)-2-mercaptoacetamide (97 mg, 0.714 mmol) in MeCN (3 mL) was stirred at 15° C. for 5 min, then concentrated under reduced pressure. The residue was purified by Prep-TLC ($SiO_2$, MeOH/$CH_2Cl_2$ 1:10 as eluent) to give 2-((4-cyano-1,2,5-oxadiazol-3-yl)thio)-N-(2-hydroxyethyl)acetamide (80 mg, 0.280 mmol) as a solid.

Step 3. 2-((4-(N'-hydroxycarbamimidoyl)-1,2,5-oxadiazol-3-yl)thio)-N-(2-hydroxyethyl)acetamide

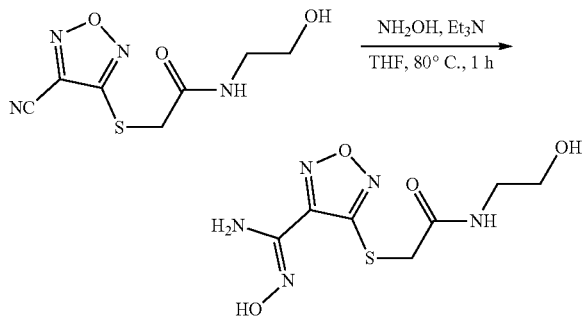

86

To a solution of 2-((4-cyano-1,2,5-oxadiazol-3-yl)thio)-N-(2-hydroxyethyl)acetamide (80 mg, 0.351 mmol) in THF (10 mL) were added triethylamine (0.4 mL, 2.87 mmol) and hydroxylamine (0.1 mL, 1.632 mmol) (in water, 50%). The mixture was stirred at 80° C. for 1 h, cooled to RT, then concentrated under reduced pressure. The residue was purified by column chromatography ($SiO_2$, MeOH/$CH_2Cl_2$ 1:10 as eluent) to give 2-((4-(N-hydroxycarbamimidoyl)-1,2,5-oxadiazol-3-yl)thio)-N-(2-hydroxyethyl)acetamide (81 mg, 0.264 mmol) as a solid.

Step 4. N-hydroxy-4-((2-((2-hydroxyethyl)amino)-2-oxoethyl)thio)-1,2,5-oxadiazole-3-carbimidoyl chloride

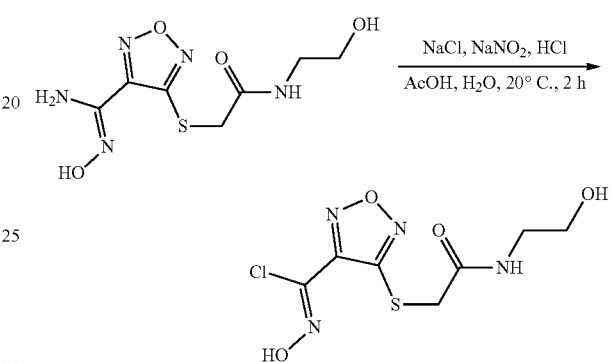

To a solution of 2-((4-(N-hydroxycarbamimidoyl)-1,2,5-oxadiazol-3-yl)thio)-N-(2-hydroxyethyl)acetamide (81 mg, 0.310 mmol) in water (2 mL), AcOH (1 mL) and 6 M HCl (0.2 mL, 1.200 mmol) at 20° C. was added sodium chloride (54.4 mg, 0.930 mmol). The reaction mixture was cooled in an ice/water/methanol bath before a solution of sodium nitrite (33 mg, 0.478 mmol) in water (0.3 mL) was added over 10 min while maintaining the temperature below 0° C. After stirring for 1.5 h, the reaction mixture was allowed to warm to RT and stirred for another 2 h. The precipitate was collected by filtration, washed with water (10 mL), taken in ethyl acetate (30 mL×2), treated with anhydrous sodium sulfate. This suspension was filtered through sodium sulfate and the filtrate was concentrated to give N-hydroxy-4-((2-((2-hydroxyethyl)amino)-2-oxoethyl)thio)-1,2,5-oxadiazole-3-carbimidoyl chloride (80 mg, 0.285 mmol) as a solid.

Step 5. 2-((4-(N-(6-fluoro-2,3-dihydro-1H-inden-1-yl)-N'-hydroxycarbamimidoyl)-1,2,5-oxadiazol-3-yl)thio)-N-(2-hydroxyethyl)acetamide

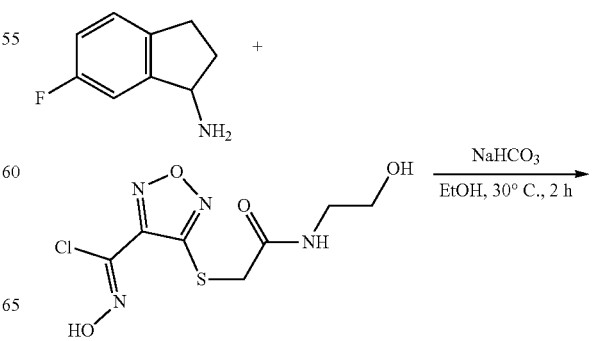

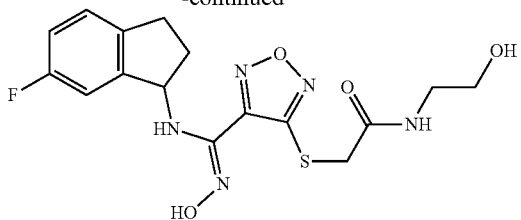

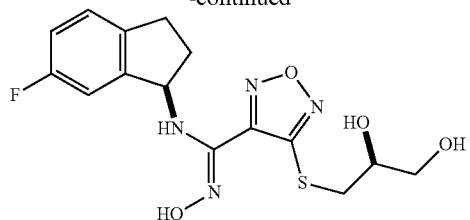

To a solution of N-hydroxy-4-((2-((2-hydroxyethyl) amino)-2-oxoethyl)thio)-1,2,5-oxadiazole-3-carbimidoyl chloride (80 mg, 0.285 mmol) and 6-fluoro-2,3-dihydro-1H-inden-1-amine (45 mg, 0.298 mmol) in EtOH (2 mL) was added sodium bicarbonate (48 mg, 0.571 mmol). The reaction mixture was stirred at 30° C. for 2 h, concentrated under reduced pressure. The residue was purified by prep-HPLC (Column Agela ASB 150×25 mm×5 um, Condition water (0.225% FA)-ACN Begin B 32, End B 62 Gradient Time (min) 10, 100% B Hold Time (min) 2, Flow Rate (mL/min) 25, Injections 3) and acetonitrile as eluents (Mobile phase A water (0.2% Formic acid), Mobile phase B acetonitrile, Detective wavelength: 220 nm.) followed by lyophilization to give 2-((4-(N-(6-fluoro-2,3-dihydro-1H-inden-1-yl)-N'-hydroxycarbamimidoyl)-1,2,5-oxadiazol-3-yl)thio)-N-(2-hydroxyethyl)acetamide (30 mg, 0.076 mmol) as a solid. m/z=: 496.1 [M+H]$^+$ $^1$H NMR (400 MHz, CD3OD) δ 7.17-7.22 (m, 1H), 6.92-6.99 (m, 2H), 5.48 (t, J=8.0 Hz, 1H), 3.95 (s, 2H), 3.60 (t, J=6.0 Hz, 2H), 3.34 (t, J=6.0 Hz, 2H), 2.87-3.00 (m, 1H), 2.70-2.84 (m, 1H), 2.50-2.63 (m, 1H), 1.87-2.01 (m, 1H).

Examples 44, 45, 46, 47: (S,S)-, (S,R), (R,S)-, and (R,R)-4-((2,3-dihydroxypropyl)thio)-N-(6-fluoro-2,3-dihydro-1H-inden-1-yl)-N'-hydroxy-1,2,5-oxadiazole-3-carboximidamide

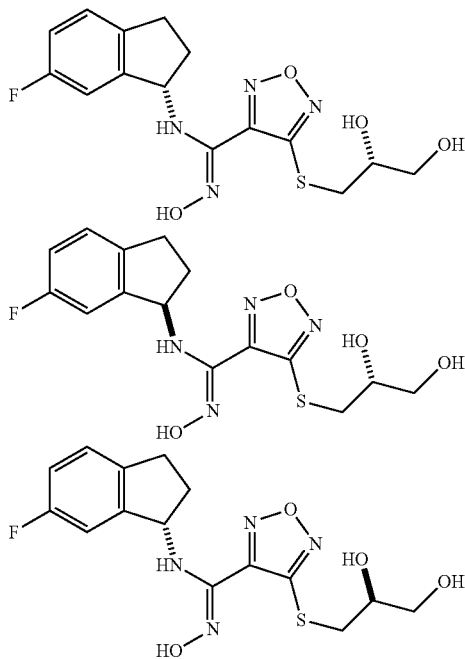

Step 1. 3-(4-((2,3-Dihydroxypropyl)thio)-1,2,5-oxadiazol-3-yl)-4-(6-fluoro-2,3-dihydro-1H-inden-1-yl)-1,24-oxadiazol-5(4H)-one

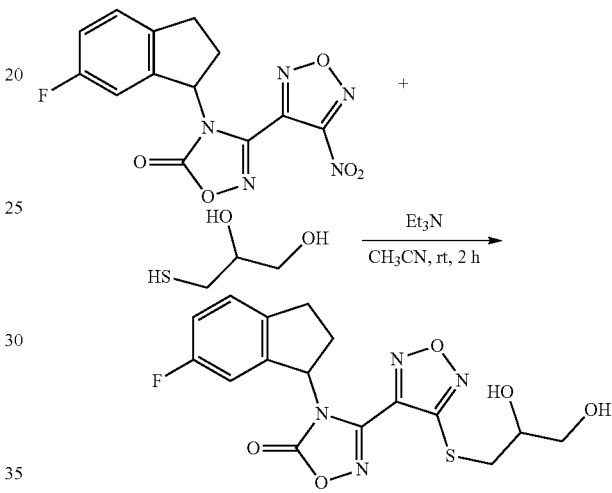

To a solution of 4-(6-fluoro-2,3-dihydro-1H-inden-1-yl)-3-(4-nitro-1,2,5-oxadiazol-3-yl)-1,2,4-oxadiazol-5(4H)-one (200 mg, 0.600 mmol) in CH$_3$CN (15 ml) were added triethylamine (164 mg, 1.618 mmol)) and 3-mercaptopropane-1,2-diol (70 mg, 0.647 mmol). The mixture was stirred at 20° C. for 2 h before the solvent was removed in vacuo to give the crude title compound (255 mg, 0.647 mmol) as an oil, which was used in the next step without further purification.

Step 2. 4-((2,3-Dihydroxypropyl)thio)-N-(6-fluoro-2,3-dihydro-1H-inden-1-yl)-N'-hydroxy-1,2,5-oxadiazole-3-carboximidamide

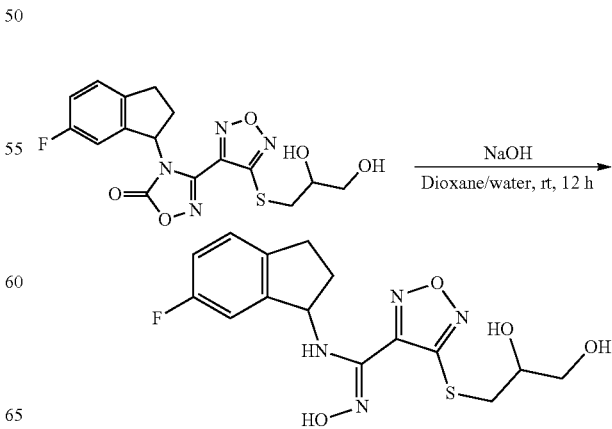

To a solution of 3-(4-((2,3-dihydroxypropyl)thio)-1,2,5-oxadiazol-3-yl)-4-(6-fluoro-2,3-dihydro-1H-inden-1-yl)-1,2,4-oxadiazol-5(4H)-one (250 mg, 0.634 mmol) in dioxane (15 mL) and water (1 ml) was added sodium hydroxide (64 mg, 1.600 mmol). The mixture was stirred at 20° C. for 12 h. The reaction mixture was acidified to a pH value of 6 with 2 M HCl, then concentrated in vacuo to give a residue which was purified by reverse phase HPLC on a GILSON 281 instrument fitted with a Phenomenex Synergi C18 (250× 21.2 mm×4 m) using water (0.2% Formic acid) and acetonitrile as eluents (Mobile phase A water (0.2% Formic acid), Mobile phase B acetonitrile, Detective wavelength: 220 nm) to give the title compound (150 mg, 0.407 mmol) as a solid.

Step 3. (S,S)-, (S,R), (R,S)-, and (R,R)-4-((2,3-dihydroxypropyl)thio)-N-(6-fluoro-2,3-dihydro-1H-inden-1-yl)-N'-hydroxy-1,2,5-oxadiazole-3-carboximidamide

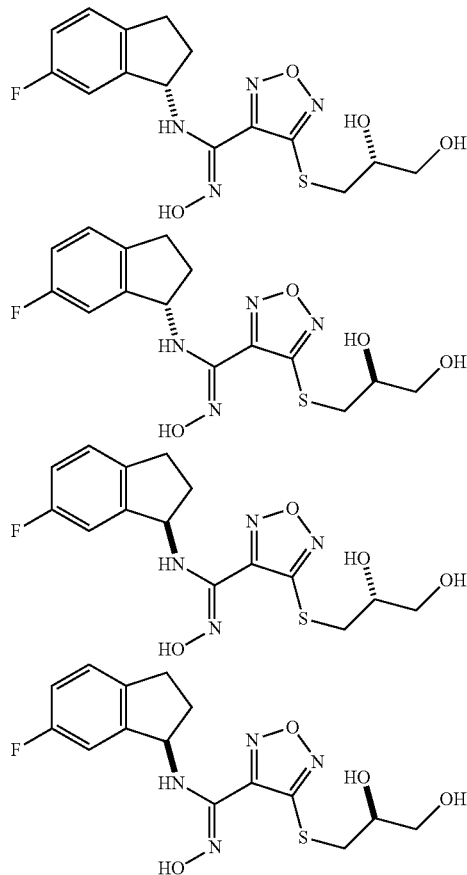

The above mixture (150 mg) was submitted for SFC chiral separation (Column: Chiralcel OD-3 100×4.6 mm I.D., 3 um; Mobile phase: A: CO₂ B: ethanol (0.05% DEA); Gradient: from 5% to 40% of B in 4.5 min and hold 40% for 2.5 min, then 5% of B for 1 min; Flow rate: 2.8 mL/min; Column temperature: 40° C.). Each of 4 isomers was obtained (20 mg) as a solid.

Example 44 (peak 1): $^1$H NMR (400 MHz, CD₃OD) δ 7.17-7.23 (m, 1H), 6.89-7.01 (m, 2H), 5.28-5.38 (m, 1H), 3.91-4.03 (m, 1H), 3.59-3.65 (m, 2H), 3.40-3.49 (m, 1H), 3.15-3.25 (m, 1H), 2.89-3.01 (m, 1H), 2.71-2.82 (m, 1H), 2.50-2.63 (m, 1H), 1.88-2.01 (m, 1H)

Example 45 (peak 2): $^1$H NMR (400 MHz, MeOD) δ 7.15-7.24 (m, 1H) 6.89-7.02 (m, 2H) 5.27-5.37 (m, 1H) 3.92-4.01 (m, 1H) 3.59-3.65 (m, 2H) 3.39-3.50 (m, 1H) 3.15-3.26 (m, 1H) 2.89-3.00 (m, 1H) 2.70-2.82 (m, 1H) 2.50-2.63 (m, 1H) 1.90-2.01 (m, 1H)

Example 46 (peak 3): $^1$H NMR (400 MHz, MeOD) δ ppm 7.15-7.23 (m, 1H) 6.89-7.02 (m, 2H) 5.27-5.36 (m, 1H) 3.92-4.00 (m, 1H) 3.59-3.64 (m, 2H) 3.40-3.48 (m, 1H) 3.14-3.26 (m, 1H) 2.89-3.00 (m, 1H) 2.70-2.83 (m, 1H) 2.51-2.59 (m, 1H) 1.91-2.02 (m, 1H)

Example 47 (peak 4): $^1$H NMR (400 MHz, MeOD) δ ppm 7.16-7.23 (m, 1H) 6.87-7.04 (m, 2H) 5.28-5.37 (m, 1H) 3.92-4.00 (m, 1H) 3.60-3.64 (m, 2H) 3.41-3.48 (m, 1H) 3.15-3.25 (m, 1H) 2.89-3.01 (m, 1H) 2.71-2.82 (m, 1H) 2.51-2.61 (m, 1H) 1.88-2.02 (m, 1H)

Examples 48 and 49. (S)— and (R)—N-ethyl-2-((4-(N-(4-fluorobicyclo[4.2.0]octa-1(6),2,4-trien-7-yl)-N'-hydroxycarbamimidoyl)-1,2,5-oxadiazol-3-yl)amino)acetamide

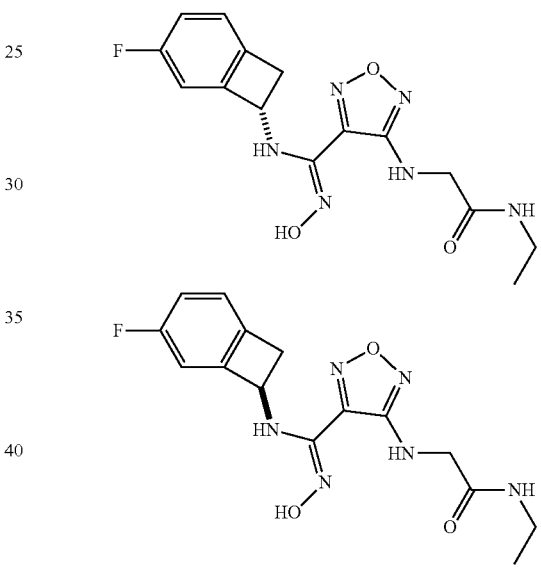

Step 1. 2-((4-Cyano-1,2,5-oxadiazol-3-yl)amino)-N-ethylacetamide

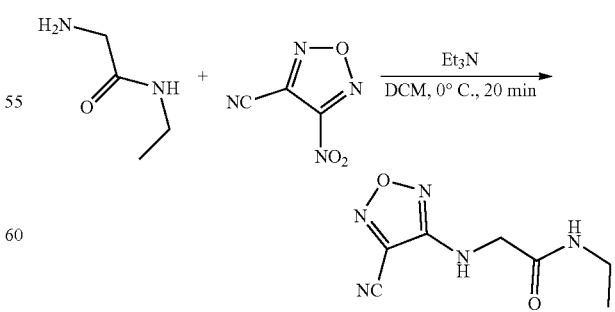

To a solution of 4-nitro-1,2,5-oxadiazole-3-carbonitrile (100 mg, 0.71 mmol) in CH₂Cl₂ (15 ml) was added triethylamine (0.2 ml, 1.44 mmol). Then a mixture of 2-amino- N-ethylacetamide hydrochloride (50 mg, 0.361 mmol) and triethylamine (0.1 ml, 0.72 mmol) in $CH_2Cl_2$ (5 ml) was added at 0° C. The reaction was stirred at 0° C. for 20 min, then concentrated under reduced pressure. The residue was purified by preparative TLC (MeOH/$CH_2Cl_2$ 1:10 as eluent) to give 2-((4-cyano-1,2,5-oxadiazol-3-yl)amino)-N-ethylacetamide (90 mg, 0.46 mmol) as an oil.

Step 2. N-ethyl-2-((4-(N-hydroxycarbamimidoyl)-1,2,5-oxadiazol-3-yl)amino)acetamide

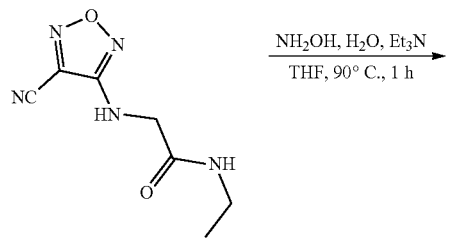

To a solution of 2-((4-cyano-1,2,5-oxadiazol-3-yl)amino)-N-ethylacetamide (190 mg, 0.97 mmol) in THF (10 ml) was added triethylamine (1.5 ml, 10.78 mmol) and hydroxylamine (0.3 ml, 4.90 mmol) (in water, 50%). The mixture was stirred at 90° C. for 1 h, cooled to RT, and concentrated under reduced pressure. The residue was purified by column chromatography (MeOH/$CH_2Cl_2$=1:10 as eluent) to give N-ethyl-2-((4-(N-hydroxycarbamimidoyl)-1,2,5-oxadiazol-3-yl)amino)acetamide (100 mg, 0.44 mmol) as a solid.

Step 3. 4-((2-(Ethylamino)-2-oxoethyl)amino)-N-hydroxy-1,2,5-oxadiazole-3-carbimidoyl chloride

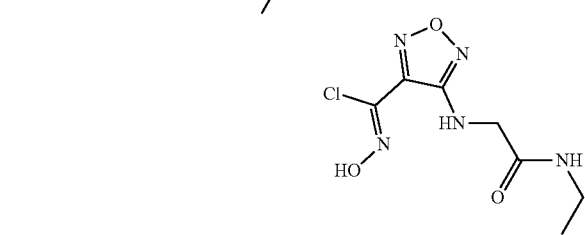

N-ethyl-2-((4-(N'-hydroxycarbamimidoyl)-1,2,5-oxadiazol-3-yl)amino)acetamide (100 mg, 0.44 mmol) was dissolved in a mixture of water (2 mL), AcOH (1 mL) and 6 M HCl (0.110 mL, 0.66 mmol). The reaction was cooled in an ice/water/methanol bath before a solution of sodium nitrite (38 mg, 0.55 mmol) in water (0.2 mL) was added over 10 min while maintaining the temperature below 0° C. After 1 h, the reaction mixture was allowed to warm to RT. The precipitate was collected by filtration, washed with water (10 mL), taken in ethyl acetate (30 mL×2), treated with anhydrous sodium sulfate. This suspension was filtered through sodium sulfate and the filtrate was concentrated to give 4-((2-(ethylamino)-2-oxoethyl)amino)-N-hydroxy-1,2,5-oxadiazole-3-carbimidoyl chloride (102 mg, 0.44 mmol) as a solid.

Step 4. N-ethyl-2-((4-(N-(4-fluorobicyclo[4.2.0]octa-1(6),2,4-trien-7-yl)-N'-hydroxycarbamimidoyl)-1,2,5-oxadiazol-3-yl)amino)acetamide

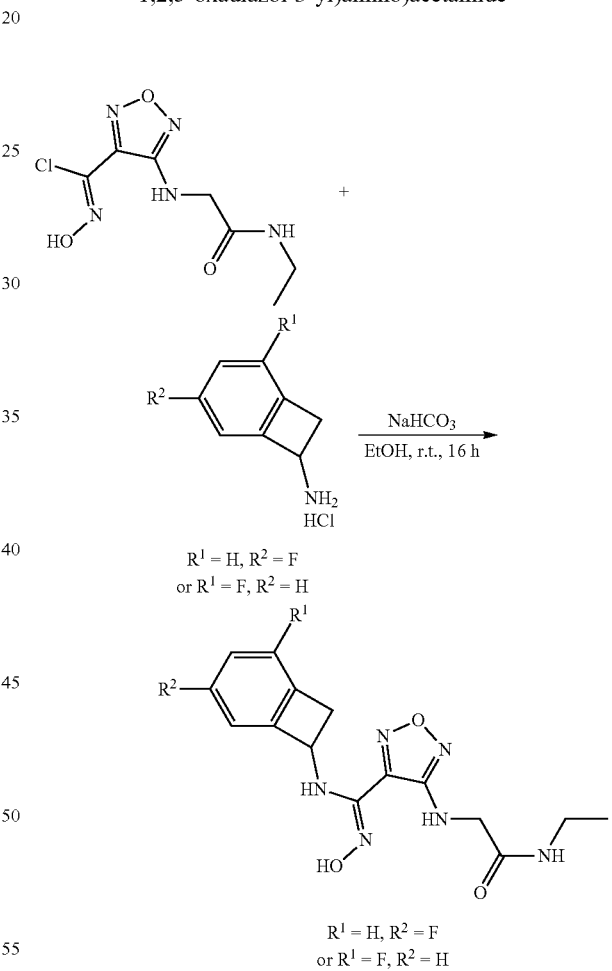

To a solution of 4/2-fluorobicyclo[4.2.0]octa-1(6),2,4-trien-7-amine (120 mg, 0.88 mmol, as a 3: mixture) in EtOH (10 ml) were added 4-((2-(ethylamino)-2-oxoethyl)amino)-N-hydroxy-1,2,5-oxadiazole-3-carbimidoyl chloride (217 mg, 0.88 mmol) and $NaHCO_3$ (184 mg, 2.19 mmol). The mixture was stirred at RT for 16 h, then concentrated under reduced pressure. The residue was purified by reverse phase HPLC on a GILSON 281 instrument fitted with a Phenomenex Synergi C18 150×30 mm×4 um using water (0.1% TFA) and acetonitrile as eluents (Mobile phase A water (0.2% Formic acid), Mobile phase B acetonitrile, Detective wavelength: 220 nm) to give N-ethyl-2-((4-(N-(4/2-fluorobicyclo[4.2.0]octa-1(6),2,4-trien-7-yl)-N'-hydroxycarbamimidoyl)-1,2,5-oxadiazol-3-yl)amino)acetamide (80 mg, 0.218 mmol) as a solid.

Step 5. (S)- and (R)—N-ethyl-2-((4-(N-(4-fluorobicyclo[4.2.0]octa-1(6),2,4-trien-7-yl)-N'-hydroxycarbamimidoyl)-1,2,5-oxadiazol-3-yl)amino)acetamide

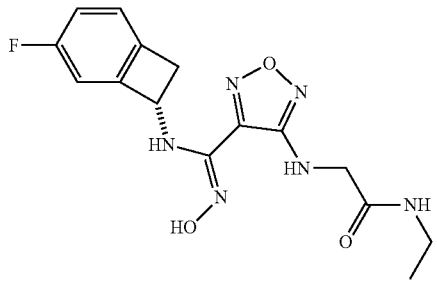

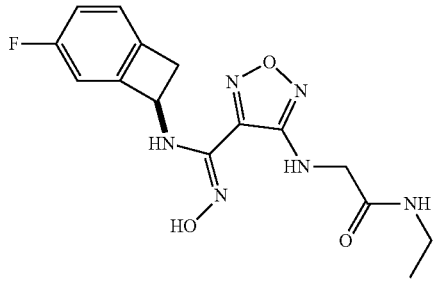

About 15 mg of each isomer was obtained as a solid from the SFC separation of 80 mg of the above racemic mixture.

Column: ChiralCel OD-H 150×4.6 mm I.D., 5 um Mobile phase: A: CO2 B: Methanol (0.05% DEA) Gradient: from 5% to 40% of B in 5.5 min and hold 40% for 3 min, then 5% of B for 1.5 min, Flow rate: 2.5 mL/min Column temperature: 40° C.

Example 48 (peak 1): LCMS: 349.1 [M+H]+; 1H NMR (400 MHz, CD3OD) δ ppm 7.13 (dd, J=7.8, 4.7 Hz, 1H), 6.96-7.04 (m, 1H), 6.88-6.94 (m, 1H), 5.64 (br d, J=2.4 Hz, 1H), 3.94 (s, 2H), 3.59 (br dd, J=14.1, 3.7 Hz, 1H), 3.25 (q, J=7.3 Hz, 2H), 3.03 (br d, J=13.9 Hz, 1H), 1.12 (t, J=7.2 Hz, 3H).

Example 49 (peak 2): LCMS: 349.1 [M+H]+; 1H NMR (400 MHz, CD3OD) δ ppm 7.13 (dd, J=7.8, 4.7 Hz, 1H), 6.96-7.04 (m, 1H), 6.88-6.94 (m, 1H), 5.64 (br d, J=2.4 Hz, 1H), 3.94 (s, 2H), 3.59 (br dd, J=14.1, 3.7 Hz, 1H), 3.25 (q, J=7.3 Hz, 2H), 3.03 (br d, J=13.9 Hz, 1H), 1.12 (t, J=7.2 Hz, 3H).

Examples 50 and 51. (S)- and (R)-2-((4-(N-(6-fluoro-2,3-dihydro-1H-inden-1-yl)-N'-hydroxy carbamimidoyl)-1,2,5-oxadiazol-3-yl)amino)-N-(2-hydroxyethyl)acetamide

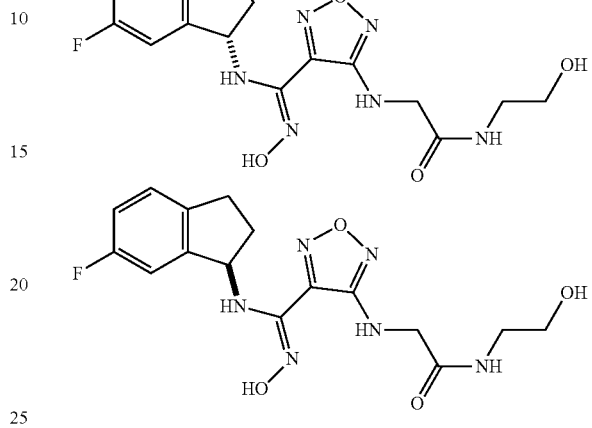

Step 1. 2-((4-(4-(6-Fluoro-2,3-dihydro-1H-inden-1-yl)-5-oxo-4,5-dihydro-1,2,4-oxadiazol-3-yl)-1,2,5-oxadiazol-3-yl)amino)-N-(2-hydroxyethyl)acetamide

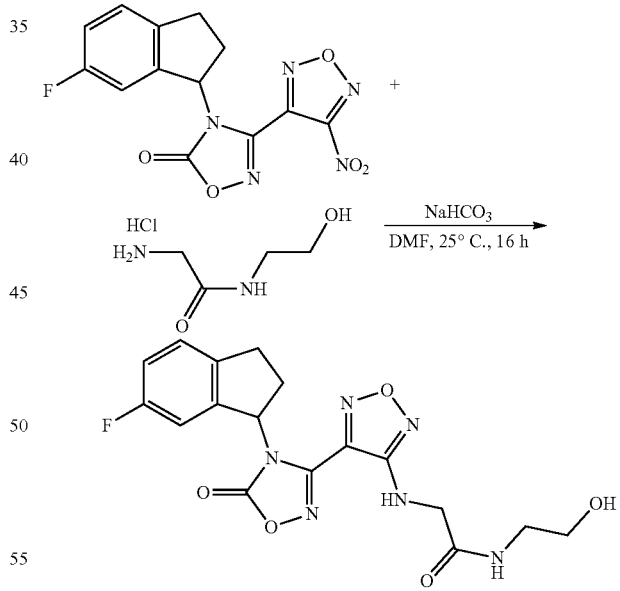

To a solution of 4-(6-fluoro-2,3-dihydro-1H-inden-1-yl)-3-(4-nitro-1,2,5-oxadiazol-3-yl)-1,2,4-oxadiazol-5(4H)-one (300 mg, 0.900 mmol) and 2-amino-N-(2-hydroxyethyl) acetamide hydrochloride (139 mg, 0.900 mmol) in DMF (5 mL) was added NaHCO3 (227 mg, 2.70 mmol). The mixture was stirred at 25° C. for 16 h before the solvent was removed in vacuo to get the crude title compound (364 mg) as an oil, which was used directly in the next step without further purification.

Step 2. 2-((4-(N-(6-fluoro-2,3-dihydro-1H-inden-1-yl)-N'-hydroxycarbamimidoyl)-1,2,5-oxadiazol-3-yl)amino)-N-(2-hydroxyethyl)acetamide

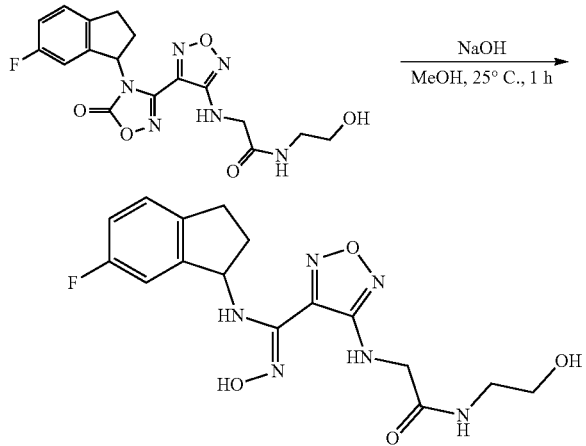

To a solution of 2-((4-(4-(6-fluoro-2,3-dihydro-1H-inden-1-yl)-5-oxo-4,5-dihydro-1,2,4-oxadiazol-3-yl)-1,2,5-oxadiazol-3-yl)amino)-N-(2-hydroxyethyl)acetamide (364 mg, 0.900 mmol) in MeOH (5 mL) and water (5 mL) was added NaOH (150 mg, 3.75 mmol) at 25° C. After stirring for 1 h, the solvent was removed in vacuo. The residue was purified by reverse phase HPLC on a GILSON 281 instrument fitted with a Waters Xbridge Prep OBD C18(150×30 mm×5 m) using water (0.225% formic acid) and acetonitrile as eluents (Mobile phase A water (0.225% formic acid), Mobile phase B acetonitrile, Detective wavelength: 220 nm) to afford the title compound (45 mg, 0.119 mmol) as a solid.

Step 3. (S)- and (R)-2-((4-(N-(6-fluoro-2,3-dihydro-1H-inden-1-yl)-N'-hydroxycarbamimidoyl)-1,2,5-oxadiazol-3-yl)amino)-N-(2-hydroxyethyl)acetamide

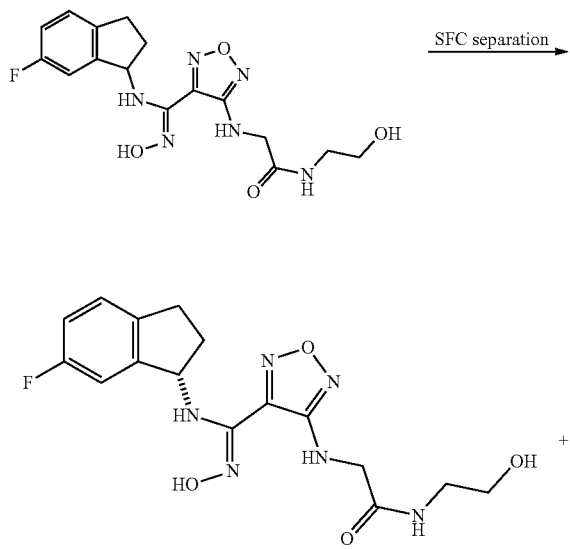

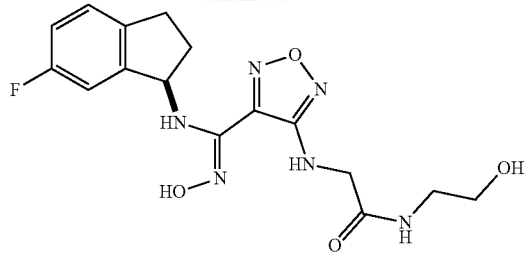

The above racemic mixture was submitted for SFC chiral separation, using the following conditions: Chiralpak AD-3 100×4.6 mm I.D., 3 um; mobile phase: A: $CO_2$ B: methanol (0.05% DEA); Gradient: from 5% to 40% of B in 4.5 min and hold 40% for 2.5 min, then 5% of B for 1 min; Flow rate: 2.8 mL/min; Column temperature: 40° C. Examples 50 and 51 (10 mg each) were obtained as a solid.

Example 50 (peak 1): $^1$H NMR (400 MHz, $CD_3OD$) δ 8.14 (br s, 1H), 7.18 (dd, J=8.2, 5.3 Hz, 1H), 6.86-6.99 (m, 2H), 5.67 (t, J=7.8 Hz, 1H), 3.96 (s, 2H), 3.58 (t, J=5.8 Hz, 2H), 3.33 (q, J=5.8 Hz, 2H), 2.86-2.99 (m, 1H), 2.68-2.82 (m, 1H), 2.57 (dtd, J=12.5, 7.6, 7.6, 2.9 Hz, 1H), 1.85-1.98 (m, 1H). m/z=379.0 [M+H]$^+$.

Example 51 (peak 2): $^1$H NMR (400 MHz, $CD_3OD$) δ 8.14 (br s, 1H), 7.18 (dd, J=8.2, 5.3 Hz, 1H), 6.86-6.99 (m, 2H), 5.67 (t, J=7.8 Hz, 1H), 3.96 (s, 2H), 3.58 (t, J=5.8 Hz, 2H), 3.33 (q, J=5.8 Hz, 2H), 2.86-2.99 (m, 1H), 2.68-2.82 (m, 1H), 2.57 (dtd, J=12.5, 7.6, 7.6, 2.9 Hz, 1H), 1.85-1.98 (m, 1H). m/z=379.0 [M+H]$^+$.

An alternative route for the synthesis of Example 50 is described below: Step 1: (S)-2-((4-(4-(6-fluoro-2,3-dihydro-1H-inden-1-yl)-5-oxo-4,5-dihydro-1,2,4-oxadiazol-3-yl)-1,2,5-oxadiazol-3-yl)amino)-N-(2-hydroxyethyl)acetamide

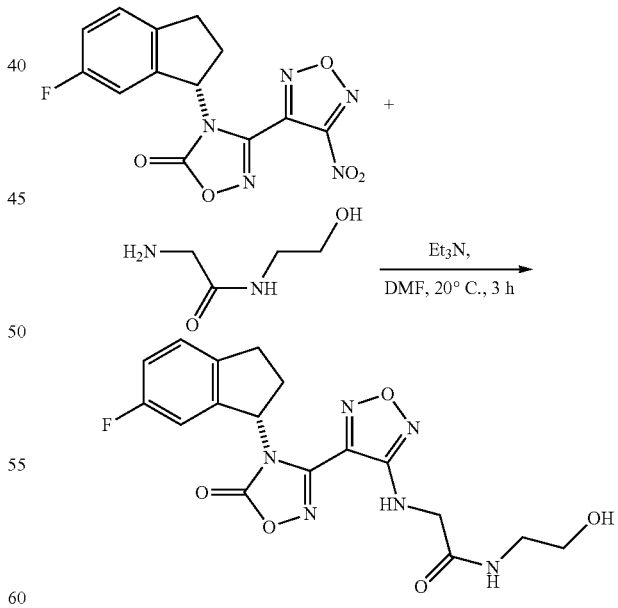

To a solution of (S)-4-(6-fluoro-2,3-dihydro-1H-inden-1-yl)-3-(4-nitro-1,2,5-oxadiazol-3-yl)-1,2,4-oxadiazol-5(4H)-one (500 mg, 1.50 mmol) in MeCN (5 mL) were added TEA (0.6 mL, 4.30 mmol) and 2-amino-N-(2-hydroxyethyl)acetamide (355 mg, 3.00 mmol) at RT. The mixture was stirred for 1 h, then concentrated in vacuo. The residue was purified by column chromatography (SiO$_2$, MeOH/CH$_2$Cl$_2$ 1:50 to 1:20 as eluent) to afford the title compound (410) as an oil. ESI MS m/z: 405.1 [M+H$^+$]

Step 2: (S)-2-((4-(N-(6-fluoro-2,3-dihydro-1H-inden-1-yl)-N'-hydroxycarbamimidoyl)-1,2,5-oxadiazol-3-yl)amino)-N-(2-hydroxyethyl)acetamide To a solution of (S)-2-((4-(4-(6-fluoro-2,3-dihydro-1H-inden-1-yl)-5-oxo-4,5-dihydro-1,2,4-oxadiazol-3-yl)-1,2,5-oxadiazol-3-yl)amino)-N-(2-hydroxyethyl)acetamide (410 mg, 1.014 mmol) in MeOH (5.00 mL) was added 2M aqueous sodium hydroxide (5 mL, 10.00 mmol) at RT. The mixture was stirred at RT for 1 h, then concentrated in vacuo. The residue was purified by reverse phase HPLC on a GILSON 281 instrument fitted with a Phenomenex Synergi C18 150*30 mm*4 um using water (0.225% FA) —CH$_3$CN to afford the title compound (220 mg) as a solid. $^1$H NMR (400 MHz, CD$_3$OD) δ 7.21 (dd, J=8.2, 5.1 Hz, 1H), 6.84-7.04 (m, 2H), 5.70 (t, J=7.7 Hz, 1H), 3.97 (s, 2H), 3.61 (t, J=5.9 Hz, 2H), 3.36 (t, J=5.8 Hz, 2H), 2.89-3.01 (m, 1H), 2.79 (dt, J=15.8, 8.2 Hz, 1H), 2.61 (dtd, J=12.5, 7.7, 7.7, 3.0 Hz, 1H), 1.95 (dq, J=12.6, 8.6 Hz, 1H); ESI MS m/z: 379.2 [M+H$^+$]

Examples 52 and 53. (S)- and (R)-2-((4-(N-(4-fluorobicyclo[4.2.0]octa-1(6),2,4-trien-7-yl)-N'-hydroxycarbamimidoyl)-1,2,5-oxadiazol-3-yl)amino)-N-(2-hydroxyethyl)acetamide Step 1. 2-((4-(4-(4/2-Fluorobicyclo[4.2.0]octa-1(6),2,4-trien-7-yl)-5-oxo-4,5-dihydro-1,2,4-oxadiazol-3-yl)-1,2,5-oxadiazol-3-yl)amino)-N-(2-hydroxyethyl)acetamide

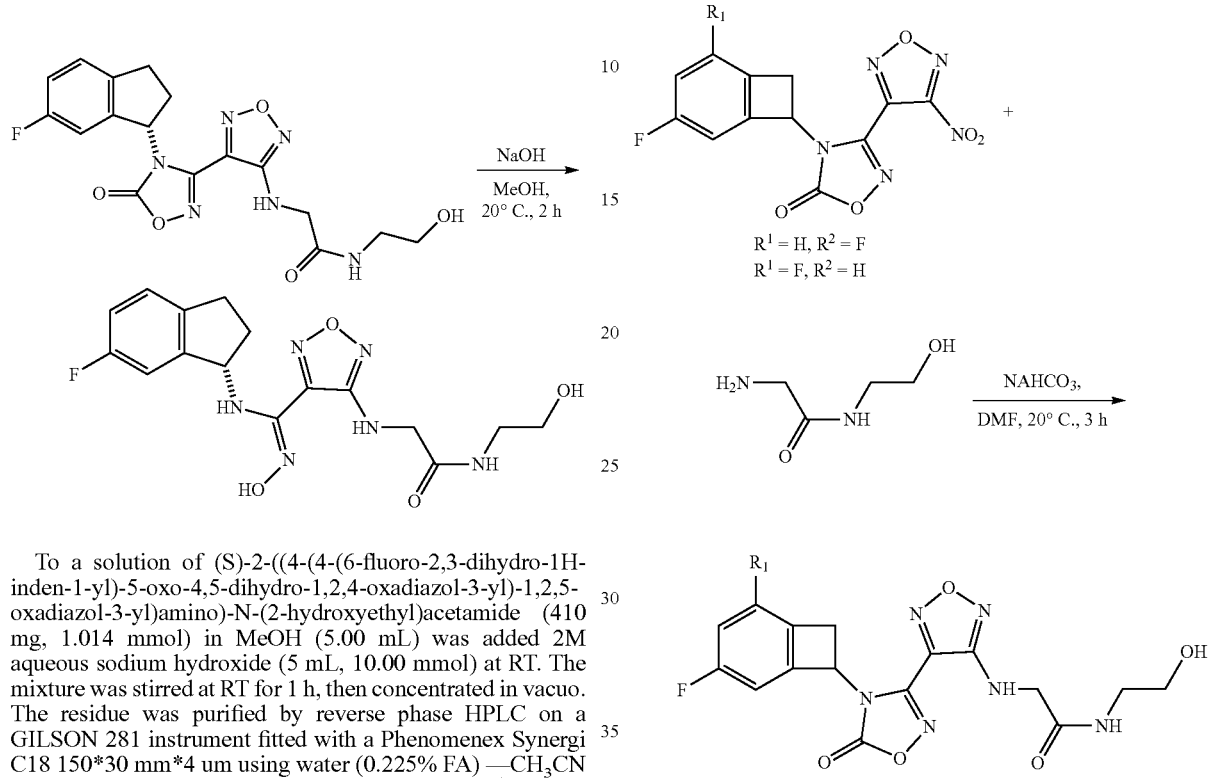

To a solution of 4-(4/2-fluorobicyclo[4.2.0]octa-1,3,5-trien-7-yl)-3-(4-nitro-1,2,5-oxadiazol-3-yl)-1,2,4-oxadiazol-5(4H)-one (Step 3, Example 40) (300 mg, 0.940 mmol, ~3:1 mixture)) and 2-amino-N-(2-hydroxyethyl)acetamide hydrochloride (145 mg, 0.940 mmol) in DMF (5 mL) was added sodium hydrogen carbonate (237 mg, 2.82 mmol). The mixture was stirred at 25° C. for 16 h, quenched by the addition of saturated NH$_4$Cl solution (50 mL), extracted with EtOAc (ca. 30 mL×2). The combined organic layers were washed with brine, dried over Na$_2$SO$_4$, filtered, and concentrated under reduced pressure. The residue was purified by prep-TLC (DCM/MeOH 10:1 as eluent) to give the title compound (150 mg, 0.365 mmol) as a solid.

Step 2. 2-((4-(N-(4/2-fluorobicyclo[4.2.0]octa-1(6),2,4-trien-7-yl)-N'-hydroxycarbamimidoyl)-1,2,5-oxadiazol-3-yl)amino)-N-(2-hydroxyethyl)acetamide

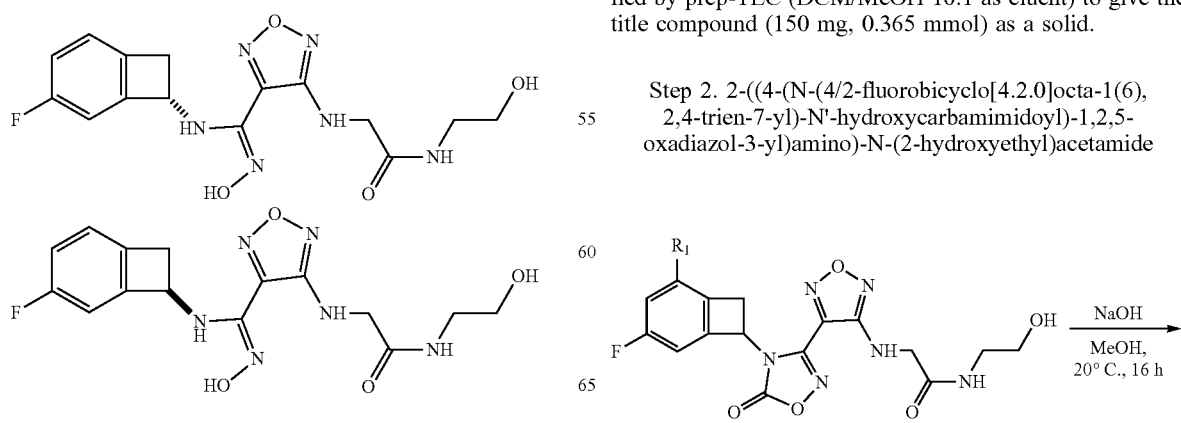

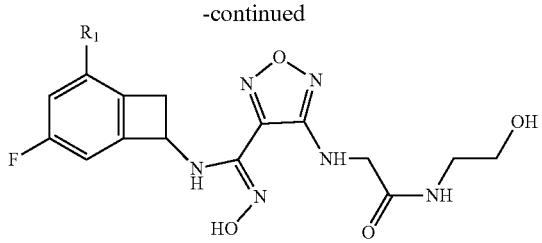

To a solution of 2-((4-(4-(4/2-fluorobicyclo[4.2.0]octa-1,3,5-trien-7-yl)-5-oxo-4,5-dihydro-1,2,4-oxadiazol-3-yl)-1,2,5-oxadiazol-3-yl)amino)-N-(2-hydroxyethyl)acetamide (150 mg, 0.384 mmol) in MeOH (5 ml) and water (5 ml) was added NaOH (77 mg, 1.921 mmol) at 25° C. The mixture was stirred at 25° C. for 16 h before the solvent was removed in vacuo. The residue was purified by reverse phase HPLC on a GILSON 281 instrument fitted with a Waters Xbridge Prep OBD C18(150×30 mm×5 m) using water (0.225% formic acid) and acetonitrile as eluents (Mobile phase A water (0.225% formic acid), Mobile phase B acetonitrile, Detective wavelength: 220 nm) to afford 2-((4-(N-(4/2-fluorobicyclo[4.2.0]octa-1,3,5-trien-7-yl)-N'-hydroxycarbamimidoyl)-1,2,5-oxadiazol-3-yl)amino)-N-(2-hydroxyethyl)acetamide (60 mg, 0.165 mmol) as a solid.

Step 3. (S)- and (R)-2-((4-(N-(4-fluorobicyclo[4.2.0]octa-1(6),2,4-trien-7-yl)-N'-hydroxycarbamimidoyl)-1,2,5-oxadiazol-3-yl)amino)-N-(2-hydroxyethyl)acetamide

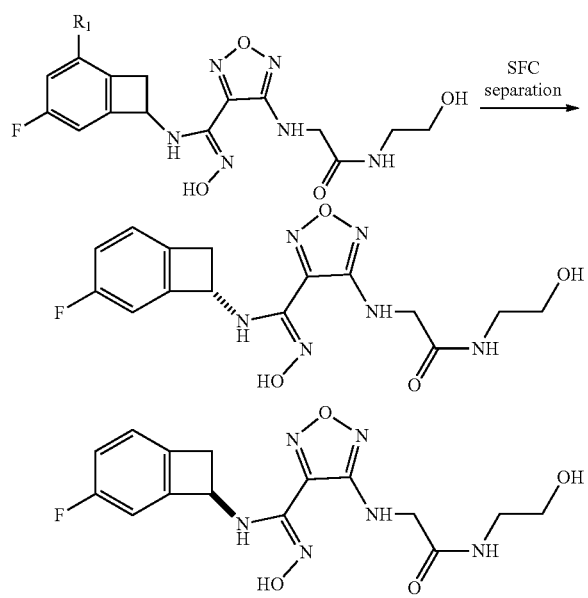

The above racemic mixture was submitted for SFC chiral separation, using the following conditions: Chiralpak AD- (250 mm×30 mm, 5 um); mobile phase: A CO$_2$, B 0.1% NH$_3$—H$_2$O, MeOH; 30% of B; Flow rate: 60 mL/min. Examples 52 and 53 (20 mg each) were obtained as a solid.

Example 52 (peak 1): $^1$H NMR (400 MHz, CD$_3$OD) δ 7.11 (dd, J=8.0, 4.5 Hz, 1H), 6.95-7.02 (m, 1H), 6.90 (br d, J=7.8 Hz, 1H), 5.63 (br s, 1H), 3.96 (s, 2H), 3.59 (t, J=5.8 Hz, 3H), 3.33 (t, J=5.9 Hz, 2H), 3.01 (br d, J=14.5 Hz, 1H). MS (ESI) m/z: 365.1

Example 53 (peak 2): $^1$H NMR (400 MHz, CD$_3$OD) δ 7.11 (dd, J=8.0, 4.5 Hz, 1H), 6.95-7.02 (m, 1H), 6.90 (br d, J=7.8 Hz, 1H), 5.63 (br s, 1H), 3.96 (s, 2H), 3.59 (t, J=5.8 Hz, 3H), 3.33 (t, J=5.9 Hz, 2H), 3.01 (br d, J=14.5 Hz, 1H). MS (ESI) m/z: 365.1

An alternative route for the synthesis of Example 52 is depicted below:

Step 1: (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)amino)-N-(2-hydroxyethyl)acetamide

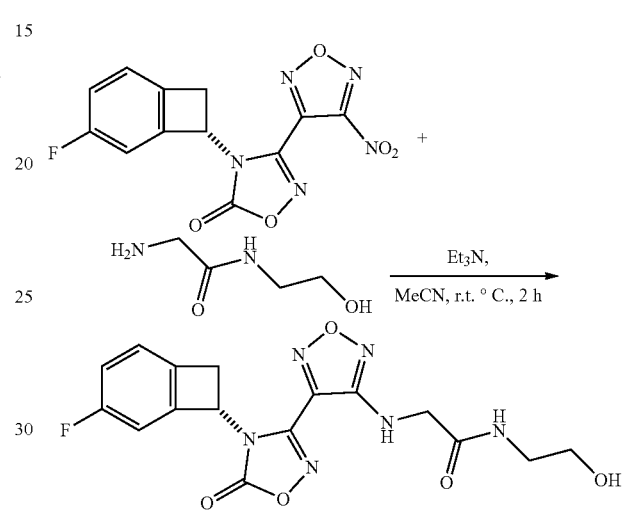

To a solution of (S)-4-(4-fluorobicyclo[4.2.0]octa-1,3,5-trien-7-yl)-3-(4-nitro-1,2,5-oxadiazol-3-yl)-1,2,4-oxadiazol-5(4H)-one (10 g, 31.3 mmol) and 2-amino-N-(2-hydroxyethyl)acetamide (7.40 g, 62.7 mmol) in MeCN (100 mL) was added TEA (13.1 mL, 94 mmol). The mixture was stirred at 25° C. for 2 h, then concentrated in vacuo to give the title compound which was used in the next step without further purification. ESI MS m/z 391.1 [M+H$^+$]

Step 2: (S)-2-((4-(N-(4-fluorobicyclo[4.2.0]octa-1(6),2,4-trien-7-yl)-N'-hydroxycarbamimidoyl)-1,2,5-oxadiazol-3-yl)amino)-N-(2-hydroxyethyl)acetamide

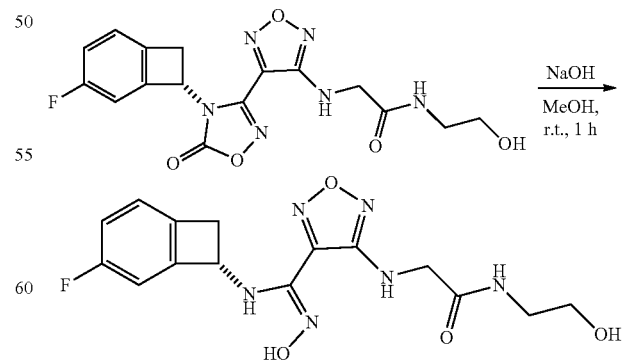

To a solution of (S)-2-((4-(4-(4-fluorobicyclo[4.2.0]octa-1,3,5-trien-7-yl)-5-oxo-4,5-dihydro-1,2,4-oxadiazol-3-yl)-1,2,5-oxadiazol-3-yl)amino)-N-(2-hydroxyethyl)acetamide (12.2 g, 31.3 mmol) in MeOH (100 mL) at 25° C. was added 2M aqueous NaOH (13.5 mL, 27 mmol). The mixture was stirred at 25° C. for 2 h, then concentrated in vacuo. The residue was purified by flash column chromatography (DCM/MeOH=20:1 as eluent) to give the title compound (4.0 g) as a solid. 1H NMR (400 MHz, CD$_3$OD) δ 7.11 (dd, J=7.8, 4.6 Hz, 1H), 6.94-7.02 (m, 1H), 6.90 (br d, J=7.0 Hz, 1H), 5.63 (br d, J=2.2 Hz, 1H), 3.96 (s, 2H), 3.54-3.61 (m, 3H), 3.33 (t, J=5.8 Hz, 2H), 3.01 (br d, J=14.2 Hz, 1H). ESI MS m/z 365.1 [M+H$^+$]

Example 54. N-(Bicyclo[4.2.0]octa-1(6),2,4-trien-7-yl)-N'-hydroxy-4-((2-(sulfamoylamino)ethyl)amino)-1,2,5-oxadiazole-3-carboximidamide

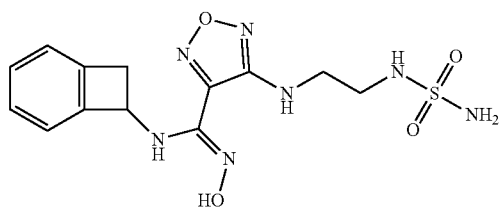 [SMILES: NS(=O)(=O)NCCNc1nonc1/C(=N/O)NC1Cc2ccccc21]

Step 1. 4-Amino-N-(bicyclo[4.2.0]octa-1(6),2,4-trien-7-yl)-N'-hydroxy-1,2,5-oxadiazole-3-carboximidamide

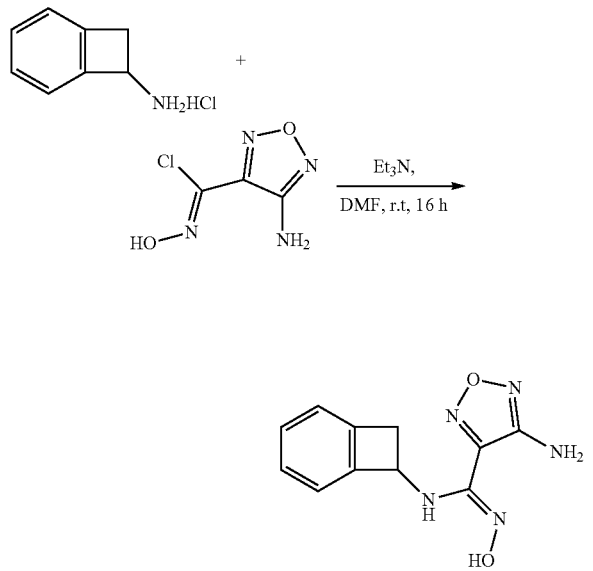

A solution of bicyclo[4.2.0]octa-1,3,5-trien-7-amine (190 mg, 1.594 mmol), 4-amino-N-hydroxy-1,2,5-oxadiazole-3-carbimidoyl chloride (259 mg, 1.594 mmol) and Et$_3$N (0.4 mL, 2.87 mmol) in DMF (7 mL) was stirred at 25° C. for 16 h, then concentrated under reduced pressure. The residue was purified by column chromatography (Pet. ether: EtOAc=PE to 5:1 as eluent) to give 4-amino-N-(bicyclo[4.2.0]octa-1,3,5-trien-7-yl)-N'-hydroxy-1,2,5-oxadiazole-3-carboximidamide (400 mg, 1.305 mmol) as a solid.

Step 2. 3-(4-Amino-1,2,5-oxadiazol-3-yl)-4-(bicyclo[4.2.0]octa-1(6),2,4-trien-7-yl)-1,2,4-oxadiazol-5(4H)-one

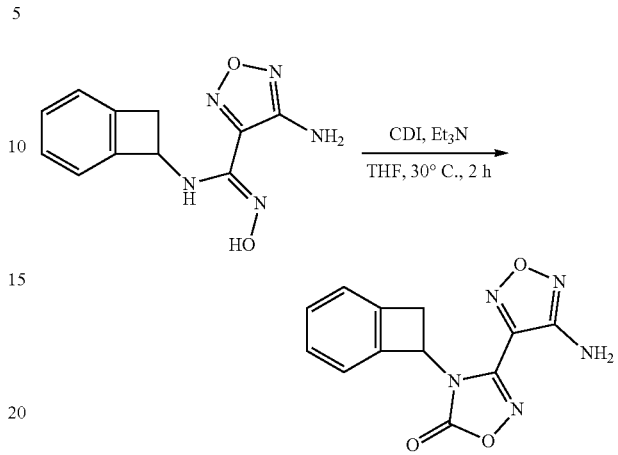

To a solution of 4-amino-N-(bicyclo[4.2.0]octa-1,3,5-trien-7-yl)-N'-hydroxy-1,2,5-oxadiazole-3-carboximidamide (0.3 g, 1.223 mmol) and CDI (0.218 g, 1.346 mmol) in THF (15 mL) was added Et$_3$N (0.3 mL, 2.152 mmol). The reaction mixture was stirred at 30° C. for 2 h under N$_2$, then concentrated in vacuo, diluted with EtOAc (50 mL), washed with water (50 mL×2). The combined organic layers were concentrated under reduced pressure. The residue was purified by column chromatography (Pet. ether:EtOAc=5:1 as eluent) to give 3-(4-amino-1,2,5-oxadiazol-3-yl)-4-(bicyclo[4.2.0]octa-1,3,5-trien-7-yl)-1,2,4-oxadiazol-5(4H)-one (290 mg, 0.962 mmol) as a solid.

Step 3. 4-(Bicyclo[4.2.0]octa-1(6),2,4-trien-7-yl)-3-(4-nitro-1,2,5-oxadiazol-3-yl)-1,2,4-oxadiazol-5(4H)-one

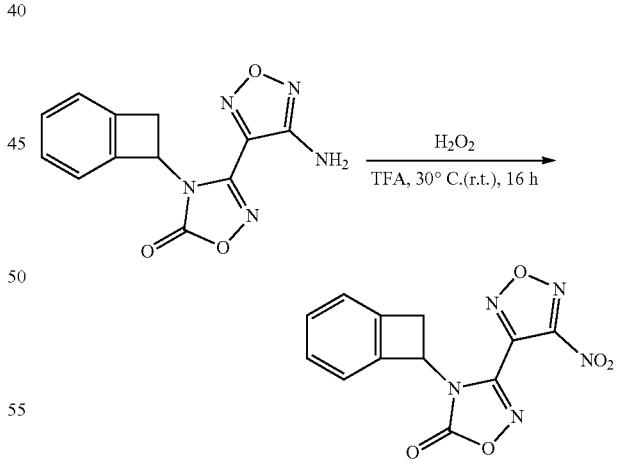

To a solution of 3-(4-amino-1,2,5-oxadiazol-3-yl)-4-(bicyclo[4.2.0]octa-1,3,5-trien-7-yl)-1,2,4-oxadiazol-5(4H)-one (290 mg, 1.069 mmol) in TFA (8 mL) was added hydrogen peroxide (30% aq., 1 mL, 1.069 mmol). The reaction mixture was stirred at 30° C. for 16 h, diluted with water (100 mL) at 0° C., extracted with DCM (100 mL×3) and the organic layers were concentrated under reduced pressure. The residue was purified by column chromatography (Pet. ether:EtOAc=PE to 5:1 as eluent) to give 4-(bicyclo[4.2.0]octa-1,3,5-trien-7-yl)-3-(4-nitro-1,2,5-oxadi-azol-3-yl)-1,2,4-oxadiazol-5(4H)-one (180 mg, 0.508 mmol) as a solid.

Step 4. N-(Bicyclo[4.2.0]octa-1(6),2,4-trien-7-yl)-N'-hydroxy-4-((2-(sulfamoylamino)ethyl)amino)-1,2,5-oxadiazole-3-carboximidamide

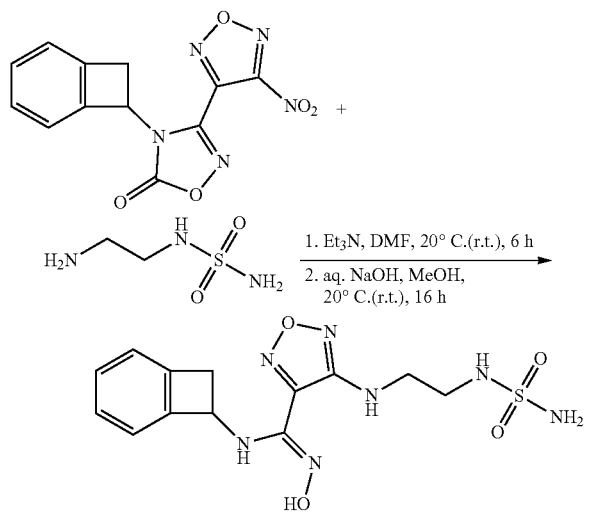

To a solution of 4-(bicyclo[4.2.0]octa-1(6),2,4-trien-7-yl)-3-(4-nitro-1,2,5-oxadiazol-3-yl)-1,2,4-oxadiazol-5(4H)-one (30 mg, 0.100 mmol) in DMF (3.00 mL) was added [(2-aminoethyl)sulfamoyl]amine (22 mg, 0.125 mmol) and $Et_3N$ (0.1 mL, 0.717 mmol). The reaction mixture was stirred at 20° C. for 6 h, concentrated in vacuo. The residue was dissolved in MeOH (3.0 mL). After addition of aqu. NaOH (2M, 1.0 mL, 2.000 mmol), the mixture was stirred at 20° C. for 16 h. The solvent was removed under reduced pressure. The residue was purified by prep-HPLC (Column Agela ASB 150×25 mm×5 um, Condition water (0.225% FA)-ACN Begin B 32, End B 62 Gradient Time (min) 10, 100% B Hold Time (min) 2, Flow Rate (mL/min) 25, Injections 3) and acetonitrile as eluents (Mobile phase A water (0.2% Formic acid), Mobile phase B acetonitrile, Detective wavelength: 220 nm.) to give N-(bicyclo[4.2.0]octa-1(6),2,4-trien-7-yl)-N'-hydroxy-4-((2-(sulfamoylamino)ethyl)amino)-1,2,5-oxadiazole-3-carboximidamide (26 mg, 0.064 mmol) as a solid. m/z 468.1 $[M+H]^+$; $^1H$ NMR (400 MHz, $CD_3OD$) δ 7.24-7.29 (m, 1H), 7.18-7.23 (m, 1H), 7.10-7.13 (m, 1H), 5.63-5.65 (m, 1H), 3.61 (dd, J=2.0 Hz, J=8.4 Hz 1H), 3.48 (q, J=6.0 Hz, 2H), 3.30 (q, J=6.0 Hz, 2H), 3.05 (d, J=8.4 Hz 1H).

Using the general methodology disclosed in the schemes, examples 29-54, and general knowledge in organic synthesis, compounds in the following Table 2 were prepared.

TABLE 2

| Examples 55-165 | | | |
|---|---|---|---|
| Ex. # | Structure | Chemical Name | Mass [M + H]+ |
| 55 |  | N-(2-((4-(N-(6-bromo-2,3-dihydro-1H-inden-1-yl)-N'-hydroxycarbamimidoyl)-1,2,5-oxadiazol-3-yl)thio)ethyl)acetamide (racemic) | 440.0 |
| 56 |  | N-(2-((4-(N-(6-bromo-2,3-dihydro-1H-inden-1-yl)-N'-hydroxycarbamimidoyl)-1,2,5-oxadiazol-3-yl)thio)ethyl)acetamide (chiral, peak 1) | 440.0 |
| 57 |  | N-(2-((4-(N-(6-bromo-2,3-dihydro-1H-inden-1-yl)-N'-hydroxycarbamimidoyl)-1,2,5-oxadiazol-3-yl)thio)ethyl)acetamide (chiral, peak 2) | 440.0 |

TABLE 2-continued

Examples 55-165

| Ex. # | Structure | Chemical Name | Mass [M + H]+ |
|---|---|---|---|
| 58 | 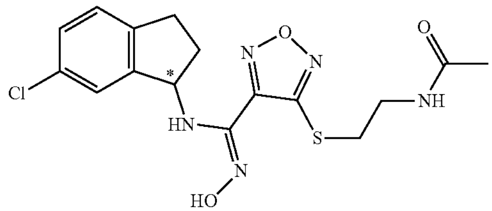 [SMILES: CC(=O)NCCSc1nonc1/C(=N/O)NC1CCc2ccc(Cl)cc21] | N-(2-((4-(N-(6-chloro-2,3-dihydro-1H-inden-1-yl)-N'-hydroxycarbamimidoyl)-1,2,5-oxadiazol-3-yl)thio)ethyl)acetamide (chiral, peak 1) | 396.1 |
| 59 | 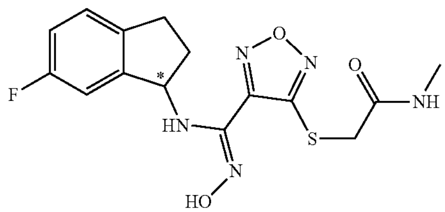 [SMILES: CNC(=O)CSc1nonc1/C(=N/O)NC1CCc2ccc(F)cc21] | 2-((4-(N-(6-fluoro-2,3-dihydro-1H-inden-1-yl)-N'-hydroxycarbadoyl)-1,2,5-oxadiazol-3-yl)thio)-N-methylacetamide (chiral peak 1) | 366.1 |
| 60 | 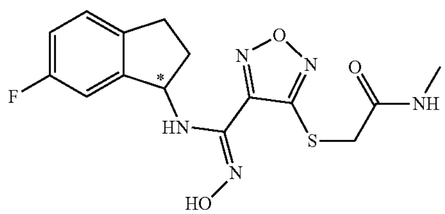 [SMILES: CNC(=O)CSc1nonc1/C(=N/O)NC1CCc2ccc(F)cc21] | 2-((4-(N-(6-fluoro-2,3-dihydro-1H-inden-1-yl)-N'-hydroxycarbamimidoyl)-1,2,5-oxadiazol-3-yl)thio)-N-methylacetamide (chiral, peak 2) | 366.1 |
| 61 | 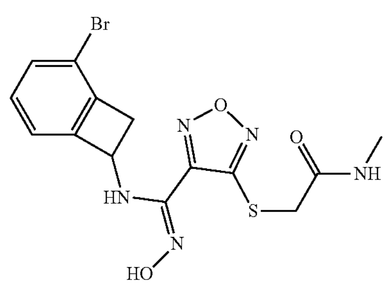 [SMILES: CNC(=O)CSc1nonc1/C(=N/O)NC1Cc2c(Br)cccc21] | 2-((4-(N-(2-bromobicyclo[4.2.0]octa-1(6),2,4-trien-7-yl)-N'-hydroxycarbamimidoyl)-1,2,5-oxadiazol-3-yl)thio)-N-methylacetamide | 412.0 |
| 62 | 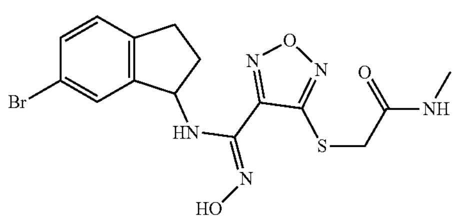 [SMILES: CNC(=O)CSc1nonc1/C(=N/O)NC1CCc2ccc(Br)cc21] | 2-((4-(N-(6-bromo-2,3-dihydro-1H-inden-1-yl)-N'-hydroxycarbamimidoyl)-1,2,5-oxadiazol-3-yl)thio)-N-methylacetamide | 426.1 |
| 63 | 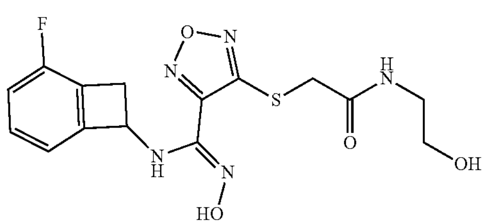 [SMILES: O=C(CSc1nonc1/C(=N/O)NC1Cc2c(F)cccc21)NCCO] | 2-((4-(N-(2-fluorobicyclo[4.2.0]octa-1(6),2,4-trien-7-yl)-N'-hydroxycarbadoyl)-1,2,5-oxadiazol-3-yl)thio)-N-(2-hydroxyethyl)acetamide | 382.1 |

TABLE 2-continued

Examples 55-165

| Ex. # | Structure | Chemical Name | Mass [M + H]+ |
|---|---|---|---|
| 64 | 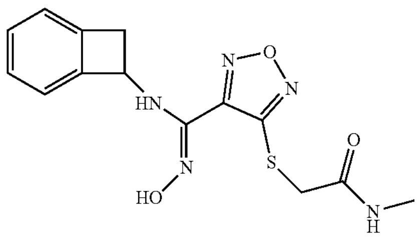 [SMILES: CNC(=O)CSc1nonc1/C(=N/O)NC1Cc2ccccc21] | 2-((4-(N-(bicyclo[4.2.0]octa-1,3,5-trien-7-yl)-N'-hydroxycarbamimidoyl)-1,2,5-oxadiazol-3-yl)thio)-N-methylacetamide | 334.1 |
| 65 | 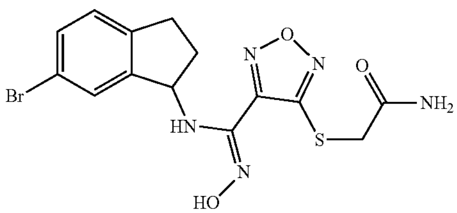 [SMILES: NC(=O)CSc1nonc1/C(=N/O)NC1CCc2ccc(Br)cc21] | 2-((4-(N-(6-bromo-2,3-dihydro-1H-inden-1-yl)-N'-hydroxycarbamimidoyl)-1,2,5-oxadiazol-3-yl)thio)acetamide | 412.0 |
| 66 | 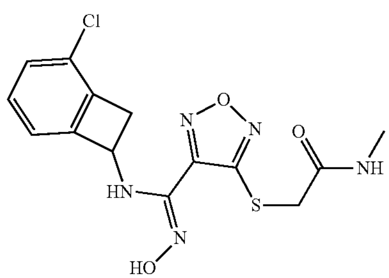 [SMILES: CNC(=O)CSc1nonc1/C(=N/O)NC1Cc2c(Cl)cccc21] | 2-((4-(N-(2-chlorobicyclo[4.2.0]octa-1(6),2,4-trien-7-yl)-N'-hydroxycarbamimidoyl)-1,2,5-oxadiazol-3-yl)thio)-N-methylacetamide | 368.1 |
| 67 | Chiral | (N-(2-((4-(N-(6,7-difluoro-2,3-dihydro-1H-inden-1-yl)-N'-hydroxycarbamimidoyl)-1,2,5-oxadiazol-3-yl)thio)ethyl)acetamide (chiral, peak 1) | 398.1 |
| 68 | Chiral | (N-(2-((4-(N-(6,7-difluoro-2,3-dihydro-1H-inden-1-yl)-N'-hydroxycarbamimidoyl)-1,2,5-oxadiazol-3-yl)thio)ethyl)acetamide (chiral, peak 2) | 398.1 |
| 69 | Chiral | (N-(2-((4-(N-(4,6-difluor-2,3-dihydro-1H-inden-1-yl)-N'-hydroxycarbamimidoyl)-1,2,5-oxadiazol-3-yl)thio)ethyl)acetamide (peak 1) | 398.1 |

TABLE 2-continued

Examples 55-165

| Ex. # | Structure | Chemical Name | Mass [M + H]+ |
|---|---|---|---|
| 70 | 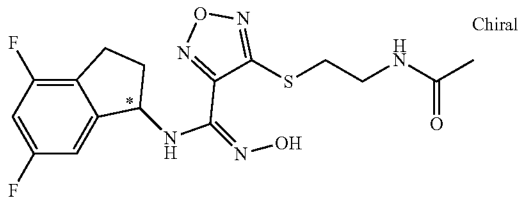 [SMILES: CC(=O)NCCSc1nonc1/C(=N\O)NC1CCc2c(F)cc(F)cc21] | (N-(2-((4-(N-(4,6-difluoro-2,3-dihydro-1H-inden-1-yl)-N'-hydroxycarbadoyl)-1,2,5-oxadiazol-3-yl)thio)ethyl)acetamide (peak 2) | 398.1 |
| 71 | 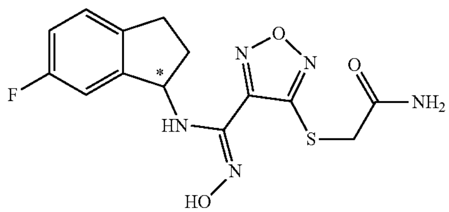 [SMILES: NC(=O)CSc1nonc1/C(=N/O)NC1CCc2ccc(F)cc21] | (2-((4-(N-(6-fluoro-2,3-dihydro-1H-inden-1-yl)-N'-hydroxycarbamimidoyl)-1,2,5-oxadiazol-3-yl)thio)acetamide (chiral, peak 1) | 352.1 |
| 72 | 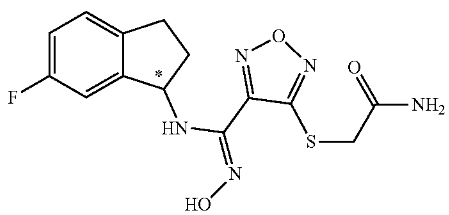 [SMILES: NC(=O)CSc1nonc1/C(=N/O)NC1CCc2ccc(F)cc21] | (2-((4-(N-(6-fluoro-2,3-dihydro-1H-inden-1-yl)-N'-hydroxycarbamimidoyl)-1,2,5-oxadiazol-3-yl)thio)acetamide (chiral, peak 2) | 352.1 |
| 73 | 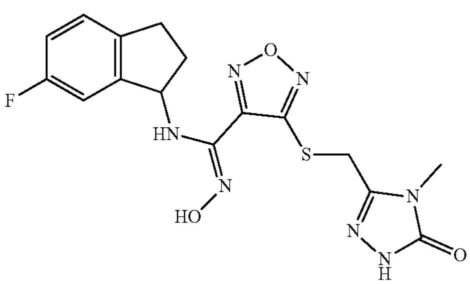 [SMILES: Cn1c(CSc2nonc2/C(=N/O)NC2CCc3ccc(F)cc32)n[nH]c1=O] | N-(6-fluoro-2,3-dihydro-1H-inden-1-yl)-N'-hydroxy-4-(((4-methyl-5-oxo-4,5-dihydro-1H-1,2,4-triazol-3-yl)methyl)thio)-1,2,5-oxadiazole-3-carboximidamide | 406.1 |
| 74 | 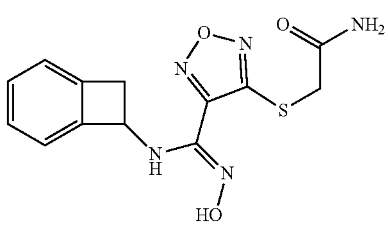 [SMILES: NC(=O)CSc1nonc1/C(=N/O)NC1Cc2ccccc21] | 2-((4-(N-(bicyclo[4.2.0]octa-1,3,5-trien-7-yl)-N'-hydroxycarbamimidoyl)-1,2,5-oxadiazol-3-yl)thio)acetamide | 320.1 |
| 75 | 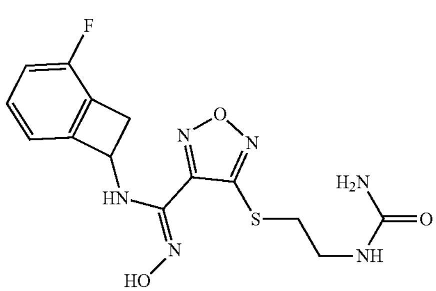 [SMILES: NC(=O)NCCSc1nonc1/C(=N/O)NC1Cc2c(F)cccc21] | N-(2-fluorobicyclo[4.2.0]octa-1(6),2,4-trien-7-yl)-N'-hydroxy-4-((2-ureidoethyl)thio)-1,2,5-oxadiazole-3-carboximidamide | 367.1 |

TABLE 2-continued

Examples 55-165

| Ex. # | Structure | Chemical Name | Mass [M + H]+ |
|---|---|---|---|
| 76 | 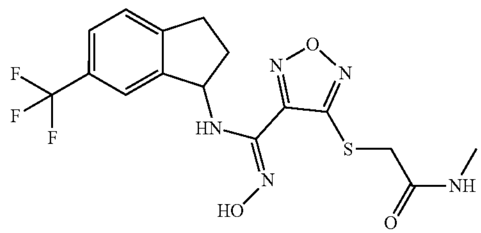 [SMILES: CNC(=O)CSc1nonc1/C(=N/O)NC1CCc2ccc(C(F)(F)F)cc21] | 2-((4-(N'-hydroxy-N-(6-(trifluoromethyl)-2,3-dihydro-1H-inden-1-yl)carbamimidoyl)-1,2,5-oxadiazol-3-yl)thio)-N-methylacetamide | 416.1 |
| 77 | 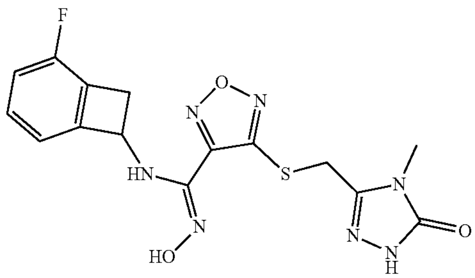 [SMILES: Cn1c(CSc2nonc2/C(=N/O)NC2Cc3c(F)cccc32)n[nH]c1=O] | N-(2-fluorobicyclo[4.2.0]octa-1(6),2,4-trien-7-yl)-N'-hydroxy-4-(((4-methyl-5-oxo-4,5-dihydro-1H-1,2,4-triazol-3-yl)methyl)thio)-1,2,5-oxadiazole-3-carboximidamide | 392.1 |
| 78 | 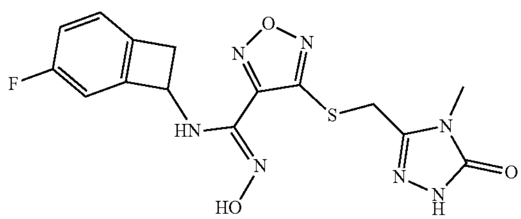 [SMILES: Cn1c(CSc2nonc2/C(=N/O)NC2Cc3ccc(F)cc32)n[nH]c1=O] | N-(4-fluorobicyclo[4.2.0]octa-1(6),2,4-trien-7-yl)-N'-hydroxy-4-(((4-methyl-5-oxo-4,5-dihydro-1H-1,2,4-triazol-3-yl)methyl)thio)-1,2,5-oxadiazole-3-carboximidamide | 392.1 |
| 79 | 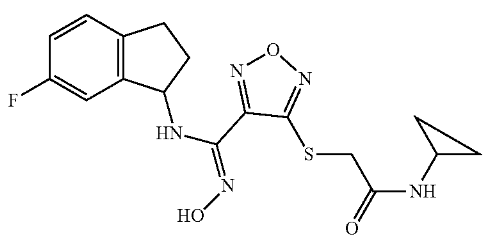 [SMILES: O=C(CSc1nonc1/C(=N/O)NC1CCc2ccc(F)cc21)NC1CC1] | N-cyclopropyl-2-((4-(N-(6-fluoro-2,3-dihydro-1H-inden-1-yl)-N'-hydroxycarbamimidoyl)-1,2,5-oxadiazol-3-yl)thio)acetamide | 392.1 |
| 80 | 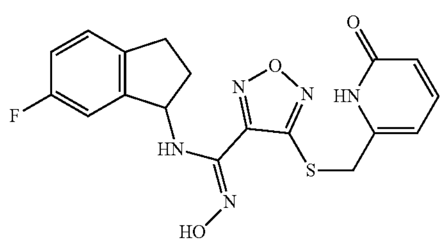 [SMILES: O=c1cccc(CSc2nonc2/C(=N/O)NC2CCc3ccc(F)cc32)[nH]1] | N-(6-fluoro-2,3-dihydro-1H-inden-1-yl)-N'-hydroxy-4-(((6-oxo-1,6-dihydropyridin-2-yl)methyl)thio)-1,2,5-oxadiazole-3-carboximidamide | 402.1 |
| 81 | 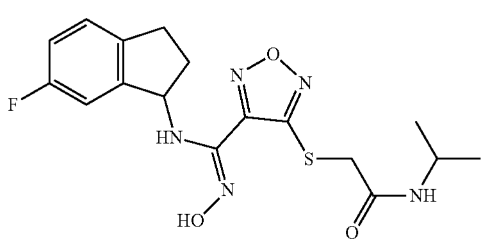 [SMILES: CC(C)NC(=O)CSc1nonc1/C(=N/O)NC1CCc2ccc(F)cc21] | 2-((4-(N-(6-fluoro-2,3-dihydro-1H-inden-1-yl)-N'-hydroxycarbamimidoyl)-1,2,5-oxadiazol-3-yl)thio)-N-isopropylacetamide | 394.1 |

TABLE 2-continued

Examples 55-165

| Ex. # | Structure | Chemical Name | Mass [M + H]+ |
|---|---|---|---|
| 82 | 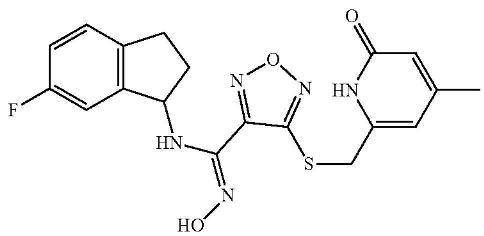 [SMILES: Cc1cc(CSc2nonc2/C(=N/O)NC2CCc3ccc(F)cc32)[nH]c(=O)c1] | N-(6-fluoro-2,3-dihydro-1H-inden-1-yl)-N'-hydroxy-4-(((4-methyl-6-oxo-1,6-dihydropyridin-2-yl)methyl)thio)-1,2,5-oxadiazole-3-carboximidamide | 416.1 |
| 83 | 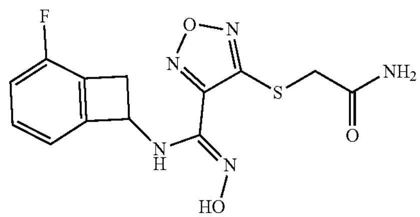 [SMILES: NC(=O)CSc1nonc1/C(=N/O)NC1Cc2c(F)cccc21] | 2-((4-(N-(2-fluorobicyclo[4.2.0]octa-1(6),2,4-trien-7-yl)-N'-hydroxycarbamimidoyl)-1,2,5-oxadiazol-3-yl)thio)acetamide | 338.1 |
| 84 | 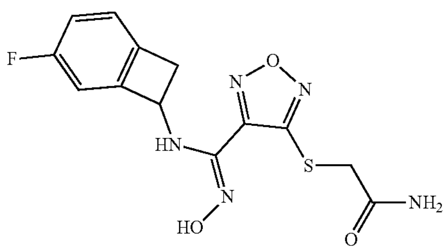 [SMILES: NC(=O)CSc1nonc1/C(=N/O)NC1Cc2ccc(F)cc21] | 2-((4-(N-(4-fluorobicyclo[4.2.0]octa-1(6),2,4-trien-7-yl)-N'-hydroxycarbamimidoyl)-1,2,5-oxadiazol-3-yl)thio)acetamide | 338.1 |
| 85 | 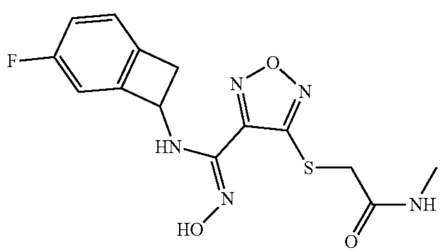 [SMILES: CNC(=O)CSc1nonc1/C(=N/O)NC1Cc2ccc(F)cc21] | (2-((4-(N-(4-fluorobicyclo[4.2.0]octa-1(6),2,4-trien-7-yl)-N'-hydroxycarbamimidoyl)-1,2,5-oxadiazol-3-yl)thio)-N-methylacetamide | 352.1 |
| 86 | 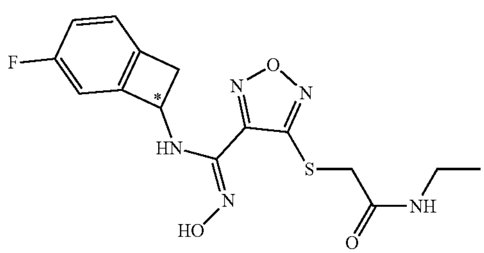 [SMILES: CCNC(=O)CSc1nonc1/C(=N/O)NC1Cc2ccc(F)cc21] | N-ethyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 1) | 366.1 |
| 87 | 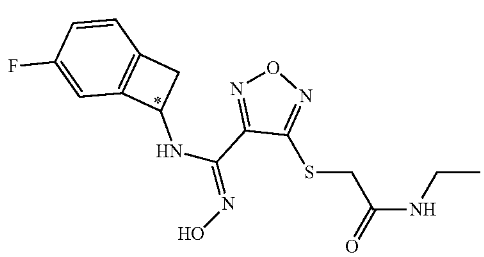 [SMILES: CCNC(=O)CSc1nonc1/C(=N/O)NC1Cc2ccc(F)cc21] | N-ethyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 2) | 366.1 |

TABLE 2-continued

Examples 55-165

| Ex. # | Structure | Chemical Name | Mass [M + H]+ |
|---|---|---|---|
| 88 | 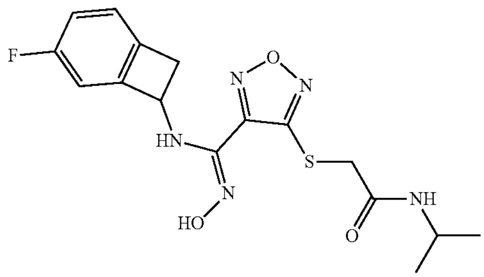 [SMILES: CC(C)NC(=O)CSc1nonc1/C(=N/O)NC1Cc2ccc(F)cc21] | 2-((4-(N-(4-fluorobicyclo[4.2.0]octa-1(6),2,4-trien-7-yl)-N'-hydroxycarbamimidoyl)-1,2,5-oxadiazol-3-yl)thio)-N-isopropylacetamide (peak 1) | 380.1 |
| 89 | 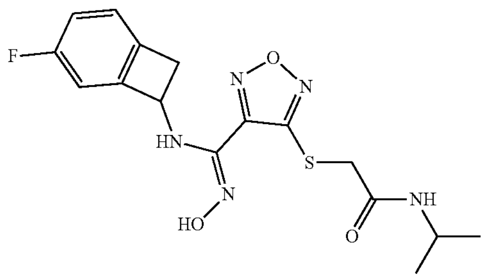 [SMILES: CC(C)NC(=O)CSc1nonc1/C(=N/O)NC1Cc2ccc(F)cc21] | 2-((4-(N-(4-fluorobicyclo[4.2.0]octa-1(6),2,4-trien-7-yl)-N'-hydroxycarbamimidoyl)-1,2,5-oxadiazol-3-yl)thio)-N-isopropylacetamide (peak 2) | 380.1 |
| 90 | 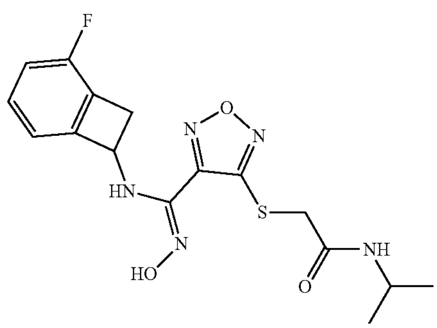 [SMILES: CC(C)NC(=O)CSc1nonc1/C(=N/O)NC1Cc2c(F)cccc21] | 2-((4-(N-(2-fluorobicyclo[4.2.0]octa-1(6),2,4-trien-7-yl)-N'-hydroxycarbamimidoyl)-1,2,5-oxadiazol-3-yl)thio)-N-isopropylacetamide | 380.1 |
| 91 | 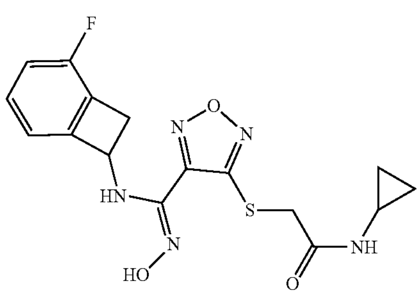 [SMILES: O=C(CSc1nonc1/C(=N/O)NC1Cc2c(F)cccc21)NC1CC1] | N-cyclopropyl-2-((4-(N-(2-fluorobicyclo[4.2.0]octa-1(6),2,4-trien-7-yl)-N'-hydroxycarbamimidoyl)-1,2,5-oxadiazol-3-yl)thio)acetamide (peak 1) | 378.1 |
| 92 | 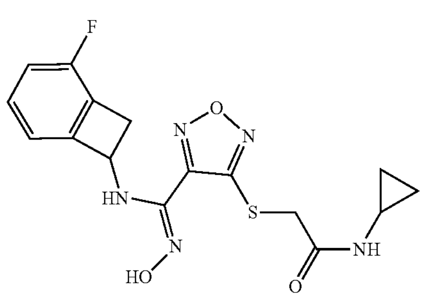 [SMILES: O=C(CSc1nonc1/C(=N/O)NC1Cc2c(F)cccc21)NC1CC1] | N-cyclopropyl-2-((4-(N-(2-fluorobicyclo[4.2.0]octa-1(6),2,4-trien-7-yl)-N'-hydroxycarbamimidoyl)-1,2,5-oxadiazol-3-yl)thio)acetamide (peak 2) | 378.1 |

TABLE 2-continued

Examples 55-165

| Ex. # | Structure | Chemical Name | Mass [M + H]+ |
|---|---|---|---|
| 93 | 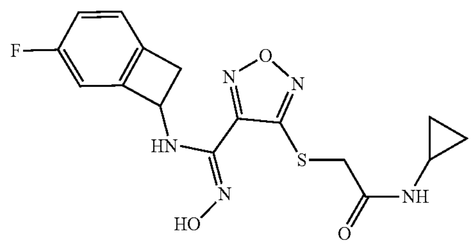 [SMILES: O=C(CSc1nonc1/C(=N/O)NC1Cc2ccc(F)cc21)NC1CC1] | N-cyclopropyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 1) | 378.1 |
| 94 | 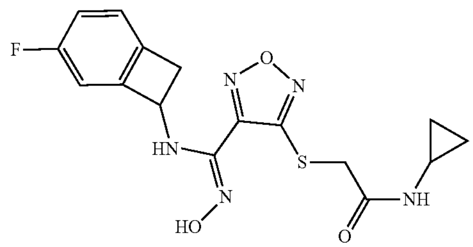 [SMILES: O=C(CSc1nonc1/C(=N/O)NC1Cc2ccc(F)cc21)NC1CC1] | N-cyclopropyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 2) | 378.1 |
| 95 | 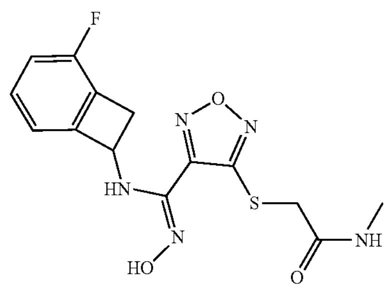 [SMILES: CNC(=O)CSc1nonc1/C(=N/O)NC1Cc2c(F)cccc21] | 2-((4-(N-(2-fluorobicyclo[4.2.0]octa-1(6),2,4-trien-7-yl)-N'-hydroxycarbamimidoyl)-1,2,5-oxadiazol-3-yl)thio)-N-methylacetamide | 352.1 |
| 96 | 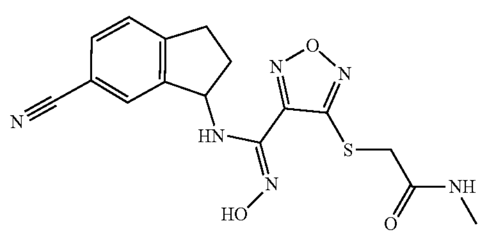 [SMILES: CNC(=O)CSc1nonc1/C(=N/O)NC1CCc2ccc(C#N)cc21] | 2-((4-(N-(6-cyano-2,3-dihydro-1H-inden-1-yl)-N'-hydroxycarbadoyl)-1,2,5-oxadiazol-3-yl)thio)-N-methylacetamide (peak 1) | 373.1 |
| 97 | 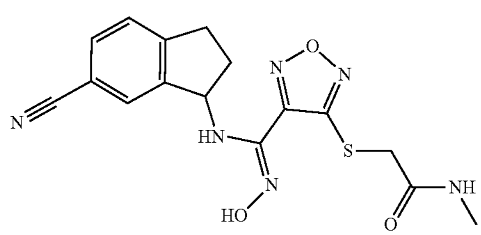 [SMILES: CNC(=O)CSc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)thio)-N-methylacetamide (peak 2) | 373.1 |
| 98 | 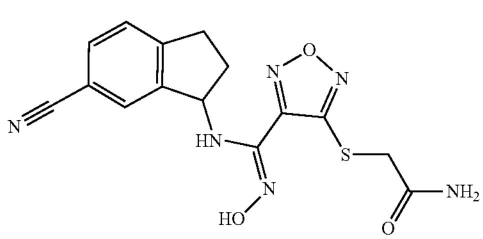 [SMILES: N#Cc1ccc2c(c1)C(N/C(=N\O)c1nonc1SCC(N)=O)CC2] | ((4-(N-(6-cyano-2,3-dihydro-1H-inden-1-yl)-N'-hydroxycarbamimidoyl)-1,2,5-oxadiazol-3-yl)thio)acetamide (peak 1) | 359.1 |

TABLE 2-continued

Examples 55-165

| Ex. # | Structure | Chemical Name | Mass [M + H]+ |
|---|---|---|---|
| 99 | 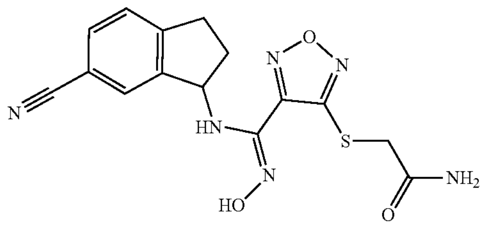 [SMILES: N#Cc1ccc2c(c1)C(N/C(=N\O)c1nonc1SCC(N)=O)CC2] | ((4-(N-(6-cyano-2,3-dihydro-1H-inden-1-yl)-N'-hydroxycarbamimidoyl)-1,2,5-oxadiazol-3-yl)thio)acetamide (peak 2) | 359.1 |
| 100 | 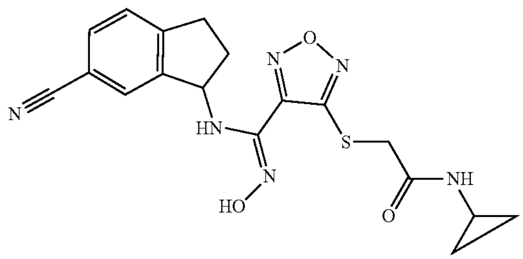 [SMILES: N#Cc1ccc2c(c1)C(N/C(=N\O)c1nonc1SCC(=O)NC1CC1)CC2] | 2-((4-(N-(6-cyano-2,3-dihydro-1H-inden-1-yl)-N'-hydroxycarbamimidoyl)-1,2,5-oxadiazol-3-yl)thio)-N-cyclopropylacetamide (peak 1) | 399.1 |
| 101 | 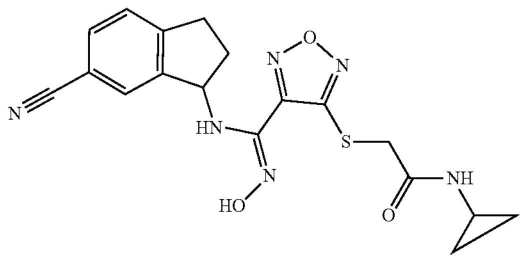 [SMILES: N#Cc1ccc2c(c1)C(N/C(=N\O)c1nonc1SCC(=O)NC1CC1)CC2] | 2-((4-(N-(6-cyano-2,3-dihydro-1H-inden-1-yl)-N'-hydroxycarbamimidoyl)-1,2,5-oxadiazol-3-yl)thio)-N-cyclopropylacetamide (peak 2) | 399.1 |
| 102 | 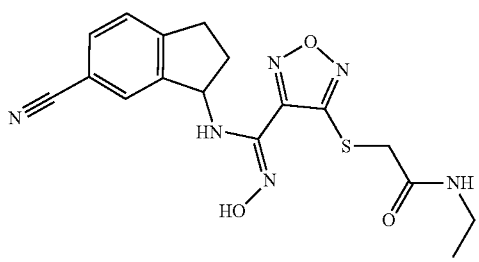 [SMILES: CCNC(=O)CSc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)thio)-N-ethylacetamide (peak 1) | 389.1 |
| 103 | 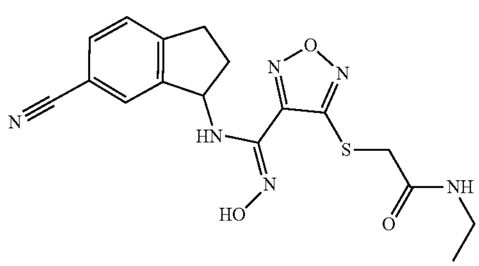 [SMILES: CCNC(=O)CSc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)thio)-N-ethylacetamide (peak 2) | 389.1 |
| 104 | 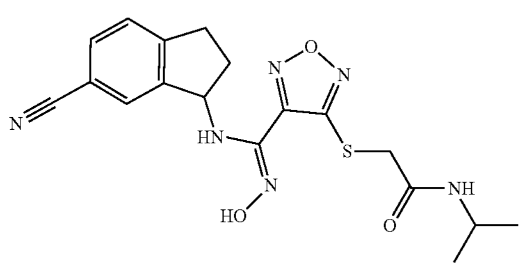 [SMILES: CC(C)NC(=O)CSc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)thio)-N-isopropylacetamide (peak 1) | 401.1 |

TABLE 2-continued

Examples 55-165

| Ex. # | Structure | Chemical Name | Mass [M + H]+ |
|---|---|---|---|
| 105 | 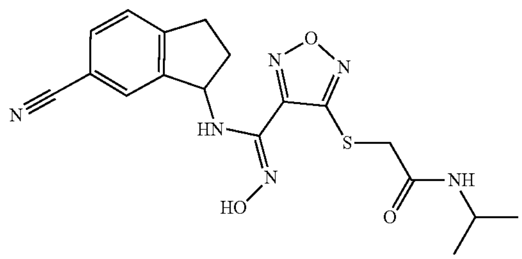 [SMILES: CC(C)NC(=O)CSc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)thio)-N-isopropylacetamide (peak 2) | 401.1 |
| 106 | 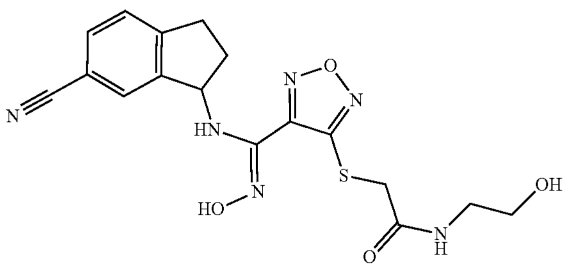 [SMILES: N#Cc1ccc2c(c1)C(N/C(=N\O)c1nonc1SCC(=O)NCCO)CC2] | 2-((4-(N-(6-cyano-2,3-dihydro-1H-inden-1-yl)-N'-hydroxycarbamimidoyl)-1,2,5-oxadiazol-3-yl)thio)-N-(2-hydroxyethyl)acetamide (peak 1) | 403.1 |
| 107 | 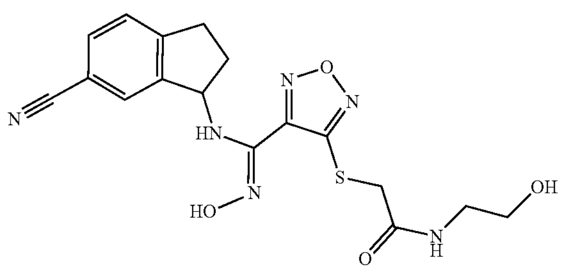 [SMILES: N#Cc1ccc2c(c1)C(N/C(=N\O)c1nonc1SCC(=O)NCCO)CC2] | 2-((4-(N-(6-cyano-2,3-dihydro-1H-inden-1-yl)-N'-hydroxycarbamimidoyl)-1,2,5-oxadiazol-3-yl)thio)-N-(2-hydroxyethyl)acetamide (peak 2) | 403.1 |
| 108 | 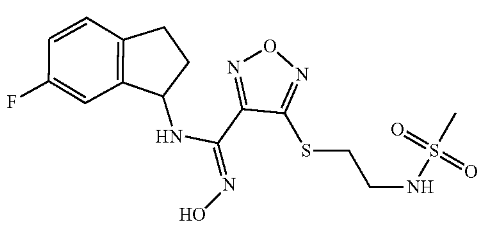 [SMILES: CS(=O)(=O)NCCSc1nonc1/C(=N/O)NC1CCc2ccc(F)cc21] | N-(6-fluoro-2,3-dihydro-1H-inden-1-yl)-N'-hydroxy-4-((2-(methylsulfonamido)ethyl)thio)-1,2,5-oxadiazole-3-carboximidamide (peak 1) | 416.1 |
| 109 | 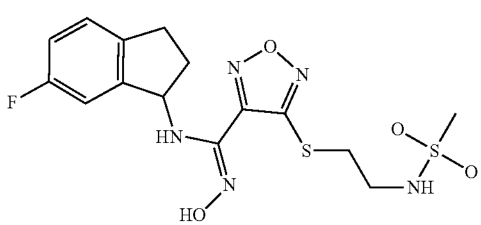 [SMILES: CS(O)(O)NCCSc1nonc1/C(=N/O)NC1CCc2ccc(F)cc21] | N-(6-fluoro-2,3-dihydro-1H-inden-1-yl)-N'-hydroxy-4-((2-(methylsulfonamido)ethyl)thio)-1,2,5-oxadiazole-3-carboximidamide (peak 2) | 416.1 |
| 110 | 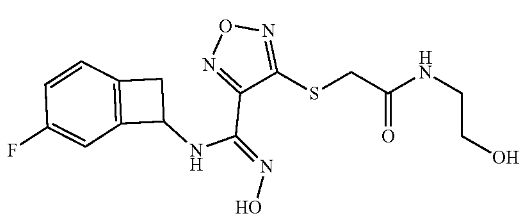 [SMILES: O=C(CSc1nonc1/C(=N/O)NC1Cc2ccc(F)cc21)NCCO] | 2-((4-(N-(4-fluorobicyclo[4.2.0]octa-1(6),2,4-trien-7-yl)-N'-hydroxycarbamimidoyl)-1,2,5-oxadiazol-3-yl)thio)-N-(2-hydroxyethyl)acetamide (peak 1) | 382.1 |

TABLE 2-continued

Examples 55-165

| Ex. # | Structure | Chemical Name | Mass [M + H]+ |
|---|---|---|---|
| 111 | 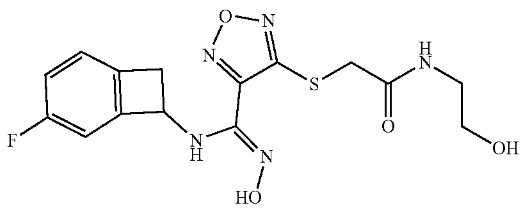 [SMILES: O=C(CSc1nonc1/C(=N/O)NC1Cc2ccc(F)cc21)NCCO] | 2-((4-(N-(4-fluorobicyclo[4.2.0]octa-1(6),2,4-trien-7-yl)-N'-hydroxycarbamimidoyl)-1,2,5-oxadiazol-3-yl)thio)-N-(2-hydroxyethyl)acetamide (peak 2) | 382.1 |
| 112 | 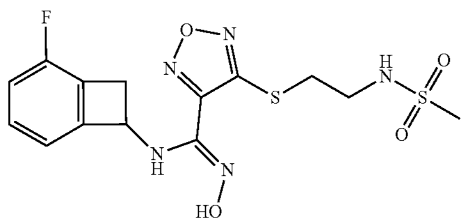 [SMILES: CS(=O)(=O)NCCSc1nonc1/C(=N/O)NC1Cc2c(F)cccc21] | N-(2-fluorobicyclo[4.2.0]octa-1(6),2,4-trien-7-yl)-N'-hydroxy-4-((2-((2-(methylsulfonamido)ethyl)thio)-1,2,5-oxadiazole-3-carboximidamide | 402.1 |
| 113 | 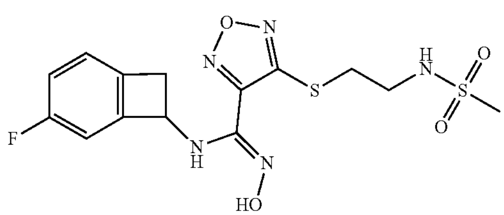 [SMILES: CS(=O)(=O)NCCSc1nonc1/C(=N/O)NC1Cc2ccc(F)cc21] | N-(4-fluorobicyclo[4.2.0]octa-1(6),2,4-trien-7-1)-N'-hydrox-4-((2-(methylsulfonamido)ethyl)thio)-1,2,5-oxadiazole-3-carboximidamide (peak 1) | 402.1 |
| 114 | 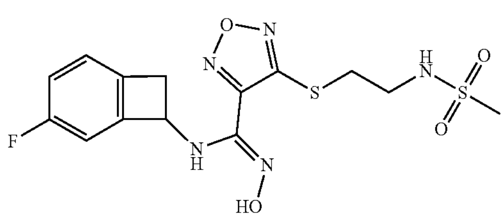 [SMILES: CS(=O)(=O)NCCSc1nonc1/C(=N/O)NC1Cc2ccc(F)cc21] | N-(4-fluorobicyclo[4.2.0]octa-1(6),2,4-trien-7-yl)-N'-hydroxy-4-((2-(methylsulfonamido)ethyl)thio)-1,2,5-oxadiazole-3-carboximidamide (peak 2) | 402.1 |
| 115 | 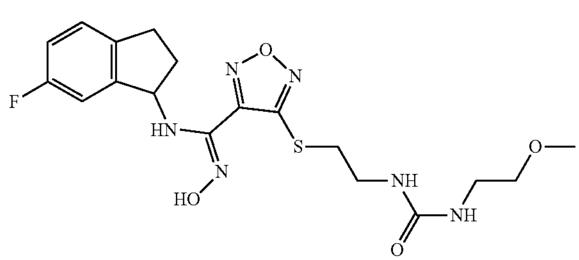 [SMILES: COCCNC(=O)NCCSc1nonc1/C(=N/O)NC1CCc2ccc(F)cc21] | N-(6-fluoro-2,3-dihydro-1H-inden-1-yl)-N'-hydroxy-4-((2-(3-(2-methoxyethyl)ureido)ethyl)thio)-1,2,5-oxadiazole-3-carboximidamide (peak 1) | 439.2 |
| 116 | 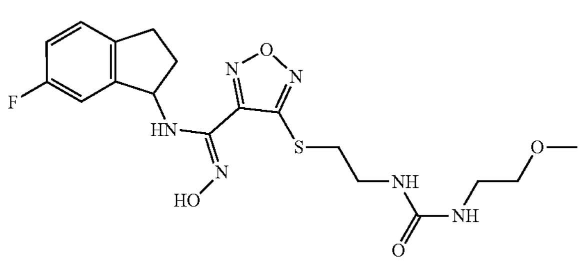 [SMILES: COCCNC(=O)NCCSc1nonc1/C(=N/O)NC1CCc2ccc(F)cc21] | N-(6-fluoro-2,3-dihydro-1H-inden-1-yl)-N'-hydroxy-4-((2-(3-(2-methoxyethyl)ureido)ethyl)thio)-1,2,5-oxadiazole-3-carboximidamide (peak 2) | 439.2 |

TABLE 2-continued

Examples 55-165

| Ex. # | Structure | Chemical Name | Mass [M + H]+ |
|---|---|---|---|
| 117 | 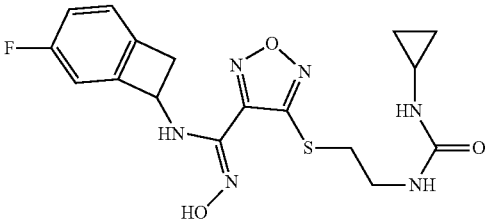 [SMILES: O=C(NCCSc1nonc1/C(=N/O)NC1Cc2ccc(F)cc21)NC1CC1] | 4-((2-(3-cyclopropylureido)ethyl)thio)-N-(4-fluorobicyclo[4.2.0]octa-1(6),2,4-trien-7-yl)-N'-hydroxy-1,2,5-oxadiazole-3-carboximidamide (peak 1) | 407.1 |
| 118 | 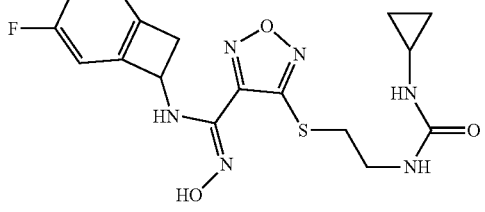 | 4-((2-(3-cyclopropylureido)ethyl)thio)-N-(4-fluorobicyclo[4.2.0]octa-1(6),2,4-trien-7-yl)-N'-hydroxy-1,2,5-oxadiazole-3-carboximidamide (peak 2) | 407.1 |
| 119 | 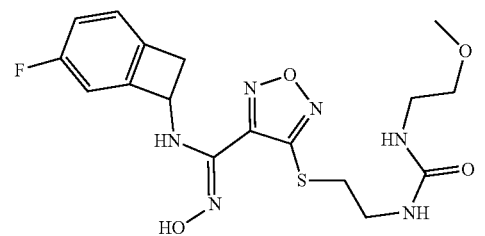 [SMILES: COCCNC(=O)NCCSc1nonc1/C(=N/O)NC1Cc2ccc(F)cc21] | N-(4-fluorobicyclo[4.2.0]octa-1(6),2,4-trien-7-yl)-N'-hydroxy-4-((2-(3-(2-methoxyethyl)ureido)ethyl)thio)-1,2,5-oxadiazole-3-carboximidamide (peak 1) | 425.1 |
| 120 | 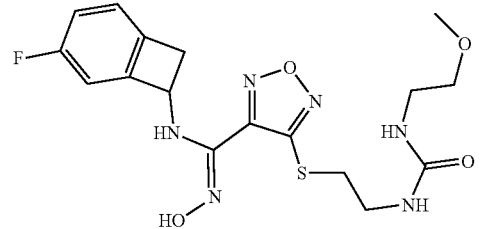 [SMILES: COCCNC(=O)NCCSc1nonc1/C(=N/O)NC1Cc2ccc(F)cc21] | N-(4-fluorobicyclo[4.2.0]octa-1(6),2,4-trien-7-yl)-N'-hydroxy-4-((2-(3-(2-methoxyethyl)ureido)ethyl)thio)-1,2,5-oxadiazole-3-carboximidamide (peak 2) | 425.1 |
| 121 | 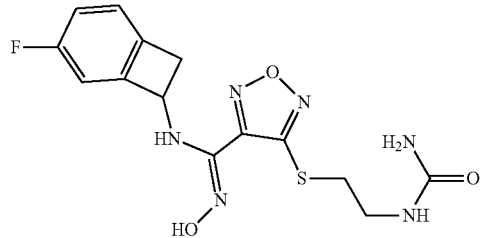 [SMILES: NC(=O)NCCSc1nonc1/C(=N/O)NC1Cc2ccc(F)cc21] | N-(4-fluorobicyclo[4.2.0]octa-1(6),2,4-trien-7-yl)-N'-hydroxy-4-((2-ureidoethyl)thio)-1,2,5-oxadiazole-3-carboximidamide | 367.1 |
| 122 | 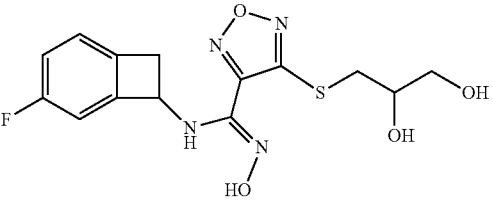 [SMILES: OCC(O)CSc1nonc1/C(=N/O)NC1Cc2ccc(F)cc21] | 4-((2,3-dihydroxypropyl)thio)-N-(4-fluorobicyclo[4.2.0]octa-1,3,5-trien-7-yl)-N'-hydroxy-1,2,5-oxadiazole-3-carboximidamide | 355.1 |

TABLE 2-continued

Examples 55-165

| Ex. # | Structure | Chemical Name | Mass [M + H]+ |
|---|---|---|---|
| 123 | 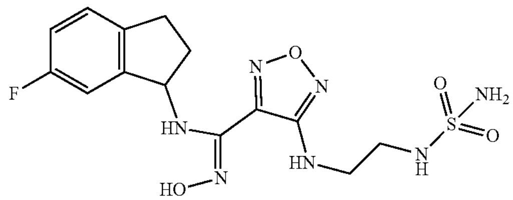 [SMILES: NS(=O)(=O)NCCNc1nonc1/C(=N/O)NC1CCc2ccc(F)cc21] | N-(6-fluoro-2,3-dihydro-1H-inden-1-yl)-N'-hydroxy-4-((2-(sulfamoylamino)ethyl)amino)-1,2,5-oxadiazole-3-carboximidamide (peak 1) | 400.1 |
| 124 | 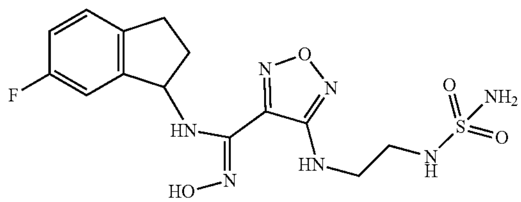 [SMILES: NS(=O)(=O)NCCNc1nonc1/C(=N/O)NC1CCc2ccc(F)cc21] | N-(6-fluoro-2,3-dihydro-1H-inden-1-yl)-N'-hydroxy-4-((2-(sulfamoylamino)ethyl)amino)-1,2,5-oxadiazole-3-carboximidamide (peak 2) | 400.1 |
| 125 | 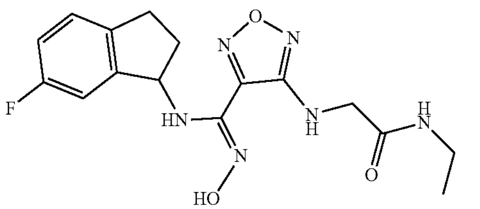 [SMILES: CCNC(=O)CNc1nonc1/C(=N/O)NC1CCc2ccc(F)cc21] | N-ethyl-2-((4-(N-(6-fluoro-2,3-dihydro-1H-inden-1-yl)-N'-hydroxycarbamimidoyl)-1,2,5-oxadiazol-3-yl)amino)acetamide | 363.1 |
| 126 | 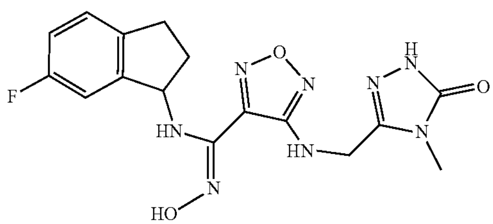 [SMILES: Cn1c(CNc2nonc2/C(=N/O)NC2CCc3ccc(F)cc32)n[nH]c1=O] | N-(6-fluoro-2,3-dihydro-1H-inden-1-yl)-N'-hydroxy-4-(((4-methyl-5-oxo-4,5-dihydro-1H-1,2,4-triazol-3-yl)methyl)amino)-1,2,5-oxadiazole-3-carboximidamide (peak 1) | 389.1 |
| 127 | 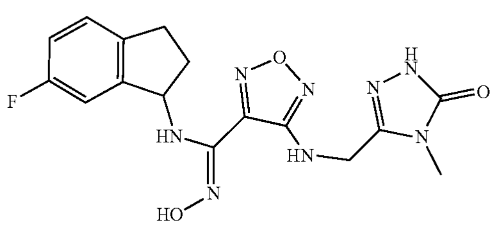 [SMILES: Cn1c(CNc2nonc2/C(=N/O)NC2CCc3ccc(F)cc32)n[nH]c1=O] | N-(6-fluoro-2,3-dihydro-1H-inden-1-yl)-N'-hydroxy-4-(((4-methyl-5-oxo-4,5-dihydro-1H-1,2,4-triazol-3-yl)methyl)amino)-1,2,5-oxadiazole-3-carboximidamide (peak 2) | 389.1 |
| 128 | 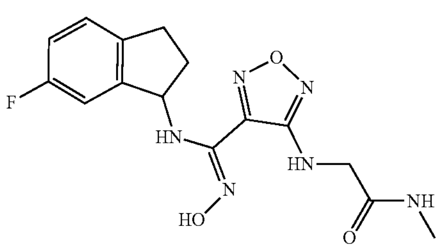 [SMILES: CNC(=O)CNc1nonc1/C(=N/O)NC1CCc2ccc(F)cc21] | (Z)-2-((4-(N-(6-fluoro-2,3-dihydro-1H-inden-1-yl)-N'-hydroxycarbamimidoyl)-1,2,5-oxadiazol-3-yl)amino)-N-methylacetamide | 349.1 |

TABLE 2-continued

Examples 55-165

| Ex. # | Structure | Chemical Name | Mass [M + H]+ |
|---|---|---|---|
| 129 | 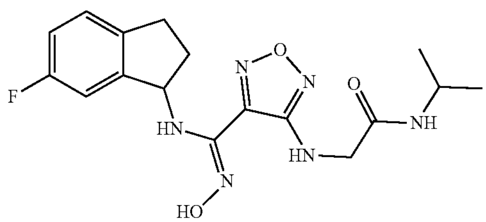 [SMILES: CC(C)NC(=O)CNc1nonc1/C(=N/O)NC1CCc2ccc(F)cc21] | 2-((4-(N-(6-fluoro-2,3-dihydro-1H-inden-1-yl)-N'-hydroxycarbamimidoyl)-1,2,5-oxadiazol-3-yl)amino)-N-isopropylacetamide (peak 1) | 377.2 |
| 130 | 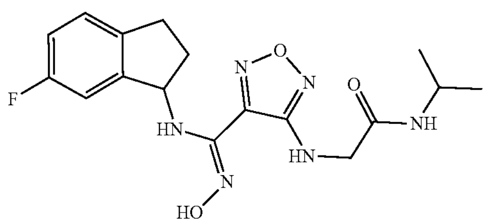 [SMILES: CC(C)NC(=O)CNc1nonc1/C(=N/O)NC1CCc2ccc(F)cc21] | 2-((4-(N-(6-fluoro-2,3-dihydro-1H-inden-1-yl)-N'-hydroxycarbamimidoyl)-1,2,5-oxadiazol-3-yl)amino)-N-isopropylacetamide (peak 2) | 377.2 |
| 131 | 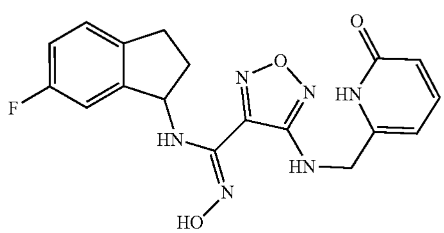 [SMILES: O=c1cccc(CNc2nonc2/C(=N/O)NC2CCc3ccc(F)cc32)[nH]1] | N-(6-fluoro-2,3-dihydro-1H-inden-1-yl)-N'-hydroxy-4-(((6-oxo-1,6-dihydropyridin-2-yl)methyl)amino)-1,2,5-oxadiazole-3-carboximidamide (peak 1) | 385.1 |
| 132 | 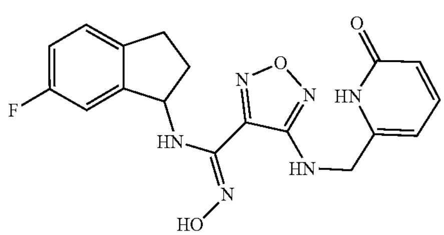 [SMILES: O=c1cccc(CNc2nonc2/C(=N/O)NC2CCc3ccc(F)cc32)[nH]1] | N-(6-fluoro-2,3-dihydro-1H-inden-1-yl)-N'-hydroxy-4-(((6-oxo-1,6-dihydropyridin-2-yl)methyl)amino)-1,2,5-oxadiazole-3-carboximidamide (peak 2) | 385.1 |
| 133 | 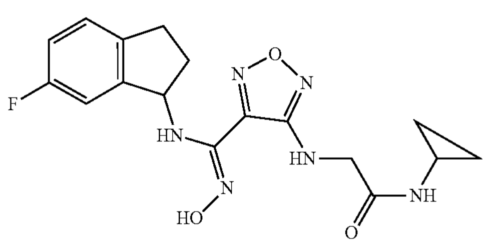 [SMILES: O=C(CNc1nonc1/C(=N/O)NC1CCc2ccc(F)cc21)NC1CC1] | N-cyclopropyl-2-((4-(N-(6-fluoro-2,3-dihydro-1H-inden-1-yl)-N'-hydroxycarbamimidoyl)-1,2,5-oxadiazol-3-yl)amino)acetamide (peak 1) | 375.2 |
| 134 | 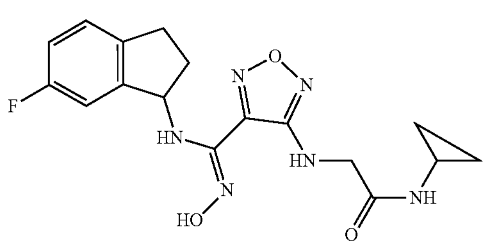 [SMILES: O=C(CNc1nonc1/C(=N/O)NC1CCc2ccc(F)cc21)NC1CC1] | N-cyclopropyl-2-((4-(N-(6-fluoro-2,3-dihydro-1H-inden-1-yl)-N'-hydroxycarbamimidoyl)-1,2,5-oxadiazol-3-yl)amino)acetamide (peak 2) | 375.2 |

TABLE 2-continued

Examples 55-165

| Ex. # | Structure | Chemical Name | Mass [M + H]+ |
|---|---|---|---|
| 135 | 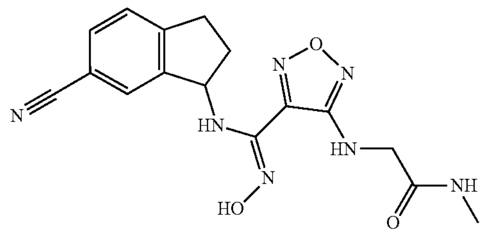 [SMILES: CNC(=O)CNc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)amino)-N-methylacetamide (peak 1) | 356.1 |
| 136 | 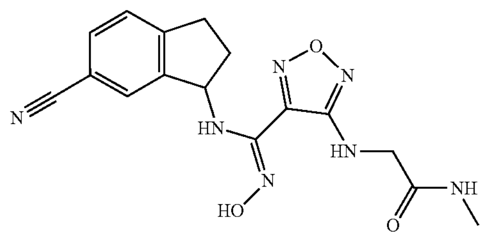 [SMILES: CNC(=O)CNc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)amino)-N-methylacetamide (peak 2) | 356.1 |
| 137 | 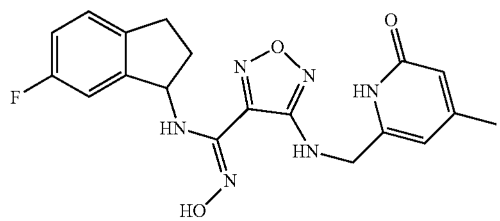 [SMILES: Cc1cc(CNc2nonc2/C(=N/O)NC2CCc3ccc(F)cc32)[nH]c(=O)c1] | N-(6-fluoro-2,3-dihydro-1H-inden-1-yl)-N'-hydroxy-4-(((4-methyl-6-oxo-1,6-dihydropyridin-2-yl)methyl)amino)-1,2,5-oxadiazole-3-carboximidamide | 399.2 |
| 138 | 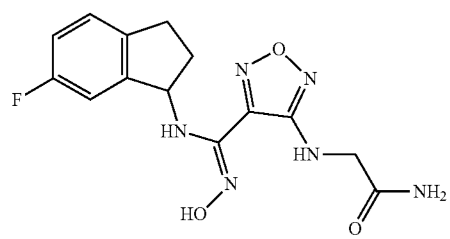 [SMILES: NC(=O)CNc1nonc1/C(=N/O)NC1CCc2ccc(F)cc21] | 2-((4-(N-(6-fluoro-2,3-dihydro-1H-inden-1-yl)-N'-hydroxycarbamimidoyl)-1,2,5-oxadiazol-3-yl)amino)acetamide (peak 1) | 335.1 |
| 139 | 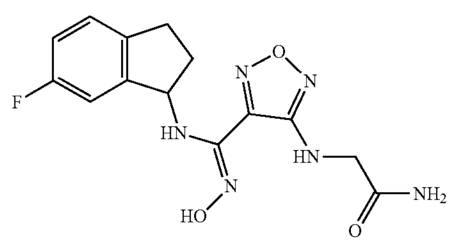 [SMILES: NC(=O)CNc1nonc1/C(=N/O)NC1CCc2ccc(F)cc21] | 2-((4-(N-(6-fluoro-2,3-dihydro-1H-inden-1-yl)-N'-hydroxycarbamimidoyl)-1,2,5-oxadiazol-3-yl)amino)acetamide (peak 2) | 335.1 |
| 140 | 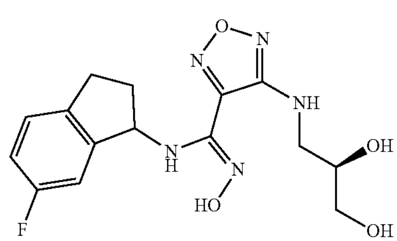 [SMILES: OC[C@H](O)CNc1nonc1/C(=N/O)NC1CCc2ccc(F)cc21] | 4-(((R)-2,3-dihydroxypropyl)amino)-N-(6-fluoro-2,3-dihydro-1H-inden-1-)-N'-hydroxy-1,2,5-oxadiazole-3-carboximidamide (peak 1) | 352.1 |

TABLE 2-continued

Examples 55-165

| Ex. # | Structure | Chemical Name | Mass [M + H]+ |
|---|---|---|---|
| 141 | 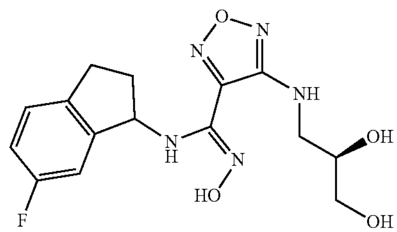 [SMILES: OC[C@H](O)CNc1nonc1/C(=N/O)NC1CCc2ccc(F)cc21] | 4-(((R)-2,3-dihydroxypropyl)amino)-N-(6-fluoro-2,3-dihydro-1H-inden-1-yl)-N'-hydroxy-1,2,5-oxadiazole-3-carboximidamide (peak 2) | 352.1 |
| 142 | 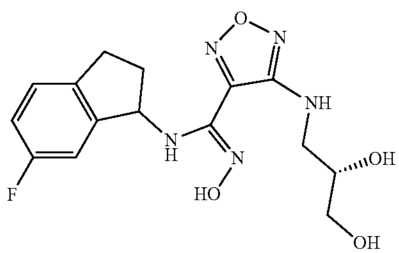 [SMILES: OC[C@@H](O)CNc1nonc1/C(=N/O)NC1CCc2ccc(F)cc21] | 4-(((S)-2,3-dihydroxypropyl)amino)-N-(6-fluoro-2,3-dihydro-1H-inden-1-yl)-N'-hydroxy-1,2,5-oxadiazole-3-carboximidamide (peak 1) | 352.1 |
| 143 | 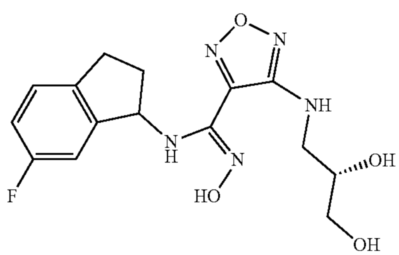 [SMILES: OC[C@@H](O)CNc1nonc1/C(=N/O)NC1CCc2ccc(F)cc21] | 4-(((S)-2,3-dihydroxypropyl)amino)-N-(6-fluoro-2,3-dihydro-1H-inden-1-yl)-N'-hydroxy-1,2,5-oxadiazole-3-carboximidamide (peak 2) | 352.1 |
| 144 | 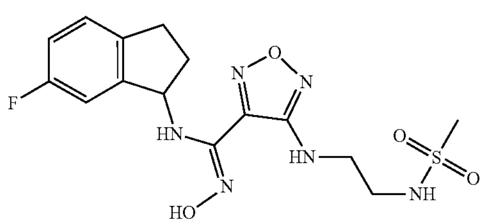 [SMILES: CS(=O)(=O)NCCNc1nonc1/C(=N/O)NC1CCc2ccc(F)cc21] | N-(6-fluoro-2,3-dihydro-1H-inden-1-yl)-N'-hydroxy-4-((2-(methylsulfonamido)ethyl)amino)-1,2,5-oxadiazole-3-carboximidamide (peak 1) | 399.1 |
| 145 | 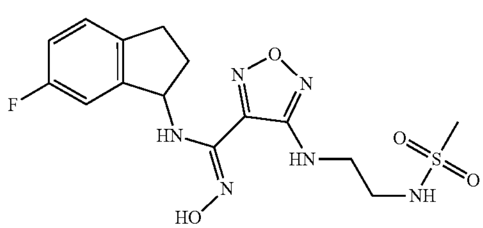 [SMILES: CS(=O)(=O)NCCNc1nonc1/C(=N/O)NC1CCc2ccc(F)cc21] | N-(6-fluoro-2,3-dihydro-1H-inden-1-yl)-N'-hydroxy-4-((2-(methylsulfonamido)ethyl)amino)-1,2,5-oxadiazole-3-carboximidamide (peak 2) | 399.1 |
| 146 | 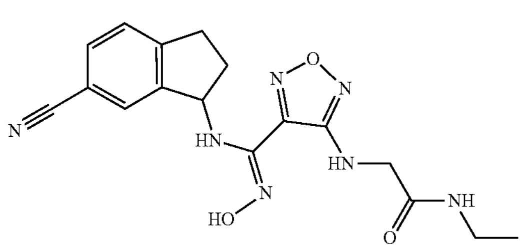 [SMILES: CCNC(=O)CNc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)amino)-N-ethylacetamide | 370.2 |

TABLE 2-continued

Examples 55-165

| Ex. # | Structure | Chemical Name | Mass [M + H]+ |
|---|---|---|---|
| 147 | 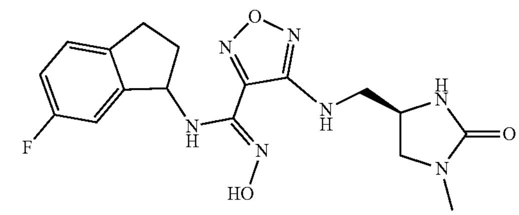 [SMILES: CN1C[C@@H](CNc2nonc2/C(=N/O)NC2CCc3ccc(F)cc32)NC1=O] | N-(6-fluoro-2,3-dihydro-1H-inden-1-yl)-N'-hydroxy-4-((((R)-1-methyl-2-oxoimidazolidin-4-yl)methyl)amino)-1,2,5-oxadiazole-3-carboximidamide | 390.2 |
| 148 | 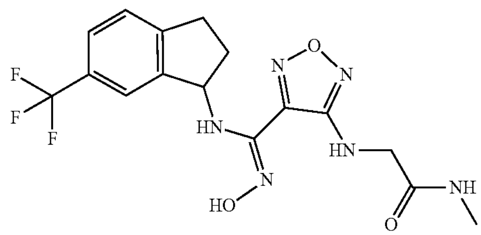 [SMILES: CNC(=O)CNc1nonc1/C(=N/O)NC1CCc2ccc(C(F)(F)F)cc21] | 2-((4-(N'-hydroxy-N-(6-(trifluoromethyl)-2,3-dihydro-1H-inden-1-yl)carbamimidoyl)-1,2,5-oxadiazol-3-yl)amino)-N-methylacetamide | 399.1 |
| 149 | 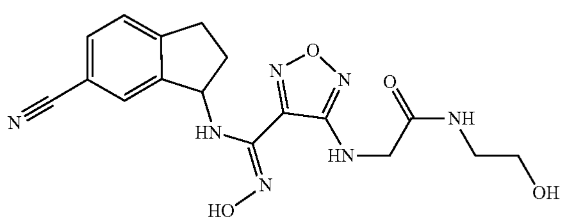 [SMILES: N#Cc1ccc2c(c1)C(N/C(=N\O)c1nonc1NCC(=O)NCCO)CC2] | 2-((4-(N-(6-cyano-2,3-dihydro-1H-inden-1-yl)-N'-hydroxycarbamimidoyl)-1,2,5-oxadiazol-3-yl)amino)-N-(2-hydroxyethyl)acetamide | 386.1 |
| 150 | 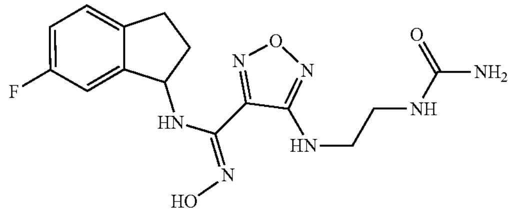 [SMILES: NC(=O)NCCNc1nonc1/C(=N/O)NC1CCc2ccc(F)cc21] | N-(6-fluoro-2,3-dihydro-1H-inden-1-yl)-N'-hydroxy-4-((2-ureidoethyl)amino)-1,2,5-oxadiazole-3-carboximidamide (peak 1) | 364.2 |
| 151 | 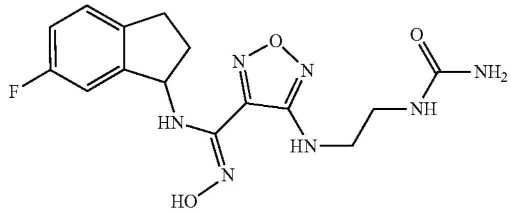 [SMILES: NC(=O)NCCNc1nonc1/C(=N/O)NC1CCc2ccc(F)cc21] | N-(6-fluoro-2,3-dihydro-1H-inden-1-yl)-N'-hydroxy-4-((2-ureidoethyl)amino)-1,2,5-oxadiazole-3-carboximidamide (peak 2) | 364.2 |
| 152 | 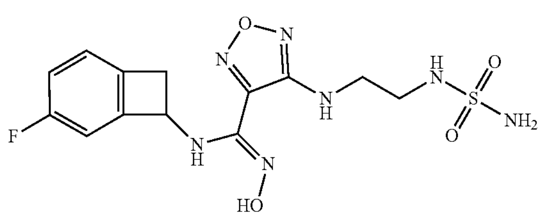 [SMILES: NS(=O)(=O)NCCNc1nonc1/C(=N/O)NC1Cc2ccc(F)cc21] | N-(4-fluorobicyclo[4.2.0]octa-1(6),2,4-trien-7-yl)-N'-hydroxy-4-((2-(sulfamoylamino)ethyl)amino)-1,2,5-oxadiazole-3-carboximidamide | 386.1 |
| 153 | 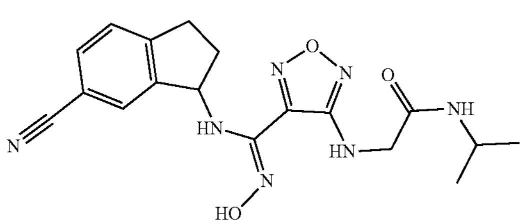 [SMILES: CC(C)NC(=O)CNc1nonc1/C(=N/O)NC1CCc2ccc(C#N)cc21] | 2-((4-(N-(6-cyano-2,3-dihydro-1H-inden-1-yl)-N'-hydroxycarbamimidoyl)-1,2,5-oxadiazol-3-yl)amino)-N-isopropylacetamide | 384.2 |

TABLE 2-continued

Examples 55-165

| Ex. # | Structure | Chemical Name | Mass [M + H]+ |
|---|---|---|---|
| 154 | 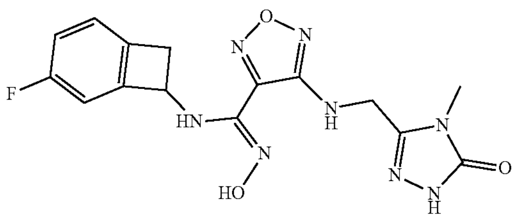 [SMILES: Cn1c(CNc2nonc2/C(=N/O)NC2Cc3ccc(F)cc32)n[nH]c1=O] | N-(4-fluorobicyclo[4.2.0]octa-1(6),2,4-trien-7-yl)-N'-hydroxy-4-(((4-methyl-5-oxo-4,5-dihydro-1H-1,2,4-triazol-3-yl)methyl)amino)-1,2,5-oxadiazole-3-carboximidamide | 375.2 |
| 155 | 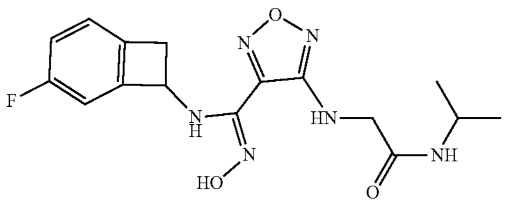 [SMILES: CC(C)NC(=O)CNc1nonc1/C(=N/O)NC1Cc2ccc(F)cc21] | 2-((4-(N-(4-fluorobicyclo[4.2.0]octa-1(6),2,4-trien-7-yl)-N'-hydroxycarbamimidoyl)-1,2,5-oxadiazol-3-yl)amino)-N-isopropylacetamide (peak 1) | 363.2 |
| 156 | 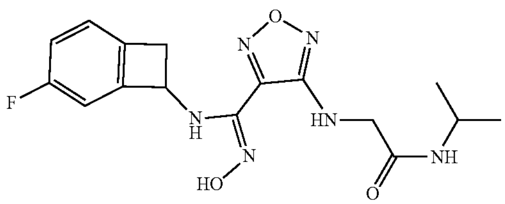 [SMILES: CC(C)NC(=O)CNc1nonc1/C(=N/O)NC1Cc2ccc(F)cc21] | 2-((4-(N-(4-fluorobicyclo[4.2.0]octa-1(6),2,4-trien-7-yl)-N'-hydroxycarbadoyl)-1,2,5-oxadiazol-3-yl)amino)-N-isopropylacetamide (peak 2) | 363.2 |
| 157 | 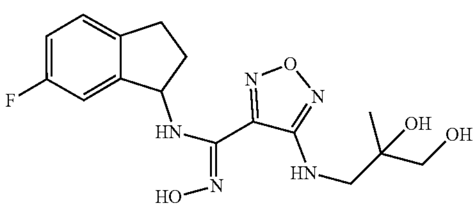 [SMILES: CC(O)(CO)CNc1nonc1/C(=N/O)NC1CCc2ccc(F)cc21] | 4-((2,3-dihydroxy-2-methylpropyl)amino)-N-(6-fluoro-2,3-dihydro-1H-inden-1-yl)-N'-hydroxy-1,2,5-oxadiazole-3-carboximidamide | 366.2 |
| 158 | 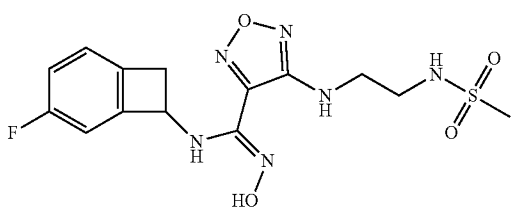 [SMILES: CS(=O)(=O)NCCNc1nonc1/C(=N/O)NC1Cc2ccc(F)cc21] | N-(4-fluorobicyclo[4.2.0]octa-1(6),2,4-trien-7-yl-N'-hydrox-4-((2-(methylsulfonamido)ethyl)amino)-1,2,5-oxadiazole-3-carboximidamide | 385.1 |
| 159 | 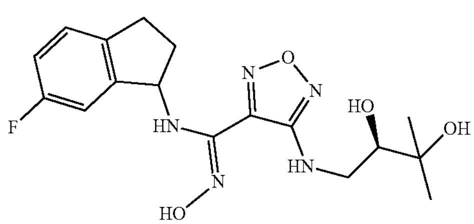 [SMILES: CC(C)(O)[C@H](O)CNc1nonc1/C(=N/O)NC1CCc2ccc(F)cc21] | 4-(((R)-2,3-dihydroxy-3-methylbutyl)amino)-N-(6-fluoro-2,3-dihydro-1H-inden-1-yl)-N'-hydroxy-1,2,5-oxadiazole-3-carboximidamide | 380.2 |
| 160 | 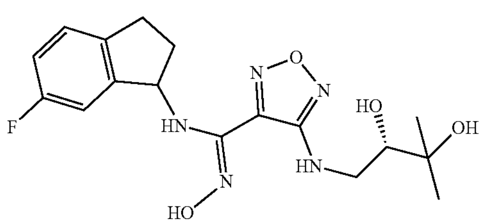 [SMILES: CC(C)(O)[C@@H](O)CNc1nonc1/C(=N/O)NC1CCc2ccc(F)cc21] | 4-(((S)-2,3-dihydroxy-3-methylbutyl)amino)-N-(6-fluoro-2,3-dihydro-1H-inden-1-yl)-N'-hydroxy-1,2,5-oxadiazole-3-carboximidamide | 380.2 |

TABLE 2-continued

Examples 55-165

| Ex. # | Structure | Chemical Name | Mass [M + H]+ |
|---|---|---|---|
| 161 | 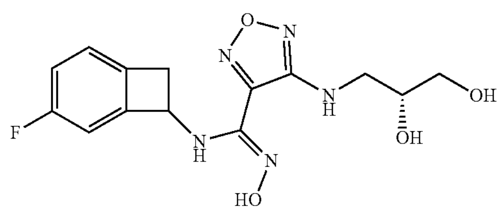 [SMILES: OC[C@H](O)CNc1nonc1/C(=N/O)NC1Cc2ccc(F)cc21] | 4-(((R)-2,3-dihydroxypropyl)amino)-N-(4-fluorobicyclo[4.2.0]octa-1,3,5-trien-7-yl)-N'-hydroxy-1,2,5-oxadiazole-3-carboximidamide | 338.1 |
| 162 | 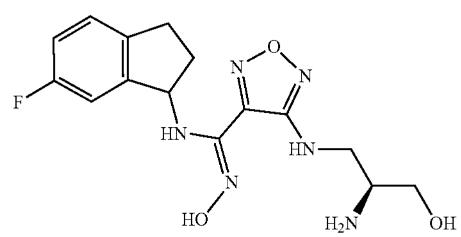 [SMILES: N[C@H](CO)CNc1nonc1/C(=N/O)NC1CCc2ccc(F)cc21] | 4-(((S)-2-amino-3-hydroxypropyl)amino)-N-(6-fluoro-2,3-dihydro-1H-inden-1-yl)-N'-hydroxy-1,2,5-oxadiazole-3-carboximidamide | 351.1 |
| 163 | 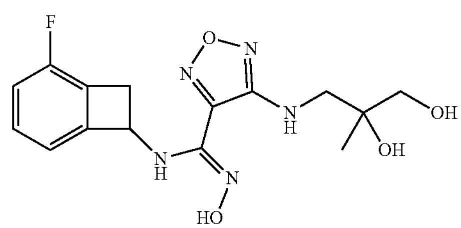 [SMILES: CC(O)(CO)CNc1nonc1/C(=N/O)NC1Cc2c(F)cccc21] | 4-((2,3-dihydroxy-2-methylpropyl)amino)-N-(2-fluorobicyclo[4.2.0]octa-1,3,5-trien-7-yl)-N'-hydroxy-1,2,5-oxadiazole-3-carboximidamide | 352.1 |
| 164 | 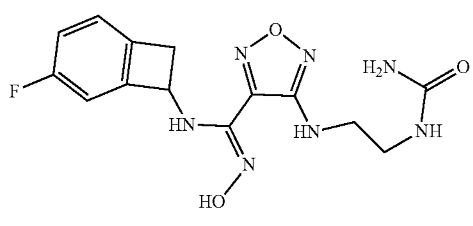 [SMILES: NC(=O)NCCNc1nonc1/C(=N/O)NC1Cc2ccc(F)cc21] | N-(4-fluorobicyclo[4.2.0]octa-1(6),2,4-trien-7-yl)-N'-hydroxy-4-((2-ureidoethyl)amino)-1,2,5-oxadiazole-3-carboximidamide | 350.1 |
| 165 | 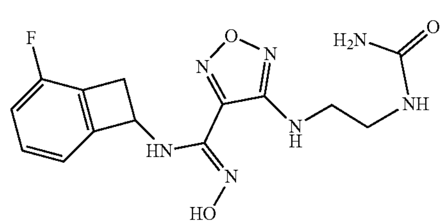 [SMILES: NC(=O)NCCNc1nonc1/C(=N/O)NC1Cc2c(F)cccc21] | N-(2-fluorobicyclo[4.2.0]octa-1(6),2,4-trien-7-yl)-N'-hydroxy-4-((2-ureidoethyl)amino)-1,2,5-oxadiazole-3-carboximidamide | 350.1 |

Examples 166 and 167. N—((S)-4-fluorobicyclo[4.2.0]octa-1(6),2,4-trien-7-yl)-N'-hydroxy-4-(((S)-2-hydroxy-3-(sulfamoylamino)propyl)amino)-1,2,5-oxadiazole-3-carboximidamide and N—((S)-4-fluorobicyclo[4.2.0]octa-1(6),2,4-trien-7-yl)-N'-hydroxy-4-(((R)-2-hydroxy-3-(sulfamoylamino)propyl)amino)-1,2,5-oxadiazole-3-carboximidamide

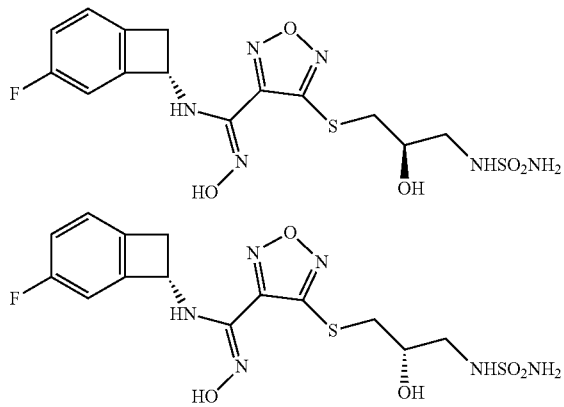

Step 1. tert-butyl (3-((4-(4-((S)-4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)-2-hydroxypropyl)carbamate

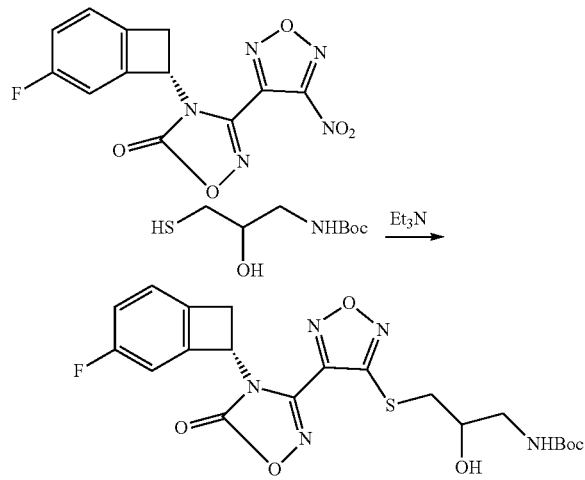

To a solution of (S)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one (224 mg, 0.70 mmol) in THF (4 mL) at RT was added a solution of tert-butyl (2-hydroxy-3-mercaptopropyl) carbamate (160 mg, 0.77 mmol) in THF (2 mL), followed by the addition of Et₃N (196 µL, 1.40 mmol). The mixture was stirred at RT for 1.5 h, then partitioned between EtOAc and sat. NaHCO₃. The organic layer was separated, washed with brine, dried over MgSO₄, and concentrated in vacuo to give the crude title compound, which was used directly in the next step. LCMS m/z 502 [M+Na]⁺.

Step 2. 3-(4-((3-amino-2-hydroxypropyl)thio)-1,2,5-oxadiazol-3-yl)-4-((S)-4-fluorobicyclo[4.2.0]octa-1(6),2,4-trien-7-yl)-1,2,4-oxadiazol-5(4H)-one

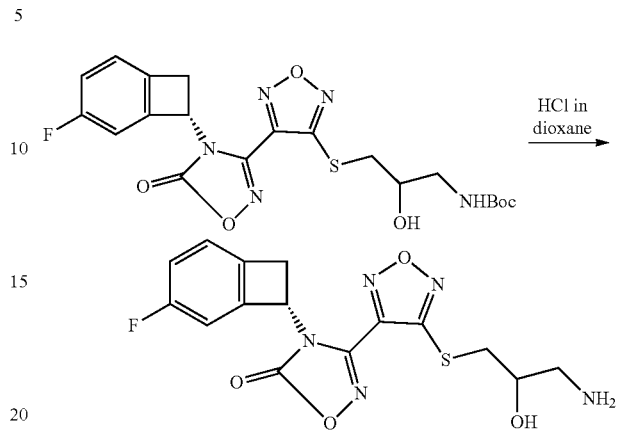

To a solution of tert-butyl (3-((4-(4-((S)-4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)-2-hydroxypropyl)carbamate (150 mg, 0.313 mmol) in dioxane (1 mL) was added HCl (4.0 M in dioxane, 2 mL). The mixture was stirred at RT for 5 h, and concentrated in vacuo to give the crude title compound, which was used directly in the next step. LCMS m/z 380 [M+1]⁺.

Step 3. tert-butyl N-(3-((4-(4-((S)-4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)-2-hydroxypropyl)sulfamoylcarbamate

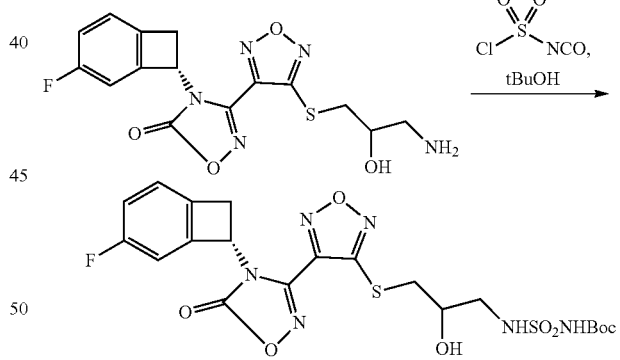

To a solution of sulfurisocyanatidic chloride (58 mg, 0.41 mmol) in CH₂Cl₂ (0.5 mL) at 0° C. was added a solution of t-BuOH (0.039 mL, 0.41 mmol) in CH₂Cl₂ (0.5 mL). The mixture was stirred at 0° C. for 1 h. The resulting solution was added into a pre-mixed mixture of 3-(4-((3-amino-2-hydroxypropyl)thio)-1,2,5-oxadiazol-3-yl)-4-((S)-4-fluorobicyclo[4.2.0]octa-1(6),2,4-trien-7-yl)-1,2,4-oxadiazol-5(4H)-one (119 mg, 0.314 mmol) and Et₃N (131 µL, 0.94 mmol) in DCM (2 mL) at 0° C. The reaction mixture was stirred at RT for 1 h, diluted with sat. NaHCO₃, and extracted with EtOAc. The organic layer was washed with brine, dried over MgSO₄, filtered, and concentrated in vacuo to give the crude title compound, which was used directly in the next step. LCMS 581 [M+1]⁺.

Step 4. N—((S)-4-fluorobicyclo[4.2.0]octa-1(6),2,4-trien-7-yl)-N'-hydroxy-4-(((S)-2-hydroxy-3-(sulfamoylamino)propyl)amino)-1,2,5-oxadiazole-3-carboximidamide and N—((S)-4-fluorobicyclo[4.2.0]octa-1(6),2,4-trien-7-yl)-N'-hydroxy-4-(((R)-2-hydroxy-3-(sulfamoylamino)propyl)amino)-1,2,5-oxadiazole-3-carboximidamide

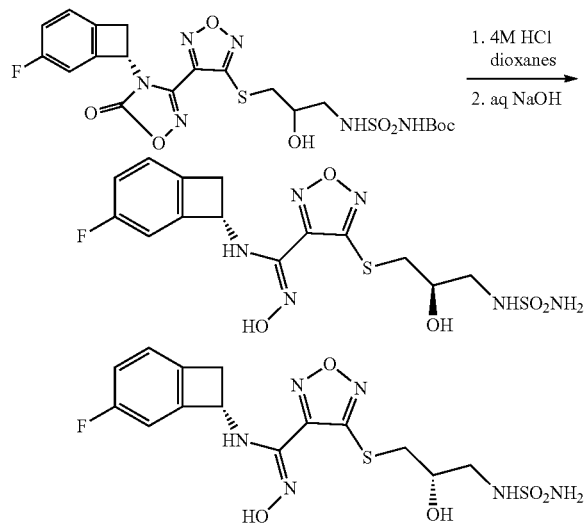

To a solution of tert-butyl N-(3-((4-(4-((S)-4-fluorobicyclo[4.2.0]octa-1(6),2,4-trien-7-yl)-5-oxo-4,5-dihydro-1,2,4-oxadiazol-3-yl)-1,2,5-oxadiazol-3-yl)thio)-2-hydroxypropyl)sulfamoylcarbamate (170 mg, 0.30 mmol) in dioxane (0.6 mL) at RT was added 4 M HCl in dioxane (2 mL). The mixture was stirred at RT for 14 h, quenched with sat NaCHO$_3$, and extracted with EtOAc. The organic layer was separated, washed with brine, dried over MgSO$_4$, filtered, and concentrated in vacuo. The residue was dissolved in THF (1 mL)/MeOH (1 mL). To the resulting solution was added 6 M aqueous NaOH (0.20 mL, 1.2 mmol). The mixture was stirred at RT for 4 h, neutralized with 2N aqueous HCl, extracted with EtOAc. The organic layer was separated, washed with aq NaHCO$_3$, brine, dried over MgSO$_4$, filtered, and concentrated in vacuo. The residue was purified by flash chromatography (0-50% EtOAc/hexanes) to give the product as a mixture of two enantiomers.

Chiral SFC separation produced the two title compounds. Chiral separation conditions: Chiralpak, AD, 21×250 (mm); Modifier: Methanol+0.25% Dimethyl Ethyl Amine; % modifier in CO$_2$: 35. Peak1: 4.4 min (tR), peak2: tR 5.5 min (tR).

Example 166 (peak 1): LCMS: 433 [M+1]$^+$; $^1$HNMR (600 MHz, DMSO-d$_6$): 10.98 (s, 1H), 7.12-7.16 (m, 1H), 7.03 (t, 1H, J=9.0 Hz), 6.91 (d, 1H, J=7.8 Hz), 6.79 (d, 1H, J=8.4 Hz), 6.46-6.56 (m, 3H), 5.32 (d, 1H, J=5.4 Hz), 5.24-5.30 (m, 1H), 3.84-3.94 (m, 1H), 3.34-3.46 (m, 2H), 3.08-3.18 (m, 2H), 2.90-3.00 (m, 2H).

Example 167 (peak 2): LCMS: 433 [M+1]$^+$; $^1$HNMR (600 MHz, DMSO-d$_6$): 10.97 (s, 1H), 7.12-7.16 (m, 1H), 7.03 (t, 1H, J=9.0 Hz), 6.91 (d, 1H, J=7.8 Hz), 6.79 (d, 1H, J=8.4 Hz), 6.46-6.56 (m, 3H), 5.32 (d, 1H, J=5.4 Hz), 5.24-5.30 (m, 1H), 3.84-3.94 (m, 1H), 3.34-3.46 (m, 2H), 3.08-3.18 (m, 2H), 2.90-3.00 (m, 2H).

Using the general methodology disclosed in the schemes, Examples 29-54 and 166-167, and general knowledge in organic synthesis, compounds in Table 3 were prepared.

TABLE 3

Examples 168-225

| Ex. # | Structure | Name | Mass [M + H]+ |
|---|---|---|---|
| 168 | 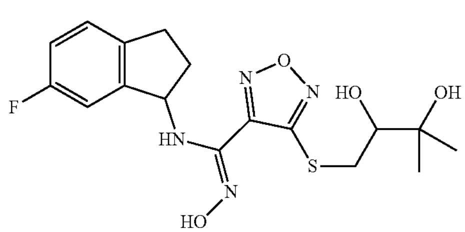 [SMILES: CC(C)(O)C(O)CSc1nonc1/C(=N/O)NC1CCc2ccc(F)cc21] | 4-[(2,3-dihydroxy-3-methylbutyl)sulfanyl]-N-(6-fluoro-2,3-dihydro-1H-inden-1-yl)-N'-hydroxy-1,2,5-oxadiazole-3-carboximidamide (peak 1) | 397.1 |
| 169 | 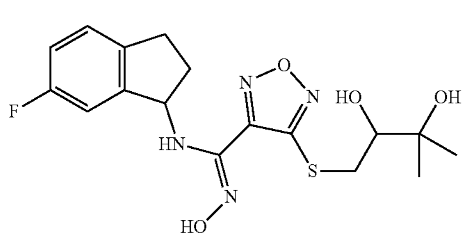 [SMILES: CC(C)(O)C(O)CSc1nonc1/C(=N/O)NC1CCc2ccc(F)cc21] | 4-[(2,3-dihydroxy-3-methylbutyl)sulfanyl]-N-(6-fluoro-2,3-dihydro-1H-inden-1-yl)-N'-hydroxy-1,2,5-oxadiazole-3-carboximidamide (peak 2) | 397.1 |

TABLE 3-continued

Examples 168-225

| Ex. # | Structure | Name | Mass [M + H]+ |
|---|---|---|---|
| 170 | 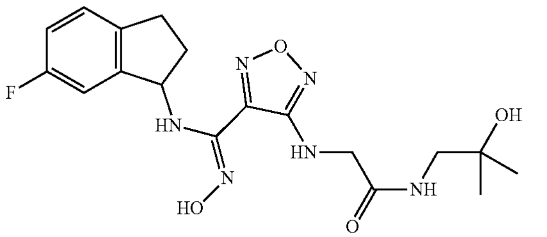 [SMILES: CC(C)(O)CNC(=O)CNc1nonc1/C(=N/O)NC1CCc2ccc(F)cc21] | N~2~-{4-[N-(6-fluoro-2,3-dihydro-1H-inden-1-yl)-N'-hydroxycarbamimidoyl]-1,2,5-oxadiazol-3-yl}-N-(2-hydroxy-2-methylpropyl)glycinamide | 407.2 |
| 171 | 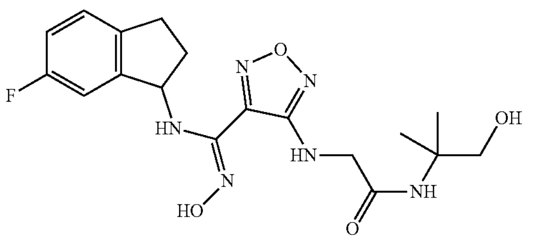 [SMILES: CC(C)(CO)NC(=O)CNc1nonc1/C(=N/O)NC1CCc2ccc(F)cc21] | N~2~-{4-[N-(6-fluoro-2,3-dihydro-1H-inden-1-yl)-N'-hydroxycarbamimidoyl]-1,2,5-oxadiazol-3-yl}-N-(2-hydroxy-2-methylpropan-2-yl)glycinamide | 407.2 |
| 172 | 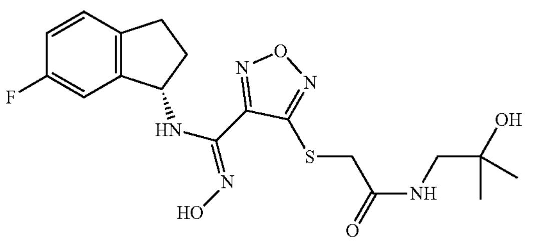 [SMILES: CC(C)(O)CNC(=O)CSc1nonc1/C(=N/O)N[C@H]1CCc2ccc(F)cc21] | 2-[(4-{N-[(1S)-6-fluoro-2,3-dihydro-1H-inden-1-yl]-N'-hydroxycarbamimidoyl}-1,2,5-oxadiazol-3-yl)sulfanyl]-N-(2-hydroxy-2-methylpropyl)acetamide | 424.1 |
| 173 | 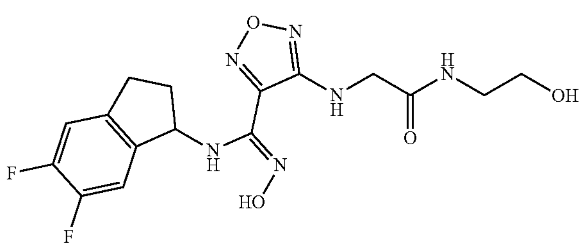 [SMILES: O=C(CNc1nonc1/C(=N/O)NC1CCc2cc(F)c(F)cc21)NCCO] | N~2~-{4-[N-(5,6-difluoro-2,3-dihydro-1H-inden-1-yl]-N'-hydroxycarbamimidoyl}-1,2,5-oxadiazol-3-yl}-N-(2-hydroxyethyl)glycinamide | 397.1 |
| 174 | 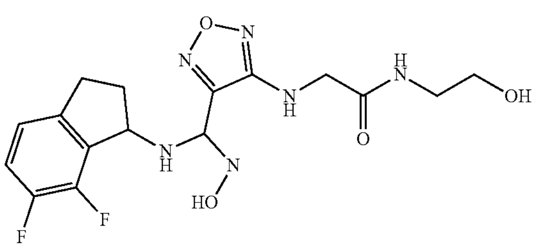 [SMILES: O=C(CNc1nonc1C(NO)NC1CCc2ccc(F)c(F)c21)NCCO] | 2-((4-(N-(6,7-difluoro-2,3-dihydro-1H-inden-1-yl)-N'-hydroxycarbamimidoyl)-1,2,5-oxadiazol-3-yl)amino)-N-(2-hydroxyethyl)acetamide | 397.1 |
| 175 | 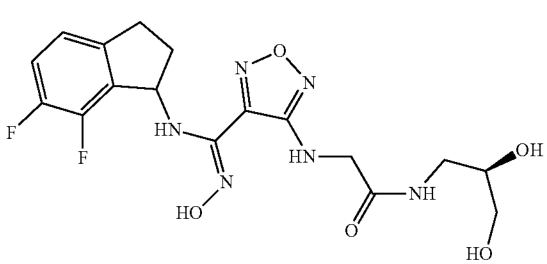 [SMILES: O=C(CNc1nonc1/C(=N/O)NC1CCc2ccc(F)c(F)c21)NC[C@@H](O)CO] | N~2~-{4-[N-(6,7-difluoro-2,3-dihydro-1H-inden-1-yl)-N'-hydroxycarbamimidoyl]-1,2,5-oxadiazol-3-yl}-N-[(2R)-2,3-dihydroxypropyl]glycinamide | 427.2 |

TABLE 3-continued

Examples 168-225

| Ex. # | Structure | Name | Mass [M + H]+ |
|---|---|---|---|
| 176 | 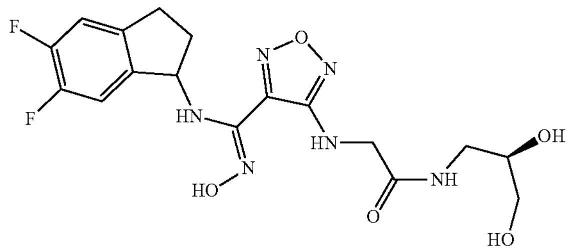 [SMILES: O=C(CNc1nonc1/C(=N/O)NC1CCc2cc(F)c(F)cc21)NC[C@@H](O)CO] | N~2~-{4-[N-(6,7-difluoro-2,3-dihydro-1H-inden-1-yl)-N'-hydroxycarbamimidoyl]-1,2,5-oxadiazol-3-yl}-N-[(2R)-2,3-dihydroxypropyl]glycinamide | 427.2 |
| 177 | 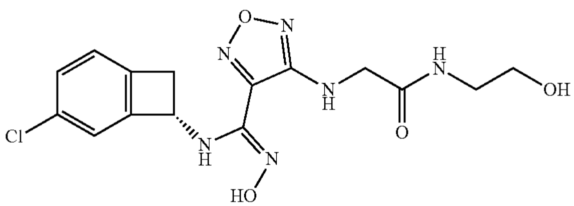 [SMILES: O=C(CNc1nonc1/C(=N/O)N[C@H]1Cc2ccc(Cl)cc21)NCCO] | N~2~-(4-{N-[(7S)-4-chlorobicyclo[4.2.0]octa-1,3,5-trien-7-yl]-N'-hydroxycarbamimidoyl}-1,2,5-oxadiazol-3-yl)-N-(2-hydroxyethyl)glycinamide | 381.1 |
| 178 | 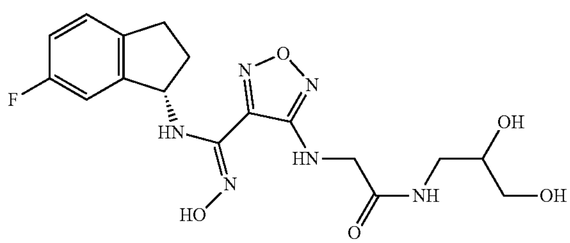 [SMILES: O=C(CNc1nonc1/C(=N/O)N[C@H]1CCc2ccc(F)cc21)NCC(O)CO] | N-(2,3-dihydroxypropyl)-N~2~-(4-{N-[(1S)-6-fluoro-2,3-dihydro-1H-inden-1-yl]-N'-hydroxycarbamimidoyl}-1,2,5-oxadiazol-3-yl)glycinamide | 409.2 |
| 179 | 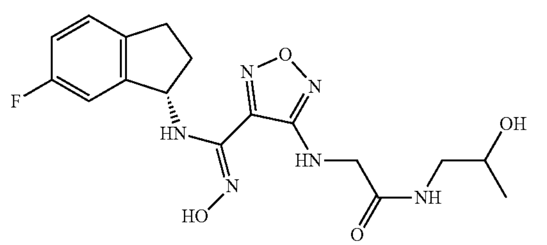 [SMILES: CC(O)CNC(=O)CNc1nonc1/C(=N/O)N[C@H]1CCc2ccc(F)cc21] | N~2~-(4-{N-[(1S)-6-fluoro-2,3-dihydro-1H-inden-1-yl]-N'-hydroxycarbamimidoyl}-1,2,5-oxadiazol-3-yl)-N-(2-hydroxypropyl)glycinamide | 393.2 |
| 180 | 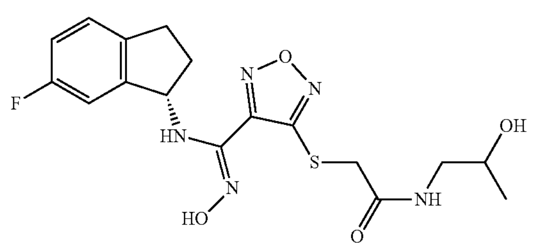 [SMILES: CC(O)CNC(=O)CSc1nonc1/C(=N/O)N[C@H]1CCc2ccc(F)cc21] | 2-[(4-{N-[(1S)-6-fluoro-2,3-dihydro-1H-inden-1-yl]-N'-hydroxycarbamimidoyl}-1,2,5-oxadiazol-3-yl)sulfanyl]-N-(2-hydroxypropyl)acetamide | 410.1 |
| 181 | 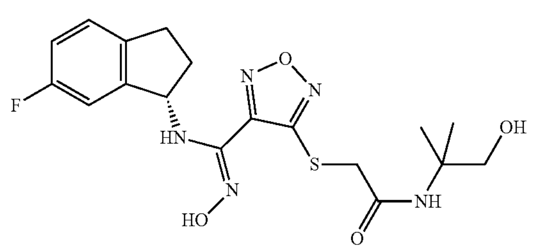 [SMILES: CC(C)(CO)NC(=O)CSc1nonc1/C(=N/O)N[C@H]1CCc2ccc(F)cc21] | 2-[(4-{N-[(1S)-6-fluoro-2,3-dihydro-1H-inden-1-yl]-N'-hydroxycarbamimidoyl}-1,2,5-oxadiazol-3-yl)sulfanyl]-N-(1-yl)acetamide | 410.1 |

US 10,988,487 B2

TABLE 3-continued

Examples 168-225

| Ex. # | Structure | Name | Mass [M + H]+ |
|---|---|---|---|
| 182 | 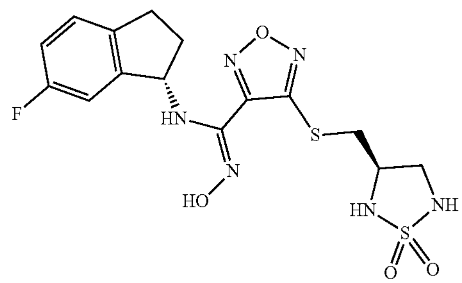 [SMILES: O=S1(=O)NC[C@H](CSc2nonc2/C(=N/O)N[C@H]2CCc3ccc(F)cc32)N1] | 4-({[(3R)-1,1-dioxo-1lambda~6~,2,5-thiadiazolidin-3-yl]methyl{sulfanyl}-N-[(1S)-6-fluoro-2,3-dihydro-1H-inden-1-yl]-N'-hydroxy-1,2,5-oxadiazole-3-carboximidamide | 429.1 |
| 183 | 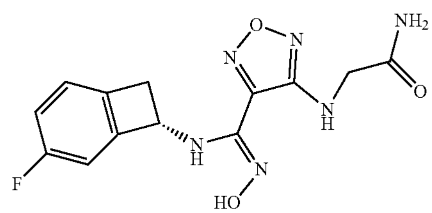 [SMILES: NC(=O)CNc1nonc1/C(=N/O)N[C@H]1Cc2ccc(F)cc21] | N~2~-(4-{N-[(7S)-4-fluorobicyclo[4.2.0]octa-1,3,5-trien-7-yl]-N'-hydroxycarbamimidoyl}-1,2,5-oxadiazol-3-yl)glycinamide | 321.1 |
| 184 | 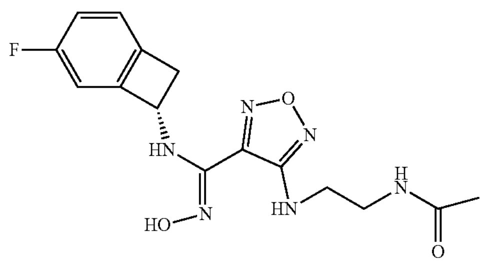 [SMILES: CC(=O)NCCNc1nonc1/C(=N/O)N[C@H]1Cc2ccc(F)cc21] | N~2~-(4-{N-[(7S)-4-fluorobicyclo[4.2.0]octa-1,3,5-trien-7-yl]-N'-hydroxycarbamimidoyl}-1,2,5-oxadiazol-3-yl)amino]ethyl}acetamide | 349.1 |
| 185 | 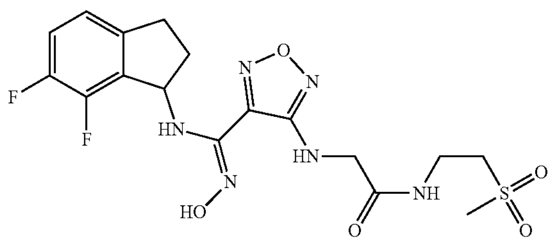 [SMILES: CS(=O)(=O)CCNC(=O)CNc1nonc1/C(=N/O)NC1CCc2ccc(F)c(F)c21] | N~2~-{4-[N-(6,7-difluoro-2,3-dihydro-1H-inden-1-yl)-N'-hydroxycarbamimidoyl]-1,2,5-oxadiazol-3-yl}-N-[2-(methylsulfonyl)ethyl)glycinamide | 459.1 |
| 186 | 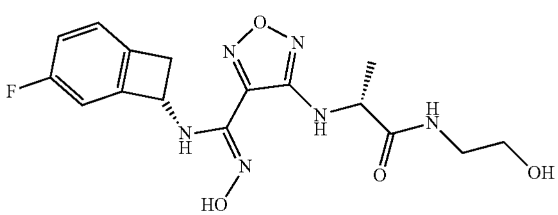 | N~2~-(4-{N-[(7S)-4-fluorobicyclo[4.2.0]octa-1,3,5-trien-7-yl]-N'-hydroxycarbamimidoyl}-1,2,5-oxadiazol-3-yl)-N-(2-hydroxyethyl)-D-alaninamide | 379.2 |
| 187 | 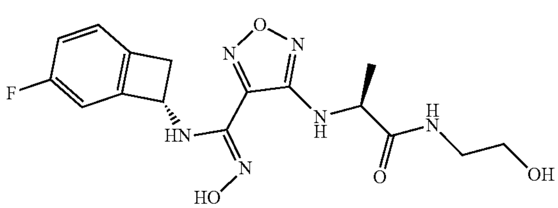 [SMILES: C[C@H](Nc1nonc1/C(=N/O)N[C@H]1Cc2ccc(F)cc21)C(=O)NCCO] | N~2~-(4-{N-[(7S)-4-fluorobicyclo[4.2.0]octa-1,3,5-trien-7-yl]-N'-hydroxycarbamimidoyl}-1,2,5-oxadiazol-3-yl)-N-(2-hydroxyethyl)-L-alaninamide | 379.2 |

TABLE 3-continued

Examples 168-225

| Ex. # | Structure | Name | Mass [M + H]+ |
|---|---|---|---|
| 188 | 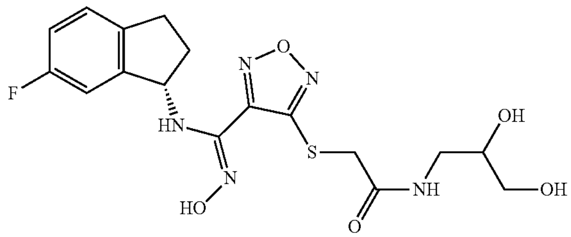 [SMILES: O=C(CSc1nonc1/C(=N/O)N[C@H]1CCc2ccc(F)cc21)NCC(O)CO] | N-(2,3-dihydroxypropyl)-2-[(4-{N-[(1S)-6-fluoro-2,3-dihydro-1H-inden-1-yl]-N'-hydroxycarbadoyl}-1,2,5-oxadiazol-3-yl)sulfanyl]acetamide | 426.1 |
| 189 | 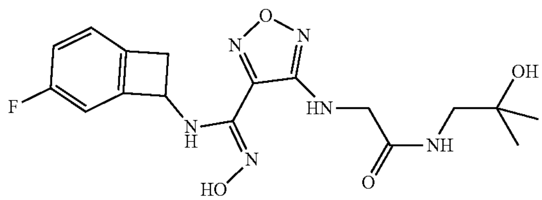 [SMILES: CC(C)(O)CNC(=O)CNc1nonc1/C(=N/O)NC1Cc2ccc(F)cc21] | N~2~-{4-[N-(4-fluorobicyclo[4.2.0]octa-1,3,5-trien-7-yl)-N'-hydroxycarbamimidoyl]-1,2,5-oxadiazol-3-yl}-N-(2-hydroxy-2-methylpropyl)glycinamide | 393.2 |
| 190 | 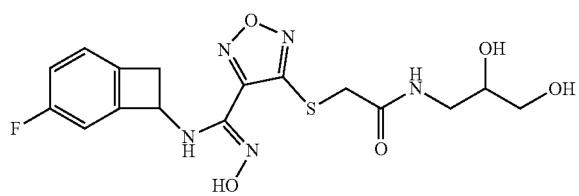 [SMILES: O=C(CSc1nonc1/C(=N/O)NC1Cc2ccc(F)cc21)NCC(O)CO] | N-(2,3-dihydroxypropyl)-2-({4-[N-(4-fluorobicyclo[4.2.0]octa-1,3,5-trien-7-yl)-N'-hydroxycarbamimidoyl]-1,2,5-oxadiazol-3-yl}sulfanyl)acetamide | 412.1 |
| 191 | 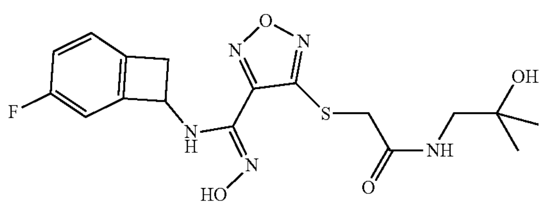 [SMILES: CC(C)(O)CNC(=O)CSc1nonc1/C(=N/O)NC1Cc2ccc(F)cc21] | 2-({4-[N-(4-fluorobicyclo[4.2.0]octa-1,3,5-trien-7-yl)-N'-hydroxycarbamimidoyl]-1,2,5-oxadiazol-3-yl}sulfanyl)-N-(2-hydroxy-2-methylpropyl)acetamide | 410.1 |
| 192 | 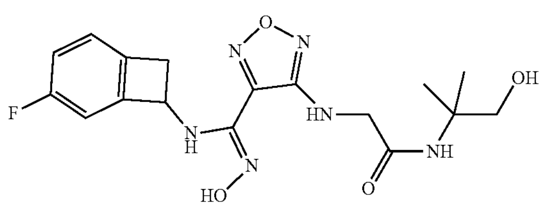 [SMILES: CC(C)(CO)NC(=O)CNc1nonc1/C(=N/O)NC1Cc2ccc(F)cc21] | N~2~-{4-[N-(4-fluorobicyclo[4.2.0]octa-1,3,5-trien-7-yl)-N'-hydroxycarbamimidoyl]-1,2,5-oxadiazol-3-yl}-N-(1-hydroxy-2-methylpropan-2-yl)glycinamide | 393.2 |
| 193 | 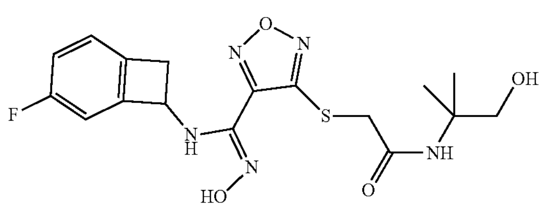 [SMILES: CC(C)(CO)NC(=O)CSc1nonc1/C(=N/O)NC1Cc2ccc(F)cc21] | 2-({4-[N-(4-fluorobicyclo[4.2.0]octa-1,3,5-trien-7-yl)-N'-hydroxycarbamimidoyl]-1,2,5-oxadiazol-3-yl}sulfanyl)-N-(1-hydroxy-2-methylpropan-2-yl)acetamide | 410.1 |
| 194 | 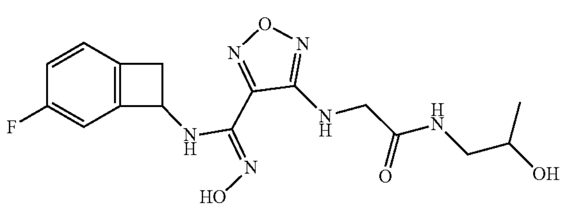 [SMILES: CC(O)CNC(=O)CNc1nonc1/C(=N/O)NC1Cc2ccc(F)cc21] | N~2~-{4-[N-(4-fluorobicyclo[4.2.0]octa-1,3,5-trien-7-)-N'-hydroxycarbamimidoyl]-1,2,5-oxadiazol-3-yl}-N-(2-hydroxypropyl)glycinamide | 379.2 |

TABLE 3-continued

Examples 168-225

| Ex. # | Structure | Name | Mass [M + H]+ |
|---|---|---|---|
| 195 | 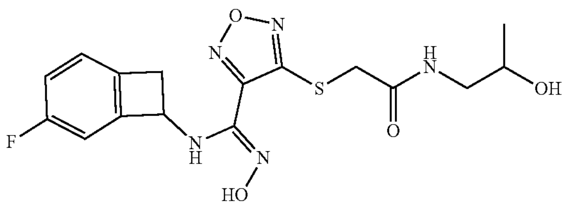 [SMILES: CC(O)CNC(=O)CSc1nonc1/C(=N/O)NC1Cc2ccc(F)cc21] | 2-({4-[N-(4-fluorobicyclo[4.2.0]octa-1,3,5-trien-7-yl)-N'-hydroxycarbamimidoyl]-1,2,5-oxadiazol-3-yl}sulfanyl)-N-(2-hydroxypropyl)acetamide | 396.1 |
| 196 | 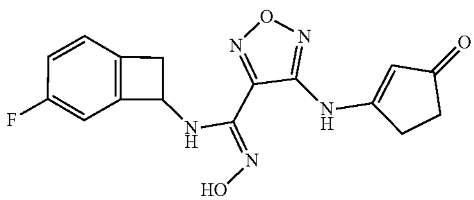 [SMILES: O=C1C=C(Nc2nonc2/C(=N/O)NC2Cc3ccc(F)cc32)CC1] | N-(4-fluorobicyclo[4.2.0]octa-1,3,5-trien-7-yl)-N'-hydroxy-4-[(3-oxocyclopent-1-en-1-yl)amino]-1,2,5-oxadiazole-3-carboximidamide | 344.1 |
| 197 | 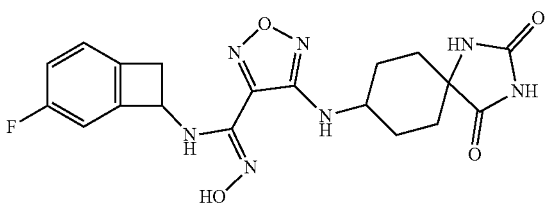 [SMILES: O=C1NC(=O)C2(CCC(Nc3nonc3/C(=N/O)NC3Cc4ccc(F)cc43)CC2)N1] | 4-[(2,4-dioxo-1,3-diazaspiro[4.5]decan-8-yl)amino]-N-(4-fluorobicyclo[4.2.0]octa-1,3,5-trien-7-yl)-N'-hydroxy-1,2,5-oxadiazole-3-carboximidamide | 430.2 |
| 198 | 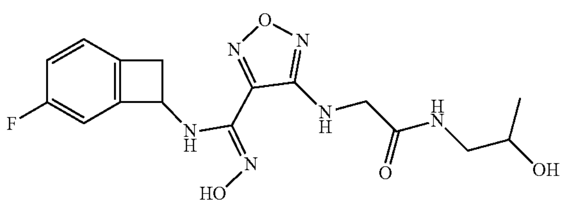 [SMILES: CC(O)CNC(=O)CNc1nonc1/C(=N/O)NC1Cc2ccc(F)cc21] | N~2~-{4-[N-(4-fluorobicyclo[4.2.0]octa-1,3,5-trien-7-yl)-N'-hydroxycarbamimidoyl]-1,2,5-oxadiazol-3-yl}-N-(2-hydroxypropyl)glycinamide | 379.2 |
| 199 | 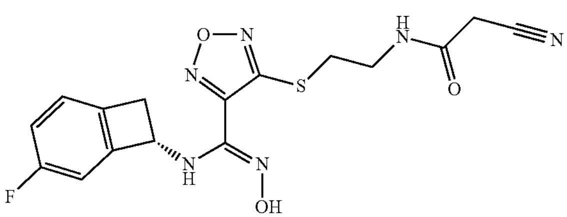 [SMILES: N#CCC(=O)NCCSc1nonc1/C(=N/O)N[C@H]1Cc2ccc(F)cc21] | 2-cyano-N-{2-[(4-{N-[(7S)-4-fluorobicyclo[4.2.0]octa-1,3,5-trien-7-yl]-N'-hydroxycarbamimidoyl}-1,2,5-oxadiazol-3-yl)sulfanyl]ethyl}acetamide | 391.1 |
| 200 | 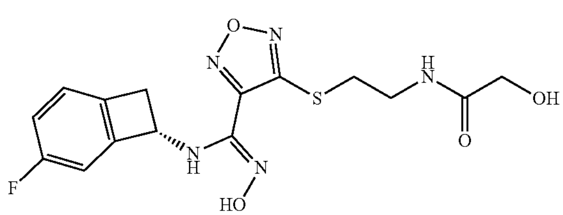 [SMILES: O=C(CO)NCCSc1nonc1/C(=N/O)N[C@H]1Cc2ccc(F)cc21] | N-{2-[(4-{N-[(7S)-4-fluorobicyclo[4.2.0]octa-1,3,5-trien-7-yl]-N'-hydroxycarbamimidoyl}-1,2,5-oxadiazol-3-yl)sulfanyl]ethyl}-2-hydroxyacetamide | 382.1 |
| 201 | 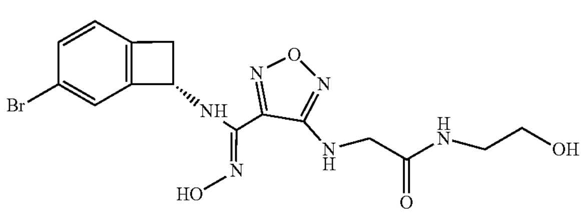 [SMILES: O=C(CNc1nonc1/C(=N/O)N[C@H]1Cc2ccc(Br)cc21)NCCO] | N~2~-(4-{N-[(7S)-4-bromobicyclo[4.2.0]octa-1,3,5-trien-7-yl]-N'-hydroxycarbamimidoyl}-1,2,5-oxadiazol-3-yl)-N-(2-hydroxyethyl)glycinamide | 425.1 |

TABLE 3-continued

Examples 168-225

| Ex. # | Structure | Name | Mass [M + H]+ |
|---|---|---|---|
| 202 | 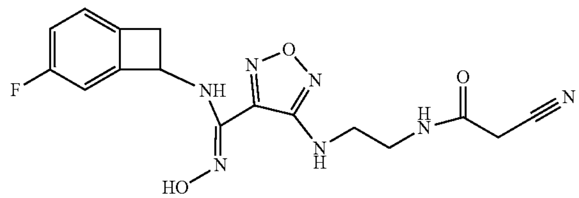 [SMILES: N#CCC(=O)NCCNc1nonc1/C(=N/O)NC1Cc2ccc(F)cc21] | 2-cyano-N-[2-({4-[N-(4-fluorobicyclo[4.2.0]octa-1,3,5-trien-7-yl)-N'-hydroxycarbamimidoyl]-1,2,5-oxadiazol-3-yl}amino)ethyl]acetamide | 374.1 |
| 203 | 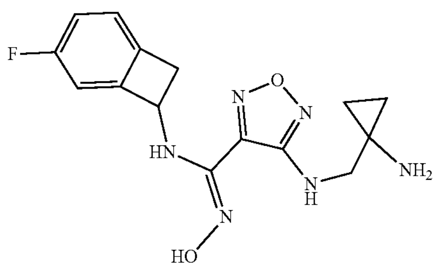 [SMILES: NC1(CNc2nonc2/C(=N/O)NC2Cc3ccc(F)cc32)CC1] | 4-{[(1-aminocyclopropyl)methyl]amino}-N-(4-fluorobicyclo[4.2.0]octa-1,3,5-trien-7-yl)-N'-hydroxy-1,2,5-oxadiazole-3-carboximidamide | 333.1 |
| 204 | 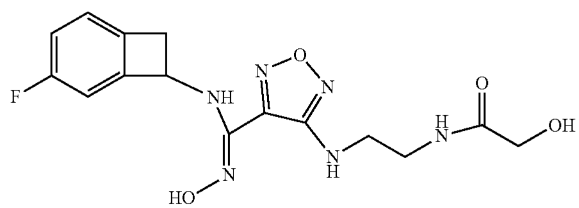 [SMILES: O=C(CO)NCCNc1nonc1/C(=N/O)NC1Cc2ccc(F)cc21] | N-[2-({4-[N-(4-fluorobicyclo[4.2.0]octa-1,3,5-trien-7-yl)-N'-hydroxycarbamimidoyl]-1,2,5-oxadiazol-3-yl}amino)ethyl]-2-hydroxyacetamide | 365.1 |
| 205 | 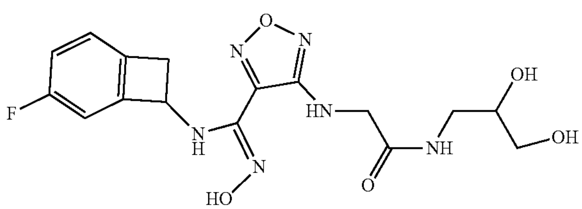 [SMILES: O=C(CNc1nonc1/C(=N/O)NC1Cc2ccc(F)cc21)NCC(O)CO] | N-(2,3-dihydroxypropyl)-N~2~-{4-[N-(4-fluorobicyclo[4.2.0]octa-1,3,5-trien-7-yl)-N'-hydroxycarbamimidoyl]-1,2,5-oxadiazol-3-yl}glycinamide | 395.1 |
| 206 | 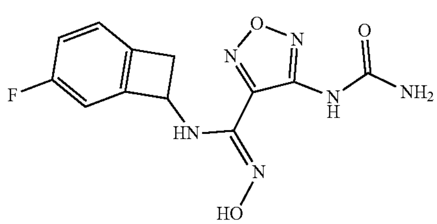 [SMILES: NC(=O)Nc1nonc1/C(=N/O)NC1Cc2ccc(F)cc21] | 4-(carbamoylamino)-N-(4-fluorobicyclo[4.2.0]octa-1,3,5-trien-7-yl)-N'-hydroxy-1,2,5-oxadiazole-3-carboximidamide | 307.1 |
| 207 | 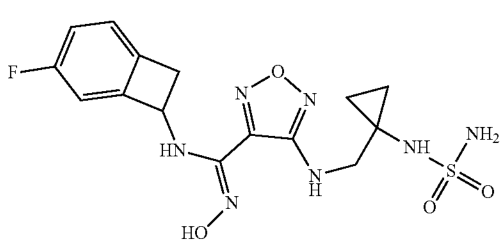 [SMILES: NS(=O)(=O)NC1(CNc2nonc2/C(=N/O)NC2Cc3ccc(F)cc32)CC1] | N-(4-fluorobicyclo[4.2.0]octa-1,3,5-trien-7-yl)-N'-hydroxy-4-({[1-(sulfamoylamino)cyclopropyl]methyl}amino)-1,2,5-oxadiazole-3-carboximidamide | 412.1 |

TABLE 3-continued

Examples 168-225

| Ex. # | Name | Mass [M + H]+ |
|---|---|---|
| 208 | N~2~-{4-[N-(3-fluorobicyclo[4.2.0]octa-1,3,5-trien-7-yl)-N'-hydroxycarbamimidoyl]-1,2,5-oxadiazol-3-yl}-N-(2-hydroxyethyl)glycinamide | 365.1 |
| 209 | N-(4-fluorobicyclo[4.2.0]octa-1,3,5-trien-7-yl)-N'-hydroxy-4-{[1-(hydroxyacetyl)azetidin-3-yl]sulfanyl}-1,2,5-oxadiazole-3-carboximidamide | 394.1 |
| 210 | 4-[(azetidin-3-yl)sulfanyl]-N-(4-fluorobicyclo[4.2.0]octa-1,3,5-trien-7-yl)-N'-hydroxy-1,2,5-oxadiazole-3-carboximidamide | 336.1 |
| 211 | N-{2-[(4-{N-[(7S)-4-fluorobicyclo[4.2.0]octa-1,3,5-trien-7-yl]-N'-hydroxycarbamimidoyl}-1,2,5-oxadiazol-3-yl)amino]propyl}acetamide | 363.2 |
| 212 | N-[(7S)-4-fluorobicyclo[4.2.0]octa-1,3,5-trien-7-yl]-N'-hydroxy-4-[(2-hydroxyethyl)amino]-1,2,5-oxadiazole-3-carboximidamide | 308.1 |
| 213 | N-[(7S)-4-fluorobicyclo[4.2.0]octa-1,3,5-trien-7-yl]-N'-hydroxy-4-{[(2S)-1-hydroxyprpan-2-yl]amino}-1,2,5-oxadiazole-3-carboximidamide | 322.1 |

TABLE 3-continued

Examples 168-225

| Ex. # | Structure | Name | Mass [M + H]+ |
|---|---|---|---|
| 214 | 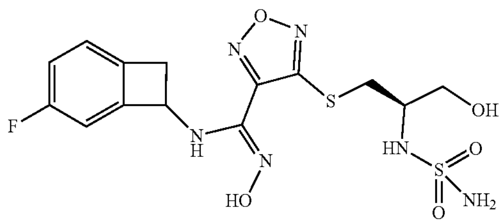 [SMILES: NS(=O)(=O)N[C@H](CO)CSc1nonc1/C(=N/O)NC1Cc2ccc(F)cc21] | N-(4-fluorobicyclo[4.2.0]octa-1,3,5-trien-7-yl)-N'-hydroxy-4-{[(2R)-3-hydroxy-2-(sulfamoylamino)propyl]sulfanyl}-1,2,5-oxadiazole-3-carboximidamide | 433.1 |
| 215 | 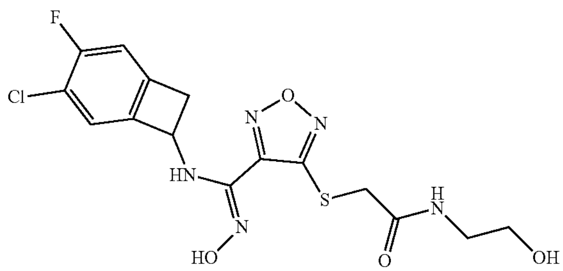 [SMILES: O=C(CSc1nonc1/C(=N/O)NC1Cc2cc(F)c(Cl)cc21)NCCO] | 2-({4-[N-(4-chloro-3-fluorobicyclo[4.2.0]octa-1,3,5-trien-7-yl)-N'-hydroxycarbamimidoyl]-1,2,5-oxadiazol-3-yl}sulfanyl)-N-(2-hydroxyethyl)acetamide | 416.1 |
| 216 | 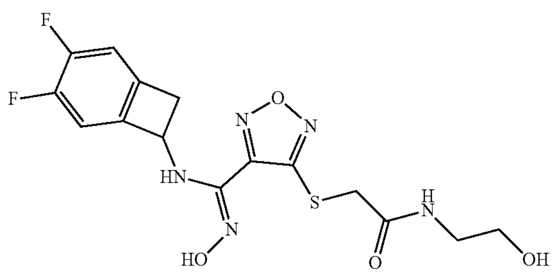 [SMILES: O=C(CSc1nonc1/C(=N/O)NC1Cc2cc(F)c(F)cc21)NCCO] | 2-({4-[N-(3,4-difluorobicyclo[4.2.0]octa-1,3,5-trien-7-yl)-N'-hydroxycarbamimidoyl]-1,2,5-oxadiazol-3-yl}sulfanyl)-N-(2-hydroxyethyl)acetamide | 400.1 |
| 217 | 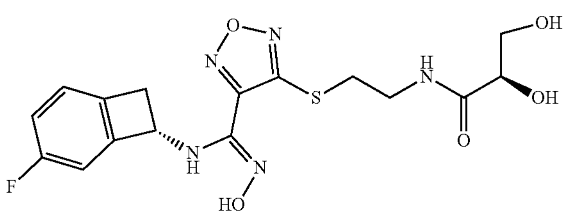 [SMILES: O=C(NCCSc1nonc1/C(=N/O)N[C@H]1Cc2ccc(F)cc21)[C@H](O)CO] | (2R)-N-{2-[(4-{N-[(7S)-4-fluorobicyclo[4.2.0]octa-1,3,5-trien-7-yl]-N'-hydroxycarbamimidoyl}-1,2,5-oxadiazol-3-yl)sulfanyl]ethyl}-2,3-dihydroxypropanamide | 412.1 |
| 218 | 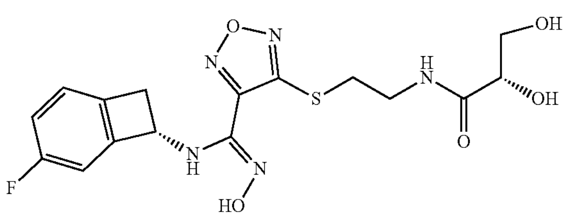 [SMILES: O=C(NCCSc1nonc1/C(=N/O)N[C@H]1Cc2ccc(F)cc21)[C@@H](O)CO] | (2S)-N-{2-[(4-{N-[(7S)-4-fluorobicyclo[4.2.0]octa-1,3,5-trien-7-yl]-N'-hydroxycarbamimidoyl}-1,2,5-oxadiazol-3-yl)sulfanyl]ethyl}-2,3-dihydroxypropanamide | 412.1 |
| 219 | 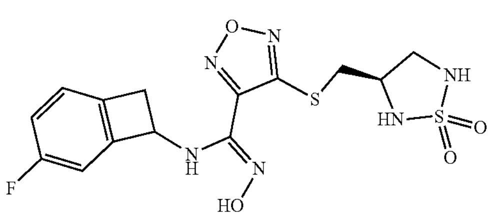 [SMILES: O=S1(=O)NC[C@H](CSc2nonc2/C(=N/O)NC2Cc3ccc(F)cc32)N1] | 4-({[(3R)-1,1-dioxo-1lambda~6~,2,5-thiadiazolidin-3-yl]methyl}sulfanyl)-N-(4-fluorobicyclo[4.2.0]octa-1,3,5-trien-7-yl)-N'-hydroxy-1,2,5-oxadiazole-3-carboximidamide | 415.1 |

TABLE 3-continued

Examples 168-225

| Ex. # | Structure | Name | Mass [M + H]+ |
|---|---|---|---|
| 220 | 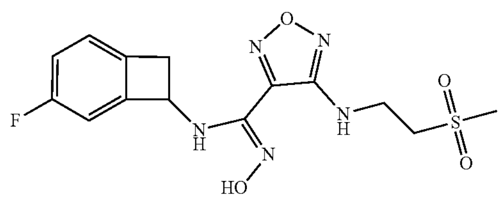 [SMILES: CS(=O)(=O)CCNc1nonc1/C(=N/O)NC1Cc2ccc(F)cc21] | N-(4-fluorobicyclo[4.2.0]octa-1,3,5-trien-7-yl)-N'-hydroxy-4-{[-(methylsulfonyl)ethyl]amino}-1,2,5-oxadiazole-3-carboximidamide | 370.1 |
| 221 | 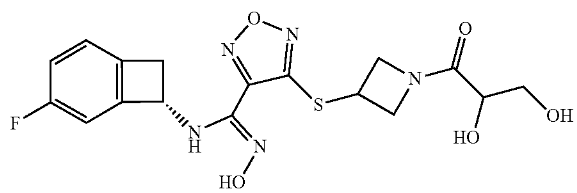 [SMILES: O=C(C(O)CO)N1CC(Sc2nonc2/C(=N/O)N[C@H]2Cc3ccc(F)cc32)C1] | 4-{[1-(2,3-dihydroxypropanoyl)azetidin-3-yl]sulfanyl}-N-[(7S)-4-fluorobicyclo[4.2.0]octa-1,3,5-trien-7-yl]-N'-hydroxy-1,2,5-oxadiazole-3-carboximidamide | 424.1 |
| 222 | 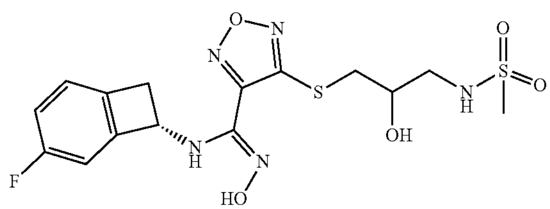 [SMILES: CS(=O)(=O)NCC(O)CSc1nonc1/C(=N/O)N[C@H]1Cc2ccc(F)cc21] | N-((S)-4-fluorobicyclo[4.2.0]octa-1(6),2,4-trien-7-yl)-N'-hydroxy-4-((2-hydroxy-3-(methylsulfonamido)propyl)thio)-1,2,5-oxadiazole-3-carboximidamide | 432.1 |
| 223 | 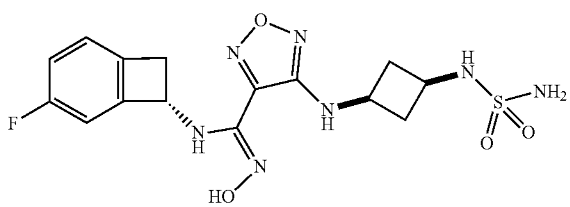 | N-((S)-4-fluorobicyclo[4.2.0]octa-1(6),2,4-trien-7-yl)-N'-hydroxy-4-((2-hydroxy-3-(sulfamoylamino)cyclobutyl)amino)-1,2,5-oxadiazole-3-carboximidamide | 412.1 |
| 224 | 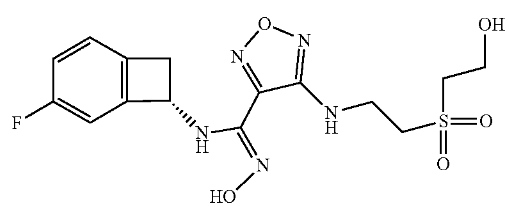 [SMILES: O=S(=O)(CCO)CCNc1nonc1/C(=N/O)N[C@H]1Cc2ccc(F)cc21] | (S)-N-(4-fluorobicyclo[4.2.0]octa-1(6),2,4-trien-7-yl)-N'-hydroxy-4-((2-((2-hydroxyethyl)sulfonyl)ethyl)amino)-1,2,5-oxadiazole-3-carboximidamide | 400.1 |
| 225 | 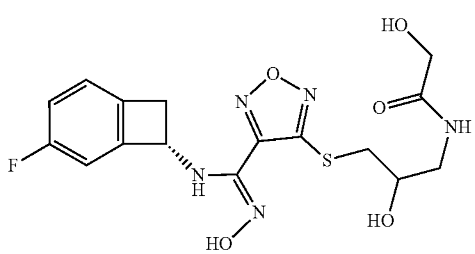 [SMILES: O=C(CO)NCC(O)CSc1nonc1/C(=N/O)N[C@H]1Cc2ccc(F)cc21] | N-(3-((4-(N-((S)-4-fluorobicyclo[4.2.0]octa-1(6),2,4-trien-7-yl)-N'-hydroxycarbamimidoyl)-1,2,5-oxadiazol-3-yl)thio)-2-hydroxypropyl)-2-hydroxyacetamide | 412.1 |
| 226 | 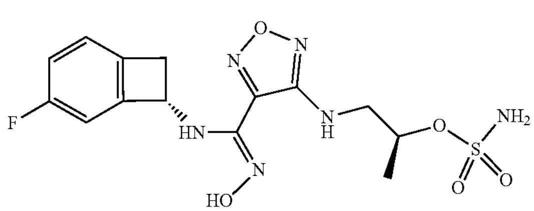 [SMILES: C[C@@H](CNc1nonc1/C(=N/O)N[C@H]1Cc2ccc(F)cc21)OS(N)(=O)=O] | (2S)-1-[(4-{N-[(7S)-4-fluorobicyclo[4.2.0]octa-1,3,5-trien-7-yl]-N'-hydroxycarbamimidoyl}-1,2,5-oxadiazol-3-yl)amino]propan-2-yl sulfamate | 401.1 |

TABLE 3-continued

Examples 168-225

| Ex. # | Structure | Name | Mass [M + H]+ |
|---|---|---|---|
| 227 | 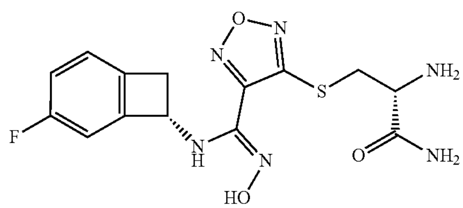 [SMILES: NC(=O)[C@@H](N)CSc1nonc1/C(=N/O)N[C@H]1Cc2ccc(F)cc21] | S-(4-{N-[(7S)-4-fluorobicyclo[4.2.0]octa-trien-7-yl]-N'-hydroxycarbamimidoyl}-1,2,5-oxadiazol-3-yl)-L-cysteinamide | 367.1 |
| 228 | 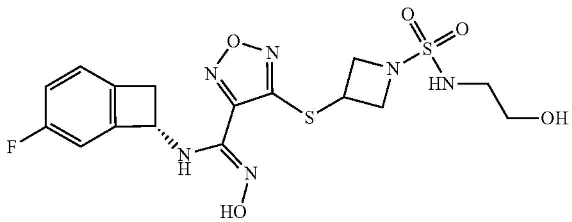 [SMILES: O=S(=O)(NCCO)N1CC(Sc2nonc2/C(=N/O)N[C@H]2Cc3ccc(F)cc32)C1] | N-[(7S)-4-fluorobicyclo[4.2.0]octa-1,3,5-trien-7-yl]-N'-hydroxy-4-({1-[(2-hydroxyethyl)sulfamoyl]azetidinin-3-yl}sulfanyl)-1,2,5-oxadiazole-3-carboximidamide | 459.1 |
| 229 | 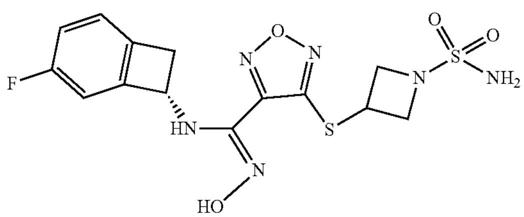 [SMILES: NS(=O)(=O)N1CC(Sc2nonc2/C(=N/O)N[C@H]2Cc3ccc(F)cc32)C1] | N-[(7S)-4-fluorobicyclo[4.2.0]octa-1,3,5-trien-7-yl]-N'-hydroxy-4-[(1-sulfamoylazetidin-3-yl)sulfanyl]-1,2,5-oxadiazole-3-carboximidamide | 415.1 |
| 230 | 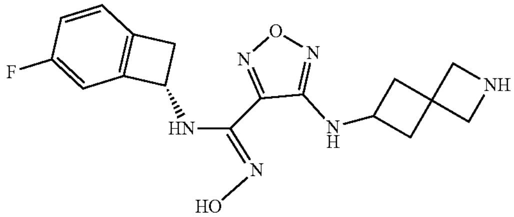 [SMILES: O/N=C(\N[C@H]1Cc2ccc(F)cc21)c1nonc1NC1CC2(CNC2)C1] | 4-[(2-azaspiro[3.3]heptan-6-yl)amino]-N-[(7S)-4-fluorobicyclo[4.2.0]octa-1,3,5-trien-7-yl]-N'-hydroxy-1,2,5-oxadiazole-3-carboximidamide | 359.1 |
| 231 | 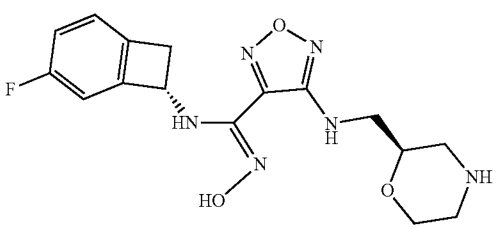 [SMILES: O/N=C(\N[C@H]1Cc2ccc(F)cc21)c1nonc1NC[C@H]1CNCCO1] | N-[(7S)-4-fluorobicyclo[4.2.0]octa-1,3,5-trien-7-yl]-N'-hydroxy-4-({[(2R)-morpholin-2-yl]methyl}amino)-1,2,5-oxadiazole-3-carboximidamide | 363.1 |
| 232 | 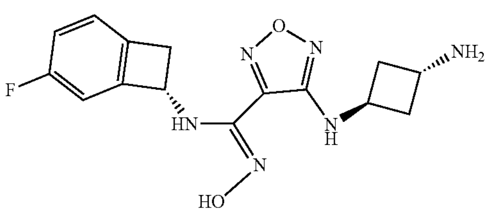 [SMILES: N[C@H]1C[C@H](Nc2nonc2/C(=N/O)N[C@H]2Cc3ccc(F)cc32)C1] | 4-[(trans-3-aminocyclobutyl)amino]-N-[(7S)-4-fluorobicyclo[4.2.0]octa-1,3,5-trien-7-yl]-N'-hydroxy-1,2,5-oxadiazole-3-carboximidamide | 333.1 |
| 233 | 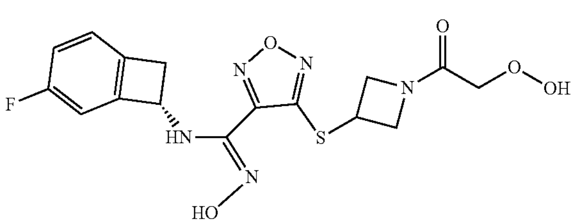 [SMILES: O=C(COO)N1CC(Sc2nonc2/C(=N/O)N[C@H]2Cc3ccc(F)cc32)C1] | N-[(7S)-4-fluorobicyclo[4.2.0]octa-1,3,5-trien-7-yl]-N'-hydroxy-4-{[1-(3-hydroxypropanoyl)azetidin-3-yl]sulfanyl}-1,2,5-oxadiazole-3-carboximidamide | 408.1 |

TABLE 3-continued

Examples 168-225

| Ex. # | Structure | Name | Mass [M + H]+ |
|---|---|---|---|
| 234 | 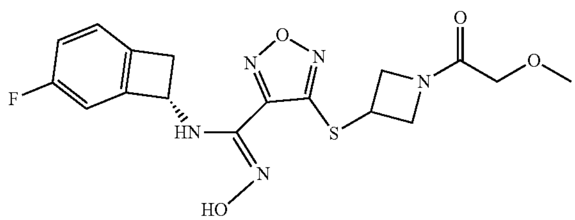 [SMILES: COCC(=O)N1CC(Sc2nonc2/C(=N/O)N[C@H]2Cc3ccc(F)cc32)C1] | N-[(7S)-4-fluorobicyclo[4.2.0]octa-1,3,5-trien-7-yl]-N'-hydroxy-4-{[1-(methoxyacetyl)azetidin-3-yl]sulfanyl}-1,2,5-oxadiazole-3-carboximidamide | 408.1 |
| 235 | 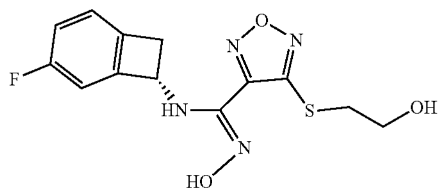 [SMILES: OCCSc1nonc1/C(=N/O)N[C@H]1Cc2ccc(F)cc21] | N-[(7S)-4-fluorobicyclo[4.2.0]octa-1,3,5-trien-7-yl]-N'-hydroxy-4-[2-hydroxyethyl)sulfanyl]-1,2,5-oxadiazole-3-carboximidamide | 325.1 |
| 236 | 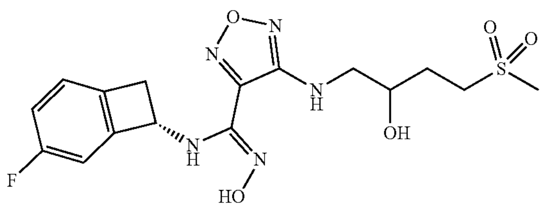 [SMILES: CS(=O)(=O)CCC(O)CNc1nonc1/C(=N/O)N[C@H]1Cc2ccc(F)cc21] | N-[(7S)-4-fluorobicyclo[4.2.0]octa-1,3,5-trien-7-yl]-N'-hydroxy-4-{[2-hydroxy-4-(methylsulfonyl)butyl]amino}-1,2,5-oxadiazole-3-carboximidamide (peak 1) | 414.1 |
| 237 | 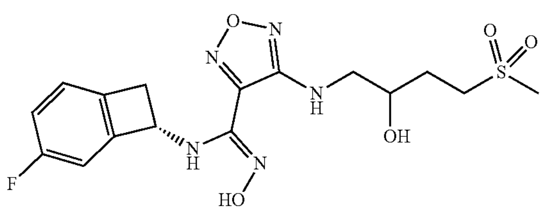 [SMILES: CS(=O)(=O)CCC(O)CNc1nonc1/C(=N/O)N[C@H]1Cc2ccc(F)cc21] | N-[(7S)-4-fluorobicyclo[4.2.0]octa-1,3,5-trien-7-yl]-N'-hydroxy-4-{[2-hydroxy-4-(methylsulfonyl)butyl]amino}-1,2,5-oxadiazole-3-carboximidamide (peak 2) | 414.1 |
| 238 | 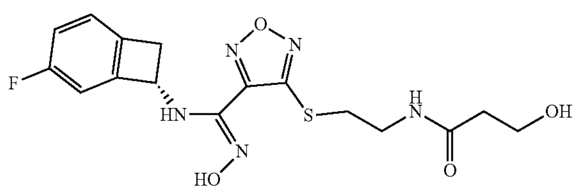 [SMILES: O=C(CCO)NCCSc1nonc1/C(=N/O)N[C@H]1Cc2ccc(F)cc21] | N-{2-[(4-{N-[(7S)-4-fluorobicyclo[4.2.0]octa-1,3,5-trien-7-yl]-N'-hydroxycaramimidoyl}-1,2,5-oxadiazol-3-yl)sulfanyl]ethyl}-3-hydroxypropanamide | 396.1 |
| 239 | 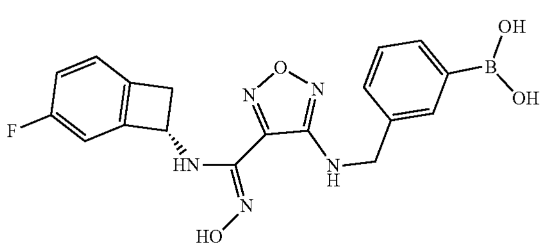 [SMILES: O/N=C(\N[C@H]1Cc2ccc(F)cc21)c1nonc1NCc1cccc(B(O)O)c1] | (3-{[(4-{N-[(7S)-4-fluorobicyclo[4.2.0]octa-1,3,5-trien-7-yl]-N'-hydroxycarbamimidoyl}-1,2,5-oxadiazol-3-yl)amino]methyl}phenyl)boronic acid | 398.1 |

TABLE 3-continued

Examples 168-225

| Ex. # | Structure | Name | Mass [M + H]+ |
|---|---|---|---|
| 240 | 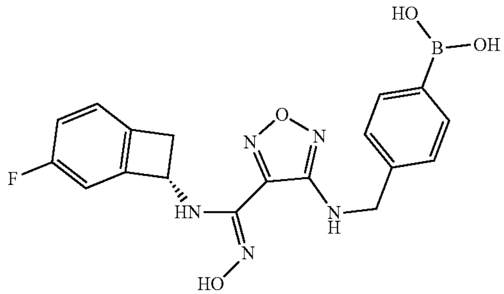 [SMILES: O/N=C(\N[C@H]1Cc2ccc(F)cc21)c1nonc1NCc1ccc(B(O)O)cc1] | (4-{[(4-{N-[(7S)-4-fluorobicyclo[4.2.0]octa-1,3,5-trien-7-yl]-N'-hydroxycarbamimidoyl}-1,2,5-oxadiazol-3-yl)amino]methyl}phenyl)boronic acid | 398.1 |
| 241 | 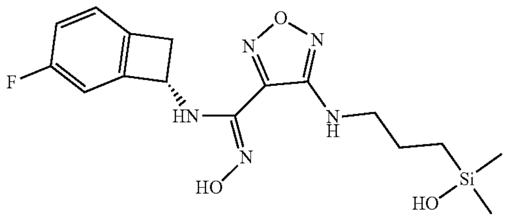 [SMILES: C[Si](C)(O)CCCNc1nonc1/C(=N/O)N[C@H]1Cc2ccc(F)cc21] | N-[(7S)-4-fluorobicyclo[4.2.0]octa-1,3,5-trien-7-yl]-N'-hydroxy-4-({3-[hydroxy(dimethyl)silyl]propyl}amino)-1,2,5-oxadiazole-3-carboximidamide | 380.2 |
| 242 | 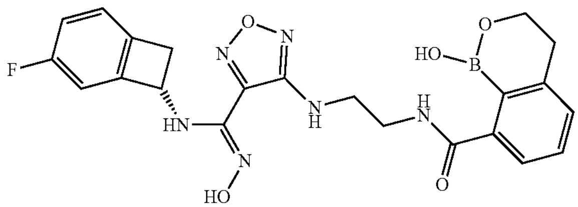 | (S,Z)-N-(2-((4-(N-(4-fluorobicyclo[4.2.0]octa-1(6),2,4-trien-7-yl)-N'-hydroxycarbamimidoyl)-1,2,5-oxadiazol-3-yl)amino)ethyl)-1-hydroxy-3,4-dihydro-1H-benzo[c][1,2]oxaborinine-8-carboxamide | 480.3 |

Biological Assays

IDO1 Enzyme Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

HIS-tagged IDO1 protein was recombinantly expressed in *Escherichia coli* using ZYP5052 autoinduction media supplemented with 500 μM delta aminolevulinic acid for 48 hours at 16 degrees Celsius. IDO1 protein was purified using $Ni^{2+}$-affinity resin and size exclusion chromatography. Purified protein was then diluted in assay buffer (50 mM Tris pH 7.0, 1% glycerol, 20 μM methylene blue, 0.05% Tween-20, 20 mM sodium ascorbate, 100 units/mL catalase to obtain a final IDO1 concentration of 40 nM. IDO1 solution (30 μM) or buffer alone (30 μM) were dispensed to wells of the assay plate using a BioRAPTR liquid dispenser (Beckman Coulter). Assay plates containing compound and IDO1 enzyme were incubated at room temperature for 30 minutes. Afterwards, 10 μL of 400 μM tryptophan in assay buffer were added to each well of the assay plate using a BioRAPTR liquid dispenser. Plates were incubated at room temperature for 60 minutes and reactions were quenched by addition of 10 μL of 0.5 M methyl isonipecotate in dimethyl sulfoxide. Plates were sealed and incubated at 37° C. for 4 hours or 50° C. for 2 h. The plates are allowed to cool and then centrifuged for 1 minute at 1000×g. The resulting fluoresence was measured in an Envision plate reader (Perkin Elmer) with a 400/25 nm excitation filter and an 510/20 nm emission filter.

The fluoresence intensity of each well was corrected for the background observed in wells that did not receive IDO1 and was expressed as a fraction of the intensity observed in wells that received IDO1 enzyme and DMSO only. Potencies were calculated by linear least squares fit to the four parameter logistic IC50 equation.

IDO1 Cellular Assay in Frozen HEK293 Cells Transiently Transfected with Human IDO1

HEK293 cells were cultured in complete HEK293 culture medium (90% DMEM, 10% heat-inactivated fetal bovine serum). When reaching sub-confluent, the cells were trypsinized and neutralized with complete medium. After spinning down, the cells were washed once with MaxCyte's EP buffer, and then resuspend in MaxCyte's EP buffer at 1×108 cells/ml. Flag-IDO1 plasmid was added to the cell suspension at a concentration of 100 μg/mL. The cell-plasmid solutions were transferred to the OC-400 processing assembly (Maxcyte), 400 l/unit and the units were placed in a Maxcyte instrument to carry out flow electroporation for transfection. The cells were then transferred to a sterile 24-well cell culture plate to recover for 20-30 minutes at 37° C. in an incubator with 5% $CO_2$. After recovery, the cells were suspended in complete culture medium at 1×106/mL and plated in cell culture flasks for 24 hours in a 37° C./5% $CO_2$ incubator. The cells were then collected and frozen down at 20×106 cells/vial in 1 mL frozen medium (90% complete HEK293 culture medium, 10% DMSO). Untransfected HREK293 WT cells were also frozen down at 5×106/vial similarly to serve as the Max-E control.

Compounds to be tested were serially diluted in ten 3-fold steps in DMSO starting from 10 mM DMSO stocks in Echo low volume plate(s). Compound dilutions or DMSO alone were then dispensed from the dilution plate(s) into the Greiner black 384-well assay plate(s) (catalog #781086, 50 nL/well) using an Echo 550 acoustic liquid handler (Labcyte)

Frozen HEK293/IDO1 and HEK293 WT cells were thawed and transferred into HEK293 assay medium (99% complete HEK293 culture medium, 1% Pen/Strep) with 20 mL medium/vial of cells. The cells were spun down at 250 g in a table top centrifuge for 5 minutes and suspended in same volume of HEK293 assay medium. The cells were counted and adjusted to density of 2×105 cells/ml in HEK293 assay medium. Sterile L-tryptophan were added to the cells with final concentration of 300 µM.

HEK293/IDO1 and HEK293 WT cells were dispensed to the respective wells of 384-well assay plates containing the compounds. The plates were incubated for about 28-30 hours at a 37° C., 5% $CO_2$ incubator. Afterwards, 12 µL of 0.5 M methyl isonipecotate in dimethyl sulfoxide were added into each well and the plates were sealed and incubated at 37° C. without $CO_2$ overnight. The plates were centrifuged for 1 minute at 200×g. The resulting fluorescence was measured in a Spectramax plate reader (Molecular Devices) with a 400 nm excitation filter and a 510 nm emission filter.

The fluorescence intensity of each well was corrected for the background observed in wells with untransfected cells and was expressed as a fraction of the intensity observed in wells of IDO1 transfected cells and DMSO only. Potencies were calculated by linear least squares fit to the four parameter logistic IC50 equation.

IDO1 Cellular Assay in Hela Cells Stimulated with IFNγ

Hela cells were cultured in complete Hela culture medium (90% EMEM, 10% heat-inactivated fetal bovine serum) and expanded to about 1×109 cells. The cells were then collected and frozen down at 10×106 cells/vial in 1 mL frozen medium (90% complete Hela culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen Hela cells were thawed and transferred into Hela assay medium (99% complete Hela culture medium, 1% Pen/Strep) with 20 mL medium/vial of cells. The cells were spun down at 250 g in a table top centrifuge for 5 minutes and suspended in same volume of Hela assay medium. The cells were then counted and adjusted to a density of 2×105 cells/ml in Hela assay medium. Sterile L-tryptophan were added to the cells with final concentration of 300 uM L-tryptophan. A small aliquot (2 mL/plate) of Hela cells were set aside and were not treated with IFNγ, to serve as the Max-E control. The rest of Hela cells were added with sterile IFNγ (Cat #285-IF, R & D systems) with a final concentration of 100 ng/mL.

Hela cells with and without IFNγ were dispensed to the respective wells of 384-well assay plates containing the compounds. The plates were incubated for about 48 hours at a 37° C., 5% $CO_2$ incubator. Afterwards, 12 µL of 0.5 M methyl isonipecotate in dimethyl sulfoxide were added into each well and the plates were sealed and incubated at 37° C. without $CO_2$ overnight. The plates were centrifuged for 1 minute at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 enzyme assay and IDO1 cellular assays described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Such a result is indicative of the intrinsic activity of the compounds in use as an inhibitor of an IDO enzyme. Specific $IC_{50}$ activity data for the exemplified compounds disclosed herein is provided in the following table.

TABLE 4

| Ex. No. | IDO1 Enzyme Assay, $IC_{50}$, nM | IDO1 HEK293 Cell Assay, $IC_{50}$, nM | IDO1 HELA Cell Assay, $IC_{50}$, nM |
| --- | --- | --- | --- |
| 1 | 78.38 | 38.57 | |
| 2 | 37.79 | 37.46 | |
| 3 | 720.9 | 518 | |
| 4 | 75.82 | 50.56 | |
| 5 | 1235 | 638.5 | |
| 6 | 2094 | 1765 | |
| 7 | 1916 | 1294 | |
| 8 | 16420 | 9399 | |
| 9 | 372.6 | 240.4 | |
| 10 | >100000 | >10000 | |
| 11 | 7432 | 7974 | |
| 12 | 23070 | 6320 | |
| 13 | 2467 | 1135 | |
| 14 | 37890 | >10000 | |
| 15 | 5333 | 3684 | |
| 16 | 11960 | 4955 | |
| 17 | 790.8 | 3030 | |
| 18 | 10110 | 8735 | |
| 19 | 6961 | >10000 | |
| 20 | 1989 | | |
| 21 | 2467 | 1135 | |
| 22 | 178.8 | 785.4 | |
| 23 | 2708 | 2843 | |
| 24 | 1739 | 2598 | |
| 25 | 337.3 | 398 | |
| 26 | 13390 | 3674 | |
| 27 | 254.6 | 350.5 | |
| 28 | 4667 | 4769 | |
| 29 | 119.8 | 152.2 | |
| 30 | 273.3 | 193.2 | |
| 31 | 11970 | 5662 | |
| 32 | 30.92 | 34.07 | 23.83 |
| 33 | 2170 | 6375 | |
| 34 | 33330 | 7456 | |
| 35 | 84.98 | 69.68 | |
| 36 | 1884 | 6663 | |
| 37 | 378.8 | 1690 | |
| 38 | 1949 | 8464 | |
| 39 | 54.14 | 79.27 | |
| 40 | 72.48 | 9.8 | 13.92 |
| 41 | 1693 | 668.1 | |
| 42 | 66.99 | 30.15 | 69.69 |
| 43 | 64.07 | 88.48 | |
| 44 | 15110 | 10000 | |
| 45 | 54580 | 10000 | |
| 46 | 112.7 | 392.3 | |
| 47 | 94.16 | 296.3 | 392.6 |
| 48 | 49.71 | 45.89 | 44.8 |
| 49 | 4321 | 6121 | |
| 50 | 53.94 | 94.2 | 84.47 |
| 51 | 12850 | >10000 | |

TABLE 4-continued

| Ex. No. | IDO1 Enzyme Assay, IC$_{50}$, nM | IDO1 HEK293 Cell Assay, IC$_{50}$, nM | IDO1 HELA Cell Assay, IC$_{50}$, nM |
|---|---|---|---|
| 52 | 65.27 | 51.39 | 49.16 |
| 53 | 1347 | 1065 | |
| 54 | 191.5 | 129.1 | |
| 55 | 1960 | 3676 | |
| 56 | 555.5 | 1770 | |
| 57 | 33140 | >10000 | |
| 58 | 85.24 | 655.5 | |
| 59 | 56.6 | 52.54 | |
| 60 | 10410 | 8350 | |
| 61 | 410.4 | 1621 | |
| 62 | 542.4 | 2412 | |
| 63 | 704.9 | 155.1 | |
| 64 | 149.9 | 125 | |
| 65 | 1386 | 3436 | |
| 66 | 632 | 1076 | |
| 67 | 38110 | >10000 | |
| 68 | 155.6 | 140.4 | |
| 69 | 109.7 | 244 | |
| 70 | 11490 | 10000 | |
| 71 | 45.12 | 110.7 | |
| 72 | 10250 | >10000 | |
| 73 | 260.4 | 809.2 | |
| 74 | 193.4 | 192.2 | |
| 75 | 512.8 | 328 | |
| 76 | 1149 | 2719 | |
| 77 | 647.6 | 145.9 | |
| 78 | 1100 | 1266 | |
| 79 | 51.19 | 120.4 | |
| 80 | 140.6 | 164.1 | |
| 81 | 103.2 | 131.6 | |
| 82 | 106.3 | 194.9 | |
| 83 | 70.87 | 55.22 | 84.94 |
| 84 | 376.6 | 287.3 | |
| 85 | 969 | 3202 | |
| 86 | 83.55 | 51.42 | 47.18 |
| 87 | 826.4 | 2454 | |
| 88 | 77.69 | 71.41 | |
| 89 | 1919 | 9346 | |
| 90 | 2204 | 6404 | |
| 91 | 326.4 | 271 | |
| 92 | 2204 | 6404 | |
| 93 | 58.99 | 90.1 | 133.1 |
| 94 | 2759 | 8049 | |
| 95 | 750.6 | 2547 | |
| 96 | 307.8 | 1607 | |
| 97 | >100000 | >10000 | |
| 98 | 461.4 | 4303 | |
| 99 | 93820 | >10000 | |
| 100 | 254.5 | 1812 | |
| 101 | 67750 | >10000 | |
| 102 | 148.8 | 663.7 | |
| 103 | 42980 | >10000 | |
| 104 | 153.6 | 853.1 | |
| 105 | >100000 | >10000 | |
| 106 | 424.4 | 839.8 | |
| 107 | >100000 | >10000 | |
| 108 | 82.64 | 20.08 | |
| 109 | 5901 | 1467 | |
| 110 | 72.75 | 13.9 | 16.5 |
| 111 | 1911 | 3278 | |
| 112 | 510.4 | 85.8 | |
| 113 | 72.67 | 23.14 | 45.71 |
| 114 | 2948 | 3730 | |
| 115 | 66.27 | 72.56 | |
| 116 | 3498 | 2624 | |
| 117 | 42.88 | 38.85 | 36.3 |
| 118 | 1097 | 1358 | |
| 119 | 81.91 | 71.64 | |
| 120 | 1608 | 4724 | |
| 121 | 98.22 | 73.6 | 225.2 |
| 122 | 87 | 117 | 239 |
| 123 | 97.85 | 30.67 | 98.03 |
| 124 | 5470 | 2952 | |
| 125 | 51.38 | 109.4 | |
| 126 | 33330 | 9948 | |
| 127 | >100000 | >10000 | |
| 128 | 120.9 | 168.4 | |
| 129 | 104.5 | 139.2 | |
| 130 | 39350 | >10000 | |
| 131 | 82.42 | 91.19 | |
| 132 | 6247 | 7947 | |
| 133 | 83.32 | 187.3 | |
| 134 | 11180 | 5320 | |
| 135 | 2456 | 3146 | |
| 136 | 76450 | >10000 | |
| 137 | 1837 | 6898 | |
| 138 | 52.43 | 206 | |
| 139 | 11600 | >10000 | |
| 140 | 239.1 | 378.3 | |
| 141 | 6919 | >10000 | |
| 142 | 173.6 | 315.4 | |
| 143 | 21100 | 10000 | |
| 144 | 88.93 | 10.05 | |
| 145 | 4356 | 1352 | |
| 146 | 1075 | 1269 | |
| 147 | 186.6 | 84.76 | |
| 148 | 2275 | 6375 | |
| 149 | 3488 | 8324 | |
| 150 | 64.99 | 86.17 | |
| 151 | 3948 | 6071 | |
| 152 | 50.3 | | 24.36 |
| 153 | 4235 | 2716 | |
| 154 | 2183 | 6365 | |
| 155 | 65.87 | 16.46 | |
| 156 | 1018 | 479.7 | |
| 157 | 253.8 | 513.3 | |
| 158 | 114.5 | 37.72 | |
| 159 | 93.11 | 104.3 | |
| 160 | 233.3 | 301.6 | |
| 161 | 89.54 | 179 | |
| 162 | 8331 | 5712 | |
| 163 | 838.6 | 592.8 | |
| 164 | 41.45 | 42.29 | 29.23 |
| 165 | 241.7 | 175 | |
| 166 | 46.66 | | 62.06 |
| 167 | 62.9 | | 51.56 |
| 168 | 103.7 | | 375.5 |
| 169 | 73.99 | | 127.6 |
| 170 | 57.95 | | 149.5 |
| 171 | 67.82 | | 193.4 |
| 172 | 82.01 | | 745.5 |
| 173 | 241.9 | | 210 |
| 174 | 372.4 | | 217.7 |
| 175 | 344.7 | | 389.3 |
| 176 | 352.2 | | 423.8 |
| 177 | 49.05 | | 160.9 |
| 178 | 62.55 | | 111.1 |
| 179 | 54.1 | | 88.2 |
| 180 | 55.35 | | 63.02 |
| 181 | 59.25 | | 78.12 |
| 182 | 78.29 | | 104.6 |
| 183 | 44.9 | | 52.82 |
| 184 | 43.07 | | 25.71 |
| 185 | 319.1 | | 440.5 |
| 186 | 138.6 | | 118.7 |
| 187 | 139.8 | | 112.8 |
| 188 | 259.1 | | 101.8 |
| 189 | 139.5 | | 58.7 |
| 190 | 97.05 | | 28.55 |
| 191 | 103.3 | | 114.2 |
| 192 | 130.2 | | 64.39 |
| 193 | 129.5 | | 37.36 |
| 194 | 62.71 | | 35.1 |
| 195 | 77.82 | | 26.73 |
| 196 | 364 | | 230.3 |
| 197 | 175 | | 59.81 |
| 198 | 66.45 | | 44.89 |
| 199 | 75.32 | | 24.36 |
| 200 | 59.32 | | 34.12 |
| 201 | 82.73 | | 167.2 |

TABLE 4-continued

| Ex. No. | IDO1 Enzyme Assay, IC$_{50}$, nM | IDO1 HEK293 Cell Assay, IC$_{50}$, nM | IDO1 HELA Cell Assay, IC$_{50}$, nM |
| --- | --- | --- | --- |
| 202 | 91.1 | | 39.22 |
| 203 | 131.9 | | 131.3 |
| 204 | 65.33 | | 84.18 |
| 205 | 56.27 | | 78.72 |
| 206 | 267.6 | | 441.2 |
| 207 | 219.7 | | 478.4 |
| 208 | 660.7 | | 326.8 |
| 209 | 60.94 | | 22.69 |
| 210 | 122 | | 488.8 |
| 211 | 136.6 | | 469 |
| 212 | 57.76 | | 51.2 |
| 213 | 175.6 | 565.7 | 321.8 |
| 214 | 195.9 | 153.8 | 79.33 |
| 215 | 261.2 | 1458 | 1126 |
| 216 | 416.9 | 136.7 | 145.7 |
| 217 | 34.64 | | 157.7 |
| 218 | 50.18 | | 47.03 |
| 219 | 209 | | 146.6 |
| 220 | 42.97 | | 69.75 |
| 221 | 34.01 | | 18.19 |
| 222 | 59.73 | | 32.97 |
| 223 | 86.35 | | 36.15 |
| 224 | 48.54 | | 42.2 |
| 225 | 69.41 | | 56.36 |
| 226 | 746.2 | | 439.6 |
| 227 | 79.17 | | 121.1 |
| 228 | 53.94 | | 48.38 |
| 229 | 50.27 | | 17.92 |
| 230 | 114.5 | | 188.5 |
| 231 | 68.46 | | 51.64 |
| 232 | 69.71 | | 56.11 |
| 233 | 45.84 | | 13.57 |
| 234 | 24.38 | | 13.24 |
| 235 | 38.93 | | 17.35 |
| 236 | 49.28 | | 63.25 |
| 237 | 43.33 | | 38.34 |
| 238 | 20.04 | | 15.54 |
| 239 | 49.91 | | 46.27 |
| 240 | 96.15 | | 61.38 |
| 241 | 900.3 | | 332.9 |
| 242 | 138.0 | | 111.8 |

IDO1 Human Whole Blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI using an Echo 555 acoustic liquid handler (Labcyte). LPS and IFNγ was prepared in RPMI to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2 isotope labeled standard of kunurenine and tryptophan was made in water at 10× concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volume of Acetonitrile. The plates was centrifuged at 4000×G for 60 min. 20 μL of supernatant was carefully transferred to a 384 well plate contain 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadruple MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., sheath gas 60 arbitrary units, Aux gas 20 arbitrary units, tube lens 85 and collision gas 1.2 mTorr. SRM chromatograms of kynurenine (Q1: 209.2>Q3: 94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and IC50 values. Compounds were titrated and IC50's were calculated by 4 parameter sigmoidal curve fitting formula.

The biological activity data of selective compounds using the IDO1 human whole blood assay described above are summarized in the table below.

TABLE 5

| Ex. No. | IDO1 human whole blood assay, IC$_{50}$, nM |
| --- | --- |
| 2 | 176.5 |
| 32 | 409.4 |
| 39 | 1176 |
| 40 | 1366 |
| 42 | 740.2 |
| 47 | 1706 |
| 48 | 346.2 |
| 50 | 827.9 |
| 52 | 238.3 |
| 59 | 605.6 |
| 83 | 397.7 |
| 86 | 554.7 |
| 93 | 956.6 |
| 110 | 331.5 |
| 113 | 430 |
| 117 | 647.6 |
| 121 | 849.2 |
| 123 | 1357 |
| 152 | 346.1 |
| 164 | 308.5 |
| 190 | 786.8 |
| 200 | 600.9 |
| 202 | 746.6 |
| 219 | 1263 |
| 221 | 624.6 |
| 228 | 1792 |
| 229 | 2177 |
| 239 | 1474 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

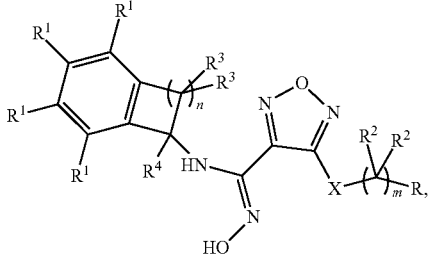

wherein:
m is 0, 1, 2, or 3; n is 1, 2, or 3,
X is —S— or —NH—;
R is selected from the group consisting of:
(a) hydrogen,
(b) $C_{1-6}$alkyl, optionally substituted with one to three substituents independently selected from the group consisting of (i) —OH, (ii) halogen, and (iii) —NH$_2$,
(c) $C_{3-6}$cycloalkyl, optionally substituted with one to three substituents independently selected from the group consisting of (i) NH$_2$, (ii) —NH—S(O)$_2$—NH$_2$ and (iii) —NH—C(O)—$C_{1-6}$alkyl, optionally substituted with —OH,
(d) $C_{4-6}$cycloalkenyl, optionally substituted with an oxo,
(e) —(C=O)—NH—R$^a$, wherein R$^a$ is selected from the group consisting of:
 (i) hydrogen,
 (ii) —$C_{1-6}$alkyl, optionally substituted with one to three substituents independently selected from the group consisting of (1) halogen, (2) —OH and (3) —S(O)$_2$—$C_{1-6}$alkyl,
 (iii) —$C_{1-6}$alkoxy, and
 (iv) —$C_{3-6}$cycloalkyl,
(f) —NR$^x$R$^y$, wherein each of R$^x$ and R$^y$ is independently selected from the group consisting of:
 (i) hydrogen,
 (ii) —(C=O)—R$^a$, wherein R$^a$ is selected from the group consisting of (1) hydrogen, and (2) —$C_{1-6}$alkyl, optionally substituted with one to three substituents independently selected from halogen and —CN, (3) —NH$_2$, (4) —NH—$C_{1-6}$alkyl, optionally substituted with —OH, —O-methyl, or —CN, (5) —NH—$C_{3-6}$cycloalkyl, and (6) heterocyclyl, optionally substituted with —OH,
 (iii) —S(O)$_2$—NH$_2$,
 (iv) —S(O)$_2$—CH$_3$, and
 (v) $C_{4-5}$cycloalkenyl, optionally substituted with one to four substituents independently selected from the group consisting of (1) oxo, (2) —$C_{1-6}$alkyl, and (3) —NH—$C_{1-6}$alkyl,
(g) a 4-, 5- or 6-membered heterocyclyl, optionally substituted with one to four substituents independently selected from the group consisting of (i) halogen, (ii) $C_{1-6}$alkyl, (iii) oxo, (iv) —C(O)—$C_{1-6}$alkyl, optionally substituted with one to three groups independently selected from —OH and —O—$C_{1-6}$alkyl, (v) —S(O)$_2$—NH$_2$ and (vi) —S(O)$_2$—NH—$C_{1-6}$alkyl, optionally substituted with —OH,
(h) —S(O)$_2$—$C_{1-6}$alkyl, optionally substituted with one to three —OH groups,
(i) —O—S(O)$_2$—NH$_2$;
(j)

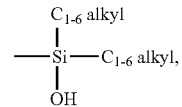

(k) a 7-, 8-, 9- or 10-membered bi-cyclic heterocyclyl, optionally substituted with one to three substituents independently selected from the group consisting of (i) halogen, (ii) $C_{1-6}$alkyl and (iii) oxo, and
(l) aryl, optionally substituted with one to three substituents independently selected from the group consisting of (i) halogen and (ii) —B(OH)$_2$;
each occurrence of R$^1$ is independently selected from the group consisting of (a) hydrogen, (b) halogen, (c) —CN, and (d) $C_{1-6}$ alkyl, optionally substituted with 1 to 3 halogens;
each occurrence of R$^2$ is independently selected from the group consisting of (a) hydrogen, (b) halogen, (c) —OH, (d) —NH$_2$ and (e) $C_{1-6}$ alkyl, optionally substituted with —OH;
each occurrence of R$^3$ is independently selected from the group consisting of (a) hydrogen, (b) halogen, (c) $C_{1-6}$ alkyl, and (d) —O—$C_{1-6}$ alkyl; and
R$^4$ is selected from the group consisting of (a) hydrogen and (b) $C_{1-4}$ alkyl.

2. The compound of claim 1, or a pharmaceutically acceptable salt thereof,
wherein: m is 0, 1, 2, or 3; n is 1, 2, or 3;
X is —S— or —NH—;
R is selected from the group consisting of:
(a) hydrogen,
(b) $C_{1-6}$alkyl, optionally substituted with one to three substituents independently selected from the group consisting of (i) —OH, (ii) halogen, and (iii) —NH$_2$,
(c) $C_{3-6}$cycloalkyl, optionally substituted with one to three substituents independently selected from the group consisting of (i) NH$_2$, (ii) —NH—S(O)$_2$—NH$_2$ and (iii) —NH—C(O)—$C_{1-6}$alkyl, optionally substituted with —OH,
(d) $C_{4-6}$cycloalkenyl, optionally substituted with an oxo,
(e) —(C=O)—NH—R$^a$, wherein R$^a$ is selected from the group consisting of:
 (i) hydrogen,
 (ii) —$C_{1-6}$alkyl, optionally substituted with one to three substituents independently selected from the group consisting of (1) halogen, (2) —OH and (3) —S(O)$_2$—$C_{1-6}$alkyl,
 (iii) —$C_{1-6}$alkoxy, and
 (iv) —$C_{3-6}$cycloalkyl,
(f) —NR$^x$R$^y$, wherein each of R$^x$ and R$^y$ is independently selected from the group consisting of:
 (i) hydrogen,
 (ii) —(C=O)—R$^a$, wherein R$^a$ is selected from the group consisting of (1) hydrogen, and (2) —$C_{1-6}$alkyl, optionally substituted with one to three substituents independently selected from halogen and —CN, (3) —NH$_2$, (4) —NH—$C_{1-6}$alkyl, optionally substituted with —OH, —O-methyl, or —CN, and (5) —NH—$C_{3-6}$cycloalkyl,
 (iii) —S(O)$_2$—NH$_2$,
 (iv) —S(O)$_2$—CH$_3$, and (v) C$_{4-5}$cycloalkenyl, optionally substituted with one to four substituents independently selected from the group consisting of (1) oxo, (2) —C$_{1-6}$alkyl, and (3) —NH—C$_{1-6}$alkyl, and (g) a 4-, 5- or 6-membered heterocyclyl, optionally substituted with one to four substituents independently selected from the group consisting of (i) halogen, (ii) C$_{1-6}$alkyl, (iii) oxo and (iv) —C(O)—C$_{1-6}$alkyl, optionally substituted with one to three —OH groups;

each occurrence of R$^1$ is independently selected from the group consisting of (a) hydrogen, (b) halogen, (c) —CN, and (d) C$_{1-6}$ alkyl, optionally substituted with 1 to 3 halogens;

each occurrence of R$^2$ is independently selected from the group consisting of (a) hydrogen, (b) halogen, and (c) —OH;

each occurrence of R$^3$ is independently selected from the group consisting of (a) hydrogen, (b) halogen, (c) C$_{1-6}$ alkyl, and (d) —O—C$_{1-6}$ alkyl; and R$^4$ is selected from the group consisting of (a) hydrogen and (b) C$_{1-4}$ alkyl.

3. The compound of claim 1, or a pharmaceutically acceptable salt thereof, wherein m is 1 or 2; and n is 1 or 2.

4. The compound of claim 1, or a pharmaceutically acceptable salt thereof, wherein R is selected from the group consisting of:
(a) C$_{1-4}$alkyl, optionally substituted with one to two —OH groups,
(b) C$_{3-4}$cycloalkyl,
(c) —(C=O)—NH—R$^a$, wherein R$^a$ is selected from the group consisting of:
(i) hydrogen,
(ii) —C$_{1-6}$alkyl,
(iii) —C$_{1-6}$alkoxy, and
(iv) —C$_{3-6}$cycloalkyl,
(d) —NR$^x$R$^y$, wherein each of R$^x$ and R$^y$ is independently selected from the group consisting of:
(i) hydrogen,
(ii) —(C=O)—C$_{1-6}$alkyl,
(iii) —S(O)$_2$—NH$_2$, and
(iv) cyclobutenyl, optionally substituted with one to three substituents independently selected from the group consisting of (1) oxo, (2) —C$_{1-4}$alkyl, and (3) —NH—C$_{1-4}$alkyl, and
(e) a 5- or 6-membered heterocyclyl, optionally substituted with one to four substituents independently selected from the group consisting of (i) C$_{1-6}$alkyl, and (ii) oxo.

5. The compound of claim 1, or a pharmaceutically acceptable salt thereof, wherein R is a 5- or 6-membered heterocyclyl selected from the group consisting of pyridinyl, pyrimidinyl, piperidinyl, triazolyl, and thiazolyl;
wherein the 5- or 6-membered heterocyclyl is optionally substituted with one to four substituents independently selected from the group consisting of (i) C$_{1-6}$alkyl, and (ii) oxo.

6. The compound of claim 1, or a pharmaceutically acceptable salt thereof, wherein each occurrence of R$^1$ is independently selected from the group consisting of (a) hydrogen, (b) halogen, (c) —CN, and (d) C$_{1-4}$ alkyl, optionally substituted with 1 to 3 halogens.

7. The compound of claim 1, or a pharmaceutically acceptable salt thereof, wherein each occurrence of R$^2$ is independently selected from the group consisting of (a) hydrogen, and (b) —OH.

8. The compound of claim 1, or a pharmaceutically acceptable salt thereof, wherein each occurrence of R$^3$ is independently selected from the group consisting of (a) hydrogen, (b) C$_{1-4}$ alkyl, and (c) —O—C$_{1-4}$ alkyl.

9. The compound of claim 1, or a pharmaceutically acceptable salt thereof, wherein:
R is selected from the group consisting of:
(a) C$_{1-4}$alkyl, optionally substituted with one to two —OH groups,
(b) C$_{3-4}$cycloalkyl,
(c) —(C=O)—NH—R$^a$, wherein R$^a$ is selected from the group consisting of (i) hydrogen, (ii) —C$_{1-6}$alkyl, and (iii) —C$_{1-6}$alkoxy,
(d) —NR$^x$R$^y$, wherein each of R$^x$ and R$^y$ is independently selected from the group consisting of (i) hydrogen, (ii) —(C=O)—C$_{1-6}$alkyl, and (iii) —S(O)$_2$—NH$_2$, and
(e) 5- or 6-membered heterocyclyl, optionally substituted with one to four substituents independently selected from the group consisting of (i) C$_{1-6}$alkyl and (ii) oxo each occurrence of R$^1$ is independently selected from the group consisting of (a) hydrogen, (b) halogen, (c) —CN, and (d) C$_{1-4}$ alkyl, optionally substituted with 1 to 3 halogens;

each occurrence of R$^2$ is independently selected from the group consisting of (a) hydrogen, and (b) —OH;

each occurrence of R$^3$ is independently selected from the group consisting of (a) hydrogen, (b) C$_{1-4}$ alkyl, and (c) —O—C$_{1-4}$ alkyl; and R$^4$ is selected from the group consisting of (a) hydrogen, and (b) C$_{1-4}$ alkyl.

10. The compound of claim 1 of formula (Ia), or a pharmaceutically acceptable salt thereof:

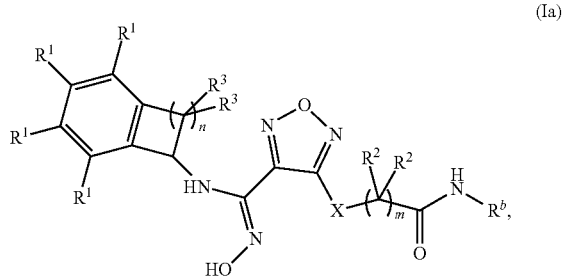

(Ia)

wherein:
m is 1, 2, or 3; n is 1 or 2;
X is —S— or —NH—;
R$^b$ is selected from the group consisting of:
(a) C$_{1-6}$alkyl, optionally substituted with one to two —OH groups,
(b) C$_{3-6}$cycloalkyl,
(c) C$_{1-6}$alkoxy, and
(d) —NR$^x$N$^y$, wherein each of R$^x$ and R$^y$ is independently selected from the group consisting of (i) hydrogen, (ii) —C$_{1-6}$alkyl, (iii) —C$_{3-6}$cycloalkyl and (iv) —(C=O)—C$_{1-6}$alkyl;

each occurrence of R$^1$ is independently selected from the group consisting of (a) hydrogen, (b) halogen, (c) —CN, and (d) C$_{1-4}$ alkyl, optionally substituted with 1 to 3 halogens;

each occurrence of R$^2$ is independently selected from the group consisting of (a) hydrogen, and (b) —OH; and each occurrence of R$^3$ is independently selected from the group consisting of (a) hydrogen, (b) C$_{1-6}$alkyl, and (c) —O—C$_{1-6}$alkyl.

11. The compound of claim 10, or a pharmaceutically acceptable salt thereof, wherein $R^b$ is selected from the group consisting of methyl, ethyl, propyl, iso-propyl, methoxy, ethoxy, propoxy and cyclopropyl.

12. The compound of claim 10, or a pharmaceutically acceptable salt thereof, wherein:
each occurrence of $R^1$ is independently selected from the group consisting of (a) hydrogen, (b) halogen, (c) —CN, and (d) —CF$_3$.

13. The compound of claim 10, or a pharmaceutically acceptable salt thereof, wherein:
each occurrence of $R^2$ is hydrogen.

14. The compound of claim 10, or a pharmaceutically acceptable salt thereof, wherein:
each occurrence of $R^3$ is independently selected from the group consisting of (a) hydrogen, (b) methyl, (c) ethyl, (d) —O-methyl, and (e) —O-ethyl.

15. The compound of claim 1 of formula (Ib), or a pharmaceutically acceptable salt thereof:

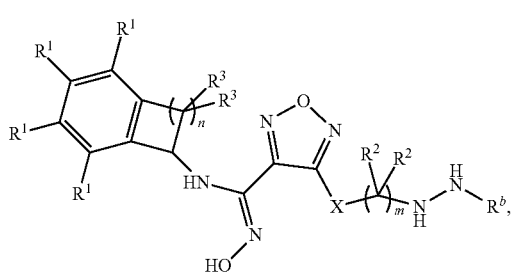

(Ib)

wherein
m is 1, 2, or 3; n is 1 or 2;
X is —S— or —NH—,
$R^b$ is selected from the group consisting of:
  (a) C$_{1-6}$alkyl, optionally substituted with one to two —OH groups, and
  (b) C$_{3-6}$cycloalkyl;
each occurrence of $R^1$ is independently selected from the group consisting of (a) hydrogen, (b) halogen, and (c) —CN;
each occurrence of $R^2$ is independently selected from the group consisting of (a) hydrogen, and (b) —OH; and
each occurrence of $R^3$ is independently selected from the group consisting of (a) hydrogen, (b) C$_{1-6}$alkyl, and (c) —O—C$_{1-6}$alkyl.

16. The compound of claim 15, or a pharmaceutically acceptable salt thereof, wherein:
each occurrence of $R^1$ is independently selected from the group consisting of (a) hydrogen, (b) halogen, and (c) —CN.

17. The compound of claim 16, or a pharmaceutically acceptable salt thereof, wherein:
each occurrence of $R^2$ is hydrogen and each occurrence of $R^3$ is independently selected from the group consisting of (a) hydrogen, (b) methyl, and (c) ethyl.

18. The compound of claim 1, or a pharmaceutically acceptable salt thereof, selected from the group consisting of:
4-Amino-N-(4-fluorobicyclo[4.2.0]octa-1,3,5-trien-7-yl)-N'-hydroxy-1,2,5-oxadiazole-3-carboximidamide,
(R)-4-Amino-N-(4-fluorobicyclo[4.2.0]octa-1,3,5-trien-7-yl)-N'-hydroxy-1,2,5-oxadiazole-3-carboximidamide,
(S)-4-Amino-N-(4-fluorobicyclo[4.2.0]octa-1,3,5-trien-7-yl)-N'-hydroxy-1,2,5-oxadiazole-3-carboximidamide,
(S)-4-amino-N-(bicyclo[4.2.0]octa-1,3,5-trien-7-yl)-N'-hydroxy-1,2,5-oxadiazole-3-carboximidamide,
(R)-4-amino-N-(bicyclo[4.2.0]octa-1,3,5-trien-7-yl)-N'-hydroxy-1,2,5-oxadiazole-3-carboximidamide,
4-Amino-N'-hydroxy-N-(7-methylbicyclo[4.2.0]octa-1,3,5-trien-7-yl)-1,2,5-oxadiazole-3-carboximidamide,
(S)-4-amino-N'-hydroxy-N-(7-methylbicyclo[4.2.0]octa-1,3,5-trien-7-yl)-1,2,5-oxadiazole-3-carboximidamide,
(R)-4-amino-N'-hydroxy-N-(7-methylbicyclo[4.2.0]octa-1,3,5-trien-7-yl)-1,2,5-oxadiazole-3-carboximidamide,
(S)-4-Amino-N-(2,3-dihydro-1H-inden-1-yl)-N'-hydroxy-1,2,5-oxadiazole-3-carboximidamide,
(R)-4-Amino-N-(2,3-dihydro-1H-inden-1-yl)-N'-hydroxy-1,2,5-oxadiazole-3-carboximidamide,
4-Amino-N-(8-fluorobicyclo[4.2.0]octa-1(6),2,4-trien-7-yl)-N'-hydroxy-1,2,5-oxadiazole-3-carboximidamide,
4-Amino-N-(8,8-difluorobicyclo[4.2.0]octa-1(6),2,4-trien-7-yl)-N'-hydroxy-1,2,5-oxadiazole-3-carboximidamide,
4-Amino-N-(6-fluoro-2,3-dihydro-1H-inden-1-yl)-N'-hydroxy-1,2,5-oxadiazole-3-carboximidamide,
4-amino-N'-hydroxy-N-(1,2,3,4-tetrahydronaphthalen-1-yl)-1,2,5-oxadiazole-3-carboximidamide, trans-4-amino-N-((1R,2R)-2-fluoro-2,3-dihydro-1H-inden-1-yl)-N'-hydroxy-1,2,5-oxadiazole-3-carboximidamide,
4-amino-N-(5-chloro-2,3-dihydro-1H-inden-1-yl)-N'-hydroxy-1,2,5-oxadiazole-3-carboximidamide,
4-amino-N'-hydroxy-N-(6-methyl-2,3-dihydro-1H-inden-1-yl)-1,2,5-oxadiazole-3-carboximidamide,
4-amino-N-(4-chloro-2,3-dihydro-1H-inden-1-yl)-N'-hydroxy-1,2,5-oxadiazole-3-carboximidamide,
4-amino-N'-hydroxy-N-(4-methyl-2,3-dihydro-1H-inden-1-yl)-1,2,5-oxadiazole-3-carboximidamideidamide,
4-amino-N-(4-fluoro-2,3-dihydro-1H-inden-1-yl)-N'-hydroxy-1,2,5-oxadiazole-3-carboximidamide,
4-amino-N-(5-fluoro-2,3-dihydro-1H-inden-1-yl)-N'-hydroxy-1,2,5-oxadiazole-3-carboximidamide,
4-amino-N-(6-bromo-2,3-dihydro-1H-inden-1-yl)-N'-hydroxy-1,2,5-oxadiazole-3-carboximidamide,
cis-4-amino-N'-hydroxy-N-(3-methyl-2,3-dihydro-1H-inden-1-yl)-1,2,5-oxadiazole-3-carboximidamide,
trans-4-amino-N'-hydroxy-N-(3-methyl-2,3-dihydro-1H-inden-1-yl)-1,2,5-oxadiazole-3-carboximidamide,
4-amino-N-(4,6-difluoro-2,3-dihydro-1H-inden-1-yl)-N'-hydroxy-1,2,5-oxadiazole-3-carboximidamide,
4-amino-N-(4-fluoro-7-methylbicyclo[4.2.0]octa-1(6),2,4-trien-7-yl)-N'-hydroxy-1,2,5-oxadiazole-3-carboximidamide,
4-amino-N-(6-cyano-2,3-dihydro-1H-inden-1-yl)-N'-hydroxy-1,2,5-oxadiazole-3-carboximidamide,
(4-amino-N-(3,3-difluoro-2,3-dihydro-1H-inden-1-yl)-N'-hydroxy-1,2,5-oxadiazole-3-carboximidamide,
N-(6-fluoro-2,3-dihydro-1H-inden-1-yl)-N'-hydroxy-4-((2-(sulfamoylamino)ethyl)thio)-1,2,5-oxadiazole-3-carboximidamide,
(S)—N-(2-((4-(N-(2,3-dihydro-1H-inden-1-yl)-N'-hydroxycarbamimidoyl)-1,2,5-oxadiazol-3-yl)thio)ethyl)acetamide,
(R)—N-(2-((4-(N-(2,3-dihydro-1H-inden-1-yl)-N'-hydroxycarbamimidoyl)-1,2,5-oxadiazol-3-yl)thio)ethyl)acetamide, (S)—N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide,
(R)—N-(2-((4-(N-(4-fluorobicyclo[4.2.0]octa-1(6),2,4-trien-7-yl)-N'-hydroxycarbamimidoyl)-1,2,5-oxadiazol-3-yl)thio)ethyl)acetamide,
(S)- or R—N-(2-((4-(N-(2-fluorobicyclo[4.2.0]octa-1(6),2,4-trien-7-yl)-N'-hydroxycarbamimidoyl)-1,2,5-oxadiazol-3-yl)thio)ethyl)acetamide,
(S)—N-(4-fluorobicyclo[4.2.0]octa-1,3,5-trien-7-yl)-N'-hydroxy-4-(((6-oxo-1,6-dihydropyridin-2-yl)methyl)thio)-1,2,5-oxadiazole-3-carboximidamide,
(R)—N-(4-fluorobicyclo[4.2.0]octa-1,3,5-trien-7-yl)-N'-hydroxy-4-(((6-oxo-1,6-dihydropyridin-2-yl)methyl)thio)-1,2,5-oxadiazole-3-carboximidamide,
(S)—N-(2-((4-(N-(2-chlorobicyclo[4.2.0]octa-1(6),2,4-trien-7-yl)-N'-hydroxycarbamimidoyl)-1,2,5-oxadiazol-3-yl)thio)ethyl)acetamide,
(R)—N-(2-((4-(N-(2-chlorobicyclo[4.2.0]octa-1(6),2,4-trien-7-yl)-N'-hydroxycarbamimidoyl)-1,2,5-oxadiazol-3-yl)thio)ethyl)acetamide,
(R)- or (S)—N-Ethyl-2-((4-(N-(6-fluoro-2,3-dihydro-1H-inden-1-yl)-N'-hydroxycarbamimidoyl)-1,2,5-oxadiazol-3-yl)thio)acetamide,
(S)—N-(4-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide,
(R)—N-(4-fluorobicyclo[4.2.0]octa-1(6),2,4-trien-7-yl)-N'-hydroxy-4-((2-(sulfamoylamino)ethyl)thio)-1,2,5-oxadiazole-3-carboximidamide,
(S)- or (R)—N-(6-fluoro-2,3-dihydro-1H-inden-1-yl)-N'-hydroxy-4-((2-ureidoethyl)thio)-1,2,5-oxadiazole-3-carboximidamide,
2-((4-(N-(6-fluoro-2,3-dihydro-1H-inden-1-yl)-N'-hydroxycarbamimidoyl)-1,2,5-oxadiazol-3-yl)thio)-N-(2-hydroxyethyl)acetamide,
(S,S)-4-((2,3-dihydroxypropyl)thio)-N-(6-fluoro-2,3-dihydro-1H-inden-1-yl)-N'-hydroxy-1,2,5-oxadiazole-3-carboximidamide,
(S,R)-4-((2,3-dihydroxypropyl)thio)-N-(6-fluoro-2,3-dihydro-1H-inden-1-yl)-N'-hydroxy-1,2,5-oxadiazole-3-carboximidamide,
(R,S)-4-((2,3-dihydroxypropyl)thio)-N-(6-fluoro-2,3-dihydro-1H-inden-1-yl)-N'-hydroxy-1,2,5-oxadiazole-3-carboximidamide,
(R,R)-4-((2,3-dihydroxypropyl)thio)-N-(6-fluoro-2,3-dihydro-1H-inden-1-yl)-N'-hydroxy-1,2,5-oxadiazole-3-carboximidamide,
(S)—N-ethyl-2-((4-(N-(4-fluorobicyclo[4.2.0]octa-1(6),2,4-trien-7-yl)-N'-hydroxycarbamimidoyl)-1,2,5-oxadiazol-3-yl)amino)acetamide,
(R)—N-ethyl-2-((4-(N-(4-fluorobicyclo[4.2.0]octa-1(6),2,4-trien-7-yl)-N'-hydroxycarbamimidoyl)-1,2,5-oxadiazol-3-yl)amino)acetamide,
(S)-2-((4-(N-(6-fluoro-2,3-dihydro-1H-inden-1-yl)-N'-hydroxycarbamimidoyl)-1,2,5-oxadiazol-3-yl)amino)-N-(2-hydroxyethyl)acetamide,
(R)-2-((4-(N-(6-fluoro-2,3-dihydro-1H-inden-1-yl)-N'-hydroxycarbamimidoyl)-1,2,5-oxadiazol-3-yl)amino)-N-(2-hydroxyethyl)acetamide,
(S)-2-((4-(N-(4-fluorobicyclo[4.2.0]octa-1(6),2,4-trien-7-yl)-N'-hydroxycarbamimidoyl)-1,2,5-oxadiazol-3-yl)amino)-N-(2-hydroxyethyl)acetamide,
(R)-2-((4-(N-(4-fluorobicyclo[4.2.0]octa-1(6),2,4-trien-7-yl)-N'-hydroxycarbamimidoyl)-1,2,5-oxadiazol-3-yl)amino)-N-(2-hydroxyethyl)acetamide,
N-(Bicyclo[4.2.0]octa-1(6),2,4-trien-7-yl)-N'-hydroxy-4-((2-(sulfamoylamino)ethyl)amino)-1,2,5-oxadiazole-3-carboximidamide,
N-(2-((4-(N-(6-bromo-2,3-dihydro-1H-inden-1-yl)-N'-hydroxycarbamimidoyl)-1,2,5-oxadiazol-3-yl)thio)ethyl)acetamide (racemic),
N-(2-((4-(N-(6-bromo-2,3-dihydro-1H-inden-1-yl)-N'-hydroxycarbamimidoyl)-1,2,5-oxadiazol-3-yl)thio)ethyl)acetamide (chiral, peak 1),
N-(2-((4-(N-(6-bromo-2,3-dihydro-1H-inden-1-yl)-N'-hydroxycarbamimidoyl)-1,2,5-oxadiazol-3-yl)thio)ethyl)acetamide (chiral, peak 2),
N-(2-((4-(N-(6-chloro-2,3-dihydro-1H-inden-1-yl)-N'-hydroxycarbamimidoyl)-1,2,5-oxadiazol-3-yl)thio)ethyl)acetamide (chiral, peak 1),
2-((4-(N-(6-fluoro-2,3-dihydro-1H-inden-1-yl)-N'-hydroxycarbamimidoyl)-1,2,5-oxadiazol-3-yl)thio)-N-methylacetamide (chiral peak 1),
2-((4-(N-(6-fluoro-2,3-dihydro-1H-inden-1-yl)-N'-hydroxycarbamimidoyl)-1,2,5-oxadiazol-3-yl)thio)-N-methylacetamide (chiral, peak 2),
2-((4-(N-(2-bromobicyclo[4.2.0]octa-1(6),2,4-trien-7-yl)-N'-hydroxycarbamimidoyl)-1,2,5-oxadiazol-3-yl)thio)-N-methylacetamide,
2-((4-(N-(6-bromo-2,3-dihydro-1H-inden-1-yl)-N'-hydroxycarbamimidoyl)-1,2,5-oxadiazol-3-yl)thio)-N-methylacetamide,
2-((4-(N-(2-fluorobicyclo[4.2.0]octa-1(6),2,4-trien-7-yl)-N'-hydroxycarbamimidoyl)-1,2,5-oxadiazol-3-yl)thio)-N-(2-hydroxyethyl)acetamide,
2-((4-(N-(bicyclo[4.2.0]octa-1,3,5-trien-7-yl)-N'-hydroxycarbamimidoyl)-1,2,5-oxadiazol-3-yl)thio)-N-methylacetamide,
2-((4-(N-(6-bromo-2,3-dihydro-1H-inden-1-yl)-N'-hydroxycarbamimidoyl)-1,2,5-oxadiazol-3-yl)thio)acetamide,
2-((4-(N-(2-chlorobicyclo[4.2.0]octa-1(6),2,4-trien-7-yl)-N'-hydroxycarbamimidoyl)-1,2,5-oxadiazol-3-yl)thio)-N-methylacetamide,
(N-(2-((4-(N-(6,7-difluoro-2,3-dihydro-1H-inden-1-yl)-N'-hydroxycarbamimidoyl)-1,2,5-oxadiazol-3-yl)thio)ethyl)acetamide (chiral, peak 1),
(N-(2-((4-(N-(6,7-difluoro-2,3-dihydro-1H-inden-1-yl)-N'-hydroxycarbamimidoyl)-1,2,5-oxadiazol-3-yl)thio)ethyl)acetamide (chiral, peak 2),
(N-(2-((4-(N-(4,6-difluoro-2,3-dihydro-1H-inden-1-yl)-N'-hydroxycarbamimidoyl)-1,2,5-oxadiazol-3-yl)thio)ethyl)acetamide (peak 1),
(N-(2-((4-(N-(4,6-difluoro-2,3-dihydro-1H-inden-1-yl)-N'-hydroxycarbamimidoyl)-1,2,5-oxadiazol-3-yl)thio)ethyl)acetamide (peak 2),
(2-((4-(N-(6-fluoro-2,3-dihydro-1H-inden-1-yl)-N'-hydroxycarbamimidoyl)-1,2,5-oxadiazol-3-yl)thio)acetamide (chiral, peak 1),
(2-((4-(N-(6-fluoro-2,3-dihydro-1H-inden-1-yl)-N'-hydroxycarbamimidoyl)-1,2,5-oxadiazol-3-yl)thio)acetamide (chiral, peak 2),
N-(6-fluoro-2,3-dihydro-1H-inden-1-yl)-N'-hydroxy-4-(((4-methyl-5-oxo-4,5-dihydro-1H-1,2,4-triazol-3-yl)methyl)thio)-1,2,5-oxadiazole-3-carboximidamide,
2-((4-(N-(bicyclo[4.2.0]octa-1,3,5-trien-7-yl)-N'-hydroxycarbamimidoyl)-1,2,5-oxadiazol-3-yl)thio)acetamide,
N-(2-fluorobicyclo[4.2.0]octa-1(6),2,4-trien-7-yl)-N'-hydroxy-4-((2-ureidoethyl)thio)-1,2,5-oxadiazole-3-carboximidamide, 2-((4-(N'-hydroxy-N-(6-(trifluoromethyl)-2,3-dihydro-1H-inden-1-yl)carbamimidoyl)-1,2,5-oxadiazol-3-yl)thio)-N-methylacetamide, N-(2-fluorobicyclo[4.2.0]octa-1(6),2,4-trien-7-yl)-N'-hydroxy-4-(((4-methyl-5-oxo-4,5-dihydro-1H-1,2,4-triazol-3-yl)methyl)thio)-1,2,5-oxadiazole-3-carboximidamide, N-(4-fluorobicyclo[4.2.0]octa-1(6),2,4-trien-7-yl)-N'-hydroxy-4-(((4-methyl-5-oxo-4,5-dihydro-1H-1,2,4-triazol-3-yl)methyl)thio)-1,2,5-oxadiazole-3-carboximidamide, N-cyclopropyl-2-((4-(N-(6-fluoro-2,3-dihydro-1H-inden-1-yl)-N'-hydroxycarbamimidoyl)-1,2,5-oxadiazol-3-yl)thio)acetamide, N-(6-fluoro-2,3-dihydro-1H-inden-1-yl)-N'-hydroxy-4-(((6-oxo-1,6-dihydropyridin-2-yl)methyl)thio)-1,2,5-oxadiazole-3-carboximidamide, 2-((4-(N-(6-fluoro-2,3-dihydro-1H-inden-1-yl)-N'-hydroxycarbamimidoyl)-1,2,5-oxadiazol-3-yl)thio)-N-isopropylacetamide, N-(6-fluoro-2,3-dihydro-1H-inden-1-yl)-N'-hydroxy-4-(((4-methyl-6-oxo-1,6-dihydropyridin-2-yl)methyl)thio)-1,2,5-oxadiazole-3-carboximidamide, 2-((4-(N-(2-fluorobicyclo[4.2.0]octa-1(6),2,4-trien-7-yl)-N'-hydroxycarbamimidoyl)-1,2,5-oxadiazol-3-yl)thio)acetamide, 2-((4-(N-(4-fluorobicyclo[4.2.0]octa-1(6),2,4-trien-7-yl)-N'-hydroxycarbamimidoyl)-1,2,5-oxadiazol-3-yl)thio)acetamide, (2-((4-(N-(4-fluorobicyclo[4.2.0]octa-1(6),2,4-trien-7-yl)-N'-hydroxycarbamimidoyl)-1,2,5-oxadiazol-3-yl)thio)-N-methylacetamide, N-ethyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 1), N-ethyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 2), 2-((4-(N-(4-fluorobicyclo[4.2.0]octa-1(6),2,4-trien-7-yl)-N'-hydroxycarbamimidoyl)-1,2,5-oxadiazol-3-yl)thio)-N-isopropylacetamide (peak 1), 2-((4-(N-(4-fluorobicyclo[4.2.0]octa-1(6),2,4-trien-7-yl)-N'-hydroxycarbamimidoyl)-1,2,5-oxadiazol-3-yl)thio)-N-isopropylacetamide (peak 2), 2-((4-(N-(2-fluorobicyclo[4.2.0]octa-1(6),2,4-trien-7-yl)-N'-hydroxycarbamimidoyl)-1,2,5-oxadiazol-3-yl)thio)-N-isopropylacetamide, N-cyclopropyl-2-((4-(N-(2-fluorobicyclo[4.2.0]octa-1(6),2,4-trien-7-yl)-N'-hydroxycarbamimidoyl)-1,2,5-oxadiazol-3-yl)thio)acetamide (peak 1), N-cyclopropyl-2-((4-(N-(2-fluorobicyclo[4.2.0]octa-1(6),2,4-trien-7-yl)-N'-hydroxycarbamimidoyl)-1,2,5-oxadiazol-3-yl)thio)acetamide (peak 2), N-cyclopropyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 1), N-cyclopropyl-2-((4-(N-(4-fluorobicyclo[4.2.0]octa-1(6),2,4-trien-7-yl)-N'-hydroxycarbamimidoyl)-1,2,5-oxadiazol-3-yl)thio)acetamide (peak 2), 2-((4-(N-(2-fluorobicyclo[4.2.0]octa-1(6),2,4-trien-7-yl)-N'-hydroxycarbamimidoyl)-1,2,5-oxadiazol-3-yl)thio)-N-methylacetamide, 2-((4-(N-(6-cyano-2,3-dihydro-1H-inden-1-yl)-N'-hydroxycarbamimidoyl)-1,2,5-oxadiazol-3-yl)thio)-N-methylacetamide (peak 1), 2-((4-(N-(6-cyano-2,3-dihydro-1H-inden-1-yl)-N'-hydroxycarbamimidoyl)-1,2,5-oxadiazol-3-yl)thio)-N-methylacetamide (peak 2), ((4-(N-(6-cyano-2,3-dihydro-1H-inden-1-yl)-N'-hydroxycarbamimidoyl)-1,2,5-oxadiazol-3-yl)thio)acetamide (peak 1), ((4-(N-(6-cyano-2,3-dihydro-1H-inden-1-yl)-N'-hydroxycarbamimidoyl)-1,2,5-oxadiazol-3-yl)thio)acetamide (peak 2), 2-((4-(N-(6-cyano-2,3-dihydro-1H-inden-1-yl)-N'-hydroxycarbamimidoyl)-1,2,5-oxadiazol-3-yl)thio)-N-cyclopropylacetamide (peak 1), 2-((4-(N-(6-cyano-2,3-dihydro-1H-inden-1-yl)-N'-hydroxycarbamimidoyl)-1,2,5-oxadiazol-3-yl)thio)-N-cyclopropylacetamide (peak 2), 2-((4-(N-(6-cyano-2,3-dihydro-1H-inden-1-yl)-N'-hydroxycarbamimidoyl)-1,2,5-oxadiazol-3-yl)thio)-N-ethylacetamide (peak 1), 2-((4-(N-(6-cyano-2,3-dihydro-1H-inden-1-yl)-N'-hydroxycarbamimidoyl)-1,2,5-oxadiazol-3-yl)thio)-N-ethylacetamide (peak 2), 2-((4-(N-(6-cyano-2,3-dihydro-1H-inden-1-yl)-N'-hydroxycarbamimidoyl)-1,2,5-oxadiazol-3-yl)thio)-N-isopropylacetamide (peak 1), 2-((4-(N-(6-cyano-2,3-dihydro-1H-inden-1-yl)-N'-hydroxycarbamimidoyl)-1,2,5-oxadiazol-3-yl)thio)-N-isopropylacetamide (peak 2), 2-((4-(N-(6-cyano-2,3-dihydro-1H-inden-1-yl)-N'-hydroxycarbamimidoyl)-1,2,5-oxadiazol-3-yl)thio)-N-(2-hydroxyethyl)acetamide (peak 1), 2-((4-(N-(6-cyano-2,3-dihydro-1H-inden-1-yl)-N'-hydroxycarbamimidoyl)-1,2,5-oxadiazol-3-yl)thio)-N-(2-hydroxyethyl)acetamide (peak 2), N-(6-fluoro-2,3-dihydro-1H-inden-1-yl)-N'-hydroxy-4-((2-(methylsulfonamido)ethyl)thio)-1,2,5-oxadiazole-3-carboximidamide (peak 1), N-(6-fluoro-2,3-dihydro-1H-inden-1-yl)-N'-hydroxy-4-((2-(methylsulfonamido)ethyl)thio)-1,2,5-oxadiazole-3-carboximidamide (peak 2), 2-((4-(N-(4-fluorobicyclo[4.2.0]octa-1(6),2,4-trien-7-yl)-N'-hydroxycarbamimidoyl)-1,2,5-oxadiazol-3-yl)thio)-N-(2-hydroxyethyl)acetamide (peak 1), 2-((4-(N-(4-fluorobicyclo[4.2.0]octa-1(6),2,4-trien-7-yl)-N'-hydroxycarbamimidoyl)-1,2,5-oxadiazol-3-yl)thio)-N-(2-hydroxyethyl)acetamide (peak 2), N-(2-fluorobicyclo[4.2.0]octa-1(6),2,4-trien-7-yl)-N'-hydroxy-4-((2-(methylsulfonamido)ethyl)thio)-1,2,5-oxadiazole-3-carboximidamide, N-(4-fluorobicyclo[4.2.0]octa-1(6),2,4-trien-7-yl)-N'-hydroxy-4-((2-(methylsulfonamido)ethyl)thio)-1,2,5-oxadiazole-3-carboximidamide (peak 1), N-(4-fluorobicyclo[4.2.0]octa-1(6),2,4-trien-7-yl)-N'-hydroxy-4-((2-(methylsulfonamido)ethyl)thio)-1,2,5-oxadiazole-3-carboximidamide (peak 2), N-(6-fluoro-2,3-dihydro-1H-inden-1-yl)-N'-hydroxy-4-((2-(3-(2-methoxyethyl)ureido)ethyl)thio)-1,2,5-oxadiazole-3-carboximidamide (peak 1), N-(6-fluoro-2,3-dihydro-1H-inden-1-yl)-N'-hydroxy-4-((2-(3-(2-methoxyethyl)ureido)ethyl)thio)-1,2,5-oxadiazole-3-carboximidamide (peak 2), 4-((2-(3-cyclopropylureido)ethyl)thio)-N-(4-fluorobicyclo[4.2.0]octa-1(6),2,4-trien-7-yl)-N'-hydroxy-1,2,5-oxadiazole-3-carboximidamide (peak 1), 4-((2-(3-cyclopropylureido)ethyl)thio)-N-(4-fluorobicyclo[4.2.0]octa-1(6),2,4-trien-7-yl)-N'-hydroxy-1,2,5-oxadiazole-3-carboximidamide (peak 2), N-(4-fluorobicyclo[4.2.0]octa-1(6),2,4-trien-7-yl)-N'-hydroxy-4-((2-(3-(2-methoxyethyl)ureido)ethyl)thio)-1,2,5-oxadiazole-3-carboximidamide (peak 1), N-(4-fluorobicyclo[4.2.0]octa-1(6),2,4-trien-7-yl)-N'-hydroxy-4-((2-(3-(2-methoxyethyl)ureido)ethyl)thio)-1,2,5-oxadiazole-3-carboximidamide (peak 2), N-(4-fluorobicyclo[4.2.0]octa-1(6),2,4-trien-7-yl)-N'-hydroxy-4-((2-ureidoethyl)thio)-1,2,5-oxadiazole-3-carboximidamide, 4-((2,3-dihydroxypropyl)thio)-N-(4-fluorobicyclo[4.2.0]octa-1,3,5-trien-7-yl)-N'-hydroxy-1,2,5-oxadiazole-3-carboximidamide, N-(6-fluoro-2,3-dihydro-1H-inden-1-yl)-N'-hydroxy-4-((2-(sulfamoylamino)ethyl)amino)-1,2,5-oxadiazole-3-carboximidamide (peak 1), N-(6-fluoro-2,3-dihydro-1H-inden-1-yl)-N'-hydroxy-4-((2-(sulfamoylamino)ethyl)amino)-1,2,5-oxadiazole-3-carboximidamide (peak 2), N-ethyl-2-((4-(N-(6-fluoro-2,3-dihydro-1H-inden-1-yl)-N'-hydroxycarbamimidoyl)-1,2,5-oxadiazol-3-yl)amino)acetamide, N-(6-fluoro-2,3-dihydro-1H-inden-1-yl)-N'-hydroxy-4-(((4-methyl-5-oxo-4,5-dihydro-1H-1,2,4-triazol-3-yl)methyl)amino)-1,2,5-oxadiazole-3-carboximidamide (peak 1), N-(6-fluoro-2,3-dihydro-1H-inden-1-yl)-N'-hydroxy-4-(((4-methyl-5-oxo-4,5-dihydro-1H-1,2,4-triazol-3-yl)methyl)amino)-1,2,5-oxadiazole-3-carboximidamide (peak 2), (Z)-2-((4-(N-(6-fluoro-2,3-dihydro-1H-inden-1-yl)-N'-hydroxycarbamimidoyl)-1,2,5-oxadiazol-3-yl)amino)-N-methylacetamide, 2-((4-(N-(6-fluoro-2,3-dihydro-1H-inden-1-yl)-N'-hydroxycarbamimidoyl)-1,2,5-oxadiazol-3-yl)amino)-N-isopropylacetamide (peak 1), 2-((4-(N-(6-fluoro-2,3-dihydro-1H-inden-1-yl)-N'-hydroxycarbamimidoyl)-1,2,5-oxadiazol-3-yl)amino)-N-isopropylacetamide (peak 2), N-(6-fluoro-2,3-dihydro-1H-inden-1-yl)-N'-hydroxy-4-(((6-oxo-1,6-dihydropyridin-2-yl)methyl)amino)-1,2,5-oxadiazole-3-carboximidamide (peak 1), N-(6-fluoro-2,3-dihydro-1H-inden-1-yl)-N'-hydroxy-4-(((6-oxo-1,6-dihydropyridin-2-yl)methyl)amino)-1,2,5-oxadiazole-3-carboximidamide (peak 2), N-cyclopropyl-2-((4-(N-(6-fluoro-2,3-dihydro-1H-inden-1-yl)-N'-hydroxycarbamimidoyl)-1,2,5-oxadiazol-3-yl)amino)acetamide (peak 1), N-cyclopropyl-2-((4-(N-(6-fluoro-2,3-dihydro-1H-inden-1-yl)-N'-hydroxycarbamimidoyl)-1,2,5-oxadiazol-3-yl)amino)acetamide (peak 2), 2-((4-(N-(6-cyano-2,3-dihydro-1H-inden-1-yl)-N'-hydroxycarbamimidoyl)-1,2,5-oxadiazol-3-yl)amino)-N-methylacetamide (peak 1), 2-((4-(N-(6-cyano-2,3-dihydro-1H-inden-1-yl)-N'-hydroxycarbamimidoyl)-1,2,5-oxadiazol-3-yl)amino)-N-methylacetamide (peak 2), N-(6-fluoro-2,3-dihydro-1H-inden-1-yl)-N'-hydroxy-4-(((4-methyl-6-oxo-1,6-dihydropyridin-2-yl)methyl)amino)-1,2,5-oxadiazole-3-carboximidamide, 2-((4-(N-(6-fluoro-2,3-dihydro-1H-inden-1-yl)-N'-hydroxycarbamimidoyl)-1,2,5-oxadiazol-3-yl)amino)acetamide (peak 1), 2-((4-(N-(6-fluoro-2,3-dihydro-1H-inden-1-yl)-N'-hydroxycarbamimidoyl)-1,2,5-oxadiazol-3-yl)amino)acetamide (peak 2), 4-(((R)-2,3-dihydroxypropyl)amino)-N-(6-fluoro-2,3-dihydro-1H-inden-1-yl)-N'-hydroxy-1,2,5-oxadiazole-3-carboximidamide (peak 1), 4-(((R)-2,3-dihydroxypropyl)amino)-N-(6-fluoro-2,3-dihydro-1H-inden-1-yl)-N'-hydroxy-1,2,5-oxadiazole-3-carboximidamide (peak 2), 4-(((S)-2,3-dihydroxypropyl)amino)-N-(6-fluoro-2,3-dihydro-1H-inden-1-yl)-N'-hydroxy-1,2,5-oxadiazole-3-carboximidamide (peak 1), 4-(((S)-2,3-dihydroxypropyl)amino)-N-(6-fluoro-2,3-dihydro-1H-inden-1-yl)-N'-hydroxy-1,2,5-oxadiazole-3-carboximidamide (peak 2), N-(6-fluoro-2,3-dihydro-1H-inden-1-yl)-N'-hydroxy-4-((2-(methylsulfonamido)ethyl)amino)-1,2,5-oxadiazole-3-carboximidamide (peak 1), N-(6-fluoro-2,3-dihydro-1H-inden-1-yl)-N'-hydroxy-4-((2-(methylsulfonamido)ethyl)amino)-1,2,5-oxadiazole-3-carboximidamide (peak 2), 2-((4-(N-(6-cyano-2,3-dihydro-1H-inden-1-yl)-N'-hydroxycarbamimidoyl)-1,2,5-oxadiazol-3-yl)amino)-N-ethylacetamide, N-(6-fluoro-2,3-dihydro-1H-inden-1-yl)-N'-hydroxy-4-(((((R)-1-methyl-2-oxoimidazolidin-4-yl)methyl)amino)-1,2,5-oxadiazole-3-carboximidamide, 2-((4-(N'-hydroxy-N-(6-(trifluoromethyl)-2,3-dihydro-1H-inden-1-yl)carbamimidoyl)-1,2,5-oxadiazol-3-yl)amino)-N-methylacetamide, 2-((4-(N-(6-cyano-2,3-dihydro-1H-inden-1-yl)-N'-hydroxycarbamimidoyl)-1,2,5-oxadiazol-3-yl)amino)-N-(2-hydroxyethyl)acetamide, N-(6-fluoro-2,3-dihydro-1H-inden-1-yl)-N'-hydroxy-4-((2-ureidoethyl)amino)-1,2,5-oxadiazole-3-carboximidamide (peak 1), N-(6-fluoro-2,3-dihydro-1H-inden-1-yl)-N'-hydroxy-4-((2-ureidoethyl)amino)-1,2,5-oxadiazole-3-carboximidamide (peak 2), 2-((4-(N-(6-cyano-2,3-dihydro-1H-inden-1-yl)-N'-hydroxycarbamimidoyl)-1,2,5-oxadiazol-3-yl)amino)-N-isopropylacetamide, N-(4-fluorobicyclo[4.2.0]octa-1(6),2,4-trien-7-yl)-N'-hydroxy-4-(((4-methyl-5-oxo-4,5-dihydro-1H-1,2,4-triazol-3-yl)methyl)amino)-1,2,5-oxadiazole-3-carboximidamide, 2-((4-(N-(4-fluorobicyclo[4.2.0]octa-1(6),2,4-trien-7-yl)-N'-hydroxycarbamimidoyl)-1,2,5-oxadiazol-3-yl)amino)-N-isopropylacetamide (peak 1), 2-((4-(N-(4-fluorobicyclo[4.2.0]octa-1(6),2,4-trien-7-yl)-N'-hydroxycarbamimidoyl)-1,2,5-oxadiazol-3-yl)amino)-N-isopropylacetamide (peak 2), 4-((2,3-dihydroxy-2-methylpropyl)amino)-N-(6-fluoro-2,3-dihydro-1H-inden-1-yl)-N'-hydroxy-1,2,5-oxadiazole-3-carboximidamide, N-(4-fluorobicyclo[4.2.0]octa-1(6),2,4-trien-7-yl)-N'-hydroxy-4-((2-(methylsulfonamido)ethyl)amino)-1,2,5-oxadiazole-3-carboximidamide, 4-(((R)-2,3-dihydroxy-3-methylbutyl)amino)-N-(6-fluoro-2,3-dihydro-1H-inden-1-yl)-N'-hydroxy-1,2,5-oxadiazole-3-carboximidamide, 4-(((S)-2,3-dihydroxy-3-methylbutyl)amino)-N-(6-fluoro-2,3-dihydro-1H-inden-1-yl)-N'-hydroxy-1,2,5-oxadiazole-3-carboximidamide, 4-(((R)-2,3-dihydroxypropyl)amino)-N-(4-fluorobicyclo[4.2.0]octa-1,3,5-trien-7-yl)-N'-hydroxy-1,2,5-oxadiazole-3-carboximidamide, 4-(((S)-2-amino-3-hydroxypropyl)amino)-N-(6-fluoro-2,3-dihydro-1H-inden-1-yl)-N'-hydroxy-1,2,5-oxadiazole-3-carboximidamide, 4-((2,3-dihydroxy-2-methylpropyl)amino)-N-(2-fluoro-bicyclo[4.2.0]octa-1,3,5-trien-7-yl)-N'-hydroxy-1,2,5-oxadiazole-3-carboximidamide, N-(4-fluorobicyclo[4.2.0]octa-1(6),2,4-trien-7-yl)-N'-hydroxy-4-((2-ureidoethyl)amino)-1,2,5-oxadiazole-3-carboximidamide, N-(2-fluorobicyclo[4.2.0]octa-1(6),2,4-trien-7-yl)-N'-hydroxy-4-((2-ureidoethyl)amino)-1,2,5-oxadiazole-3-carboximidamide, N—((S)-4-fluorobicyclo[4.2.0]octa-1(6),2,4-trien-7-yl)-N'-hydroxy-4-(((S)-2-hydroxy-3-(sulfamoylamino)propyl)amino)-1,2,5-oxadiazole-3-carboximidamide, N—((S)-4-fluorobicyclo[4.2.0]octa-1(6),2,4-trien-7-yl)-N'-hydroxy-4-(((R)-2-hydroxy-3-(sulfamoylamino)propyl)amino)-1,2,5-oxadiazole-3-carboximidamide, 4-[(2,3-dihydroxy-3-methylbutyl)sulfanyl]-N-(6-fluoro-2,3-dihydro-1H-inden-1-yl)-N'-hydroxy-1,2,5-oxadiazole-3-carboximidamide (peak 1), 4-[(2,3-dihydroxy-3-methylbutyl)sulfanyl]-N-(6-fluoro-2,3-dihydro-1H-inden-1-yl)-N'-hydroxy-1,2,5-oxadiazole-3-carboximidamide (peak 2), N~2~-{4-[N-(6-fluoro-2,3-dihydro-1H-inden-1-yl)-N'-hydroxycarbamimidoyl]-1,2,5-oxadiazol-3-yl}-N-(2-hydroxy-2-methylpropyl)glycinamide, N~2~-{4-[N-(6-fluoro-2,3-dihydro-1H-inden-1-yl)-N'-hydroxycarbamimidoyl]-1,2,5-oxadiazol-3-yl}-N-(1-hydroxy-2-methylpropan-2-yl)glycinamide, 2-[(4-{N-[(1 S)-6-fluoro-2,3-dihydro-1H-inden-1-yl]-N'-hydroxycarbamimidoyl}-1,2,5-oxadiazol-3-yl)sulfanyl]-N-(2-hydroxy-2-methylpropyl)acetamide, N~2~-{4-[N-(5,6-difluoro-2,3-dihydro-1H-inden-1-yl)-N'-hydroxycarbamimidoyl]-1,2,5-oxadiazol-3-yl}-N-(2-hydroxyethyl)glycinamide, 2-((4-(N-(6,7-difluoro-2,3-dihydro-1H-inden-1-yl)-N'-hydroxycarbamimidoyl)-1,2,5-oxadiazol-3-yl)amino)-N-(2-hydroxyethyl)acetamide, N~2~-{4-[N-(6,7-difluoro-2,3-dihydro-1H-inden-1-yl)-N'-hydroxycarbamimidoyl]-1,2,5-oxadiazol-3-yl}-N-[(2R)-2,3-dihydroxypropyl]glycinamide, N~2~-{4-[N-(5,6-difluoro-2,3-dihydro-1H-inden-1-yl)-N'-hydroxycarbamimidoyl]-1,2,5-oxadiazol-3-yl}-N-[(2R)-2,3-dihydroxypropyl]glycinamide, N~2~-(4-{N-[7 S)-4-chlorobicyclo[4.2.0]octa-1,3,5-trien-7-yl]-N'-hydroxycarbamimidoyl}-1,2,5-oxadiazol-3-yl)-N-(2-hydroxyethyl)glycinamide, N-(2,3-dihydroxypropyl)-N~2~-(4-{N-[(1 S)-6-fluoro-2,3-dihydro-1H-inden-1-yl]-N'-hydroxycarbamimidoyl}-1,2,5-oxadiazol-3-yl)glycinamide, N~2~-(4-{N-[(1 S)-6-fluoro-2,3-dihydro-1H-inden-1-yl]-N'-hydroxycarbamimidoyl}-1,2,5-oxadiazol-3-yl)-N-(2-hydroxypropyl)glycinamide, 2-[(4-{N-[(1 S)-6-fluoro-2,3-dihydro-1H-inden-1-yl]-N'-hydroxycarbamimidoyl}-1,2,5-oxadiazol-3-yl)sulfanyl]-N-(2-hydroxypropyl)acetamide, 2-[(4-{N-[(1 S)-6-fluoro-2,3-dihydro-1H-inden-1-yl]-N'-hydroxycarbamimidoyl}-1,2,5-oxadiazol-3-yl)sulfanyl]-N-(1-hydroxy-2-methylpropan-2-yl)acetamide, 4-({[(3R)-1,1-dioxo-1lambda~6~,2,5-thiadiazolidin-3-yl]methyl}sulfanyl)-N-[(1 S)-6-fluoro-2,3-dihydro-1H-inden-1-yl]-N'-hydroxy-1,2,5-oxadiazole-3-carboximidamide, N~2~-(4-{N-[(7S)-4-fluorobicyclo[4.2.0]octa-1,3,5-trien-7-yl]-N'-hydroxycarbamimidoyl}-1,2,5-oxadiazol-3-yl)glycinamide, N-{2-[(4-{N-[(7S)-4-fluorobicyclo[4.2.0]octa-1,3,5-trien-7-yl]-N'-hydroxycarbamimidoyl}-1,2,5-oxadiazol-3-yl)amino]ethyl}acetamide, N~2~-{4-[N-(6,7-difluoro-2,3-dihydro-1H-inden-1-yl)-N'-hydroxycarbamimidoyl]-1,2,5-oxadiazol-3-yl}-N-[2-(methyl sulfonyl)ethyl]glycinamide, N~2~-(4-{N-[(7S)-4-fluorobicyclo[4.2.0]octa-1,3,5-trien-7-yl]-N'-hydroxycarbamimidoyl}-1,2,5-oxadiazol-3-yl)-N-(2-hydroxyethyl)-D-alaninamide, N~2~-(4-{N-[(7S)-4-fluorobicyclo[4.2.0]octa-1,3,5-trien-7-yl]-N'-hydroxycarbamimidoyl}-1,2,5-oxadiazol-3-yl)-N-(2-hydroxyethyl)-L-alaninamide, N-(2,3-dihydroxypropyl)-2-[(4-{N-[(1 S)-6-fluoro-2,3-dihydro-1H-inden-1-yl]-N-hydroxycarbamimidoyl}-1,2,5-oxadiazol-3-yl)sulfanyl]acetamide, N~2~-{4-[N-(4-fluorobicyclo[4.2.0]octa-1,3,5-trien-7-yl)-N'-hydroxycarbamimidoyl]-1,2,5-oxadiazol-3-yl}-N-(2-hydroxy-2-methylpropyl)glycinamide, N-(2,3-dihydroxypropyl)-2-({4-[N-(4-fluorobicyclo[4.2.0]octa-1,3,5-trien-7-yl)-N'-hydroxycarbamimidoyl]-1,2,5-oxadiazol-3-yl}sulfanyl)acetamide, 2-({4-[N-(4-fluorobicyclo[4.2.0]octa-1,3,5-trien-7-yl)-N'-hydroxycarbamimidoyl]-1,2,5-oxadiazol-3-yl}sulfanyl)-N-(2-hydroxy-2-methylpropyl)acetamide, N~2~-{4-[N-(4-fluorobicyclo[4.2.0]octa-1,3,5-trien-7-yl)-N'-hydroxycarbamimidoyl]-1,2,5-oxadiazol-3-yl}-N-(1-hydroxy-2-methylpropan-2-yl)glycinamide, 2-({4-[N-(4-fluorobicyclo[4.2.0]octa-1,3,5-trien-7-yl)-N'-hydroxycarbamimidoyl]-1,2,5-oxadiazol-3-yl}sulfanyl)-N-(1-hydroxy-2-methylpropan-2-yl)acetamide, N~2~-{4-[N-(4-fluorobicyclo[4.2.0]octa-1,3,5-trien-7-yl)-N'-hydroxycarbamimidoyl]-1,2,5-oxadiazol-3-yl}-N-(2-hydroxypropyl)glycinamide, 2-({4-[N-(4-fluorobicyclo[4.2.0]octa-1,3,5-trien-7-yl)-N'-hydroxycarbamimidoyl]-1,2,5-oxadiazol-3-yl}sulfanyl)-N-(2-hydroxypropyl)acetamide, N-(4-fluorobicyclo[4.2.0]octa-1,3,5-trien-7-yl)-N'-hydroxy-4-[(3-oxocyclopent-1-en-1-yl)amino]-1,2,5-oxadiazole-3-carboximidamide, 4-[(2,4-dioxo-1,3-diazaspiro[4.5]decan-8-yl)amino]-N-(4-fluorobicyclo[4.2.0]octa-1,3,5-trien-7-yl)-N'-hydroxy-1,2,5-oxadiazole-3-carboximidamide, N~2~-{4-[N-(4-fluorobicyclo[4.2.0]octa-1,3,5-trien-7-yl)-N'-hydroxycarbamimidoyl]-1,2,5-oxadiazol-3-yl}-N-(2-hydroxypropyl)glycinamide, 2-cyano-N-{2-[(4-{N-[(7S)-4-fluorobicyclo[4.2.0]octa-1,3,5-trien-7-yl]-N'-hydroxycarbamimidoyl}-1,2,5-oxadiazol-3-yl)sulfanyl]ethyl}acetamide, N-{2-[(4-{N-[(7S)-4-fluorobicyclo[4.2.0]octa-1,3,5-trien-7-yl]-N-hydroxycarbamimidoyl}-1,2,5-oxadiazol-3-yl)sulfanyl]ethyl}-2-hydroxyacetamide, N~2~-(4-{N-[(7S)-4-bromobicyclo[4.2.0]octa-1,3,5-trien-7-yl]-N'-hydroxycarbamimidoyl}-1,2,5-oxadiazol-3-yl)-N-(2-hydroxyethyl)glycinamide, 2-cyano-N-[2-({4-[N-(4-fluorobicyclo[4.2.0]octa-1,3,5-trien-7-yl)-N'-hydroxycarbamimidoyl]-1,2,5-oxadiazol-3-yl}amino)ethyl]acetamide, 4-{[(1-aminocyclopropyl)methyl]amino}-N-(4-fluorobicyclo[4.2.0]octa-1,3,5-trien-7-yl)-N'-hydroxy-1,2,5-oxadiazole-3-carboximidamide, N-[2-({4-[N-(4-fluorobicyclo[4.2.0]octa-1,3,5-trien-7-yl)-N'-hydroxycarbamimidoyl]-1,2,5-oxadiazol-3-yl}amino)ethyl]-2-hydroxyacetamide, N-(2,3-dihydroxypropyl)-N~2~-{4-[N-(4-fluorobicyclo[4.2.0]octa-1,3,5-trien-7-yl)-N'-hydroxycarbamimidoyl]-1,2,5-oxadiazol-3-yl}glycinamide, 4-(carbamoylamino)-N-(4-fluorobicyclo[4.2.0]octa-1,3,5-trien-7-yl)-N'-hydroxy-1,2,5-oxadiazole-3-carboximidamide, N-(4-fluorobicyclo[4.2.0]octa-1,3,5-trien-7-yl)-N'-hydroxy-4-({[1-(sulfamoylamino)cyclopropyl]methyl}amino)-1,2,5-oxadiazole-3-carboximidamide, N~2~-{4-[N-(3-fluorobicyclo[4.2.0]octa-1,3,5-trien-7-yl)-N'-hydroxycarbamimidoyl]-1,2,5-oxadiazol-3-yl}-N-(2-hydroxyethyl)glycinamide, N-(4-fluorobicyclo [4.2.0]octa-1,3,5-trien-7-yl)-N'-hydroxy-4-{[1-(hydroxyacetyl)azetidin-3-yl]sulfanyl}-1,2,5-oxadiazole-3-carboximidamide, 4-[(azetidin-3-yl)sulfanyl]-N-(4-fluorobicyclo [4.2.0]octa-1,3,5-trien-7-yl)-N'-hydroxy-1,2,5-oxadiazole-3-carboximidamide, N-{2-[(4-{N-[(7S)-4-fluorobicyclo[4.2.0]octa-1,3,5-trien-7-yl]-N'-hydroxycarbamimidoyl}-1,2,5-oxadiazol-3-yl)amino]propyl}acetamide, N-[(7 S)-4-fluorobicyclo[4.2.0]octa-1,3,5-trien-7-yl]-N'-hydroxy-4-[(2-hydroxyethyl)amino]-1,2,5-oxadiazole-3-carboximidamide, N-[(7S)-4-fluorobicyclo[4.2.0]octa-1,3,5-trien-7-yl]-N'-hydroxy-4-{[(2 S)-1-hydroxypropan-2-yl]amino}-1,2,5-oxadiazole-3-carboximidamide, N-(4-fluorobicyclo[4.2.0]octa-1,3,5-trien-7-yl)-N'-hydroxy-4-{[(2R)-3-hydroxy-2-(sulfamoylamino)propyl]sulfanyl}-1,2,5-oxadiazole-3-carboximidamide, 2-({4-[N-(4-chloro-3-fluorobicyclo[4.2.0]octa-1,3,5-trien-7-yl)-N'-hydroxycarbamimidoyl]-1,2,5-oxadiazol-3-yl}sulfanyl)-N-(2-hydroxyethyl)acetamide, 2-({4-[N-(3,4-difluorobicyclo[4.2.0]octa-1,3,5-trien-7-yl)-N'-hydroxycarbamimidoyl]-1,2,5-oxadiazol-3-yl}sulfanyl)-N-(2-hydroxyethyl)acetamide, (2R)—N-{2-[(4-{N-[(7S)-4-fluorobicyclo[4.2.0]octa-1,3,5-trien-7-yl]-N-hydroxycarbamimidoyl}-1,2,5-oxadiazol-3-yl)sulfanyl]ethyl}-2,3-dihydroxypropanamide, (2S)—N-{2-[(4-{N-[(7S)-4-fluorobicyclo[4.2.0]octa-1,3,5-trien-7-yl]-N-hydroxycarbamimidoyl}-1,2,5-oxadiazol-3-yl)sulfanyl]ethyl}-2,3-dihydroxypropanamide, 4-({[(3R)-1,1-dioxo-1lambda~6~,2,5-thiadiazolidin-3-yl]methyl}sulfanyl)-N-(4-fluorobicyclo[4.2.0]octa-1,3,5-trien-7-yl)-N'-hydroxy-1,2,5-oxadiazole-3-carboximidamide, N-(4-fluorobicyclo[4.2.0]octa-1,3,5-trien-7-yl)-N'-hydroxy-4-{[2-(methyl sulfonyl)ethyl]amino}-1,2,5-oxadiazole-3-carboximidamide, 4-{[1-(2,3-dihydroxypropanoyl)azetidin-3-yl]sulfanyl}-N-[(7S)-4-fluorobicyclo[4.2.0]octa-1,3,5-trien-7-yl]-N'-hydroxy-1,2,5-oxadiazole-3-carboximidamide, N—((S)-4-fluorobicyclo[4.2.0]octa-1(6),2,4-trien-7-yl)-N'-hydroxy-4-((2-hydroxy-3-(methylsulfonamido)propyl)thio)-1,2,5-oxadiazole-3-carboximidamide, N—((S)-4-fluorobicyclo[4.2.0]octa-1(6),2,4-trien-7-yl)-N'-hydroxy-4-(((1 s,3R)-3-(sulfamoylamino)cyclobutyl)amino)-1,2,5-oxadiazole-3-carboximidamide, (S)—N-(4-fluorobicyclo [4.2.0]octa-1 (6),2,4-trien-7-yl)-N'-hydroxy-4-((2-((2-hydroxyethyl)sulfonyl)ethyl)amino)-1,2,5-oxadiazole-3-carboximidamide, N-(3-((4-(N—((S)-4-fluorobicyclo[4.2.0]octa-1(6),2,4-trien-7-yl)-N'-hydroxycarbamimidoyl)-1,2,5-oxadiazol-3-yl)thio)-2-hydroxypropyl)-2-hydroxyacetamide, (2S)-1-[(4-{N-[(7S)-4-fluorobicyclo[4.2.0]octa-1,3,5-trien-7-yl]-N'-hydroxycarbamimidoyl}-1,2,5-oxadiazol-3-yl)amino]propan-2-yl sulfamate, S-(4-{N-[(7S)-4-fluorobicyclo[4.2.0]octa-1,3,5-trien-7-yl]-N'-hydroxycarbamimidoyl}-1,2,5-oxadiazol-3-yl)-L-cysteinamide, N-[(7S)-4-fluorobicyclo[4.2.0]octa-1,3,5-trien-7-yl]-N'-hydroxy-4-({1-[(2-hydroxyethyl)sulfamoyl]azetidin-3-yl}sulfanyl)-1,2,5-oxadiazole-3-carboximidamide, N-[(7S)-4-fluorobicyclo[4.2.0]octa-1,3,5-trien-7-yl]-N'-hydroxy-4-[(1-sulfamoylazetidin-3-yl)sulfanyl]-1,2,5-oxadiazole-3-carboximidamide, 4-[(2-azaspiro[3.3]heptan-6-yl)amino]-N-[(7 S)-4-fluorobicyclo[4.2.0]octa-1,3,5-trien-7-yl]-N'-hydroxy-1,2,5-oxadiazole-3-carboximidamide, N-[(7 S)-4-fluorobicyclo[4.2.0]octa-1,3,5-trien-7-yl]-N'-hydroxy-4-({[(2R)-morpholin-2-yl]methyl}amino)-1,2,5-oxadiazole-3-carboximidamide, 4-[(trans-3-aminocyclobutyl)amino]-N-[(7S)-4-fluorobicyclo[4.2.0]octa-1,3,5-trien-7-yl]-N'-hydroxy-1,2,5-oxadiazole-3-carboximidamide, N-[(7S)-4-fluorobicyclo[4.2.0]octa-1,3,5-trien-7-yl]-N'-hydroxy-4-{[1-(3-hydroxypropanoyl)azetidin-3-yl]sulfanyl}-1,2,5-oxadiazole-3-carboximidamide, N-[(7S)-4-fluorobicyclo[4.2.0]octa-1,3,5-trien-7-yl]-N'-hydroxy-4-{[1-(methoxyacetyl)azetidin-3-yl]sulfanyl}-1,2,5-oxadiazole-3-carboximidamide, N-[(7S)-4-fluorobicyclo[4.2.0]octa-1,3,5-trien-7-yl]-N'-hydroxy-4-[(2-hydroxyethyl)sulfanyl]-1,2,5-oxadiazole-3-carboximidamide, N-[(7 S)-4-fluorobicyclo[4.2.0]octa-1,3,5-trien-7-yl]-N'-hydroxy-4-{[2-hydroxy-4-(methylsulfonyl)butyl]amino}-1,2,5-oxadiazole-3-carboximidamide (peak 1), N-[(7 S)-4-fluorobicyclo[4.2.0]octa-1,3,5-trien-7-yl]-N'-hydroxy-4-{[2-hydroxy-4-(methylsulfonyl)butyl]amino}-1,2,5-oxadiazole-3-carboximidamide (peak 2), N-{2-[(4-{N-[(7S)-4-fluorobicyclo[4.2.0]octa-1,3,5-trien-7-yl]-N'-hydroxycarbamimidoyl}-1,2,5-oxadiazol-3-yl)sulfanyl]ethyl}-3-hydroxypropanamide, (3-{[(4-{N-[(7S)-4-fluorobicyclo[4.2.0]octa-1,3,5-trien-7-yl]-N'-hydroxycarbamimidoyl}-1,2,5-oxadiazol-3-yl)amino]methyl}phenyl)boronic acid, (4-{[(4-{N-[(7S)-4-fluorobicyclo[4.2.0]octa-1,3,5-trien-7-yl]-N'-hydroxycarbamimidoyl}-1,2,5-oxadiazol-3-yl)amino]methyl}phenyl)boronic acid, N-[(7S)-4-fluorobicyclo[4.2.0]octa-1,3,5-trien-7-yl]-N'-hydroxy-4-({3-[hydroxy(dimethyl)silyl]propyl}amino)-1,2,5-oxadiazole-3-carboximidamide, and (S,Z)-N-(2-((4-(N-(4-fluorobicyclo[4.2.0]octa-1(6),2,4-trien-7-yl)-N'-hydroxycarbamimidoyl)-1,2,5-oxadiazol-3-yl)amino)ethyl)-1-hydroxy-3,4-dihydro-1H-benzo[c][1,2]oxaborinine-8-carboxamide.

19. A composition which comprises an inert carrier and a compound of claim 1 or a pharmaceutically acceptable salt thereof.

20. A method for treating an IDO-associated disease or disorder in a mammalian subject which comprises administering to the subject an effective amount of a compound of claim 1 or a pharmaceutically acceptable salt thereof, wherein the disease or disorder is selected from a cancer of the colon, pancreas, breast, prostate, lung, brain, ovary, cervix, testes, renal, head and neck, lymphoma, leukemia, and melanoma.

* * * * *